United States Patent
Bartley et al.

(10) Patent No.: US 11,193,133 B2
(45) Date of Patent: Dec. 7, 2021

(54) MODULATION OF EXPRESSION OF ACYLTRANSFERASES TO MODIFY HYDROXYCINNAMIC ACID CONTENT

(71) Applicant: The Regents of the University of California, Oakland, CA (US)

(72) Inventors: Laura E. Bartley, Norman, OK (US); Pamela Ronald, Davis, CA (US); Henrik Vibe Scheller, Millbrae, CA (US)

(73) Assignee: The Regents of the University of California, Oakland, CA (US)

( * ) Notice: Subject to any disclaimer, the term of this patent is extended or adjusted under 35 U.S.C. 154(b) by 115 days.

(21) Appl. No.: 16/659,230

(22) Filed: Oct. 21, 2019

(65) Prior Publication Data

US 2020/0140877 A1     May 7, 2020

Related U.S. Application Data

(60) Division of application No. 15/652,115, filed on Jul. 17, 2017, now Pat. No. 10,450,578, which is a division of application No. 14/746,779, filed on Jun. 22, 2015, now Pat. No. 9,708,624, which is a continuation-in-part of application No. PCT/US2013/077266, filed on Dec. 20, 2013.

(60) Provisional application No. 61/745,247, filed on Dec. 21, 2012.

(51) Int. Cl.
*C12N 15/82* (2006.01)
*C12N 9/10* (2006.01)

(52) U.S. Cl.
CPC ....... *C12N 15/8246* (2013.01); *C12N 9/1025* (2013.01)

(58) Field of Classification Search
CPC ................................................ C12N 15/8246
See application file for complete search history.

(56) References Cited

U.S. PATENT DOCUMENTS

| | | | |
|---|---|---|---|
| 9,708,624 | B2 | 7/2017 | Bartley et al. |
| 10,450,578 | B2 | 10/2019 | Bartley et al. |
| 2005/0086712 | A1 | 4/2005 | Meyer et al. |
| 2008/0305521 | A1 | 12/2008 | Alves et al. |
| 2009/0253732 | A1 | 10/2009 | Gregory et al. |
| 2010/0143915 | A1 | 6/2010 | Ronald et al. |
| 2013/0203973 | A1 | 8/2013 | Wilkerson et al. |
| 2013/0219547 | A1 | 8/2013 | Wilkerson et al. |
| 2015/0020234 | A1 | 1/2015 | Wilkerson et al. |
| 2015/0307892 | A1 | 10/2015 | Bartley et al. |

FOREIGN PATENT DOCUMENTS

| | | |
|---|---|---|
| WO | 2008034648 A1 | 8/2008 |
| WO | 2012103555 A2 | 8/2012 |
| WO | 2014100742 A2 | 6/2014 |
| WO | 2014100742 A3 | 10/2014 |

OTHER PUBLICATIONS

Piston, F. et al., Planta (2010) vol. 231, pp. 677-691. (Year: 2010).*
International Search Report and Written Opinion from International Application No. PCT/US2013/077266, dated Jul. 14, 2014, 18 pages.
Bartley et al. (2013) "Overexpression of a Bahd Acyltransferase, Osat1O, Alters Rice Cell Wall Hydroxycinnamic Acid Content and Saccharification," Plant Physiol., 161(4):1615-1633.
Casler et al. (2006) "Relationships of fibre, lignin, and phenolics to in vitro fibre digestibility in three perennial grasses," Animal Feed Science and Technology, 125:151-161.
Lanoue et al. (2010} "De novo biosynthesis of defense root exudates in response to Fusarium attack in barley," New Phytologist, 185:577-588.
Lin et al., (2016) "Cell Wall Composition and Candidate Biosynthesis Gene Expression During Rice Development," Plant Cell Physiol., 57 (10): 2058-2075.
MacAdam et al. (2002) "Relationship of growth cessation with the formation of diferulate cross-links and p-coumaroylated lignins in tall fescue leaf blades," Planta, 215:785-793.
Mitchell et al. (2007) A novel bioinformatics approach identifies candidate genes for the synthesis and feruloylation of arabinoxylan. Plant Physiol 144:43-53.
Molina et al. (2009) "Identification of an *Arabidopsis* Feruloyl-CoA Transferase Required for Suberin Synthesis 1 [W] [OAJ]." Plant Physiol., 151:1317-1328.
Piston et al. (2010) "Down-regulation of four putative arabinoxylan feruloyl transferase genes from family PF02458 reduces esterlinked ferulate content in rice cell walls," Planta, 231:677-691.
Rautengarten et al. (2012) "*Arabidopsis* Deficient in Cutin Ferulate encodes a transferase required for feruloylation of omega-hydroxy fatty acids in cutin polyester," Plant Physiol., 158:654-665.
Tuominen et al. (2011) "Differential Phylogenetic Expansions in BAHD Acyltransferases Across Five Angiosperm Taxa and Evidence of Divergent Expression Among Populus Paralogues," BMC Genomics, 12:236 (17 pages).
UniProt Accession No. Q69UE6 (Q69UE6_0RYSJ), "Putative 10-deacetylbaccatinl!l-10-0-acetyl transferase," ver. 1, Sep. 2004, retreived from the internet at uniprot.org/uniprot/Q69UE6 on Mar. 19, 2014 (2 pages).
Unno et al. (2007) "Structural and mutational studies of anthocyanin malonyltransferases establish the features of BAHD enzyme catalysis," J. Biol. Chem., 282:15812-15822.
Wilkerson et al. (2014) "Monolignol Ferulate Transferase Introduces Chemically Labile Linkages into the Lignin Backbone," Science, 344(6179):90-93.
Withers et al. (2012) "Identification of grass-specific enzyme that acylates monolignols with p-coumarate," J. Biol. Chem., 287:8347-8355.
GenBank Accession AAM08506.1, Apr. 4, 2020, Putative 10-deacetylbaccatin III-10-O-acetyl transferase [*Oryza sativa* Japonica Group].

* cited by examiner

*Primary Examiner* — Russell Kallis
(74) *Attorney, Agent, or Firm* — Robin C. Chiang; Lawrence Berkeley National Laboratory

(57) ABSTRACT

The invention provides methods of engineering plants to modulate hydroxycinnamic acid content. The invention additionally provides compositions and methods comprising such plants.

15 Claims, 42 Drawing Sheets

Specification includes a Sequence Listing.

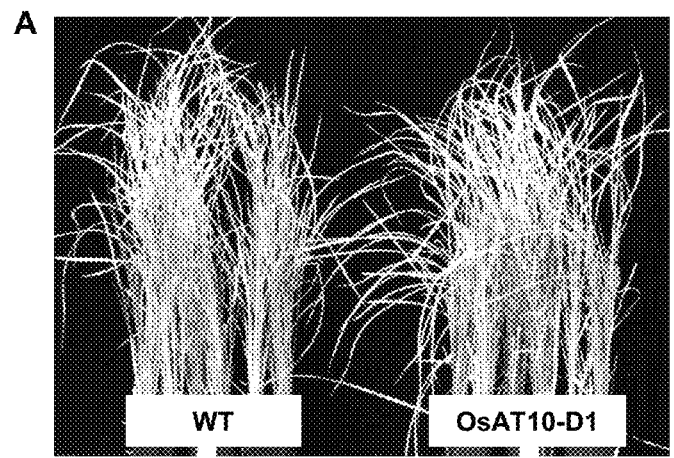
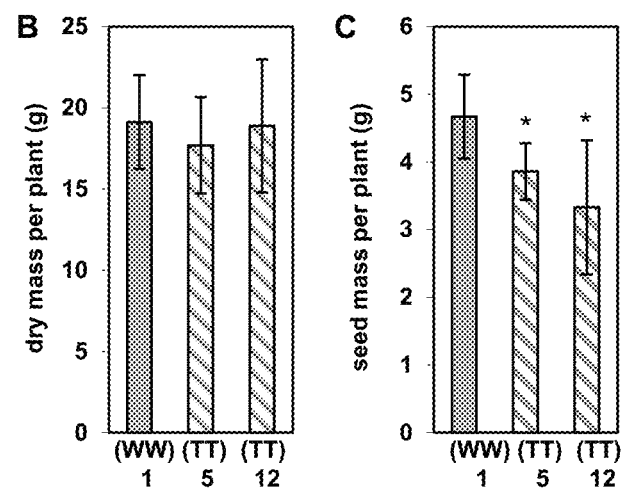
FIGS. 4A-4C

FIG. 21A-21C Multiple sequence alignment of the PFAM domain of OsAT10 and related proteins. "fl" indicates that the full length sequence is included.

CLUSTAL 2.0.10 multiple sequence alignment

```
LOC_Os06g39390.1_OsAT10fl      MGVFAVTKVSEGPVRPSA-ATPSETLPLAWDRYPTHRGLVESVHIYLRR
Bradi1g36990.1_BdAT10          ---FTVTKLSEGPVRPSA-DTPSETLPLAWDRYPTHRGLVESTHIYCSG
Sb10g023150.1_SbAT10           ----AVTKVSEGPVRPSA-ATPSETLPLAWDRYPTHRGLVESVHIYLRR
LOC_Os06g39390.1_OsAT10        ---FKVTRISEGPVKPAS-STPEETLPLAWDRYPTHRGLVESMHIFR--
Sb03g003390.1_SbAT9            MGVFAVTKVSEGPVRPSA-ATPSDTLPLAWDRYPTHRGLVESVHIYRDA
Bradi1g36990.1_BdAT10fl        ---FKVTRISEGPVKPASPDTPGHTLPLAWDRYPTHRGLVESMHIFR--
Bradi2g05480.1_BdAT9           ---FKVTRISEGAVKPAA-ATPEETLPLAWDRYPTHRGLVESMHIFR--
LOC_Os01g09010.1_OsAT9         ---FKVTRISEGAVKPAA-ATPEETLPLAWDRYPTHRGLVESMHIFR--

LOC_Os06g39390.1_OsAT10fl      ----DDAAVEAPCADGGVIVEGKK----KNNKPAAVVRGALADALVHY
Bradi1g36990.1_BdAT10          ---------------------KKNNN-NSKKPPAAVVRSALADALVHY
Sb10g023150.1_SbAT10           ----DDVAKMLLPPQAPAAATKKKKEVTTKSKKSPAAVVRGALADALVLY
LOC_Os06g39390.1_OsAT10        ----DDAAVEAPCADGGVIVEGKK----KNNKPAAVVRGALADALVHY
Sb03g003390.1_SbAT9            FQPPPAPEAAAAAAEEEEDQEKKKNNN-NSKKPAAVVRSALADALVHY
Bradi1g36990.1_BdAT10fl        --------------------------------SGADAAPGVIRDALAKALVFF
Bradi2g05480.1_BdAT9           --------------------------------SGADAAPGVIRDALARALVFF
LOC_Os01g09010.1_OsAT9         --------------------------------SGADAAPGVIRDALARALVFF
                                                                : .**. ** . **

LOC_Os06g39390.1_OsAT10fl      YPFAGRIVEDERSPGRP---------------------AVLCSGEGVY
Bradi1g36990.1_BdAT10          YPFAGRIVEDAAKPGRP---------------------AVLCCAEGVY
Sb10g023150.1_SbAT10           YPFAGRIVED--VPGRP---------------------AVLCSAEGVY
LOC_Os06g39390.1_OsAT10        YPFAGRIVEDERSPGRP---------------------AVLCSGEGVY
Sb03g003390.1_SbAT9            YPLAGRIVEGDQPGCP----------------------AIRCTADGVY
Bradi1g36990.1_BdAT10fl        YPFAGRIVEDAAKPGRP---------------------AVLCCAEGVY
Bradi2g05480.1_BdAT9           YPLAGRIVEPEKEAAAAAAAAAGENGDGEKKAPAASFPLGVRCAGDGVY
LOC_Os01g09010.1_OsAT9         YPLAGRIVEPEAGSPA----------------------IRCTADGVY
                               **:******                               : :*.*

LOC_Os06g39390.1_OsAT10fl      FVEAAANCTLADVNHLERPLLLSKEDLVPCPTPEQWPVEPHNSLAMIQVT
Bradi1g36990.1_BdAT10          FVEATANCTLADVNFLERPLLLGKEDLVPYPAPELWAVEPHNTLAMIQVT
Sb10g023150.1_SbAT10           FVEAAANCTLADVNFLERPLLLSKEDLVPCPTPDLWPVEPHNSLAMIQVT
LOC_Os06g39390.1_OsAT10        FVEAAANCTLADVNFLERPLLLSKEDLVPCPTPEQWPVEPHNSLAMIQVT
Sb03g003390.1_SbAT9            FAEAVADCSLEDVRFLERPLLPKEDLVPYPGDDRWTVEPHNTIMMQIT
Bradi1g36990.1_BdAT10fl        FVEATANCTLADVNFLERPLLLGKEDLVPYPAPELWAVEPHNTLAMIQVT
Bradi2g05480.1_BdAT9           FAEAEAECSLEDVRFLERPLLPKEDLVPYPGPDKWSVEPHNTIMMQIT
LOC_Os01g09010.1_OsAT9         FAEAAADCSLEDVRFLERPLLLPKEDLVPYPGDDRWGVEPHNTIMMQIT
                               *.** ** ..* ****** ****** *  :  * ..****:.: *:.:*
```

```
LOC_Os01g09010.1_OsAT9          QMTFNYESIYVSDWSKLGFAEVDYGFGPPKFAGPLVNNDFIASVVILKAP
                                **:*:**********  :****:*.*  ******

LOC_Os06g39390.1_OsAT10f1       APLAGTRLLASCVTKEHADDFAARMREDLV---------
Bradi1g36990.1_BdAT10           APLAGTRLLASCVTKEHAEGF------------------
Sb10g023150.1_SbAT10            ---------------------------------------
LOC_Os06g39390.1_OsAT10         ---------------------------------------
Sb03g003390.1_SbAT9             LPLDGTRMLASCVTKEHSDEF------------------
Bradi1g36990.1_BdAT10f1         APLAGTRLLASCVTKEHAEGFASRMREDIA---------
Bradi2g05480.1_BdAT9            LPLDGTRMLASCVTKEHSDEFV-----------------
LOC_Os01g09010.1_OsAT9          LPLDGTRMLASCVTKEHSEEFVR----------------
```

FIG. 21C

FIGS. 22A-22C. Multiple sequence alignment of PFAM domains of proteins closely related to OsAT15

```
LOC_Os10g03390.1_OsAT18      ----VTKSPPEIVRPSEPVTTTAATGK------IIFSPFDKPLAT-VPV
LOC_Os10g03360.1_OsAt17      ----VTKSPPEIVRPSEPVTTTAATSK------VIFSPLDRPLAI-VPI
LOC_Os10g01920.1_OsAT15fl    MSIVVSKSAPVVVRPSEP--ATSTADK------ILLSTLDKPVAT-IPV
LOC_Os10g01920.1_OsAt15      ---APVVVRPSEP--ATSTADK------ILLSTLDKPVAT-IPV
LOC_Os10g02000.1_OsAt14      ------VVVRPSQPPVKTTSGSK------IVLSPMDKPSSM-MPT
LOC_Os10g01930.1_OsAt13      ------
LOC_Os10g01800.1_OsAt16      ------VVVGADDQ--QSSGAGT------IDLSSFDKSLGP-LPI
Bradi5g01770.1               ------

LOC_Os10g03390.1_OsAT18      VVLQVFEHP----------------------------IHEPVETIRRGLSH-
LOC_Os10g03360.1_OsAt17      VVLQVFEHP----------------------------IHEPVETIRRGLSR-
LOC_Os10g01920.1_OsAT15fl    TVLLAFDHP----------------------------IHDATAETIKTALAQ-
LOC_Os10g01920.1_OsAt15      TVLLAFDHP----------------------------IHDATAETIKTALAQ-
LOC_Os10g02000.1_OsAt14      TVLLAFDHPTI--------------------------QSECTAETIKRGLAQ-
LOC_Os10g01930.1_OsAt13      --------------------------------------ALAQ-
LOC_Os10g01800.1_OsAt16      
Bradi5g01770.1               TVLLVFDHP----------------------------IKDPVESIKKALSQS LOC_Os10g03390.1_OsAT18      -ALVHYYPLAGRLAG------DDY---------------DD
LOC_Os10g03360.1_OsAt17      -ALVHYYPLAGRLAG------DDY---------------DD
LOC_Os10g01920.1_OsAT15fl    -SLVHYYPIAGRISC--DN--DDG---------------GH
LOC_Os10g01920.1_OsAt15      -SLVHYYPIAGRISC--DN--DDG---------------GH
LOC_Os10g02000.1_OsAt14      -ALVPYYPIAGRLSC--DD--D-----------------
LOC_Os10g01930.1_OsAt13      -ALVHYYPIAGRLSCNDDE--DGG---------------GD
LOC_Os10g01800.1_OsAt16      
Bradi5g01770.1               LAVDHYHPMAGRLTP------DGGA--------------

LOC_Os10g03390.1_OsAT18      VHIDCT------GEGVTIVAASAN-CTVKQLMRDIDG-RLPDPSTAVQR
LOC_Os10g03360.1_OsAt17      VHIDCT------GEGVTVTFVAANAD-CTVKELVRDIDC-RSPDAAKAVIR
LOC_Os10g01920.1_OsAT15fl    FYIDCTG-----EDLGVTFVAASAN-CTMEELMCLVDD-QAPDDETAVVQ
LOC_Os10g01920.1_OsAt15      FYIDCTG-----EDLGVTFVAASAN-CTMEELMCLVDD-QAPDDETAVVQ
LOC_Os10g02000.1_OsAt14      FYIDCT------EBLGVTFVAASAN-CTMEELMCCVDD-QPPDAETAVVQ
LOC_Os10g01930.1_OsAt13      FYIDCT------SELGVMFVAASAD-CTMEELMRVADN-QPTDDETAVVQ
LOC_Os10g01800.1_OsAt16      ---IACTG----EGVSFVGASVS-CALADQHLPL--------LKD
Bradi5g01770.1

LOC_Os10g03390.1_OsAT18      ELIVDDNPAYGFG------RADPLILMQ----VTTFTCGGFVIG
LOC_Os10g03360.1_OsAt17      ELIVD-YPANGFG------RADPLVLMQ----VTAFACGGFVVG
LOC_Os10g01920.1_OsAT15fl    QLAFNCTPDD--------LHHRLLWVQ----VTTLNCGGFVVG
LOC_Os10g01920.1_OsAt15      QLAFNCTPDD--------LHHRLLWVQ----VTTLNCGGFVVG
```

FIG. 22A

```
LOC_Os10g02000.1_OsAT14       QLAFNCTPDDDH------LPHCLLWVQ---------------VTTLSCGGFVVG
LOC_Os10g01930.1_OsAt13       QLAFNCTPDD--------LHHRLLWMQ---------------VTTLSCGGFVVG
LOC_Os10g01800.1_OsAt16       QLAFNCTPDVGDD-----GPPPLLWVQ---------------VTTLSCGGFVVG
Bradi5g01770.1                DLAMG-YPGDWCR-----PEDPLVQMQ---------------VTEFSCGGFVVG
                              :*.:  *               * :.*:             ** :.*****:*

LOC_Os10g03390.1_OsAT18       VTWNHGAADGPGIAQFLQAVGELARGLPT---------TSVIPVR---SDK
LOC_Os10g03360.1_OsAt17       VTWNHGAADGFGIAQFLQAVGELARGLPT---------PAVTPVR---WDG
LOC_Os10g01920.1_OsAT15fl     VTWSHGVADGPGIAQFIQAVGELARGLPS---------PSVVPVR---LDD
LOC_Os10g01920.1_OsAt15       VTWSHGVADGPGIAQFIQAVGELARGLPS---------PSVVPVR---LDD
LOC_Os10g02000.1_OsAT14       VTWNHAVADGFGIAQFIQAVGELARGLPSA--------PSVTPVR---LDD
LOC_Os10g01930.1_OsAt13       VTWNHGLADGFGMAQFIQAVGELTRGLPS---------PSVVPVR---LDD
LOC_Os10g01800.1_OsAt16       VTWSHGLADGVGIAQFIQAVGELARGLPS---------PSIVPVR---QDD
Bradi5g01770.1                VTWNHVMADGAGMAQFLRAIGELARGLPS---------PSVVPVR---SS.
                              *** *  **  * ** :*:*** ****:.         ** *:*   .

LOC_Os10g03390.1_OsAT18       SLQA---MSSST-VMAAKQFMFG----------------VK-PTTLALHS
LOC_Os10g03360.1_OsAt17       WAQA---VAPST-VMASKRFMFG----------------VKAPTRLALHS
LOC_Os10g01920.1_OsAT15fl     KIAT-QAVPPF-TMAVHRFISG-----------------LKPVSNLDVRN
LOC_Os10g01920.1_OsAt15       KIAT-QAVPPF-TMAVHRFISG-----------------LKPVSNLDVRN
LOC_Os10g02000.1_OsAT14       QNN---AVSPF-TMAFMQLADR-----------------HKVP-DLTFNN
LOC_Os10g01930.1_OsAt13       DNNATQAIPPF-AMAVYQFMSSSS---------------HKASIDHTFNN
LOC_Os10g01800.1_OsAt16       IVAT-QVVPPF-TMALLQFLPG-----------------LKPLDLTFNN
Bradi5g01770.1                SLLP--CIPPS-VVAAQRAMMA-----------------VASKDMASLD
                                .:   .  *  ..  :                      .

LOC_Os10g03390.1_OsAT18       ITIPARVINGVR---GPTP-------TCTVFEAVAAVMNRCRTRV
LOC_Os10g03360.1_OsAt17       ITIPARTIDGVR---GAT--------ACTMFEAVAAAALWRCRTRV
LOC_Os10g01920.1_OsAT15fl     VTVSSSLINHII-VGARRRA------TVFEAVAAVLWQCRTRV
LOC_Os10g01920.1_OsAt15       VTVSSSLINHII-VGARRRA------TVFEAVAAVLWQCRTRV
LOC_Os10g02000.1_OsAT14       VTVPSRLMDHI--IRGRTIN------VTVFEAVAAVLWQCRTRA
LOC_Os10g01930.1_OsAt13       ITVPSLIDHIR-FRGRFTNDD-----VTVFEAVAAVLWQCRTRA
LOC_Os10g01800.1_OsAt16       VTVPTSLINHIRRFRGRRTNDDG--GQHSTTTITAFEAVAAVLWKCRTRA
Bradi5g01770.1                FTIPSSAIARIKGQWADAN------AHEQPCTVFEAVTALLWLCRTRA
                              :*::               .       *   ****.::.*. * **:.

LOC_Os10g03390.1_OsAT18       VMS-----DPDAP-----------TVLAITVNS----RKYVG-------
LOC_Os10g03360.1_OsAt17       VMS-----DPDAP-----------TVLAITVNS----RKHVG-------
LOC_Os10g01920.1_OsAT15fl     VMT-----DPEAP-----------AVLLFAVNA----RKYLG-------
LOC_Os10g01920.1_OsAt15       VMT-----DPEAP-----------AVLLFAVNA----RKYLG-------
LOC_Os10g02000.1_OsAT14       VMT-----NPEAP-----------AVLLFAVNA----RKYLG-------
LOC_Os10g01930.1_OsAt13       VMK-----NPEAP-----------AVLLFAVNA----RKYLG-------
LOC_Os10g01800.1_OsAt16       VMA-----SPEAP-----------AILVFVVNA----RKYLAG------
Bradi5g01770.1                VVTAK-DDDELP-----------VGMVFPSNV----RQQLG-------
                              *:       *  *           .::: :*     *  :*

LOC_Os10g03390.1_OsAT18       ----VKDGYYGNCATMQMAVARSGVVAD-----
```

```
LOC_Os10g03360.1_OsAt17      ----VKDGYYGNCATVHMAVARSGAVAG-------
LOC_Os10g01920.1_OsAT15fl    ----AKDGYYGCCTAMHMAVSKSGTVAN-------
LOC_Os10g01920.1_OsAt15      ----AKDGYYGCCTAMHMAVSKSGTVAN-------
LOC_Os10g02000.1_OsAt14      ----AKDGYYGNCSTMHVAVAKSGAVAN-------
LOC_Os10g01930.1_OsAt13      ----AKDGYYGNCSTMHVAVAKSGAVAN-------
LOC_Os10g01800.1_OsAt16      ----VNDGYYGNCSMMHMAMAKSGAVAN-------
Bradi5g01770.1               AEAGYYGNCLAAQLVQATTGAPA------------
                                 .****.*  ::  :  :*.*

LOC_Os10g03390.1_OsAT18      --GDMMEVVRTIRRA----KEEIP----ERLKK---GD-
LOC_Os10g03360.1_OsAt17      --GDMTEAVRAIRRA----KEEIP----ERLKK---GD-
LOC_Os10g01920.1_OsAT15fl    --GDIMKLVGIIRRA----KEQIP----ERLKAD DGE-
LOC_Os10g01920.1_OsAt15      --GDIMKLVGIIRRA----KEQIP----EQLKADDGE-
LOC_Os10g02000.1_OsAt14      --ADINDIVDIIRRA----KERIP----EQLKMTGGSDM
LOC_Os10g01930.1_OsAt13      --ADINDIVDIIRRA----KERIP----EQLKMTGGSDM
LOC_Os10g01800.1_OsAt16      --GDIMDVVEIIRRA----KERIP----EQFGE---GSD
Bradi5g01770.1               INGLVKLIKRA----KDGG----DQQQPL---
                               :*.***.*     ::          ::

LOC_Os10g03390.1_OsAT18      ------------------AIAELSKG-QLSGYES--VLLVTCWRNIG--FEAVDFG
LOC_Os10g03360.1_OsAt17      -------------------VIGELSKE-QLGGYES--VLLVTCWRNIG--FEAVDYG
LOC_Os10g01920.1_OsAT15fl    -------------------MMLRTMVGEKQVNGYES--LLYLTSWRNIG--FEDVDFG
LOC_Os10g01920.1_OsAt15      -------------------MMLRTMVGEKQVNGYES--LLYLTSWRNIG--FEDVDFG
LOC_Os10g02000.1_OsAt14      -------------------TMLRELADDHRLDGYES--LLYLTSWRNIG--FEDVDFG
LOC_Os10g01930.1_OsAt13      -------------------TMLRELADDHRLDGYES--LLYLTSWRNIG--FEDVDFG
LOC_Os10g01800.1_OsAt16      -------------------RMVRELSDGQQVDGYES--LLYLTSWRNIG--LEEVDFG
Bradi5g01770.1               -------------------HQG------AAVGWYD---TLLVSSWRNLG--FEAAEFG
                                                  :          * :: ****.*   *. ..:*

LOC_Os10g03390.1_OsAT18      -GGRTARVMTTYEQSGVRPL--------CVVCLPWQGEEDEGARV------
LOC_Os10g03360.1_OsAt17      -GGRTARVMTTYEQGRVRPM--------CVVCLPWQGEEEBGA--------
LOC_Os10g01920.1_OsAT15fl    -SGKTARVMT-YPPRMLSMMPR----IAPICFMLKATEEGVRVMSDCVTAD
LOC_Os10g01920.1_OsAt15      -SGKTARVMT-Y----------------------------------------
LOC_Os10g02000.1_OsAt14      -SGKTARVM---------------------------------------
LOC_Os10g01930.1_OsAt13      -SGKTARVMT-YPQRVVLSM--------------------------------
LOC_Os10g01800.1_OsAt16      -SGKTARVM---------------------------------------
Bradi5g01770.1               GGAPARVM-WHQRQTVLPI--------CVVCPPCKGKDDGVNVMSMCVRPE
                              .* ****

LOC_Os10g03390.1_OsAT18      ---------------
LOC_Os10g03360.1_OsAt17      ---------------
LOC_Os10g01920.1_OsAT15fl    HADAFYQEIAKLKATT
LOC_Os10g01920.1_OsAt15      ---------------
LOC_Os10g02000.1_OsAt14      ---------------
LOC_Os10g01930.1_OsAt13      ---------------
LOC_Os10g01800.1_OsAt16      ---------------
Bradi5g01770.1               HADSFQ---------
```

FIGS. 23A-23E. Multiple sequence alignment of PFAM domains of proteins related to OsAT7

```
Sb09g005480.1_SbAT7          ----------TVERLAQRLVPPAE--PTPTGP----------HRLSWLDRYPT
Bradi2g33980.1_BdAT7         -------PVERLAQRLVAPAG--PTPEGP----------LRLSWLDRYPT
LOC_Os05g08640.1_OsAT7fl     MAAAAPDKAVERLSQKLVHPSS--PTPSAP----------LRLSWLDRYPT
Bradi2g04980.1_BdAT6A        ------VSRLPQRLVLPAE--PTPAGP----------LRLSWLDRYPT
Bradi2g04990.1_BdAT6B        ------SVSRLAQRLVLPAE--PTPSGP----------LRLSWLDRYPT
Sb03g003830.1_SbAT6          --------PARLVVPAE--PTPAGP----------LHLSWLDRYPT
LOC_Os01g08380.1_OsAT6       --------SVERLGQRRVVPAE--PTPAGP----------LRLSWLDRYPT
Sb10g023160.1_SbAT8          -------TVTRLAQRVVAPSA--PTPRGQ----------LPLSWLDRYPT
LOC_Os06g39470.1_OsAT8       -------TVTRVAQRVVAPSA--ATPGGA----------LPLSWLDRYPT
Bradi5g15600.1_BdAT8A        ---------------------------------------LPLSWLDRYPT
Bradi1g36980.1_BdAT8B        -------TVTRVAQRVVAPSA--PTPGGE----------LPLSWLDRYPT Sb09g005480.1_SbAT7          QMALIESLHVFKPDPARDGV--------------------SPAATIER
Bradi2g33980.1_BdAT7         QMALIESLHVFKPDMAREGD--------------------SPARAVER
LOC_Os05g08640.1_OsAT7fl     QMALIESLHVFKPDPARDAAGQG-----------------LAPARAIET
Bradi2g04980.1_BdAT6A        QMALIESLHVFKPAPAHDG---------------------ADPARTIER
Bradi2g04990.1_BdAT6B        QMALIESLHVFKPAPARHAD--------------------ACPGPARTIER
Sb03g003830.1_SbAT6          QMALIESLHVFKAAPATATGGIDG----------------GAAASPARTIER
LOC_Os01g08380.1_OsAT6       QMALIESLHVFKPALDRAIGGDD-----------------VAVGPARTIER
Sb10g023160.1_SbAT8          QRALIESLHVFKGRAD-AEA--------------------PARAIER
LOC_Os06g39470.1_OsAT8       QRALIESLHVFKGRADAAVA--------------------PAAAIER
Bradi5g15600.1_BdAT8A        ------------------------------------------------
Bradi1g36980.1_BdAT8B        QRALIESLHVFKGRAGATEG--------------------PVKAIER Sb09g005480.1_SbAT7          ALAR--ALVDYYPLAGRLAVS-AG-GQLH
Bradi2g33980.1_BdAT7         ALAR--ALVDYYPLAGRLAVS-DA-GELQ
LOC_Os05g08640.1_OsAT7fl     ALAR--ALVEYYPLAGRLAVSRDS-GELQ
Bradi2g04980.1_BdAT6A        ALAQ--ALVRYYPLAGRLAFTDDG-GQSH
Bradi2g04990.1_BdAT6B        ALAQ--ALVRYYPLAGRLAFTDDG-GQSH
Sb03g003830.1_SbAT6          ALAR--ALVHYYPLAGRLVLSESG-AQQA
LOC_Os01g08380.1_OsAT6       ALAR--ALVHYYPLAGRLAFSDSG--EVC
Sb10g023160.1_SbAT8          ALAG--ALVSYYPIAGRLAVSADE-GQLV
LOC_Os06g39470.1_OsAT8       ALAA--ALVSYYPIAGRLAERGDG-GELV
Bradi5g15600.1_BdAT8A        ------------------------------
Bradi1g36980.1_BdAT8B        ALAA--ALVSYYPLAGRLAVPADG-GELV Sb09g005480.1_SbAT7          --VDCS------AEG-VWFIEAAVR-CRLDDVDY-----LEYP---LQIPKD
Bradi2g33980.1_BdAT7         --VDCR------DGG-VWFIEAAVR-CRLEDVDY-----LEYP---LAVDKD
LOC_Os05g08640.1_OsAT7fl     --VDCCGGAGGHGG-VWFIEAAVP-CRLEDVDY-----LEYP---LAISKD
Bradi2g04980.1_BdAT6A        --VDCGGP---GSG-VWFTEAAAA-CGLEDVDY-----LEHP---MMIPKD
```

FIG. 23A

```
Bradi2g04990.1_BdAT6B      ---VDCGGP----RSG-VWFTEAEAA-CGLEDVDY-----LEHP----MMISKD
Sb03g003830.1_SbAT6        ---VDCS------NAG-VWFTEAEAA-CTLEDVDY-----LEAP----LMIPKD
LOC_Os01g08380.1_OsAT6     ---VDCG------DAG-VWFTEAEAS-CSLEDVDY-----LEYP----MMVPKD
Sb10g023160.1_SbAT8        ---VDCT------GEG-VWFIEASAS-CTLEDVDY-----LEYP----LMVPKD
LOC_Os06g39470.1_OsAT8     ---VDCT------GEG-VWFIEATAS-CSLEDVDY-----LEYP----LMVDKD
Bradi5g15600.1_BdAT8A      ------------------------------------------------------
Bradi1g36980.1_BdAT8B      ---VDCT------GEG-VWFLEAAAG-CTLEDVDY-----LEYP----LMMPKD Sb09g005480.1_SbAT7        DLLP--HPLPRPSH--DEESKLILLVQ--------------VTAFACGGFVVG
Bradi2g33980.1_BdAT7       ELLP--HPRPKPTH--EEESKLILLVQ--------------VTTFDCGGFVVG
LOC_Os05g08640.1_OsAT7f1   ELLP--HPRPRPTR--DEEDKLILLVQ--------------VTTFACGGFVVG
Bradi2g04980.1_BdAT6A      ALLP---PTPHAAEE-GDERRLVLLVQ--------------VTSFACGGFVVG
Bradi2g04990.1_BdAT6B      ELLP---PTP-AAEE-GDERRLVLLVQ--------------VTSFACGGFVVG
Sb03g003830.1_SbAT6        DLLP---PTPAAGDE-EDERALVLLVQ--------------VTSFACGGFVVG
LOC_Os01g08380.1_OsAT6     ELLP---PTPAG----EEERELVLLVQ--------------VTAFACGGFVVG
Sb10g023160.1_SbAT8        ELLP-HPTYPPESDP-LPEDSLILLVQ--------------VTQFACGGFVVG
LOC_Os06g39470.1_OsAT8     ELLP-HPTYP-ASES-HPEDSLILLVQ--------------VTQFACGGFVVG
Bradi5g15600.1_BdAT8A      ------------------------------------------VMQFACGGFVVG
Bradi1g36980.1_BdAT8B      ELLP-HPTYP-AADP-LPEDSFILLVQ--------------VTQFACGGFVVG
                            *     ********

Sb09g005480.1_SbAT7        FRFSHAVADGLGAAKFMAAVGELARGAE--------QVSVPPVWARDAI
Bradi2g33980.1_BdAT7       FRFSHAVADGPGAAQFMGAVGELARGAG--------RISVPPAWGRDAI
LOC_Os05g08640.1_OsAT7f1   FRFSHAVADGPGAAQFMGAVGELARGGE--------RITVAPSWGRDAV
Bradi2g04980.1_BdAT6A      FRFSHAVADGPGAAQFMAAVGDLARGAE--------SLSMEPQWGRDAV
Bradi2g04990.1_BdAT6B      FRFSHAVADGPGAAQFMAAVGDLARGAE--------SLSMEPQWGRDAV
Sb03g003830.1_SbAT6        FRFSHAVADGPGAAQFMNAVGELARGAEN-------ALSVVPQWGRDAI
LOC_Os01g08380.1_OsAT6     FRFSHAVADGPGAAQFMAAVGELARGAG--------GVSVDPVWGRDAI
Sb10g023160.1_SbAT8        FRFSHAVADGPGAAQFMTAVGDMARGHA--------APLVAPAWGREAI
LOC_Os06g39470.1_OsAT8     FRFSHAVADGPGAAQFMTAVGEIARGRA--------APALAPAWGRDAI
Bradi5g15600.1_BdAT8A      FRFSHAVADGPGAAQFTTAAGEIAPGRA--------GPSVKAAWGREAI
Bradi1g36980.1_BdAT8B      FRFSHAVADGPGAAQFMTAVGEIARGRA--------GPSVKPAWGREAI
                          **********  ****:* ****:*  *          :  . *.*:*:
```

```
LOC_Os01g08380.1_OsAT6    ----AGFYGNCYYIMRVSAPAGKVAGS-------------------
Sb10g023160.1_SbAT8       ----GGFYGNCYYIMRVSAAAAEAVADA------------------
LOC_Os06g39470.1_OsAT8    ----DGFYGNCYYIMRVTAAAGAVADA-------------------
Bradi5g15600.1_BdAT8A     ----DGFYGYCYYIMRVSAPAEAVSDA-------------------
Bradi1g36980.1_BdAT8B     ----DGFYGNCYYIMRVSAPAEAVSDA-------------------
                              ****  ********:::.*  *:

Sb09g005480.1_SbAT7       -SVTDVVRIIREG--KKRLPSELARWAAGED---------------
Bradi2g33980.1_BdAT7      -SMADVVKIIKEG--KKRLPSEFARWAAGEM---------------
LOC_Os05g08640.1_OsAT7fl  -SVTDVVRMIREG--KKRLPSEFARWAAGEM---------------
Bradi2g04980.1_BdAT6A     -SVPEVVKIIKDG--KRRMPAEFARWASGEAG--------------
Bradi2g04990.1_BdAT6B     -SVPEVVKIIKDG--KRRMPAEFARWASGEAG--------------
Sb03g003830.1_SbAT6       -SVTEVVKIIKDG--KRRMPAEFARWAAGEVG--------------
LOC_Os01g08380.1_OsAT6    -SVTEVVKIIKDG--KRRMPSEFSRWAAGDM---------------
Sb10g023160.1_SbAT8       -SVYDVVRLIREG--KKRLPAEFARWSAGDT---------------
LOC_Os06g39470.1_OsAT8    -SVNDVVRLIREG--KKRLPGEFARWSGGGG---------------
Bradi5g15600.1_BdAT8A     -PLHDVVRLIHDG--KKR-----------------------------
Bradi1g36980.1_BdAT8B     -PLHEVVRLIREG--KKRLPSEFARWSRGEM---------------
                           .:  **:: :.*   **:  *:*

Sb09g005480.1_SbAT7       ----------GGVDPYQIT----SDYR----TLLVSDWTRLG-FAEVDYG-WGPP
Bradi2g33980.1_BdAT7      ----------AGVDPYQIT----SDYR----TLLVSDWTRLG-FAEVDYG-WGPP
LOC_Os05g08640.1_OsAT7fl  ----------AGVDPYRIT----SDYR----TLLVSDWTRLG-FAEVDYG-WGPP
Bradi2g04980.1_BdAT6A     ----------AGGEDPYRIT---SDYR----TLLVSDWTRLG-FAEVDYG-WGPP
Bradi2g04990.1_BdAT6B     ----------AGGEDPYRIT---SDYR----TLLVSDWTRLG-FAEVDYG-WGPP
Sb03g003830.1_SbAT6       ----------AAGVDPYQIT---SDYR----TLLVSDWTRLG-FAEVDYG-WGPP
LOC_Os01g08380.1_OsAT6    ----------AGGDPYQIT----SDYR----TLLVSDWTRLG-FAEVDYG-WGPP
Sb10g023160.1_SbAT8       ----------GG-VDPYRIT---SDYR----TLLVSDWSRLG-FAEVDYG-WGCP
LOC_Os06g39470.1_OsAT8    ----------GGEDDPYRIT---SDYR----TLLVSDWSRLG-FAEVDYG-WGAP
Bradi5g15600.1_BdAT8A     ----------NG--DPYRIT---SDCR----TLLVSDWSRLG-FAEVDYG-WGAP
Bradi1g36980.1_BdAT8B Sb09g005480.1_SbAT7       AHVVPLT-----------------------------
Bradi2g33980.1_BdAT7      AHVVPLT-----------------------------
LOC_Os05g08640.1_OsAT7fl  GHVVPLTNLDYIATC------ILVKPWAHKPGARLITQCVTPDRVTAFHD
Bradi2g04980.1_BdAT6A     AHVVPLT-----------------------------
Bradi2g04990.1_BdAT6B     AHVVPLT-----------------------------
Sb03g003830.1_SbAT6       AHVVPLT-----------------------------
LOC_Os01g08380.1_OsAT6    AHVVPLT-----------------------------
Sb10g023160.1_SbAT8       VHVVPLTNLDYIATC---------ILVRPSA-----
LOC_Os06g39470.1_OsAT8    VHVVPLTNLDYIATC---------ILVRPSA-----
Bradi5g15600.1_BdAT8A     ------------------------------------
Bradi1g36980.1_BdAT8B     VHVVPLTNLDYIATC---------ILVRPS------
```

```
Sb09g005480.1_SbAT7        ------------
Bradi2g33980.1_BdAT7       ------------
LOC_Os05g08640.1_OsAT7f1   AMVDIN------
Bradi2g04980.1_BdAT6A      ------------
Bradi2g04990.1_BdAT6B      ------------
Sb03g003830.1_SbAT6        ------------
LOC_Os01g08380.1_OsAT6     ------------
Sb10g023160.1_SbAT8        ------------
LOC_Os06g39470.1_OsAT8     ------------
Bradi5g15600.1_BdAT8A      ------------
Bradi1g36980.1_BdAT8B      ------------
```

FIG. 23E

FIGS. 24A-24D. Multiple sequence alignment of PFAM domains of proteins related to AT5

FIG. 24A

```
Sb09g005680.1           ------------------AAAETT------AHIINLSSFDKALAF-FPVTS
Bradi2g43510.1          ----------PALVPP--VGPTPRGA------LPLSSIDKTAAVRVSVDF
Bradi4g06070.1          -TVNRKSQSFVKPAAPTPTPQTP------PPLLELSAIDRVPGLRHTVRS
LOC_Os05g19910.1        -TVMRKSRNFVGP--SPFTPPAE------ITTTLELSSIDRVPGLRHTVRS
Sb08g005680.1           -TVTRKSQSFVVPSSSSAPVPTT------AETLELSAIDRVPGLRHTVRS
CAC09063-BanAAT-Clade-V -AVTRSRSLVTP--CGVTPTGS------LGLSAIDRVPGLRHMVRS
LOC_Os01g18744.1        --VVRTNREFVRP--SAATPPSS------GELIELSIIDRVVGLRHLVRS
Bradi2g36910.1          FTVTRTSKSLVPPSSSSPTPAATEDDAPVPVIMRLSTIDRVPGLRHILVS
Sb09g002910.1           -PVTRTNRSLVPP--SSATPQET------LRLSVIDRVAGLRHLVRS
LOC_Os05g04584.1        FTVTRTSRSLVAP--SSPTPAET------LPLSVIDRVAGLRHLVRS
                                                         *  :** :. ..  *

Sb09g005680.1           FHIFDHA---------IHRPAE-TVRSALSRALVHYYPVAGRAVEDS
Bradi2g43510.1          IQVFPPSTDGASAGD---------QVA-AMRDGFARALVPYYPVAGRIAEPT
Bradi4g06070.1          LHVFRPPPHGDGAACS--------RPAE-VIRAALARALVEYPAFAGRLVVGG
LOC_Os05g19910.1        LHVFRRHKNSGPVVDG--DSRRPAA-VIRAALARALADYPAFAGRFVGSL
Sb08g005680.1           LHVFRRKADDDAAAAAAASRRPAE-VIRAALSRALVDYRPFAGRFVGSL
CAC09063-BanAAT-Clade-V LHVFRQG---------REPAR--IIREALSKALVKYYPFAGRFVDDP
LOC_Os01g18744.1        LHIFSAAAPSGGDAKP------SPAR-VIKEALGKALVDYYPFAGRFVDGG
Bradi2g36910.1          LHAFDGHGVVAGEDDE-ERIRWPAR-VVREALGKALVDYYPFAGRFVVDE
Sb09g002910.1           LHVFAGGENKKQAAP-------PAK-SLREALGKALVDYYPFAGRFVEED
LOC_Os05g04584.1        LHVFEAGGRNGGGE--------PARVVIREALGKALVEYHPFAGRFVEGD
                        :                  .   ::   *** . * .::***.

Sb09g005680.1           S--GDLRIACTGEGVGFVAASANCSLADVKLF-DPP---FGALLKELAVGL
Bradi2g43510.1          P--GDLVVDCTGEGVWFVEAAASCSLADVNGL-ERP---LLIPKGELIP-R
Bradi4g06070.1          SG-SDCGVACTGDGAWFVEAAAGCNLEDVNEL-DYP---LVVCEEELLPTA
LOC_Os05g19910.1        LA-GDACVACTGEGAWFVEAAADCSLDDVNGL-EYP---LMISEEELLP-A
Sb08g005680.1           YA-GEACVECTDEGAWFVEAVADCSLDDVNGLDDYP---LMVSEEELLP-A
CAC09063-BanAAT-Clade-V EGGGEVRVACTGEGAWFVEAKADCSLEDVKYL-DLP---LMIPEDALLP-K
LOC_Os01g18744.1        GGPGSARVECTGEGAWFVEAAAGCSLDDVNGL-DHP---LMIPEDDLLP-D
Bradi2g36910.1          E--GEVGVKCSGEGAWFVEAKAECSLEEARHLDGNPMEMVIPKEDLLP-E
Sb09g002910.1           ---GEVRVACTGEGAWFVEAAAACSLEEVRHL-DHP---MLIPKEELLP-E
LOC_Os05g04584.1        GG-GEVAVACTGEGAWFVEATAACSLEEVKLL-DHP---MVIPKEELLP-E
                            .   *  ** *** *** .  :*   :             *
```

FIG. 24B

```
Sb09g005680.1         GAEGFRPSDPLLLVQ---------------VTEEFSCGGFVVGVTRNHVVADGTG
Bradi2g43510.1        PPPEEKLEDLILMAQ---------------VTKFTCGGFAVGICFSHLVFDGQG
Bradi4g06070.1        PEGELDPTSIPVMMQLMSEMTLWHKTVTEEFSCGGFVVGLVAVHTFADGLG
LOC_Os05g19910.1      PEDGVDPTSIPVMMQ---------------VTEEFTCGGFILGLVAVHTLADGLG
Sb08g005680.1         PEEGVDPTSIPMMMQ---------------VTEEFSCGGFVVGLVAVHTLADGLG
CAC09063-BanAAT-Clade-V  PCPGLNPLDLPLMLQ---------------VTEFVGGGFVVGLISVHTIADGLG
LOC_Os01g18744.1      AAPGVHPLDLIPLMMQ---------------VTEEFSCGGFVVGLISVHTMADGLG
Bradi2g36910.1        PIPGVDPLDIPLIMQ---------------VTEEFTCGGFVVGLISVHTIADGLG
Sb09g002910.1         PAPGVNPLDMPLMMQ---------------VTEEFTCGGFVVGLISVHTIADGLG
LOC_Os05g04584.1      PAPDVQPLDIPLMMQ---------------VTEEFTCGGFVVGLISVHTIADGLG
                       .              :               *    *** :*:  *  **   *

Sb09g005680.1         FAQFLQAVGELARG-------LPRPAVFPVSCGD---DSLPELPPFVDAMEK
Bradi2g43510.1        AAQFLKAAGELARG-------LPAPSVAPVWDRDAIPDPPKLPR-------G
Bradi4g06070.1        AAQFINAIAEFARG-------LNRPTVNPIWARATIPNPPKFPP-------G
LOC_Os05g19910.1      AAQFITAVAELARG-------MDKLRVAPVWDRSLIPNPPKLPP-------G
Sb08g005680.1         AAQFINAISEFARG-------LDKLTIAPVWARSLIPNPPKLPP-------A
CAC09063-BanAAT-Clade-V  VVQFINAVAELARG-------LPKPTVEPAWSREVIPNPPKLPP-------G
LOC_Os01g18744.1      AGQFINAVGDYARG-------LDRFRVSPVWAREAIPSPPKLPP-------G
Bradi2g36910.1        AGQFINAVADYARG-------LPKPRVSPVWARDLVPDPPKMP--------A
Sb09g002910.1         AGQFINAVADYARGGATAGAVTRFRITPIWARDVIPDPPKMP---------A
LOC_Os05g04584.1      AGQFINAVADYARG-------LAKPRVSPVWARDAIPDPPRMP--------A
                     . **:.*  : **        :     .          ..

Sb09g005680.1         AQVTLEPRDFAYLDITVPSRCINRIKAGFARHAAAAAESGGP-CTVFEAV
Bradi2g43510.1        PPPSFTAFNFVTQVVEISPENLARIKEDFKA------ATGETCSTFDAV
Bradi4g06070.1        PPPSFQSFGFQHFATDIRPDRIAHAKAEYLK------ATGTH-CSAFDVA
LOC_Os05g19910.1      PPPSFQSFGFQHFSTDVTSDRIAHVKAEYFQ------TFGQY-CSTFDVA
Sb08g005680.1         PPPSFESFGFKHFVMDVTFDNIAHVKTEYFQ------ANGQY-CSTFDVA
CAC09063-BanAAT-Clade-V  GPPVFPSFKLLHATVDLSPDHIDHVKSRHLE------LTGQR-CSTFDVA
LOC_Os01g18744.1      PPPELKMFQLRHVTADLSLDSINKAKSAYFA------ATGHR-CSTFDVA
Bradi2g36910.1        PPPKLELLDLRHFTVDLSPDHIAKVKSQYFA------STGHR-CSAFDVV
Sb09g002910.1         PPPRLDLLDLVYFTTDLSPDHIAKVKSSYLE------STGQR-CSAFDVC
LOC_Os05g04584.1      PPPRLELLDLRYFTVDLSPDHIAKVKSAFFE------STGHR-CSAFDVC
                         :      :  .  :   .              ..   *: *.::
```

```
Sb09g005680.1             MAVLWQCRTRAIMS-DPDT----------------PAPLIFAANVRKHA----G------
Bradi2g43510.1            TAVVFKCRALAVELPDTA--------------------EVRLGFAASTRHLL----QGVLP-
Bradi4g06070.1            VAKVWQARTRAVRY-GPEA--------------------QVQVCFFANTRHLL----GELLP-
LOC_Os05g19910.1          TAKVWQARTRAVGY-KPEI--------------------QVHVCFFANTRHLL----TQVLP-
Sb08g005680.1             IAKVWQARTRAIKY-NPDV--------------------KVHVCFFANTRHLL----TRELP-
CAC09063-BanAAT-Clade-V   IANLWQSRTRAINL-DPGV--------------------DVHVCFFANTRHLI----RQVLLP-
LOC_Os01g18744.1          IAKTWQARTRALRLPEPTS----------------RVNLCFFANTRHLIM-AGAAAWPA
Bradi2g36910.1            VAVTWQSRTRALRLAGAGYD-----------------DVHVCFFANTRHLM----LHGGA-
Sb09g002910.1             VARTWQARVRALRLPDAAA-----------------PVHVCFFANTRHLL----PATAAAP-
LOC_Os05g04584.1          VAKTWQARTRALVAAAAAGDDDQERRTVRVCFFANTRHLMLKGDGAAA-
                              *  :: .*: :                    .   * *..  *:

Sb09g005680.1             -------AKRGYYGNCITSAVVVPTSGEVA-NGDINDVLRLIKRAKQPIPY
Bradi2g43510.1            -------SVDGYYGNCVYPVGITRSSKTIR-EAALTEVVGVMREAKEALTV
Bradi4g06070.1            -------EGFYGNCFFPVTVKARAGDVAGSKDLLGIIRMIRDGKARLPL
LOC_Os05g19910.1          -------KDGGYYGNCFYPVTVTAIAEDVA-TKELLDVIKIIRDGKARLPM
Sb08g005680.1             -------NDGGFYGNCFYPVTVTATAEGVA-SGGLHDVIRMIRDGKARLPL
CAC09063-BanAAT-Clade-V   PAAGGNGNGFYGNCFYPVTVPVSVVAESGAVE-AADVAGVVGMIREAKARLPA
LOC_Os01g18744.1          -------GAAGFYGNCFYPVRATCGSAEVA-SADVAGVVKVVRDAKARLAG
Bradi2g36910.1            -------ASGFYGNCFYTVKATRPSGEVA-AADIVDVVRAIRDAKARLAA
Sb09g002910.1             -------AATGFYGNCFYPVAAVASGGEVA-GADIVDVVRIVRDAKARLAA
LOC_Os05g04584.1          
                                 *:*****      . :        :              *

Sb09g005680.1             QFWKNNSADDDAGDDEEGGRHVKEPRPEGGLSLSMEQLDVTLGYNAFDVT
Bradi2g43510.1            RFTDWMRGG---------AKDDH-----------YNVPLDYGTVTVS
Bradi4g06070.1            EFADWASGLGGGGAGDKMKFVQDDP---------YELRFEHNVLFVS
LOC_Os05g19910.1          EFAKWASGD---------VKVDP-----------YALTFEHNVLFVS
Sb08g005680.1             EFAKWSMGD---------VKVDP-----------YQLTFKHNVLFVS
CAC09063-BanAAT-Clade-V   EFAKWAAGD---------FKDDP-----------YELSFTYNSLFVS
LOC_Os01g18744.1          DFARWAAGD---------FREDP-----------YELSFTYDSLFVS
Bradi2g36910.1            DVARWAVGG---------FEQDP-----------YELTFTYDSLFVS
Sb09g002910.1             DFARWAAGG---------FDRDP-----------YELTFTYDSLFVS
LOC_Os05g04584.1          DVARWAVGG---------FEEDP-----------YELTFTYDSLFVS
                          :                                .
```

FIG. 24C

```
Sb09g005680.1          SWRNLGADAVDFGGGRPARVM--CWLDRMAVPHCVACLP--CNKDGGNVL
Bradi2g43510.1         DWSRVGFNEVDYGFGEPGYVFTLN-------------------------
Bradi4g06070.1         DWTRLGFLEVDYGWGVPSHVIPFNYADYMAVA-VLGAPP--APVKGTRVM
LOC_Os05g19910.1       DWTRLGFFEVDYGWGTPNHIIPFTYADYMAVA-VLGAPP--MPKKGTRIM
Sb08g005680.1          DWTRLGFFEVDYGWGVPNHIIPFTYADYMAVA-VLGAPPTTVKNKGTRIM
CAC09063-BanAAT-Clade-V DWTRLGFLDVDYGWGKPLHVIPFAYLDIMAVG-IIGAPP--APQKGTRVM
LOC_Os01g18744.1       DWTRLGFLEADYGWGPPSHVIPFAYYPFMAVA-IIGAPP--VPKTGARIM
Bradi2g36910.1         DWTRLGFLEADYGWGPPAHVVPFSYHPFMAVA-VIGAPP--KPKLGSRVM
Sb09g002910.1          DWTRLGFLEADYGWGTPTHVVPFSYHPFMAVA-VIGAPP--APKPGARIM
LOC_Os05g04584.1       DWTRLGFLDADYGWGTPSHVVPFSYHPFMAVA-VIGAPP--APKLGARVM
                        *  .:*    .  *   *:. *  *   ::

Sb09g005680.1          ARCVREEHVDAF------
Bradi2g43510.1         ------------DDVN--
Bradi4g06070.1         TQCVEEKHLKEFRDEME-
LOC_Os05g19910.1       TQCVENKCIKEFQDEMK-
Sb08g005680.1          TQCVEEKHLMEFKDEMKA
CAC09063-BanAAT-Clade-V AQCVEKEHMQAFLEEMK-
LOC_Os01g18744.1       TQCVEDDHLPAFKEEI--
Bradi2g36910.1         TMCVEEDHLPEFRDQMN-
Sb09g002910.1          TMCVQEQHLPEFQEQMN-
LOC_Os05g04584.1       TMCVEEAHLPEFRDQMN-
```

```
Query_14679    1  MTIKEVQVVSKKNVKPSVPTFDHH--KTCKLIAFD-QIAFPDQVPIIYFY----NSSNIHR------IREQLVKSLSETLT  68
Query_14681    1  MVAVTVMRKSRNFVGFSPPTPPAEITTTLELSSIDRVPGLRHNVRSLHVFRRHKNSGPVVDGDSRRPAAVIRAALARALA   80

Query_14679   69  KFYPLAGRFV-----QDGFYVDCHDEGVLIVEAEVNIPLNEFIGQAKKHIQLIHDLVPKNFKDIHSYENPIVGLQNSYFK  144
Query_14681   81  DYPAFAGRFVGSLLAGDACVACTGEGANFVEAAADCSLDDVNGLEYPLMISEEELLPAPEDGVDPT--SIPVMMQVTEFT  158

Query_14679  145  CGGLAICHYLSHVADGYTRAAFTKEHHFTTHGIIHGDQLVSSSPIHFELAILVPAREL$TVIKPAVMPPHKIKEIKVVT   224
Query_14681  159  CGGFILGLVAVHTLADGLGAAQFITAVAELARGH----DKLRVAPV-WDRSLIPNPPKLPPG------PPPSFQSFGFQH  227

Query_14679  225  RRFLFDENAISAFKDHVIKSESVHRPTRVEVVTSVLMKALINQSKLPS---STLYFELNFRGKTGINTPPLDHHFSLCGS  301
Query_14681  228  FSTDVTSDRIAHVKAEYFQT-FGQYCSTFDVATAKVWQARTRAVGYKPEIQVHVCFFANTRHLL---TQVLPKDGGYYGN  303

Query_14679  302  FYTQVPTRFRGGNQTRQDLELHELVKLLRGKLRNTLAKCSEINTADGLFLERASNFNIIQEDLEDEQVDVRIFTTLCRMP  381
Query_14681  304  CFYPVTVT-------AIAEDVATKELLDVIKIIRDGKARLPKE--------FAKWASGDVKVDPYALTFEHNVLFVSDWTRLG  371

Query_14679  382  LYETEFGKNKPERVTIPER--HLKIVFLLDTKCGTGIERLVSHDEADHLQFELDPTISAFAS*  442
Query_14681  372  FFEVDYGWGTPNHIIPFTYADYMAVAVLGAPPMPKKGTRIMTQCVENKCIKEFQDEMKAFI*-  433
```

>OsAT5_LOC_Os05g19910.1 (Query 14681)
MVAVTVMRKSRNFVGPSPPTPPAEITTTLELSSIDRVPGLRHNVRSLHVFRRHKNSGPVV
DGDSRRPAAVIRAALARALADYPAFAGRFVGSLLAGDACVACTGEGAWFVEAAADCSLDD
VNGLEYPLMISEEELLPAPEDGVDPTSIPVMMQVTEFTCGGFILGLVAVHTLADGLGAAQ
FITAVAELARGMDKLRVAPVWDRSLIPNPPKLPPGPPPSFQSFGFQHFSTDVTSDRIAHV
KAEYFQTFGQYCSTFDVATAKVWQARTRAVGYKPEIQVHVCFFANTRHLLTQVLPKDGGY
YGNCFYPVTVTAIAEDVATKELLDVIKIIRDGKARLPMEFAKWASGDVKVDPYALTFEHN
VLFVSDWTRLGFFEVDYGWGTPNHIIPFTYADYMAVAVLGAPPMPKKGTRIMTQCVENKC
IKEFQDEMKAFI*

FIG. 29

|  | Coumaric Acid | Ferulic Acid | Sinapic Acid |
|---|---|---|---|
| Coumaryl Alcohol | NA | ✓ | NA |
| Coniferyl Alcohol | ✓[1] | ✓ | NA |
| Sinapyl Alcohol | NA | NA | NA |

NA: No activity
[1] Detected product with same retention time as ferulic acid adduct

SEQUENCE LISTING

<160> NUMBER OF SEQ ID NOS: 102

<210> SEQ ID NO 1
<211> LENGTH: 1332
<212> TYPE: DNA
<213> ORGANISM: Oryza sativa

<400> SEQUENCE: 1

```
atgggcgtct cgccgtcac caaggtgtcc gagggccccg tccggccgtc cgcagcgacg      60
ccgtcggaga cgctgccgct cgcctgggtc gaccgctacc cgacgcaccg cggcctcgtc     120
gagtccgtgc acatctaccc ccgccgcgac gacgccgccg tcgaggcgcc gtcgccgac     180 ggcggcgtca tcgtcgaggg aaagaagaag aataataagc cggcggcggc ggtggtgcgc     240
```

```
ggcgcgctgg cggacgcgct ggtgcactac tacccgttcg cggggcggat cgtggaggac      300
gagcggtcgc cggggcggcc tgccgtgctg tgctccggcg agggcgtcta cttcgtggag      360
gccgccgcca actgcaccct cgccgacgtc aaccacctgg agcggccgct gctgctgtcc      420
aaggaggacc tcgtgccgtg cccgacgccg agcagtggc ccgtcgagcc gcacaacagc      480
ctcgccatga tccaggtgac gacgttcacc tgcggcggct tcgtgatcgg ctgcgcacc      540 aaccacgcg tggcggacgg caccggcgcc gcccagttca tgaacgccgt cggcgacctc      600
gcccgcggcc tcccggagcc gcgggtgaag ccgatctggg cgcgcgaccg cttcccggac      660
ccggacatca gcccggcccc gctgccggag ctccccgtgc tgccgctcca gtacatcgcc      720
ttcgacttcc ccgccgccta cctcggcaag ctcaaggcgc agtacgccgc caccgccggc      780
gccagcaaga tctgctccgc cttcgacatc gtcatcgcca agctctggca gtgccggacg      840
cgcgccatcg ccgccgaccc cgccgcggcc gtcaagctct gcttcttcgc cagcgcccgc      900
caggtgctcg gcctggagac cggctactgg ggcaacgcca tcttcccggt gaaggtgtcc      960
gcggcggcgg gggaggtggc ggcgtcgtcg gtgatcgagc tcgtcggcgt ggtccgggag      1020
gcgaagcggc ggatggccgg cgagtgcctg cgctgggcgg aggggcgcac cggcggcgcc      1080
gacccgttcc agatgacgtt cgactacgag tccgtgtacg tgtcggactg gagcaagctc      1140
gggttcaacg acgtcgacta cgggtacggc gcgccgtcgg cggcggggcc gctggtgaac      1200
tgcgacctca tctcgtcggt gatcgtcatg cgggcgccgg cgccgctcgc cggcacgcgg      1260
ctgctggcga gctgcgtcac caaggagcac gccgacgact cgccgccag gatgagggag      1320 gatctcgtct aa                                                         1332

<210> SEQ ID NO 2
<211> LENGTH: 443
<212> TYPE: PRT
<213> ORGANISM: Oryza sativa

<400> SEQUENCE: 2

Met Gly Val Phe Ala Val Thr Lys Val Ser Glu Gly Pro Val Arg Pro
1               5                   10                  15

Ser Ala Ala Thr Pro Ser Glu Thr Leu Pro Leu Ala Trp Val Asp Arg
            20                  25                  30

Tyr Pro Thr His Arg Gly Leu Val Glu Ser Val His Ile Tyr Leu Arg
        35                  40                  45

Arg Asp Asp Ala Ala Val Glu Ala Pro Cys Ala Asp Gly Gly Val Ile
    50                  55                  60

Val Glu Gly Lys Lys Lys Asn Asn Lys Pro Ala Ala Val Val Arg
65                  70                  75                  80

Gly Ala Leu Ala Asp Ala Leu Val His Tyr Tyr Pro Phe Ala Gly Arg
                85                  90                  95

Ile Val Glu Asp Glu Arg Ser Pro Gly Arg Pro Ala Val Leu Cys Ser
            100                 105                 110

Gly Glu Gly Val Tyr Phe Val Glu Ala Ala Ala Asn Cys Thr Leu Ala
        115                 120                 125

Asp Val Asn His Leu Glu Arg Pro Leu Leu Ser Lys Glu Asp Leu
    130                 135                 140

Val Pro Cys Pro Thr Pro Glu Gln Trp Pro Val Glu Pro His Asn Ser
145                 150                 155                 160

Leu Ala Met Ile Gln Val Thr Thr Phe Thr Cys Gly Gly Phe Val Ile
                165                 170                 175
```

Gly Leu Arg Thr Asn His Ala Val Ala Asp Gly Thr Gly Ala Ala Gln
            180                 185                 190

Phe Met Asn Ala Val Gly Asp Leu Ala Arg Gly Leu Pro Glu Pro Arg
        195                 200                 205

Val Lys Pro Ile Trp Ala Arg Asp Arg Phe Pro Asp Pro Asp Ile Lys
    210                 215                 220

Pro Gly Pro Leu Pro Glu Leu Pro Val Leu Pro Leu Gln Tyr Ile Ala
225                 230                 235                 240

Phe Asp Phe Pro Ala Ala Tyr Leu Gly Lys Leu Lys Ala Gln Tyr Ala
            245                 250                 255

Ala Thr Ala Gly Ala Ser Lys Ile Cys Ser Ala Phe Asp Ile Val Ile
        260                 265                 270

Ala Lys Leu Trp Gln Cys Arg Thr Arg Ala Ile Ala Ala Asp Pro Ala
    275                 280                 285

Ala Ala Val Lys Leu Cys Phe Phe Ala Ser Ala Arg Gln Val Leu Gly
290                 295                 300

Leu Glu Thr Gly Tyr Trp Gly Asn Ala Ile Phe Pro Val Lys Val Ser
305                 310                 315                 320

Ala Ala Ala Gly Glu Val Ala Ala Ser Ser Val Ile Glu Leu Val Gly
            325                 330                 335

Val Val Arg Glu Ala Lys Arg Arg Met Ala Gly Glu Cys Leu Arg Trp
        340                 345                 350

Ala Glu Gly Arg Thr Gly Gly Ala Asp Pro Phe Gln Met Thr Phe Asp
    355                 360                 365

Tyr Glu Ser Val Tyr Val Ser Asp Trp Ser Lys Leu Gly Phe Asn Asp
370                 375                 380

Val Asp Tyr Gly Tyr Gly Ala Pro Ser Ala Ala Gly Pro Leu Val Asn
385                 390                 395                 400

Cys Asp Leu Ile Ser Ser Val Ile Val Met Arg Ala Pro Ala Pro Leu
            405                 410                 415

Ala Gly Thr Arg Leu Leu Ala Ser Cys Val Thr Lys Glu His Ala Asp
        420                 425                 430

Asp Phe Ala Ala Arg Met Arg Glu Asp Leu Val
    435                 440

<210> SEQ ID NO 3
<211> LENGTH: 1305
<212> TYPE: DNA
<213> ORGANISM: Oryza sativa

<400> SEQUENCE: 3
atgagtattg tggtgagcaa gtcagcgccg gtggtcgtcc ggccatcgga gccggccaca      60
tcgacggccg acaagatcct tctgtcaact ttggacaagc tgttgccac gataccagtg     120 accgtgctac ttgcgttcga ccaccccatc catgacgcca ccgcggagac catcaagacg     180
gctctcgctc aatcactcgt ccactactat cctatcgccg ccgcatttc ctgcgacaat      240 gacgacggcg gccatttcta catcgactgc accggcgagg atctcggggt cacgttcgtg     300
gccgcgtccg ccaactgcac catggaggag ctcatgtgtc tcgtcgacga ccaggctccc     360
gacgacgaga cagcggtggt gcagcagctc gccttcaact gcacgcccga cgaccttcat     420
caccgtctgc tgtgggtgca ggtcaccact ctcaactgtg gaggcttcgt cgtcggggtg     480
acatggagcc atggcgtggc tgacggtccc ggcatagcac agttcataca agccgtcggc     540
gagctcgccc gtggcctgcc atcgccgtcc gtcgtcccgg tcaggttgga cgacaagatc     600

-continued

```
gcaacccaag ccgtacctcc cttcaccatg gccgttcatc gcttcatatc cggcctcaag      660
ccagtatcaa acctcgacgt acgcaacgtc accgtctcat ctagccttat caaccacatc      720
atcgtcggag ctcgtcgtcg tgccaccgtg ttcgaggcgg tcgccgccgt gctctggcag      780
tgccgtacac gggtggtgat gacggatcct gaggcccccg ccgtgctgct cttcgcggtg      840
aacgcacgca agtacctcgg cgccaaggac ggctactacg gatgctgcac cgccatgcac      900
atggccgtgt ccaagtccgg cacggtggcc aacggcgaca tcatgaagtt ggtcggcatc      960
atacgccgcg ccaaggagca gataccggag cagctgaagg cagacgacgg cgagatgatg     1020
ctacggacga tggtagggga gaagcaggtg aatggatacg agagcctgct ctacttgaca     1080
tcctggcgaa acatcgggtt cgaggacgtc gatttcggca gcgggaagac ggcgagggtg     1140
atgacctacc cgccgaggat gctgtccatg atgcccagga ttgcgcccat ctgcttcatg     1200
ctcaaggcca cagaggaagg ggtcagggtc atgtcagact gtgttacggc tgaccacgcc     1260
gatgccttct atcaagaaat agccaagctc aaagccacca cctga                    1305
```

<210> SEQ ID NO 4
<211> LENGTH: 434
<212> TYPE: PRT
<213> ORGANISM: Oryza sativa

<400> SEQUENCE: 4

```
Met Ser Ile Val Val Ser Lys Ser Ala Pro Val Val Arg Pro Ser
1               5                   10                  15

Glu Pro Ala Thr Ser Thr Ala Asp Lys Ile Leu Leu Ser Thr Leu Asp
                20                  25                  30

Lys Pro Val Ala Thr Ile Pro Val Thr Val Leu Leu Ala Phe Asp His
                35                  40                  45

Pro Ile His Asp Ala Thr Ala Glu Thr Ile Lys Thr Ala Leu Ala Gln
        50                  55                  60

Ser Leu Val His Tyr Tyr Pro Ile Ala Gly Arg Ile Ser Cys Asp Asn
65                  70                  75                  80

Asp Asp Gly Gly His Phe Tyr Ile Asp Cys Thr Gly Glu Asp Leu Gly
                85                  90                  95

Val Thr Phe Val Ala Ala Ser Ala Asn Cys Thr Met Glu Glu Leu Met
                100                 105                 110

Cys Leu Val Asp Asp Gln Ala Pro Asp Asp Glu Thr Ala Val Val Gln
        115                 120                 125

Gln Leu Ala Phe Asn Cys Thr Pro Asp Asp Leu His His Arg Leu Leu
    130                 135                 140

Trp Val Gln Val Thr Thr Leu Asn Cys Gly Gly Phe Val Val Gly Val
145                 150                 155                 160

Thr Trp Ser His Gly Val Ala Asp Gly Pro Gly Ile Ala Gln Phe Ile
                165                 170                 175

Gln Ala Val Gly Glu Leu Ala Arg Gly Leu Pro Ser Pro Ser Val Val
                180                 185                 190

Pro Val Arg Leu Asp Asp Lys Ile Ala Thr Gln Ala Val Pro Pro Phe
        195                 200                 205

Thr Met Ala Val His Arg Phe Ile Ser Gly Leu Lys Pro Val Ser Asn
    210                 215                 220

Leu Asp Val Arg Asn Val Thr Val Ser Ser Leu Ile Asn His Ile
225                 230                 235                 240

Ile Val Gly Ala Arg Arg Arg Ala Thr Val Phe Glu Ala Val Ala Ala
```

```
                245                 250                 255
Val Leu Trp Gln Cys Arg Thr Arg Val Val Met Thr Asp Pro Glu Ala
            260                 265                 270
Pro Ala Val Leu Leu Phe Ala Val Asn Ala Arg Lys Tyr Leu Gly Ala
        275                 280                 285
Lys Asp Gly Tyr Tyr Gly Cys Cys Thr Ala Met His Met Ala Val Ser
    290                 295                 300
Lys Ser Gly Thr Val Ala Asn Gly Asp Ile Met Lys Leu Val Gly Ile
305                 310                 315                 320
Ile Arg Arg Ala Lys Glu Gln Ile Pro Glu Gln Leu Lys Ala Asp Asp
                325                 330                 335
Gly Glu Met Met Leu Arg Thr Met Val Gly Glu Lys Gln Val Asn Gly
            340                 345                 350
Tyr Glu Ser Leu Leu Tyr Leu Thr Ser Trp Arg Asn Ile Gly Phe Glu
        355                 360                 365
Asp Val Asp Phe Gly Ser Gly Lys Thr Ala Arg Val Met Thr Tyr Pro
    370                 375                 380
Pro Arg Met Leu Ser Met Met Pro Arg Ile Ala Pro Ile Cys Phe Met
385                 390                 395                 400
Leu Lys Ala Thr Glu Glu Gly Val Arg Val Met Ser Asp Cys Val Thr
                405                 410                 415
Ala Asp His Ala Asp Ala Phe Tyr Gln Glu Ile Ala Lys Leu Lys Ala
            420                 425                 430
Thr Thr

<210> SEQ ID NO 5
<211> LENGTH: 1320
<212> TYPE: DNA
<213> ORGANISM: Oryza sativa

<400> SEQUENCE: 5
atggcggcgg cggcgccgga caaggcggtg gagcggctgt cccagaagct ggtgcacccg      60
tcgtccccca cgccgtcggc cccgctccgc ctctcctggc tcgaccgcta ccccacccag     120
atggcgctca tcgagtcgct ccacgtcttc aagcccgacc ggcgaggga cgccgcgggg      180 caggggctcg cccccgcgcg cgccatcgag acggccctcg cgagagccct cgtcgagtac     240
tacccgctcg ccgggaggct cgccgtctcc cggactccg gcgagctcca ggtggattgc      300
tgcggcggcg ccggcggcca tggcggggtg tggttcatcg aggcggctgt cccgtgccgg     360
ctcgaggacg tggattacct cgagtaccct ctcgccatct ccaaggacga gctgctcccc     420
cacccgcgcc cccgcccac ccgcgacgag gaagacaagc tcatcctgct cgtccaggtg      480
acgacgttcg cgtgcggcgg gttcgtggtg gggttcaggt tcagccacgc ggtggcggac     540
ggcccggggg cggcgcagtt catgggcgcg gtcggcgagc tcgcccgcgg cggcgagcgc     600
atcacggtgg ccccgtcgtg ggggcgcgac gcggtgcccg accggccgg cgccatggtc      660 ggcgccctcc cggagccggc cggcgcgtcc cgcctcgagt acctcgccat cgacatctcc     720
gccgactaca tcaaccactt caagtcccag ttcgcggcgg ccaccggcgg cgcccgctgc     780
tccgccttcg aggtgctcat cgccaaggca tggcagagcc gcaccgcgc cgccgcgttc      840 gaccccctcga cgccgatcaa cctctccttc gccatgaacg cccggccgct cctcctcccg    900
cgcggcggcg ccgggttcta cggcaactgc tactacatca tgcgggtggc ctccaccgcc    960
gggagggtgg cgacggcgag cgtcaccgac gtggtgagga tgatccggga ggggaagaag    1020
```

-continued

```
cggctcccgt cggagttcgc gcggtgggcc gccggagaga tggccggagt cgacccgtac    1080
cagatcacct ccgactaccg gacgctgctg gtctccgact ggacgcggct gggcttcgcc    1140
gaggtggact acgggtgggg cccaccgggc cacgtcgtgc cgctcacgaa cctggactac    1200
atcgccacgt gtatcctcgt caagccctgg gcccacaaac caggggcacg gctcatcacc    1260
cagtgcgtca cacccgaccg cgtcaccgcc ttccacgacg ccatggtgga catcaactaa    1320
```

<210> SEQ ID NO 6
<211> LENGTH: 439
<212> TYPE: PRT
<213> ORGANISM: Oryza sativa

<400> SEQUENCE: 6

```
Met Ala Ala Ala Pro Asp Lys Ala Val Glu Arg Leu Ser Gln Lys
1               5                   10                  15

Leu Val His Pro Ser Ser Pro Thr Pro Ser Ala Pro Leu Arg Leu Ser
                20                  25                  30

Trp Leu Asp Arg Tyr Pro Thr Gln Met Ala Leu Ile Glu Ser Leu His
            35                  40                  45

Val Phe Lys Pro Asp Pro Ala Arg Asp Ala Ala Gly Gln Gly Leu Ala
        50                  55                  60

Pro Ala Arg Ala Ile Glu Thr Ala Leu Ala Arg Ala Leu Val Glu Tyr
65                  70                  75                  80

Tyr Pro Leu Ala Gly Arg Leu Ala Val Ser Arg Asp Ser Gly Glu Leu
                85                  90                  95

Gln Val Asp Cys Cys Gly Gly Ala Gly Gly His Gly Gly Val Trp Phe
            100                 105                 110

Ile Glu Ala Ala Val Pro Cys Arg Leu Glu Asp Val Asp Tyr Leu Glu
        115                 120                 125

Tyr Pro Leu Ala Ile Ser Lys Asp Glu Leu Leu Pro His Pro Arg Pro
        130                 135                 140

Arg Pro Thr Arg Asp Glu Glu Asp Lys Leu Ile Leu Leu Val Gln Val
145                 150                 155                 160

Thr Thr Phe Ala Cys Gly Gly Phe Val Val Gly Phe Arg Phe Ser His
                165                 170                 175

Ala Val Ala Asp Gly Pro Gly Ala Ala Gln Phe Met Gly Ala Val Gly
            180                 185                 190

Glu Leu Ala Arg Gly Gly Glu Arg Ile Thr Val Ala Pro Ser Trp Gly
        195                 200                 205

Arg Asp Ala Val Pro Asp Pro Ala Gly Ala Met Val Gly Ala Leu Pro
    210                 215                 220

Glu Pro Ala Gly Ala Ser Arg Leu Glu Tyr Leu Ala Ile Asp Ile Ser
225                 230                 235                 240

Ala Asp Tyr Ile Asn His Phe Lys Ser Gln Phe Ala Ala Thr Gly
                245                 250                 255

Gly Ala Arg Cys Ser Ala Phe Glu Val Leu Ile Ala Lys Ala Trp Gln
            260                 265                 270

Ser Arg Thr Arg Ala Ala Ala Phe Asp Pro Ser Thr Pro Ile Asn Leu
        275                 280                 285

Ser Phe Ala Met Asn Ala Arg Pro Leu Leu Leu Pro Arg Gly Gly Ala
        290                 295                 300

Gly Phe Tyr Gly Asn Cys Tyr Tyr Ile Met Arg Val Ala Ser Thr Ala
305                 310                 315                 320

Gly Arg Val Ala Thr Ala Ser Val Thr Asp Val Val Arg Met Ile Arg
```

325                 330                 335
Glu Gly Lys Lys Arg Leu Pro Ser Glu Phe Ala Arg Trp Ala Ala Gly
            340                 345                 350

Glu Met Ala Gly Val Asp Pro Tyr Gln Ile Thr Ser Asp Tyr Arg Thr
            355                 360                 365

Leu Leu Val Ser Asp Trp Thr Arg Leu Gly Phe Ala Glu Val Asp Tyr
        370                 375                 380

Gly Trp Gly Pro Pro Gly His Val Val Pro Leu Thr Asn Leu Asp Tyr
385                 390                 395                 400

Ile Ala Thr Cys Ile Leu Val Lys Pro Trp Ala His Lys Pro Gly Ala
                405                 410                 415

Arg Leu Ile Thr Gln Cys Val Thr Pro Asp Arg Val Thr Ala Phe His
            420                 425                 430

Asp Ala Met Val Asp Ile Asn
            435

<210> SEQ ID NO 7
<211> LENGTH: 1299
<212> TYPE: DNA
<213> ORGANISM: Oryza sativa

<400> SEQUENCE: 7
atggtcgctg tcaccgtgat gaggaagtcc cggaacttcg tcgggccgtc tcctccgacg        60
ccgccggccg agatcacgac gacgctcgag ctgtcgtcca tcgaccgcgt gcccgggctg       120
cgccacaacg tgcggtccct gcacgtgttc cgccgccaca agaacagcgg gcccgtcgtc       180
gacggtgata gcaggaggcc ggccgccgtg atccgcgcgg cgctcgcccg ggcgctggcg       240
gactacccgg cgttcgccgg ccgattcgtc ggctccctgc tggccggcga cgcctgcgtc       300
gcgtgcaccg gcgagggcgc gtggttcgtg gaggcagccg cggactgcag cctcgacgac       360
gtgaacggcc tcgagtaccc gctcatgatc tccgaggagg agctgctgcc tgccccccgag      420 gacggcgtcg accctaccag tattccagtc atgatgcagg tgactgaatt cacttgtgga       480
ggatttatct tgggccttgt ggcagtccac acccttgctg atggacttgg agcagcacaa       540
ttcatcactg cagtagctga attggcccgt ggcatggaca agctcagggt ggctcccgtg       600
tgggatcgct cgctgatacc gaacccacct aagctccctc ctgggccacc accatcgttc       660
cagtcctttg gttttcagca tttctccaca gatgtcacct ctgaccgtat agctcacgtg       720
aaggctgagt acttccagac ctttggccag tattgttcca cctttgatgt tgctactgct       780
aaggtttggc aggccaggac acgggccgtc gggtacaaac cggagatcca ggtccatgtg       840
tgtttctttg caaacacgcg tcacctgctc acgcaggttc tcccaaaaga tgggggctac       900
tatggcaact gcttttatcc agtgactgtg acagcaatag ctgaggatgt tgccaccaaa       960
gagttgcttg atgtgatcaa gataattcgg gatggaaagg cgaggctccc catggagttt      1020
gcaaagtggg cttcagggga tgtgaaagtt gatccctacg cattgacatt tgaacacaat      1080 gtgcttttg tgtctgattg gacgaggtta ggattcttcg aggtagacta tgggtggggt        1140
acacctaatc acatcatacc attcacttat gcagactaca tggcagtcgc agtgcttggt      1200
gctccaccaa tgccaaagaa agggacccgg attatgcaca gtgtgtggga gaacaagtgt      1260
atcaaggagt ccaagatgga gatgaaggcc ttcatataa                            1299

<210> SEQ ID NO 8
<211> LENGTH: 432
<212> TYPE: PRT

<213> ORGANISM: Oryza sativa

<400> SEQUENCE: 8

```
Met Val Ala Val Thr Val Met Arg Lys Ser Arg Asn Phe Val Gly Pro
1               5                   10                  15
Ser Pro Pro Thr Pro Pro Ala Glu Ile Thr Thr Thr Leu Glu Leu Ser
                20                  25                  30
Ser Ile Asp Arg Val Pro Gly Leu Arg His Asn Val Arg Ser Leu His
            35                  40                  45
Val Phe Arg Arg His Lys Asn Ser Gly Pro Val Val Asp Gly Asp Ser
        50                  55                  60
Arg Arg Pro Ala Ala Val Ile Arg Ala Ala Leu Ala Arg Ala Leu Ala
65                  70                  75                  80
Asp Tyr Pro Ala Phe Ala Gly Arg Phe Val Gly Ser Leu Leu Ala Gly
                85                  90                  95
Asp Ala Cys Val Ala Cys Thr Gly Glu Gly Ala Trp Phe Val Glu Ala
                100                 105                 110
Ala Ala Asp Cys Ser Leu Asp Val Asn Gly Leu Glu Tyr Pro Leu
            115                 120                 125
Met Ile Ser Glu Glu Leu Leu Pro Ala Pro Glu Asp Gly Val Asp
        130                 135                 140
Pro Thr Ser Ile Pro Val Met Met Gln Val Thr Glu Phe Thr Cys Gly
145                 150                 155                 160
Gly Phe Ile Leu Gly Leu Val Ala Val His Thr Leu Ala Asp Gly Leu
                165                 170                 175
Gly Ala Ala Gln Phe Ile Thr Ala Val Ala Glu Leu Ala Arg Gly Met
                180                 185                 190
Asp Lys Leu Arg Val Ala Pro Val Trp Asp Arg Ser Leu Ile Pro Asn
            195                 200                 205
Pro Pro Lys Leu Pro Pro Gly Pro Pro Pro Ser Phe Gln Ser Phe Gly
        210                 215                 220
Phe Gln His Phe Ser Thr Asp Val Thr Ser Asp Arg Ile Ala His Val
225                 230                 235                 240
Lys Ala Glu Tyr Phe Gln Thr Phe Gly Gln Tyr Cys Ser Thr Phe Asp
                245                 250                 255
Val Ala Thr Ala Lys Val Trp Gln Ala Arg Thr Arg Ala Val Gly Tyr
                260                 265                 270
Lys Pro Glu Ile Gln Val His Val Cys Phe Phe Ala Asn Thr Arg His
            275                 280                 285
Leu Leu Thr Gln Val Leu Pro Lys Asp Gly Tyr Tyr Gly Asn Cys
        290                 295                 300
Phe Tyr Pro Val Thr Val Thr Ala Ile Ala Glu Asp Val Ala Thr Lys
305                 310                 315                 320
Glu Leu Leu Asp Val Ile Lys Ile Ile Arg Asp Gly Lys Ala Arg Leu
                325                 330                 335
Pro Met Glu Phe Ala Lys Trp Ala Ser Gly Asp Val Lys Val Asp Pro
                340                 345                 350
Tyr Ala Leu Thr Phe Glu His Asn Val Leu Phe Val Ser Asp Trp Thr
            355                 360                 365
Arg Leu Gly Phe Phe Glu Val Asp Tyr Gly Trp Gly Thr Pro Asn His
        370                 375                 380
Ile Ile Pro Phe Thr Tyr Ala Asp Tyr Met Ala Val Ala Val Leu Gly
385                 390                 395                 400
```

```
Ala Pro Pro Met Pro Lys Lys Gly Thr Arg Ile Met Thr Gln Cys Val
                405                 410                 415
Glu Asn Lys Cys Ile Lys Glu Phe Gln Asp Glu Met Lys Ala Phe Ile
            420                 425                 430

<210> SEQ ID NO 9
<211> LENGTH: 373
<212> TYPE: PRT
<213> ORGANISM: Brachypodium distachyon

<400> SEQUENCE: 9

Lys Lys Asn Asn Asn Ser Lys Lys Pro Pro Ala Ala Val Val Arg
1               5                   10                  15

Ser Ala Leu Ala Asp Ala Leu Val His Tyr Tyr Pro Phe Ala Gly Arg
                20                  25                  30

Ile Val Glu Asp Ala Ala Lys Pro Gly Arg Pro Ala Val Leu Cys Cys
            35                  40                  45

Ala Glu Gly Val Tyr Phe Val Glu Ala Thr Ala Asn Cys Thr Leu Ala
        50                  55                  60

Asp Val Asn Phe Leu Glu Arg Pro Leu Leu Leu Gly Lys Glu Asp Leu
65                  70                  75                  80

Val Pro Tyr Pro Ala Pro Glu Leu Trp Ala Val Glu Pro His Asn Thr
                85                  90                  95

Leu Ala Met Ile Gln Val Thr Thr Phe Thr Cys Gly Gly Phe Val Leu
                100                 105                 110

Gly Leu Arg Thr Asn His Ala Val Ala Asp Gly Thr Gly Ala Ala Gln
            115                 120                 125

Phe Leu Asn Ala Val Gly Asp Leu Ala Arg Gly Leu Gln Glu Pro Arg
        130                 135                 140

Val Lys Pro Val Trp Ala Arg Asp Arg Phe Pro Asp Pro Asp Ile Gln
145                 150                 155                 160

Pro Gly Pro Leu Pro Glu Leu Pro Val Leu Ala Leu Glu Tyr Ile Ala
                165                 170                 175

Phe Asp Phe Pro Val Thr Tyr Ile Asp Lys Ile Lys Ser Glu Tyr Asn
                180                 185                 190

Ala Cys Ser Gly Gly Lys His Cys Ser Gly Phe Asp Ile Val Ile Ala
            195                 200                 205

Lys Leu Trp Gln Ser Arg Thr Arg Ala Ile Gly Ile Pro Glu Ser
        210                 215                 220

Ser Pro Ser Ala Asp Val Lys Leu Cys Phe Phe Ala Ser Ala Arg His
225                 230                 235                 240

Val Leu Lys Ile Glu Pro Gly Tyr Trp Gly Asn Ala Ile Phe Pro Val
                245                 250                 255

Lys Val Thr Ala Ala Glu Lys Val Ala Gly Ser Ser Val Val Glu
                260                 265                 270

Leu Val Ser Ile Val Arg Glu Ala Lys Lys Gln Met Ala Glu Asp Cys
            275                 280                 285

Leu Ser Trp Ala Glu Gly Arg Thr Gly Gly Arg Asp Pro Phe Gln Met
        290                 295                 300

Ser Phe Asp Tyr Glu Ser Val Tyr Val Ser Asp Trp Ser Lys Leu Gly
305                 310                 315                 320

Phe Ser Asp Val Asp Tyr Gly Tyr Gly Thr Pro Met Thr Ala Gly Pro
                325                 330                 335

Leu Val Asn Cys Asp Leu Ile Ala Ser Val Ile Val Met Lys Ala Pro
            340                 345                 350
```

Ala Pro Leu Ala Gly Thr Arg Leu Leu Ala Ser Cys Val Thr Lys Glu
        355                 360                 365

His Ala Glu Gly Phe
    370

<210> SEQ ID NO 10
<211> LENGTH: 399
<212> TYPE: PRT
<213> ORGANISM: Sorghum bicolor

<400> SEQUENCE: 10

Phe Thr Val Thr Lys Leu Ser Glu Gly Pro Val Arg Pro Ser Ala Asp
1               5                   10                  15

Thr Pro Ser Glu Thr Leu Pro Leu Ala Trp Val Asp Arg Tyr Pro Thr
            20                  25                  30

His Arg Gly Leu Val Glu Ser Thr His Ile Tyr Cys Ser Gly Asp Asp
        35                  40                  45

Val Ala Lys Met Leu Leu Pro Pro Gln Ala Pro Ala Ala Thr Lys
    50                  55                  60

Lys Lys Glu Val Thr Thr Lys Ser Lys Ser Pro Ala Ala Val Val
65                  70                  75                  80

Arg Gly Ala Leu Ala Asp Ala Leu Val Leu Tyr Tyr Pro Phe Ala Gly
                85                  90                  95

Arg Ile Val Glu Asp Val Pro Gly Arg Pro Ala Val Leu Cys Ser Ala
            100                 105                 110

Glu Gly Val Tyr Phe Val Glu Ala Ala Ala Asn Cys Thr Leu Ala Asp
        115                 120                 125

Val Asn Phe Leu Glu Arg Pro Leu Leu Leu Ala Lys Glu Gln Leu Val
130                 135                 140

Pro Cys Pro Thr Pro Asp Leu Trp Pro Val Glu Pro His Asn Ser Leu
145                 150                 155                 160

Ala Met Ile Gln Val Thr Thr Phe Thr Cys Gly Gly Phe Val Val Gly
                165                 170                 175

Leu Arg Thr Asn His Ala Val Ala Asp Gly Thr Gly Ala Ala Gln Phe
            180                 185                 190

Leu Asn Ala Val Gly Asp Leu Ala Arg Gly Leu Pro Glu Pro Arg Val
        195                 200                 205

Lys Pro Ile Trp Gly Arg Asp Arg Phe Pro Asp Pro Asp Ile Lys Pro
    210                 215                 220

Gly Pro Leu Pro Glu Leu Pro Val Leu Ala Leu Glu Tyr Ile Ala Phe
225                 230                 235                 240

Asp Phe Pro Thr Ala Tyr Leu Asp Lys Leu Lys Ser Gln Tyr Ala Ala
                245                 250                 255

Ser Thr Gly Gly Lys Ile Cys Ser Gly Phe Asp Ile Val Ile Ala Lys
            260                 265                 270

Leu Trp Gln Cys Arg Thr Arg Ala Ile Ile Asp Ala Ala Ala Gly Ala
        275                 280                 285

Asp Asp Val Arg Leu Cys Phe Phe Ala Ser Val Arg His Val Leu Lys
    290                 295                 300

Leu Glu Pro Gly Tyr Tyr Gly Asn Ala Ile Phe Pro Val Lys Val Gln
305                 310                 315                 320

Ala Pro Ala Glu Lys Val Ala Gly Ser Ser Val Val Glu Leu Val Gly
                325                 330                 335

Met Val Arg Glu Ala Lys Arg Arg Met Ala Glu Glu Cys Leu Arg Trp

```
              340                 345                 350
Ala Glu Asp Arg Thr Gly Gly Val Asp Pro Phe Gln Met Thr Phe Asn
            355                 360                 365

Tyr Glu Ser Val Tyr Val Ser Asp Trp Ser Lys Leu Gly Phe Thr Asp
        370                 375                 380

Val Asp Tyr Gly Tyr Gly Ala Pro Met Ser Ala Gly Pro Leu Val
385                 390                 395

<210> SEQ ID NO 11
<211> LENGTH: 395
<212> TYPE: PRT
<213> ORGANISM: Oryza sativa

<400> SEQUENCE: 11

Ala Val Thr Lys Val Ser Glu Gly Pro Val Arg Pro Ser Ala Ala Thr
1               5                   10                  15

Pro Ser Glu Thr Leu Pro Leu Ala Trp Val Asp Arg Tyr Pro Thr His
            20                  25                  30

Arg Gly Leu Val Glu Ser Val His Ile Tyr Leu Arg Arg Asp Asp Ala
        35                  40                  45

Ala Val Glu Ala Pro Cys Ala Asp Gly Val Ile Val Glu Gly Lys
    50                  55                  60

Lys Lys Asn Asn Lys Pro Ala Ala Val Val Arg Gly Ala Leu Ala
65                  70                  75                  80

Asp Ala Leu Val His Tyr Tyr Pro Phe Ala Gly Arg Ile Val Glu Asp
                85                  90                  95

Glu Arg Ser Pro Gly Arg Pro Ala Val Leu Cys Ser Gly Glu Gly Val
            100                 105                 110

Tyr Phe Val Glu Ala Ala Asn Cys Thr Leu Ala Asp Val Asn His
        115                 120                 125

Leu Glu Arg Pro Leu Leu Leu Ser Lys Glu Asp Leu Val Pro Cys Pro
    130                 135                 140

Thr Pro Glu Gln Trp Pro Val Glu Pro His Asn Ser Leu Ala Met Ile
145                 150                 155                 160

Gln Val Thr Thr Phe Thr Cys Gly Gly Phe Val Ile Gly Leu Arg Thr
                165                 170                 175

Asn His Ala Val Ala Asp Gly Thr Gly Ala Ala Gln Phe Met Asn Ala
            180                 185                 190

Val Gly Asp Leu Ala Arg Gly Leu Pro Glu Pro Arg Val Lys Pro Ile
        195                 200                 205

Trp Ala Arg Asp Arg Phe Pro Asp Pro Asp Ile Lys Pro Gly Pro Leu
    210                 215                 220

Pro Glu Leu Pro Val Leu Pro Leu Gln Tyr Ile Ala Phe Asp Phe Pro
225                 230                 235                 240

Ala Ala Tyr Leu Gly Lys Leu Lys Ala Gln Tyr Ala Ala Thr Ala Gly
                245                 250                 255

Ala Ser Lys Ile Cys Ser Ala Phe Asp Ile Val Ile Ala Lys Leu Trp
            260                 265                 270

Gln Cys Arg Thr Arg Ala Ile Ala Ala Asp Pro Ala Ala Ala Val Lys
        275                 280                 285

Leu Cys Phe Phe Ala Ser Ala Arg Gln Val Leu Gly Leu Glu Thr Gly
    290                 295                 300

Tyr Trp Gly Asn Ala Ile Phe Pro Val Lys Val Ser Ala Ala Ala Gly
305                 310                 315                 320
```

-continued

```
Glu Val Ala Ala Ser Ser Val Ile Glu Leu Val Gly Val Val Arg Glu
                325                 330                 335

Ala Lys Arg Arg Met Ala Gly Glu Cys Leu Arg Trp Ala Glu Gly Arg
            340                 345                 350

Thr Gly Gly Ala Asp Pro Phe Gln Met Thr Phe Asp Tyr Glu Ser Val
        355                 360                 365

Tyr Val Ser Asp Trp Ser Lys Leu Gly Phe Asn Asp Val Asp Tyr Gly
    370                 375                 380

Tyr Gly Ala Pro Ser Ala Ala Gly Pro Leu Val
385                 390                 395
```

<210> SEQ ID NO 12
<211> LENGTH: 405
<212> TYPE: PRT
<213> ORGANISM: Sorghum bicolor

<400> SEQUENCE: 12

```
Phe Lys Val Thr Arg Ile Ser Glu Gly Pro Val Lys Pro Ala Ser Ser
1               5                   10                  15

Thr Pro Glu Glu Thr Leu Pro Leu Ala Trp Val Asp Arg Tyr Pro Thr
            20                  25                  30

His Arg Gly Leu Val Glu Ser Met His Ile Phe Arg Ser Gly Ala Asp
        35                  40                  45

Ala Ala Pro Ala Val Ile Arg Ala Ala Leu Gly Lys Ala Leu Ala Phe
    50                  55                  60

Phe Tyr Pro Leu Ala Gly Arg Ile Val Glu Gly Asp Gln Pro Gly Cys
65                  70                  75                  80

Pro Ala Ile Arg Cys Thr Ala Asp Gly Val Tyr Phe Ala Glu Ala Val
                85                  90                  95

Ala Asp Cys Ser Leu Glu Asp Val Arg Phe Leu Glu Arg Pro Leu Leu
            100                 105                 110

Leu Pro Lys Glu Asp Leu Val Pro Tyr Pro Gly Asp Asp Arg Trp Thr
        115                 120                 125

Val Glu Pro His Asn Thr Ile Met Met Met Gln Ile Thr Lys Phe Thr
    130                 135                 140

Cys Gly Gly Phe Val Met Gly Leu Arg Phe Asn His Ala Ser Ala Asp
145                 150                 155                 160

Gly Met Gly Ala Ala Gln Phe Ile Asn Ala Val Gly Asp Met Ala Arg
                165                 170                 175

Gly Leu Thr Glu Pro Lys Val Leu Pro Val Trp His Arg Glu Lys Phe
            180                 185                 190

Pro Asn Pro Asn Ile Lys Pro Gly Pro Leu Pro Glu Leu Pro Val Leu
        195                 200                 205

Ala Leu Asp Tyr Val Val Leu Asp Phe Pro Thr Pro Tyr Ile Asp Asp
    210                 215                 220

Leu Lys Arg Gln Tyr Lys Ala His Ser Gly Lys Phe Cys Ser Gly Phe
225                 230                 235                 240

Asp Val Leu Thr Ala Lys Leu Trp Gln Cys Arg Thr Arg Ala Leu Ala
                245                 250                 255

Leu Asp Pro Ala Thr Glu Val Lys Leu Cys Phe Phe Ala Ser Val Arg
            260                 265                 270

His Leu Leu Lys Leu Asp Arg Gly Tyr Tyr Gly Asn Ser Ile Phe Pro
        275                 280                 285

Val Lys Met Ser Ala Pro Ala Glu Lys Val Leu Ala Ser Ser Ile Leu
    290                 295                 300
```

```
Glu Val Val Asp Met Ile Arg Glu Ala Lys Asp Arg Met Ala Val Glu
305                 310                 315                 320

Phe Phe Arg Phe Ala Lys Glu Thr Asp Gln Asp Pro Phe Gln Met
            325                 330                 335

Thr Phe Asn Tyr Glu Ser Ile Tyr Val Ser Asp Trp Ser Lys Leu Gly
            340                 345                 350

Phe Ser Asp Val Asp Tyr Gly Phe Gly Pro Pro Met Phe Ala Gly Pro
            355                 360                 365

Leu Val Asn Asn Asp Phe Ile Ala Ser Val Val Ile Leu Lys Ala Pro
370                 375                 380

Leu Pro Leu Asp Gly Thr Arg Met Leu Ala Ser Cys Val Thr Lys Glu
385                 390                 395                 400

His Ser Asp Glu Phe
                405

<210> SEQ ID NO 13
<211> LENGTH: 454
<212> TYPE: PRT
<213> ORGANISM: Brachypodium distachyon

<400> SEQUENCE: 13

Met Gly Val Phe Ala Val Thr Lys Val Ser Glu Gly Pro Val Arg Pro
1               5                   10                  15

Ser Ala Ala Thr Pro Ser Asp Thr Leu Pro Leu Ala Trp Val Asp Arg
                20                  25                  30

Tyr Pro Thr His Arg Gly Leu Val Glu Ser Val His Ile Tyr Arg Asp
            35                  40                  45

Ala Phe Gln Pro Pro Pro Ala Pro Glu Ala Ala Ala Ala Ala Ala Ala
        50                  55                  60

Glu Glu Glu Glu Asp Gln Glu Lys Lys Lys Asn Asn Asn Asn Ser Lys
65                  70                  75                  80

Lys Pro Pro Ala Ala Val Val Arg Ser Ala Leu Ala Asp Ala Leu Val
                85                  90                  95

His Tyr Tyr Pro Phe Ala Gly Arg Ile Val Glu Asp Ala Ala Lys Pro
            100                 105                 110

Gly Arg Pro Ala Val Leu Cys Cys Ala Glu Gly Val Tyr Phe Val Glu
        115                 120                 125

Ala Thr Ala Asn Cys Thr Leu Ala Asp Val Asn Phe Leu Glu Arg Pro
130                 135                 140

Leu Leu Leu Gly Lys Glu Asp Leu Val Pro Tyr Pro Ala Pro Glu Leu
145                 150                 155                 160

Trp Ala Val Glu Pro His Asn Thr Leu Ala Met Ile Gln Val Thr Thr
                165                 170                 175

Phe Thr Cys Gly Gly Phe Val Leu Gly Leu Arg Thr Asn His Ala Val
            180                 185                 190

Ala Asp Gly Thr Gly Ala Ala Gln Phe Leu Asn Ala Val Gly Asp Leu
        195                 200                 205

Ala Arg Gly Leu Gln Glu Pro Arg Val Lys Pro Val Trp Ala Arg Asp
210                 215                 220

Arg Phe Pro Asp Pro Asp Ile Gln Pro Gly Pro Leu Pro Glu Leu Pro
225                 230                 235                 240

Val Leu Ala Leu Glu Tyr Ile Ala Phe Asp Phe Pro Val Thr Tyr Ile
                245                 250                 255

Asp Lys Ile Lys Ser Glu Tyr Asn Ala Cys Ser Gly Gly Lys His Cys
```

```
                    260                 265                 270
Ser Gly Phe Asp Ile Val Ile Ala Lys Leu Trp Gln Ser Arg Thr Arg
                275                 280                 285

Ala Ile Ile Gly Ile Pro Glu Ser Pro Ser Ala Asp Val Lys Leu
            290                 295                 300

Cys Phe Phe Ala Ser Ala Arg His Val Leu Lys Ile Glu Pro Gly Tyr
305                 310                 315                 320

Trp Gly Asn Ala Ile Phe Pro Val Lys Val Thr Ala Ala Glu Lys
                325                 330                 335

Val Ala Gly Ser Ser Val Val Glu Leu Val Ser Ile Val Arg Glu Ala
                340                 345                 350

Lys Lys Gln Met Ala Glu Asp Cys Leu Ser Trp Ala Glu Gly Arg Thr
                355                 360                 365

Gly Gly Arg Asp Pro Phe Gln Met Ser Phe Asp Tyr Glu Ser Val Tyr
                370                 375                 380

Val Ser Asp Trp Ser Lys Leu Gly Phe Ser Asp Val Asp Tyr Gly Tyr
385                 390                 395                 400

Gly Thr Pro Met Thr Ala Gly Pro Leu Val Asn Cys Asp Leu Ile Ala
                405                 410                 415

Ser Val Ile Val Met Lys Ala Pro Ala Pro Leu Ala Gly Thr Arg Leu
                420                 425                 430

Leu Ala Ser Cys Val Thr Lys Glu His Ala Gly Phe Ala Ser Arg
                435                 440                 445

Met Arg Glu Asp Ile Ala
    450

<210> SEQ ID NO 14
<211> LENGTH: 431
<212> TYPE: PRT
<213> ORGANISM: Brachypodium distachyon

<400> SEQUENCE: 14

Phe Lys Val Thr Arg Ile Ser Glu Gly Pro Val Lys Pro Ala Ser Pro
1               5                   10                  15

Asp Thr Pro Gly His Thr Leu Pro Leu Ala Trp Val Asp Arg Tyr Pro
                20                  25                  30

Thr His Arg Gly Leu Val Glu Ser Met His Ile Phe Arg Ser Gly Ala
                35                  40                  45

Asp Ala Ala Pro Gly Val Ile Arg Asp Ala Leu Ala Lys Ala Leu Val
            50                  55                  60

Phe Phe Tyr Pro Leu Ala Gly Arg Ile Val Glu Pro Glu Lys Glu Ala
65                  70                  75                  80

Ala Ala Ala Ala Ala Ala Ala Gly Glu Asn Gly Asp Gly Glu
                85                  90                  95

Lys Lys Ala Pro Ala Ala Ser Phe Pro Leu Gly Val Arg Cys Ala Gly
                100                 105                 110

Asp Gly Val Tyr Phe Ala Glu Ala Glu Ala Glu Cys Ser Leu Glu Asp
                115                 120                 125

Val Arg Phe Leu Glu Arg Pro Leu Leu Leu Pro Lys Glu Asp Leu Val
            130                 135                 140

Pro Tyr Pro Gly Pro Asp Lys Trp Ser Val Glu Pro His Asn Thr Ile
145                 150                 155                 160

Met Met Met Gln Ile Thr Lys Phe Thr Cys Gly Gly Phe Val Met Gly
                165                 170                 175
```

Leu Arg Phe Asn His Ala Ser Ala Asp Gly Met Gly Ala Ala Gln Phe
            180                 185                 190

Ile Lys Ala Val Gly Asp Met Ala Arg Gly Leu Pro Glu Pro Ala Val
        195                 200                 205

Lys Pro Val Trp Asp Arg Glu Lys Phe Pro Asn Pro Ser Ile Lys Pro
    210                 215                 220

Gly Pro Leu Pro Glu Leu Pro Val Leu Ala Leu Asp Tyr Ile Val Leu
225                 230                 235                 240

Asp Phe Pro Thr Gly Tyr Ile Asp Gly Leu Lys Ala Gln Tyr Lys Ala
                245                 250                 255

His Ser Gly Lys Phe Cys Ser Gly Phe Asp Val Leu Thr Ala Lys Leu
            260                 265                 270

Trp Gln Cys Arg Thr Arg Ala Leu Asn Leu Glu Pro Gly Ala Thr Val
        275                 280                 285

Lys Leu Cys Phe Phe Ala Ser Val Arg His Leu Leu Lys Leu Asp Pro
    290                 295                 300

Gly Tyr Tyr Gly Asn Ser Ile Phe Pro Val Lys Met Ser Ala Pro Ser
305                 310                 315                 320

Glu Lys Val Leu Gly Ser Ser Val Met Glu Val Ile Asp Met Ile Arg
                325                 330                 335

Glu Ala Lys Gln Arg Met Ala Val Glu Phe Gln Phe Ala Lys Glu
            340                 345                 350

Glu Thr Lys Gln Asp Pro Phe Gln Met Ser Phe Asp Tyr Glu Ser Ile
        355                 360                 365

Tyr Val Ser Asp Trp Ser Lys Leu Gly Phe Ser Asp Val Asp Tyr Gly
    370                 375                 380

Phe Gly Pro Pro Met Phe Ala Gly Pro Leu Val Asn Asn Asp Phe Ile
385                 390                 395                 400

Ala Ser Val Val Ile Leu Lys Ala Pro Leu Pro Leu Asp Gly Thr Arg
                405                 410                 415

Met Leu Ala Ser Cys Val Thr Lys Glu His Ser Asp Glu Phe Val
            420                 425                 430

<210> SEQ ID NO 15
<211> LENGTH: 356
<212> TYPE: PRT
<213> ORGANISM: Oryza sativa

<400> SEQUENCE: 15

Phe Lys Val Thr Arg Ile Ser Glu Gly Ala Val Lys Pro Ala Ala Ala
1               5                   10                  15

Thr Pro Glu Glu Thr Leu Pro Leu Ala Trp Val Asp Arg Tyr Pro Thr
            20                  25                  30

His Arg Gly Leu Val Glu Ser Met His Ile Phe Arg Ser Gly Ala Asp
        35                  40                  45

Ala Ala Pro Gly Val Ile Arg Asp Ala Leu Ala Arg Leu Val Phe
    50                  55                  60

Phe Tyr Pro Leu Ala Gly Arg Ile Val Glu Pro Gly Ala Gly Ser Pro
65                  70                  75                  80

Ala Ile Arg Cys Thr Ala Asp Gly Val Tyr Phe Ala Glu Ala Ala Ala
                85                  90                  95

Asp Cys Ser Leu Glu Asp Val Arg Phe Leu Glu Arg Pro Leu Leu Leu
            100                 105                 110

Pro Lys Glu Asp Leu Val Pro Tyr Pro Gly Asp Asp Arg Trp Gly Val
        115                 120                 125

```
Glu Pro His Asn Thr Ile Met Met Met Gln Ile Thr Lys Phe Thr Cys
        130                 135                 140

Gly Gly Phe Val Met Gly Leu Arg Phe Asn His Ala Ser Ala Asp Gly
145                 150                 155                 160

Met Gly Ala Ala Gln Phe Ile Asn Ala Val Gly Asp Met Ala Arg Gly
                165                 170                 175

Leu Pro Glu Pro Arg Val Lys Pro Val Trp Asp Arg Glu Lys Phe Pro
            180                 185                 190

Asn Pro Ser Ile Lys Pro Gly Pro Leu Pro Gly Leu Pro Val Leu Ala
        195                 200                 205

Leu Asp Tyr Ile Val Leu Asp Phe Pro Thr Gly Tyr Ile Asp Gly Leu
    210                 215                 220

Lys Ala Gln Tyr Lys Ala His Ser Gly Lys Phe Cys Ser Gly Phe Asp
225                 230                 235                 240

Val Leu Thr Ala Lys Leu Trp Gln Cys Arg Thr Arg Ala Leu Asn Leu
                245                 250                 255

Glu Pro Gly Ala Thr Val Lys Leu Cys Phe Phe Ala Ser Val Arg His
            260                 265                 270

Leu Leu Lys Leu Asp Arg Gly Tyr Tyr Gly Asn Ser Ile Phe Pro Val
        275                 280                 285

Lys Met Ser Ala Pro Ser Glu Thr Val Leu Ser Ser Ser Val Met Glu
    290                 295                 300

Val Val Asp Met Ile Arg Gln Ala Lys Glu Arg Met Ala Val Glu Phe
305                 310                 315                 320

Phe Gln Phe Ala Lys Glu Glu Thr Glu Gln Asp Pro Phe Leu Pro Leu
                325                 330                 335

Asp Gly Thr Arg Met Leu Ala Ser Cys Val Thr Lys Glu His Ser Glu
            340                 345                 350

Glu Phe Val Arg
        355

<210> SEQ ID NO 16
<211> LENGTH: 398
<212> TYPE: PRT
<213> ORGANISM: Oryza sativa

<400> SEQUENCE: 16

Val Thr Lys Ser Pro Pro Glu Ile Val Arg Pro Ser Glu Pro Val Thr
1               5                   10                  15

Thr Thr Ala Ala Thr Gly Lys Ile Ile Phe Ser Pro Phe Asp Lys Pro
                20                  25                  30

Leu Ala Thr Val Pro Val Val Leu Gln Val Phe Glu His Pro Ile
            35                  40                  45

His Glu Pro Val Glu Thr Ile Arg Arg Gly Leu Ser His Ala Leu Val
        50                  55                  60

His Tyr Tyr Pro Leu Ala Gly Arg Leu Ala Gly Asp Tyr Asp Asp
65                  70                  75                  80

Val His Ile Asp Cys Thr Gly Glu Gly Val Thr Ile Val Ala Ala Ser
                85                  90                  95

Ala Asn Cys Thr Val Lys Gln Leu Met Arg Asp Ile Asp Gly Arg Leu
                100                 105                 110

Pro Asp Pro Ser Thr Ala Val Gln Arg Glu Leu Ile Val Asp Asp Asn
            115                 120                 125

Pro Ala Tyr Gly Phe Gly Arg Ala Asp Pro Leu Ile Leu Met Gln Val
```

```
                130             135             140
Thr Thr Phe Thr Cys Gly Gly Phe Val Ile Gly Val Thr Trp Asn His
145                 150             155                 160

Gly Ala Ala Asp Gly Phe Gly Ile Ala Gln Phe Leu Gln Ala Val Gly
                165             170             175

Glu Leu Ala Arg Gly Leu Pro Thr Thr Ser Val Ile Pro Val Arg Ser
                180             185             190

Asp Lys Ser Leu Gln Ala Met Ser Ser Ser Thr Val Met Ala Ala Lys
            195             200             205

Gln Phe Met Phe Gly Val Lys Pro Thr Thr Leu Ala Leu His Ser Ile
        210             215             220

Thr Ile Pro Ala Arg Val Ile Asn Gly Val Arg Gly Pro Thr Pro Thr
225             230             235             240

Cys Thr Val Phe Glu Ala Val Ala Val Met Trp Arg Cys Arg Thr
                245             250             255

Arg Val Val Met Ser Asp Pro Asp Ala Pro Thr Val Leu Ala Ile Thr
            260             265             270

Val Asn Ser Arg Lys Tyr Val Gly Val Lys Asp Gly Tyr Tyr Gly Asn
        275             280             285

Cys Ala Thr Met Gln Met Ala Val Ala Arg Ser Gly Val Val Ala Asp
    290             295             300

Gly Asp Met Met Glu Val Val Arg Thr Ile Arg Arg Ala Lys Glu Glu
305             310             315             320

Ile Pro Glu Arg Leu Lys Lys Gly Asp Ala Ile Ala Glu Leu Ser Lys
                325             330             335

Gly Gln Leu Ser Gly Tyr Glu Ser Val Leu Val Thr Cys Trp Arg
                340             345             350

Asn Ile Gly Phe Glu Ala Val Asp Phe Gly Gly Arg Thr Ala Arg
                355             360             365

Val Met Thr Thr Tyr Glu Gln Ser Gly Val Arg Pro Leu Cys Val Val
            370             375             380

Cys Leu Pro Trp Gln Gly Glu Glu Asp Glu Gly Ala Arg Val
385                 390             395

<210> SEQ ID NO 17
<211> LENGTH: 395
<212> TYPE: PRT
<213> ORGANISM: Oryza sativa

<400> SEQUENCE: 17

Val Thr Lys Ser Pro Pro Glu Ile Val Arg Pro Ser Glu Pro Val Thr
1               5               10              15

Thr Thr Ala Ala Thr Ser Lys Val Ile Phe Ser Pro Leu Asp Arg Pro
            20              25              30

Leu Ala Ile Val Pro Ile Val Val Leu Gln Val Phe Glu His Pro Ile
        35              40              45

His Glu Pro Val Glu Thr Ile Arg Arg Gly Leu Ser Arg Ala Leu Val
    50              55              60

His Tyr Tyr Pro Leu Ala Gly Arg Leu Ala Gly Asp Asp Tyr Asp Asp
65              70              75              80

Val His Ile Asp Cys Thr Gly Glu Gly Val Thr Phe Val Ala Ala Asn
            85              90              95

Ala Asp Cys Thr Val Lys Glu Leu Val Arg Asp Ile Asp Cys Arg Ser
            100             105             110
```

```
Pro Asp Ala Ala Lys Ala Val Ile Arg Glu Leu Ile Val Asp Tyr Pro
            115                 120                 125

Ala Asn Gly Phe Gly Arg Ala Asp Pro Leu Val Leu Met Gln Val Thr
        130                 135                 140

Ala Phe Ala Cys Gly Gly Phe Val Val Gly Val Thr Trp Asn His Gly
145                 150                 155                 160

Ala Ala Asp Gly Phe Gly Ile Ala Gln Phe Leu Gln Ala Val Gly Glu
                165                 170                 175

Leu Ala Arg Gly Leu Pro Thr Pro Ala Val Thr Pro Val Arg Trp Asp
            180                 185                 190

Gly Trp Ala Gln Ala Val Ala Pro Ser Thr Val Met Ala Ser Lys Arg
        195                 200                 205

Phe Met Phe Gly Val Lys Ala Pro Thr Arg Leu Ala Leu His Ser Ile
210                 215                 220

Thr Ile Pro Ala Arg Thr Ile Asp Gly Val Arg Gly Ala Thr Ala Cys
225                 230                 235                 240

Thr Met Phe Glu Ala Val Ala Ala Leu Trp Arg Cys Arg Thr Arg
                245                 250                 255

Val Val Met Ser Asp Pro Asp Ala Pro Thr Val Leu Ala Ile Thr Val
            260                 265                 270

Asn Ser Arg Lys His Val Gly Val Lys Asp Gly Tyr Tyr Gly Asn Cys
        275                 280                 285

Ala Thr Val His Met Ala Val Ala Arg Ser Gly Ala Val Ala Gly Gly
            290                 295                 300

Asp Met Thr Glu Ala Val Arg Ala Ile Arg Arg Ala Lys Glu Glu Ile
305                 310                 315                 320

Pro Glu Arg Leu Lys Lys Gly Asp Val Ile Gly Glu Leu Ser Lys Glu
                325                 330                 335

Gln Leu Gly Gly Tyr Glu Ser Val Leu Leu Val Thr Cys Trp Arg Asn
            340                 345                 350

Ile Gly Phe Glu Ala Val Asp Tyr Gly Gly Arg Thr Ala Arg Val
        355                 360                 365

Met Thr Thr Tyr Glu Gln Gly Arg Val Arg Pro Met Cys Val Val Cys
370                 375                 380

Leu Pro Trp Gln Gly Glu Glu Glu Gly Ala
385                 390                 395

<210> SEQ ID NO 18
<211> LENGTH: 375
<212> TYPE: PRT
<213> ORGANISM: Oryza sativa

<400> SEQUENCE: 18

Ala Pro Val Val Val Arg Pro Ser Glu Pro Ala Thr Ser Thr Ala Asp
1               5                   10                  15

Lys Ile Leu Leu Ser Thr Leu Asp Lys Pro Val Ala Thr Ile Pro Val
            20                  25                  30

Thr Val Leu Leu Ala Phe Asp His Pro Ile His Asp Ala Thr Ala Glu
        35                  40                  45

Thr Ile Lys Thr Ala Leu Ala Gln Ser Leu Val His Tyr Tyr Pro Ile
    50                  55                  60

Ala Gly Arg Ile Ser Cys Asp Asn Asp Gly Gly His Phe Tyr Ile
65                  70                  75              80

Asp Cys Thr Gly Glu Asp Leu Gly Val Thr Phe Val Ala Ala Ser Ala
                85                  90                  95
```

Asn Cys Thr Met Glu Glu Leu Met Cys Leu Val Asp Gln Ala Pro
                100                 105                 110

Asp Asp Glu Thr Ala Val Val Gln Gln Leu Ala Phe Asn Cys Thr Pro
            115                 120                 125

Asp Asp Leu His His Arg Leu Leu Trp Val Gln Val Thr Thr Leu Asn
        130                 135                 140

Cys Gly Gly Phe Val Val Gly Val Thr Trp Ser His Gly Val Ala Asp
145                 150                 155                 160

Gly Pro Gly Ile Ala Gln Phe Ile Gln Ala Val Gly Glu Leu Ala Arg
                165                 170                 175

Gly Leu Pro Ser Pro Ser Val Val Pro Val Arg Leu Asp Asp Lys Ile
            180                 185                 190

Ala Thr Gln Ala Val Pro Pro Phe Thr Met Ala Val His Arg Phe Ile
        195                 200                 205

Ser Gly Leu Lys Pro Val Ser Asn Leu Asp Val Arg Asn Val Thr Val
    210                 215                 220

Ser Ser Ser Leu Ile Asn His Ile Ile Val Gly Ala Arg Arg Arg Ala
225                 230                 235                 240

Thr Val Phe Glu Ala Val Ala Ala Val Leu Trp Gln Cys Arg Thr Arg
                245                 250                 255

Val Val Met Thr Asp Pro Glu Ala Pro Ala Val Leu Leu Phe Ala Val
            260                 265                 270

Asn Ala Arg Lys Tyr Leu Gly Ala Lys Asp Gly Tyr Tyr Gly Cys Cys
        275                 280                 285

Thr Ala Met His Met Ala Val Ser Lys Ser Gly Thr Val Ala Asn Gly
    290                 295                 300

Asp Ile Met Lys Leu Val Gly Ile Ile Arg Arg Ala Lys Glu Gln Ile
305                 310                 315                 320

Pro Glu Gln Leu Lys Ala Asp Asp Gly Glu Met Met Leu Arg Thr Met
                325                 330                 335

Val Gly Glu Lys Gln Val Asn Gly Tyr Glu Ser Leu Leu Tyr Leu Thr
            340                 345                 350

Ser Trp Arg Asn Ile Gly Phe Glu Asp Val Asp Phe Gly Ser Gly Lys
        355                 360                 365

Thr Ala Arg Val Met Thr Tyr
    370                 375

<210> SEQ ID NO 19
<211> LENGTH: 261
<212> TYPE: PRT
<213> ORGANISM: Oryza sativa

<400> SEQUENCE: 19

Glu Thr Ala Val Val Gln Gln Leu Ala Phe Asn Cys Thr Pro Asp Asp
1               5                   10                  15

Asp His Leu Pro His Cys Leu Leu Trp Val Gln Val Thr Thr Leu Ser
            20                  25                  30

Cys Gly Gly Phe Val Val Gly Val Thr Trp Asn His Ala Val Ala Asp
        35                  40                  45

Gly Phe Gly Ile Ala Gln Phe Ile Gln Ala Val Gly Glu Leu Ala Arg
    50                  55                  60

Gly Leu Pro Ser Ala Pro Ser Val Thr Pro Val Arg Leu Asp Asp Gln
65                  70                  75                  80

Asn Asn Ala Val Ser Pro Phe Thr Met Ala Phe Met Gln Leu Ala Asp 85                  90                  95
Arg His Lys Val Pro Asp Leu Thr Phe Asn Val Thr Val Pro Ser
                100                 105                 110

Arg Leu Met Asp His Ile Ile Arg Gly Arg Thr Thr Asn Val Thr Val
            115                 120                 125

Phe Glu Ala Val Ala Ala Val Leu Trp Gln Cys Arg Thr Arg Ala Val
        130                 135                 140

Met Thr Asn Pro Glu Ala Pro Ala Val Leu Leu Phe Ala Val Asn Ala
145                 150                 155                 160

Arg Lys Tyr Leu Gly Ala Lys Asp Gly Tyr Tyr Gly Asn Cys Ser Thr
                165                 170                 175

Met His Val Ala Val Ala Lys Ser Gly Ala Val Ala Asn Ala Asp Ile
                180                 185                 190

Asn Asp Ile Val Asp Ile Ile Arg Arg Ala Lys Glu Arg Ile Pro Glu
                195                 200                 205

Gln Leu Lys Met Thr Gly Gly Ser Asp Met Thr Met Leu Arg Glu Leu
                210                 215                 220

Ala Asp Asp His Arg Leu Asp Gly Tyr Glu Ser Leu Leu Tyr Leu Thr
225                 230                 235                 240

Ser Trp Arg Asn Ile Gly Phe Glu Asp Val Asp Phe Gly Ser Gly Lys
                245                 250                 255

Thr Ala Arg Val Met
                260

<210> SEQ ID NO 20
<211> LENGTH: 391
<212> TYPE: PRT
<213> ORGANISM: Oryza sativa

<400> SEQUENCE: 20

Val Val Val Arg Pro Ser Gln Pro Pro Val Lys Thr Thr Ser Gly Ser
1               5                   10                  15

Lys Ile Val Leu Ser Pro Met Asp Lys Pro Ser Ser Met Met Pro Thr
                20                  25                  30

Thr Val Leu Leu Ala Phe Asp His Pro Thr Ile Gln Ser Glu Cys Thr
            35                  40                  45

Ala Glu Thr Ile Lys Arg Gly Leu Ala Gln Ala Leu Val Pro Tyr Tyr
        50                  55                  60

Pro Ile Ala Gly Arg Leu Ser Cys Asp Asp Gly Asp Phe Tyr Ile
65                  70                  75                  80

Asp Cys Thr Gly Glu Glu Leu Gly Val Thr Phe Val Ala Ala Ser Ala
                85                  90                  95

Asn Cys Thr Met Glu Glu Leu Met Cys Cys Val Asp Asp Gln Pro Pro
                100                 105                 110

Asp Ala Glu Thr Ala Val Val Gln Gln Leu Ala Phe Asn Cys Thr Pro
            115                 120                 125

Asp Asp Leu His His Arg Leu Leu Trp Met Gln Val Thr Thr Leu Ser
        130                 135                 140

Cys Gly Gly Phe Val Val Gly Val Thr Trp Asn His Gly Leu Ala Asp
145                 150                 155                 160

Gly Phe Gly Met Ala Gln Phe Ile Gln Ala Val Gly Glu Leu Thr Arg
                165                 170                 175

Gly Leu Pro Ser Pro Ser Val Val Pro Val Arg Leu Asp Asp Asn
                180                 185                 190

```
Asn Ala Thr Gln Ala Ile Pro Pro Phe Ala Met Ala Val Tyr Gln Phe
            195                 200                 205

Met Ser Ser Ser Ser His Lys Ala Ser Ile Asp His Thr Phe Asn Asn
210                 215                 220

Ile Thr Val Pro Ser Ser Leu Ile Asp His Ile Arg Phe Arg Gly Arg
225                 230                 235                 240

Arg Thr Asn Asp Asp Val Thr Val Phe Glu Ala Val Ala Ala Val Leu
                245                 250                 255

Trp Gln Cys Arg Thr Arg Ala Val Met Lys Asn Pro Glu Ala Pro Ala
            260                 265                 270

Val Leu Leu Phe Ala Val Asn Ala Arg Lys Tyr Leu Gly Ala Lys Asp
            275                 280                 285

Gly Tyr Tyr Gly Asn Cys Ser Thr Met His Val Ala Val Ala Lys Ser
290                 295                 300

Gly Ala Val Ala Asn Ala Asp Ile Asn Asp Ile Val Asp Ile Ile Arg
305                 310                 315                 320

Arg Ala Lys Glu Arg Ile Pro Glu Gln Leu Lys Met Thr Gly Gly Ser
                325                 330                 335

Asp Met Thr Met Leu Arg Glu Leu Ala Asp Asp His Arg Leu Asp Gly
                340                 345                 350

Tyr Glu Ser Leu Leu Tyr Leu Thr Ser Trp Arg Asn Ile Gly Phe Glu
            355                 360                 365

Asp Val Asp Phe Gly Ser Gly Lys Thr Ala Arg Val Met Thr Tyr Pro
            370                 375                 380

Gln Arg Val Val Leu Ser Met
385                 390

<210> SEQ ID NO 21
<211> LENGTH: 336
<212> TYPE: PRT
<213> ORGANISM: Oryza sativa

<400> SEQUENCE: 21

Ala Leu Ala Gln Ala Leu Val His Tyr Tyr Pro Ile Ala Gly Arg Leu
1               5                   10                  15

Ser Cys Asn Asp Asp Glu Asp Gly Gly Gly Asp Phe Tyr Ile Asp Cys
                20                  25                  30

Thr Ser Glu Leu Gly Val Met Phe Val Ala Ala Ser Ala Asp Cys Thr
            35                  40                  45

Met Glu Glu Leu Met Arg Val Ala Asp Asn Gln Pro Thr Asp Asp Glu
50                  55                  60

Thr Ala Val Val Gln Gln Leu Ala Phe Asn Cys Thr Pro Asp Val Gly
65                  70                  75                  80

Asp Asp Gly Pro Pro Pro Leu Leu Trp Val Gln Val Thr Thr Leu Ser
                85                  90                  95

Cys Gly Gly Phe Val Val Gly Val Thr Trp Ser His Gly Leu Ala Asp
            100                 105                 110

Gly Val Gly Ile Ala Gln Phe Ile Gln Ala Val Gly Glu Leu Ala Arg
            115                 120                 125

Gly Leu Pro Ser Pro Ser Ile Val Pro Val Arg Gln Asp Asp Ile Val
130                 135                 140

Ala Thr Gln Val Val Pro Pro Phe Thr Met Ala Leu Leu Gln Phe Leu
145                 150                 155                 160

Pro Gly Leu Lys Pro Leu Asp Leu Thr Phe Asn Asn Val Thr Val Pro
                165                 170                 175
```

```
Thr Ser Leu Ile Asn His Ile Arg Arg Phe Arg Gly Arg Thr Asn
            180                 185                 190

Asp Asp Gly Gly Gln His Ser Thr Thr Ile Thr Ala Phe Glu Ala
            195                 200                 205

Val Ala Ala Val Leu Trp Lys Cys Arg Thr Arg Ala Val Met Ala Ser
210                 215                 220

Pro Glu Ala Pro Ala Ile Leu Val Phe Val Asn Ala Arg Lys Tyr
225                 230                 235                 240

Leu Ala Gly Val Asn Asp Gly Tyr Tyr Gly Asn Cys Ser Met Met His
            245                 250                 255

Met Ala Met Ala Lys Ser Gly Ala Val Ala Asn Gly Asp Ile Met Asp
            260                 265                 270

Val Val Glu Ile Ile Arg Arg Ala Lys Glu Arg Ile Pro Glu Gln Phe
            275                 280                 285

Gly Glu Gly Ser Asp Arg Met Val Arg Glu Leu Ser Asp Gly Gln Gln
            290                 295                 300

Val Asp Gly Tyr Glu Ser Leu Leu Tyr Leu Thr Ser Trp Arg Asn Ile
305                 310                 315                 320

Gly Leu Glu Glu Val Asp Phe Gly Ser Gly Lys Thr Ala Arg Val Met
            325                 330                 335

<210> SEQ ID NO 22
<211> LENGTH: 389
<212> TYPE: PRT
<213> ORGANISM: Brachypodium distachyon

<400> SEQUENCE: 22

Val Val Val Gly Ala Asp Asp Gln Gln Ser Ser Gly Ala Gly Thr Ile
1               5                   10                  15

Asp Leu Ser Ser Phe Asp Lys Ser Leu Gly Pro Leu Pro Ile Thr Val
            20                  25                  30

Leu Leu Val Phe Asp His Pro Ile Lys Asp Pro Val Glu Ser Ile Lys
            35                  40                  45

Lys Ala Leu Ser Gln Ser Leu Ala Val Asp His Tyr His Pro Met Ala
50                  55                  60

Gly Arg Leu Thr Pro Asp Gly Ala Ile Ala Cys Thr Gly Glu Gly
65                  70                  75                  80

Val Ser Phe Val Gly Ala Ser Val Ser Cys Ala Leu Ala Asp Gln His
            85                  90                  95

Leu Pro Leu Leu Lys Asp Asp Leu Ala Met Gly Tyr Pro Gly Asp Trp
            100                 105                 110

Cys Arg Pro Glu Asp Pro Leu Val Gln Met Gln Val Thr Glu Phe Ser
            115                 120                 125

Cys Gly Gly Phe Val Val Gly Val Thr Trp Asn His Val Met Ala Asp
            130                 135                 140

Gly Ala Gly Met Ala Gln Phe Leu Arg Ala Ile Gly Glu Leu Ala Arg
145                 150                 155                 160

Gly Leu Pro Ser Pro Ser Val Val Pro Val Arg Ser Ser Ser Leu Leu
            165                 170                 175

Pro Cys Ile Pro Pro Ser Val Val Ala Ala Gln Arg Ala Met Met Ala
            180                 185                 190

Val Ala Ser Lys Asp Met Ala Ser Leu Asp Phe Thr Ile Pro Ser Ser
            195                 200                 205

Ala Ile Ala Arg Ile Lys Gly Gln Trp Ala Asp Ala Asn Ala His Glu
```

```
            210                 215                 220
Gln Pro Cys Thr Val Phe Glu Ala Val Thr Ala Leu Leu Trp Leu Cys
225                 230                 235                 240

Arg Thr Arg Ala Val Val Thr Ala Lys Asp Asp Glu Leu Pro Val
                245                 250                 255

Gly Met Val Phe Pro Ser Asn Val Arg Gln Gln Leu Gly Ala Glu Ala
                260                 265                 270

Gly Tyr Tyr Gly Asn Cys Leu Ala Ala Gln Leu Val Gln Ala Thr Thr
            275                 280                 285

Gly Ala Pro Ala Ile Asn Gly Leu Val Lys Leu Ile Lys Arg Ala Lys
            290                 295                 300

Asp Gly Gly Asp Gln Gln Gln Pro Leu His Gln Gly Ala Ala Val Gly
305                 310                 315                 320

Trp Tyr Asp Thr Leu Leu Val Ser Ser Trp Arg Asn Leu Gly Phe Glu
                325                 330                 335

Ala Ala Glu Phe Gly Gly Gly Ala Pro Ala Arg Val Met Trp His Gln
                340                 345                 350

Arg Gln Thr Val Leu Pro Ile Cys Val Val Cys Pro Pro Cys Lys Gly
            355                 360                 365

Lys Asp Asp Gly Val Asn Val Met Ser Met Cys Val Arg Pro Glu His
            370                 375                 380

Ala Asp Ser Phe Gln
385

<210> SEQ ID NO 23
<211> LENGTH: 392
<212> TYPE: PRT
<213> ORGANISM: Sorghum bicolor

<400> SEQUENCE: 23

Thr Val Glu Arg Leu Ala Gln Arg Leu Val Pro Pro Ala Glu Pro Thr
1               5                   10                  15

Pro Thr Gly Pro His Arg Leu Ser Trp Leu Asp Arg Tyr Pro Thr Gln
                20                  25                  30

Met Ala Leu Ile Glu Ser Leu His Val Phe Lys Pro Asp Pro Ala Arg
            35                  40                  45

Asp Gly Val Ser Pro Ala Thr Ile Glu Arg Ala Leu Ala Arg Ala
    50                  55                  60

Leu Val Asp Tyr Tyr Pro Leu Ala Gly Arg Leu Ala Val Ser Ala Gly
65                  70                  75                  80

Gly Gln Leu His Val Asp Cys Ser Ala Glu Gly Val Trp Phe Ile Glu
                85                  90                  95

Ala Ala Val Arg Cys Arg Leu Asp Asp Val Asp Tyr Leu Glu Tyr Pro
            100                 105                 110

Leu Gln Ile Pro Lys Asp Asp Leu Leu Pro His Pro Leu Pro Arg Pro
        115                 120                 125

Ser His Asp Glu Glu Ser Lys Leu Ile Leu Leu Val Gln Val Thr Ala
    130                 135                 140

Phe Ala Cys Gly Gly Phe Val Val Gly Phe Arg Phe Ser His Ala Val
145                 150                 155                 160

Ala Asp Gly Leu Gly Ala Ala Lys Phe Met Ala Ala Val Gly Glu Leu
                165                 170                 175

Ala Arg Gly Ala Glu Gln Val Ser Val Pro Pro Val Trp Ala Arg Asp
            180                 185                 190
```

```
Ala Ile Pro Asp Pro Gly Ala Leu Val Gly Ser Leu Pro Asp Pro
        195                 200                 205

Thr Gly Ala Lys Arg Leu Glu Tyr Leu Ala Ile Asp Ile Ser Ala Asp
210                 215                 220

Tyr Ile Asp His Phe Lys Ser Gln Phe Ala Ala Thr Gly Gly
225                 230                 235                 240

Arg Cys Ser Ser Phe Glu Val Leu Ile Ala Lys Ala Trp Gln Ser Arg
                245                 250                 255

Thr Arg Ala Ala Gly Phe Asp Asp Pro Ala Ser Thr Pro Val Gln Leu
                260                 265                 270

Cys Phe Ala Met Asn Ala Arg Pro Leu Leu Leu Ala Gly Gly Ser Gly
            275                 280                 285

Gly Thr Arg Ser Pro Arg Gly Gly Gly Gly Ala Gly Phe Tyr Gly
        290                 295                 300

Asn Cys Tyr Tyr Ile Met Arg Val Ser Ser Thr Ala Asp Arg Val Ala
305                 310                 315                 320

Ser Ser Ser Val Thr Asp Val Val Arg Ile Ile Arg Glu Gly Lys Lys
                325                 330                 335

Arg Leu Pro Ser Glu Leu Ala Arg Trp Ala Ala Gly Glu Asp Gly Gly
                340                 345                 350

Val Asp Pro Tyr Gln Ile Thr Ser Asp Tyr Arg Thr Leu Leu Val Ser
            355                 360                 365

Asp Trp Thr Arg Leu Gly Phe Ala Glu Val Asp Tyr Gly Trp Gly Pro
            370                 375                 380

Pro Ala His Val Val Pro Leu Thr
385                 390

<210> SEQ ID NO 24
<211> LENGTH: 381
<212> TYPE: PRT
<213> ORGANISM: Brachypodium distachyon

<400> SEQUENCE: 24

Pro Val Glu Arg Leu Ala Gln Arg Leu Val Ala Pro Ala Gly Pro Thr
1               5                   10                  15

Pro Glu Gly Pro Leu Arg Leu Ser Trp Leu Asp Arg Tyr Pro Thr Gln
                20                  25                  30

Met Ala Leu Ile Glu Ser Leu His Val Phe Lys Pro Asp Met Ala Arg
            35                  40                  45

Glu Gly Asp Ser Pro Ala Arg Ala Val Glu Arg Ala Leu Ala Arg Ala
        50                  55                  60

Leu Val Asp Tyr Tyr Pro Leu Ala Gly Arg Leu Ala Val Ser Asp Ala
65                  70                  75                  80

Gly Glu Leu Gln Val Asp Cys Arg Asp Gly Gly Val Trp Phe Ile Glu
                85                  90                  95

Ala Ala Val Arg Cys Arg Leu Glu Asp Val Asp Tyr Leu Glu Tyr Pro
            100                 105                 110

Leu Ala Val Asp Lys Asp Glu Leu Leu Pro His Pro Arg Pro Lys Pro
        115                 120                 125

Thr His Glu Glu Glu Ser Lys Leu Ile Leu Leu Val Gln Val Thr Thr
    130                 135                 140

Phe Asp Cys Gly Gly Phe Val Val Gly Phe Arg Phe Ser His Ala Val
145                 150                 155                 160

Ala Asp Gly Pro Gly Ala Ala Gln Phe Met Gly Ala Val Gly Glu Leu
                165                 170                 175
```

```
Ala Arg Gly Ala Gly Arg Ile Ser Val Pro Pro Ala Trp Gly Arg Asp
            180                 185                 190

Ala Ile Pro Asp Pro Ala Gly Ala Leu Val Gly Arg Leu Pro Glu Pro
        195                 200                 205

Ala Gly Ala Lys Arg Leu Glu Tyr Leu Ala Ile Asp Ile Ser Ala Asp
    210                 215                 220

Tyr Ile Asn His Phe Lys Ala Gln Phe Ala Ala Thr Gly Gly Ala
225                 230                 235                 240

Arg Cys Ser Ala Phe Glu Val Leu Ile Ala Lys Ala Trp Gln Ser Arg
                245                 250                 255

Thr Arg Ala Ala Gly Phe Asp Glu Glu Ser Pro Val His Leu Ser Phe
                260                 265                 270

Ala Met Asn Ala Arg Pro Leu Leu His Ala Arg Leu Pro Ser Gly Gly
            275                 280                 285

Ala Gly Phe Tyr Gly Asn Cys Tyr Tyr Ile Met Arg Val Ser Ser Thr
        290                 295                 300

Ala Gly Lys Val Ala Ser Ser Met Ala Asp Val Val Lys Ile Ile
305                 310                 315                 320

Lys Glu Gly Lys Lys Arg Leu Pro Ser Glu Phe Ala Arg Trp Ala Ala
                325                 330                 335

Gly Glu Met Ala Gly Val Asp Pro Tyr Gln Ile Thr Ser Asp Tyr Arg
            340                 345                 350

Thr Leu Leu Val Ser Asp Trp Thr Arg Leu Gly Phe Ala Glu Val Asp
        355                 360                 365

Tyr Gly Trp Gly Pro Pro Ala His Val Val Pro Leu Thr
    370                 375                 380

<210> SEQ ID NO 25
<211> LENGTH: 387
<212> TYPE: PRT
<213> ORGANISM: Brachypodium distachyon

<400> SEQUENCE: 25

Val Ser Arg Leu Pro Gln Arg Leu Val Leu Pro Ala Glu Pro Thr Pro
1               5                   10                  15

Ala Gly Pro Leu Arg Leu Ser Trp Leu Asp Arg Tyr Pro Thr Gln Met
            20                  25                  30

Ala Leu Ile Glu Ser Leu His Val Phe Lys Pro Ala Pro Ala His Asp
        35                  40                  45

Gly Ala Asp Pro Ala Arg Thr Ile Glu Arg Ala Leu Ala Gln Ala Leu
    50                  55                  60

Val Arg Tyr Tyr Pro Leu Ala Gly Arg Leu Ala Phe Thr Asp Asp Gly
65                  70                  75                  80

Gly Gln Ser His Val Asp Cys Gly Gly Pro Gly Ser Gly Val Trp Phe
                85                  90                  95

Thr Glu Ala Ala Ala Cys Gly Leu Glu Asp Val Asp Tyr Leu Glu
            100                 105                 110

His Pro Met Met Ile Pro Lys Asp Ala Leu Leu Pro Pro Thr Pro His
        115                 120                 125

Ala Ala Glu Glu Gly Asp Glu Arg Arg Leu Val Leu Val Gln Val
    130                 135                 140

Thr Ser Phe Ala Cys Gly Gly Phe Val Gly Phe Arg Phe Ser His
145                 150                 155                 160

Ala Val Ala Asp Gly Pro Gly Ala Ala Gln Phe Met Ala Ala Val Gly
```

-continued

```
                165                 170                 175
Asp Leu Ala Arg Gly Ala Glu Ser Leu Ser Met Glu Pro Gln Trp Gly
            180                 185                 190

Arg Asp Ala Val Pro Asp Pro Ala Gly Ala Val Val Gly Ala Leu Pro
        195                 200                 205

Asp Pro Ala Gly Ala Lys Arg Leu Glu Tyr Leu Ala Met Asp Ile Ser
    210                 215                 220

Ala Asp Tyr Ile Asp His Phe Lys Ser Gln Tyr Asn Ser Ser Asn Asn
225                 230                 235                 240

Gly Gly Gly Ala Arg Cys Ser Ala Phe Glu Val Leu Val Ala Lys Ala
                245                 250                 255

Trp Gln Ser Arg Thr Arg Ala Ala Gly Phe Asp Pro Ser Ala Thr Val
            260                 265                 270

His Leu Cys Phe Ala Met Asn Ala Arg Pro Leu Leu His Ala Ser Leu
        275                 280                 285

Pro Ser Ala Gly Ala Gly Phe Tyr Gly Asn Cys Tyr Tyr Ile Met Arg
    290                 295                 300

Val Ser Ala Pro Ala Gly Lys Val Ser Gly Ser Val Pro Glu Val
305                 310                 315                 320

Val Lys Ile Ile Lys Asp Gly Lys Arg Arg Met Pro Ala Glu Phe Ala
                325                 330                 335

Arg Trp Ala Ser Gly Glu Ala Gly Ala Gly Glu Asp Pro Tyr Arg
            340                 345                 350

Ile Thr Ser Asp Tyr Arg Thr Leu Leu Val Ser Asp Trp Thr Arg Leu
        355                 360                 365

Gly Phe Ala Glu Val Asp Tyr Gly Trp Gly Pro Pro Ala His Val Val
    370                 375                 380

Pro Leu Thr
385

<210> SEQ ID NO 26
<211> LENGTH: 366
<212> TYPE: PRT
<213> ORGANISM: Brachypodium distachyon

<400> SEQUENCE: 26

Ser Val Ser Arg Leu Ala Gln Arg Leu Val Leu Pro Ala Glu Pro Thr
1               5                   10                  15

Pro Ser Gly Pro Leu Arg Leu Ser Trp Leu Asp Arg Tyr Pro Thr Gln
            20                  25                  30

Met Ala Leu Ile Glu Ser Leu His Val Phe Lys Pro Ala Pro Ala Arg
        35                  40                  45

His Ala Asp Ala Cys Pro Gly Pro Ala Arg Thr Ile Glu Arg Ala Leu
    50                  55                  60

Ala Gln Ala Leu Val Arg Tyr Tyr Pro Leu Ala Gly Arg Leu Ala Phe
65                  70                  75                  80

Thr Asp Asp Gly Gly Gln Ser His Val Asp Cys Gly Gly Pro Arg Ser
                85                  90                  95

Gly Val Trp Phe Thr Glu Ala Glu Ala Ala Cys Gly Leu Glu Asp Val
            100                 105                 110

Asp Tyr Leu Glu His Pro Met Met Ile Ser Lys Asp Glu Leu Leu Pro
        115                 120                 125

Pro Thr Pro Ala Ala Glu Glu Gly Asp Glu Arg Arg Leu Val Leu Leu
    130                 135                 140
```

```
Val Gln Val Thr Ser Phe Ala Cys Gly Gly Phe Val Val Gly Phe Arg
145                 150                 155                 160

Phe Ser His Ala Val Ala Asp Gly Pro Gly Ala Gln Phe Met Ala
            165                 170                 175

Ala Val Gly Asp Leu Ala Arg Gly Ala Glu Ser Leu Ser Met Glu Pro
            180                 185                 190

Gln Trp Gly Arg Asp Ala Val Pro Asp Pro Ala Gly Ala Val Val Gly
            195                 200                 205

Ala Leu Pro Asp Pro Ala Gly Ala Lys Arg Leu Glu Tyr Leu Ala Met
            210                 215                 220

Asp Ile Ser Ala Asp Tyr Ile Asp His Phe Lys Ala Gln Tyr Asn Ser
225                 230                 235                 240

Thr Asn Asn Gly Gly Ala Arg Cys Ser Ala Phe Glu Val Leu Val Ala
                245                 250                 255

Lys Ala Trp Gln Ser Arg Thr Arg Ala Ala Gly Phe Asp Pro Ser Thr
            260                 265                 270

Thr Val His Leu Cys Phe Ala Met Asn Ala Arg Pro Leu Leu His Ala
            275                 280                 285

Ser Leu Pro Ser Ala Gly Ser Val Pro Glu Val Val Lys Ile Ile Lys
            290                 295                 300

Asp Gly Lys Arg Arg Met Pro Ala Glu Phe Ala Arg Trp Ala Ser Gly
305                 310                 315                 320

Glu Ala Gly Ala Gly Gly Glu Asp Pro Tyr Arg Ile Thr Ser Asp Tyr
                325                 330                 335

Arg Thr Leu Leu Val Ser Asp Trp Thr Arg Leu Gly Phe Ala Glu Val
            340                 345                 350

Asp Tyr Gly Trp Gly Pro Pro Ala His Val Val Pro Leu Thr
            355                 360                 365

<210> SEQ ID NO 27
<211> LENGTH: 390
<212> TYPE: PRT
<213> ORGANISM: Sorghum bicolor

<400> SEQUENCE: 27

Pro Ala Arg Leu Val Val Pro Ala Glu Pro Thr Pro Ala Gly Pro Leu
1               5                   10                  15

His Leu Ser Trp Leu Asp Arg Tyr Pro Thr Gln Met Ala Leu Ile Glu
            20                  25                  30

Ser Leu His Val Phe Lys Ala Ala Pro Ala Thr Ala Thr Gly Gly Ile
            35                  40                  45

Asp Gly Gly Ala Ala Ser Pro Ala Arg Thr Ile Glu Arg Ala Leu
50                  55                  60

Ala Arg Ala Leu Val His Tyr Tyr Pro Leu Ala Gly Arg Leu Val Leu
65                  70                  75                  80

Ser Glu Ser Gly Ala Gln Gln Ala Val Asp Cys Ser Asn Ala Gly Val
            85                  90                  95

Trp Phe Thr Glu Ala Glu Ala Ala Cys Thr Leu Glu Asp Val Asp Tyr
            100                 105                 110

Leu Glu Ala Pro Leu Met Ile Pro Lys Asp Asp Leu Leu Pro Pro Thr
            115                 120                 125

Pro Ala Ala Gly Asp Glu Glu Asp Glu Arg Ala Leu Val Leu Leu Val
            130                 135                 140

Gln Val Thr Ser Phe Ala Cys Gly Gly Phe Val Val Gly Phe Arg Phe
145                 150                 155                 160
```

```
Ser His Ala Val Ala Asp Gly Pro Gly Ala Ala Gln Phe Met Asn Ala
                165                 170                 175

Val Gly Glu Leu Ala Arg Gly Ala Glu Asn Ala Leu Ser Val Val Pro
            180                 185                 190

Gln Trp Gly Arg Asp Ala Ile Pro Asp Pro Ala Ala Leu Val Gly
        195                 200                 205

Arg Leu Pro Thr Pro Asp Ala Asp Ser Lys Arg Leu Glu Tyr Leu Ala
    210                 215                 220

Ile Asp Ile Ser Ala Asp Tyr Ile Asn His Phe Lys Ala Gln Tyr Ser
225                 230                 235                 240

Ala Ala His Ala Gly Ala Ala Trp Cys Ser Ala Phe Glu Val Leu Ile
                245                 250                 255

Ala Lys Ala Trp Gln Ser Arg Thr Arg Ala Ala Gly Phe Asp Pro Asp
            260                 265                 270

Ser Pro Val His Leu Cys Phe Ala Met Asn Ala Arg Pro Met Leu His
        275                 280                 285

Ala Ser Leu Pro Arg Gly Gly Ala Gly Phe Tyr Gly Asn Cys Tyr Tyr
    290                 295                 300

Ile Met Arg Val Ser Ala Pro Ala Gly Lys Val Ala Gly Ser Ser Val
305                 310                 315                 320

Thr Glu Val Val Lys Ile Ile Lys Asp Gly Lys Arg Met Pro Ala
                325                 330                 335

Glu Phe Ala Arg Trp Ala Ala Gly Glu Val Gly Ala Ala Gly Val Asp
            340                 345                 350

Pro Tyr Gln Ile Thr Ser Asp Tyr Arg Thr Leu Leu Val Ser Asp Trp
        355                 360                 365

Thr Arg Leu Gly Phe Ala Glu Val Asp Tyr Gly Trp Gly Pro Pro Ala
    370                 375                 380

His Val Val Pro Leu Thr
385                 390

<210> SEQ ID NO 28
<211> LENGTH: 389
<212> TYPE: PRT
<213> ORGANISM: Oryza sativa

<400> SEQUENCE: 28

Ser Val Glu Arg Leu Gly Gln Arg Arg Val Val Pro Ala Glu Pro Thr
1               5                   10                  15

Pro Ala Gly Pro Leu Arg Leu Ser Trp Leu Asp Arg Tyr Pro Thr Gln
            20                  25                  30

Met Ala Leu Ile Glu Ser Leu His Val Phe Lys Pro Ala Leu Asp Arg
        35                  40                  45

Ala Ile Gly Gly Asp Asp Val Ala Val Gly Pro Ala Arg Thr Ile Glu
    50                  55                  60

Arg Ala Leu Ala Arg Ala Leu Val His Tyr Tyr Pro Leu Ala Gly Arg
65                  70                  75                  80

Leu Ala Phe Ser Asp Ser Gly Glu Val Cys Val Asp Cys Gly Asp Ala
                85                  90                  95

Gly Val Trp Phe Thr Glu Ala Glu Ala Ser Cys Ser Leu Glu Asp Val
            100                 105                 110

Asp Tyr Leu Glu Tyr Pro Met Met Val Pro Lys Asp Glu Leu Leu Pro
        115                 120                 125

Pro Thr Pro Ala Gly Glu Glu Glu Arg Glu Leu Val Leu Leu Val Gln
```

```
                130             135             140
Val Thr Ala Phe Ala Cys Gly Gly Phe Val Val Gly Phe Arg Phe Ser
145                 150                 155                 160

His Ala Val Ala Asp Gly Pro Gly Ala Ala Gln Phe Met Ala Ala Val
                165                 170                 175

Gly Glu Leu Ala Arg Gly Ala Gly Val Ser Val Asp Pro Val Trp
                180                 185                 190

Gly Arg Asp Ala Ile Pro Asp Pro Ala Ala Val Ile Gly Ser Leu
                195                 200                 205

Pro Asp Pro Ala Gly Ala Lys Arg Leu Glu Tyr Leu Ala Val Asp Ile
210                 215                 220

Ser Ala Asp Tyr Ile Asn His Phe Lys Asn Gln Tyr Asn Ala Glu Ala
225                 230                 235                 240

His Ala Ala Ala Ala Gly Val Ala Arg Cys Ser Ala Phe Glu Val Leu
                245                 250                 255

Ile Ala Lys Ala Trp Arg Ser Arg Thr Arg Ala Ala Gly Phe Glu Pro
                260                 265                 270

Asp Thr Thr Val Asn Leu Cys Phe Ala Met Asn Ala Arg Pro Leu Leu
                275                 280                 285

His Ala Ser Leu Pro Arg Gly Gly Ala Gly Phe Tyr Gly Asn Cys Tyr
                290                 295                 300

Tyr Ile Met Arg Val Ser Ala Pro Ala Gly Lys Val Ala Gly Ser Ser
305                 310                 315                 320

Val Thr Glu Val Val Lys Ile Ile Lys Asp Gly Lys Arg Arg Met Pro
                325                 330                 335

Ser Glu Phe Ser Arg Trp Ala Ala Gly Asp Met Ala Gly Gly Asp Pro
                340                 345                 350

Tyr Gln Ile Thr Ser Asp Tyr Arg Thr Leu Leu Val Ser Asp Trp Thr
                355                 360                 365

Arg Leu Gly Phe Ala Glu Val Asp Tyr Gly Trp Gly Pro Pro Ala His
                370                 375                 380

Val Val Pro Leu Thr
385

<210> SEQ ID NO 29
<211> LENGTH: 402
<212> TYPE: PRT
<213> ORGANISM: Sorghum bicolor

<400> SEQUENCE: 29

Thr Val Thr Arg Leu Ala Gln Arg Val Val Ala Pro Ser Ala Pro Thr
1               5                   10                  15

Pro Arg Gly Gln Leu Pro Leu Ser Trp Leu Asp Arg Tyr Pro Thr Gln
                20                  25                  30

Arg Ala Leu Ile Glu Ser Leu His Val Phe Lys Gly Arg Ala Asp Ala
            35                  40                  45

Glu Ala Pro Ala Arg Ala Ile Glu Arg Ala Leu Ala Gly Ala Leu Val
        50                  55                  60

Ser Tyr Tyr Pro Ile Ala Gly Arg Leu Ala Val Ser Ala Asp Glu Gly
65                  70                  75                  80

Gln Leu Val Val Asp Cys Thr Gly Glu Gly Val Trp Phe Ile Glu Ala
                85                  90                  95

Ser Ala Ser Cys Thr Leu Glu Asp Val Asp Tyr Leu Glu Tyr Pro Leu
                100                 105                 110
```

```
Met Val Pro Lys Asp Glu Leu Leu Pro His Pro Thr Tyr Pro Pro Glu
            115                 120                 125

Ser Asp Pro Leu Pro Glu Asp Ser Leu Ile Leu Leu Val Gln Val Thr
        130                 135                 140

Gln Phe Ala Cys Gly Gly Phe Val Val Gly Phe Arg Phe Ser His Ala
145                 150                 155                 160

Val Ala Asp Gly Pro Gly Ala Ala Gln Phe Met Thr Ala Val Gly Asp
                165                 170                 175

Met Ala Arg Gly His Ala Ala Pro Leu Val Ala Pro Ala Trp Gly Arg
            180                 185                 190

Glu Ala Ile Pro Asn Pro Pro Gly Ala Ala Val Gly Ala Leu Pro Val
        195                 200                 205

Pro Thr Glu Leu Arg Leu Gln Tyr Leu Ala Met Asp Ile Ser Thr Asp
210                 215                 220

Tyr Ile Glu His Phe Lys Ser Arg Phe Leu Glu Gln Thr Gly Gly Gln
225                 230                 235                 240

Gln Arg Cys Ser Ala Phe Glu Val Leu Ile Ala Lys Ala Trp Gln Ser
                245                 250                 255

Arg Thr Arg Ala Ala Arg Phe Glu Pro Gly Ser Pro Val His Val Cys
            260                 265                 270

Phe Ala Met Asn Ala Arg Pro Ala Leu Ala Arg Leu Gly Asp Gly Lys
        275                 280                 285

Pro Pro Ala Pro Leu Pro Gly Gly Phe Tyr Gly Asn Cys Tyr Tyr Ile
290                 295                 300

Met Arg Val Ser Ala Ala Ala Glu Ala Val Ala Asp Ala Ser Val Tyr
305                 310                 315                 320

Asp Val Val Arg Leu Ile Arg Glu Gly Lys Lys Arg Leu Pro Ala Glu
                325                 330                 335

Phe Ala Arg Trp Ser Ala Gly Asp Thr Gly Val Asp Pro Tyr Arg
            340                 345                 350

Ile Thr Ser Asp Tyr Arg Thr Leu Leu Val Ser Asp Trp Ser Arg Leu
        355                 360                 365

Gly Phe Ala Glu Val Asp Tyr Gly Trp Gly Cys Pro Val His Val Val
370                 375                 380

Pro Leu Thr Asn Leu Asp Tyr Ile Ala Thr Cys Ile Leu Val Arg Pro
385                 390                 395                 400

Ser Ala

<210> SEQ ID NO 30
<211> LENGTH: 392
<212> TYPE: PRT
<213> ORGANISM: Oryza sativa

<400> SEQUENCE: 30

Thr Val Thr Arg Val Ala Gln Arg Val Val Ala Pro Ser Ala Ala Thr
1               5                   10                  15

Pro Gly Gly Ala Leu Pro Leu Ser Trp Leu Asp Arg Tyr Pro Thr Gln
            20                  25                  30

Arg Ala Leu Ile Glu Ser Leu His Val Phe Lys Gly Arg Ala Asp Ala
        35                  40                  45

Ala Val Ala Pro Ala Ala Ile Glu Arg Ala Leu Ala Ala Ala Leu
    50                  55                  60

Val Ser Tyr Tyr Pro Ile Ala Gly Arg Leu Ala Glu Arg Gly Asp Gly
65                  70                  75                  80
```

```
Gly Glu Leu Val Val Asp Cys Thr Gly Glu Gly Val Trp Phe Ile Glu
                85                  90                  95
Ala Thr Ala Ser Cys Ser Leu Glu Asp Val Asp Tyr Leu Glu Tyr Pro
            100                 105                 110
Leu Met Val Asp Lys Asp Glu Leu Leu Pro His Pro Thr Tyr Pro Ala
        115                 120                 125
Ser Glu Ser His Pro Glu Asp Ser Leu Ile Leu Leu Val Gln Val Thr
    130                 135                 140
Gln Phe Ala Cys Gly Gly Phe Val Val Gly Phe Arg Phe Ser His Ala
145                 150                 155                 160
Val Ala Asp Gly Pro Gly Ala Ala Gln Phe Met Thr Ala Val Gly Glu
                165                 170                 175
Ile Ala Arg Gly Arg Ala Ala Pro Ala Leu Ala Pro Ala Trp Gly Arg
            180                 185                 190
Asp Ala Ile Pro Cys Pro Pro Ser Ala Ala Val Gly Pro Leu Pro Val
        195                 200                 205
Pro Thr Glu Leu Arg Leu Gln Tyr Leu Ala Met Asp Ile Ser Thr Asp
    210                 215                 220
Tyr Ile Asp His Phe Lys Ala Arg Phe Leu Glu Gln Thr Gly His Arg
225                 230                 235                 240
Cys Ser Ala Phe Glu Val Leu Ile Ala Lys Ala Trp Gln Ser Arg Thr
                245                 250                 255
Arg Ala Ala Gly Phe Ala Pro Gly Ser Pro Val His Val Cys Phe Ala
            260                 265                 270
Met Asn Ala Arg Pro Val Leu Arg Arg Ala Leu Pro Asp Gly Phe Tyr
        275                 280                 285
Gly Asn Cys Tyr Tyr Ile Met Arg Val Thr Ala Ala Ala Gly Ala Val
    290                 295                 300
Ala Asp Ala Ser Val Asn Asp Val Val Arg Leu Ile Arg Glu Gly Lys
305                 310                 315                 320
Lys Arg Leu Pro Gly Glu Phe Ala Arg Trp Ser Gly Gly Gly Gly Gly
                325                 330                 335
Gly Val Asp Pro Tyr Arg Ile Thr Ser Asp Tyr Arg Thr Leu Leu Val
            340                 345                 350
Ser Asp Trp Ser Arg Leu Gly Phe Ala Glu Val Asp Tyr Gly Trp Gly
        355                 360                 365
Cys Pro Val His Val Pro Leu Thr Asn Leu Asp Tyr Ile Ala Thr
    370                 375                 380
Cys Ile Leu Val Arg Pro Ser Ala
385                 390

<210> SEQ ID NO 31
<211> LENGTH: 170
<212> TYPE: PRT
<213> ORGANISM: Brachypodium distachyon

<400> SEQUENCE: 31

Val Met Gln Phe Ala Cys Gly Gly Phe Val Val Gly Phe Arg Phe Ser
1               5                   10                  15
His Ala Val Ala Asp Gly Pro Gly Ala Ala Gln Phe Thr Thr Ala Ala
            20                  25                  30
Gly Glu Ile Ala Pro Gly Arg Ala Gly Pro Ser Val Lys Ala Ala Trp
        35                  40                  45
Gly Arg Glu Ala Ile Pro Thr Glu Leu Arg Leu Gln Tyr Leu Ala Met
    50                  55                  60
```

Asp Ile Ser Thr Asp Tyr Ile Glu His Phe Lys Ala Arg Phe Leu Glu
65                  70                  75                  80

His Ala Gly Pro Lys Cys Ser Ala Phe Glu Val Leu Ile Ala Lys Ala
            85                  90                  95

Trp Gln Ala Arg Thr Arg Ala Ala Arg Phe Ala Cys Gly Thr Pro Val
        100                 105                 110

His Val Cys Phe Ala Met Asn Ala Arg Ser Ala Leu Pro Thr Ser Pro
    115                 120                 125

Arg Ala Ile Pro Asp Gly Phe Tyr Gly Tyr Cys Tyr Tyr Ile Met Arg
130                 135                 140

Val Ser Ala Pro Ala Glu Ala Val Ser Asp Ala Pro Leu His Asp Val
145                 150                 155                 160

Val Arg Leu Ile His Asp Gly Lys Lys Arg
            165                 170

<210> SEQ ID NO 32
<211> LENGTH: 393
<212> TYPE: PRT
<213> ORGANISM: Brachypodium distachyon

<400> SEQUENCE: 32

Thr Val Thr Arg Val Ala Gln Arg Val Ala Pro Ser Ala Pro Thr
1               5                   10                  15

Pro Gly Gly Glu Leu Pro Leu Ser Trp Leu Asp Arg Tyr Pro Thr Gln
            20                  25                  30

Arg Ala Leu Ile Glu Ser Leu His Val Phe Lys Gly Arg Ala Gly Ala
        35                  40                  45

Thr Glu Gly Pro Val Lys Ala Ile Glu Arg Ala Leu Ala Ala Ala Leu
    50                  55                  60

Val Ser Tyr Tyr Pro Leu Ala Gly Arg Leu Ala Val Pro Ala Asp Gly
65                  70                  75                  80

Gly Glu Leu Val Val Asp Cys Thr Gly Glu Gly Val Trp Phe Leu Glu
            85                  90                  95

Ala Ala Ala Gly Cys Thr Leu Glu Asp Val Asp Tyr Leu Glu Tyr Pro
        100                 105                 110

Leu Met Met Pro Lys Asp Glu Leu Leu Pro His Pro Thr Tyr Pro Ala
    115                 120                 125

Ala Asp Pro Leu Pro Glu Asp Ser Phe Ile Leu Leu Val Gln Val Thr
130                 135                 140

Gln Phe Ala Cys Gly Gly Phe Val Val Gly Phe Arg Phe Ser His Ala
145                 150                 155                 160

Val Ala Asp Gly Pro Gly Ala Ala Gln Phe Met Thr Ala Val Gly Glu
            165                 170                 175

Ile Ala Arg Gly Arg Ala Gly Pro Ser Val Lys Pro Ala Trp Gly Arg
        180                 185                 190

Glu Ala Ile Pro Ser Pro Ala Ala Pro Val Gly Pro Leu Pro
    195                 200                 205

Val Pro Thr Glu Leu Arg Leu Gln Tyr Leu Ala Met Asp Ile Ser Thr
210                 215                 220

Asp Tyr Ile Glu His Phe Lys Ala Arg Phe Leu Glu Gln Ala Gly His
225                 230                 235                 240

Arg Cys Ser Ala Phe Glu Val Leu Ile Ala Lys Ala Trp Gln Ala Arg
            245                 250                 255

Thr Arg Ala Ala Arg Phe Ala Pro Gly Thr Pro Val His Val Cys Phe

```
            260                 265                 270
Ala Met Asn Ala Arg Ser Ala Leu Pro Gln Pro Arg Ala Val Pro Asp
            275                 280                 285

Gly Phe Tyr Gly Asn Cys Tyr Tyr Ile Met Arg Val Ser Ala Pro Ala
        290                 295                 300

Glu Ala Val Ser Asp Ala Pro Leu His Glu Val Val Arg Leu Ile Arg
305                 310                 315                 320

Glu Gly Lys Lys Arg Leu Pro Ser Glu Phe Ala Arg Trp Ser Arg Gly
                325                 330                 335

Glu Met Asn Gly Asp Pro Tyr Arg Ile Thr Ser Asp Cys Arg Thr Leu
            340                 345                 350

Leu Val Ser Asp Trp Ser Arg Leu Gly Phe Ala Glu Val Asp Tyr Gly
        355                 360                 365

Trp Gly Ala Pro Val His Val Val Pro Leu Thr Asn Leu Asp Tyr Ile
    370                 375                 380

Ala Thr Cys Ile Leu Val Arg Pro Ser
385                 390

<210> SEQ ID NO 33
<211> LENGTH: 422
<212> TYPE: PRT
<213> ORGANISM: Sorghum bicolor

<400> SEQUENCE: 33

Ala Ala Ala Glu Thr Thr Ala His Ile Ile Asn Leu Ser Ser Phe Asp
1               5                   10                  15

Lys Ala Leu Ala Phe Phe Pro Val Thr Ser Phe His Ile Phe Asp His
                20                  25                  30

Ala Ile His Arg Pro Ala Glu Thr Val Arg Ser Ala Leu Ser Arg Ala
            35                  40                  45

Leu Val His Tyr Tyr Pro Val Ala Gly Arg Ala Val Glu Asp Ser Ser
        50                  55                  60

Gly Asp Leu Arg Ile Ala Cys Thr Gly Glu Gly Val Gly Phe Val Ala
65                  70                  75                  80

Ala Ser Ala Asn Cys Ser Leu Ala Asp Val Lys Leu Phe Asp Pro Pro
                85                  90                  95

Phe Gly Ala Leu Leu Lys Glu Leu Ala Val Gly Leu Gly Ala Glu Gly
            100                 105                 110

Phe Arg Pro Ser Asp Pro Leu Leu Leu Val Gln Val Thr Glu Phe Ser
        115                 120                 125

Cys Gly Gly Phe Val Val Gly Val Thr Arg Asn His Val Val Ala Asp
130                 135                 140

Gly Thr Gly Phe Ala Gln Phe Leu Gln Ala Val Gly Glu Leu Ala Arg
145                 150                 155                 160

Gly Leu Pro Arg Pro Ala Val Phe Pro Val Ser Cys Gly Asp Ser
                165                 170                 175

Leu Pro Glu Leu Pro Pro Phe Val Asp Ala Met Glu Lys Ala Gln Val
            180                 185                 190

Thr Leu Glu Pro Arg Asp Phe Ala Tyr Leu Asp Ile Thr Val Pro Ser
        195                 200                 205

Arg Cys Ile Asn Arg Ile Lys Ala Gly Phe Ala Arg His Ala Ala Ala
    210                 215                 220

Ala Ala Glu Ser Gly Gly Pro Cys Thr Val Phe Glu Ala Val Met Ala
225                 230                 235                 240
```

Val Leu Trp Gln Cys Arg Thr Arg Ala Ile Met Ser Asp Pro Asp Thr
            245                 250                 255

Pro Ala Pro Leu Ile Phe Ala Ala Asn Val Arg Lys His Ala Gly Ala
        260                 265                 270

Lys Arg Gly Tyr Tyr Gly Asn Cys Ile Thr Ser Ala Val Val Pro
    275                 280                 285

Thr Ser Gly Glu Val Ala Asn Gly Asp Ile Asn Asp Val Leu Arg Leu
290                 295                 300

Ile Lys Arg Ala Lys Gln Pro Ile Pro Tyr Gln Phe Trp Lys Asn Asn
305                 310                 315                 320

Ser Ala Asp Asp Ala Gly Asp Glu Glu Gly Arg His Val
            325                 330                 335

Lys Glu Pro Arg Pro Glu Gly Gly Leu Ser Leu Ser Met Glu Gln Leu
            340                 345                 350

Asp Val Thr Leu Gly Tyr Asn Ala Phe Asp Val Thr Ser Trp Arg Asn
            355                 360                 365

Leu Gly Ala Asp Ala Val Asp Phe Gly Gly Arg Pro Ala Arg Val
370                 375                 380

Met Cys Trp Leu Asp Arg Met Ala Val Pro His Cys Val Ala Cys Leu
385                 390                 395                 400

Pro Cys Asn Lys Asp Gly Asn Val Leu Ala Arg Cys Val Arg Glu
            405                 410                 415

Glu His Val Asp Ala Phe
            420

<210> SEQ ID NO 34
<211> LENGTH: 374
<212> TYPE: PRT
<213> ORGANISM: Brachypodium distachyon

<400> SEQUENCE: 34

Pro Ala Leu Val Pro Val Gly Pro Thr Pro Arg Gly Ala Leu Pro
1               5                   10                  15

Leu Ser Ser Ile Asp Lys Thr Ala Ala Val Arg Val Ser Val Asp Phe
            20                  25                  30

Ile Gln Val Phe Pro Pro Ser Thr Asp Gly Ala Ser Ala Gly Asp Gln
        35                  40                  45

Val Ala Ala Met Arg Asp Gly Phe Ala Arg Ala Leu Val Pro Tyr Tyr
    50                  55                  60

Pro Val Ala Gly Arg Ile Ala Glu Pro Thr Pro Gly Asp Leu Val Val
65                  70                  75                  80

Asp Cys Thr Gly Glu Gly Val Trp Phe Val Glu Ala Ala Ser Cys
            85                  90                  95

Ser Leu Ala Asp Val Asn Gly Leu Glu Arg Pro Leu Leu Ile Pro Lys
            100                 105                 110

Gly Glu Leu Ile Pro Arg Pro Pro Glu Glu Lys Leu Glu Asp Leu
        115                 120                 125

Ile Leu Met Ala Gln Val Thr Lys Phe Thr Cys Gly Gly Phe Ala Val
    130                 135                 140

Gly Ile Cys Phe Ser His Leu Val Phe Asp Gly Gln Gly Ala Ala Gln
145                 150                 155                 160

Phe Leu Lys Ala Ala Gly Glu Leu Ala Arg Gly Leu Pro Ala Pro Ser
            165                 170                 175

Val Ala Pro Val Trp Asp Arg Asp Ala Ile Pro Asp Pro Pro Lys Leu
            180                 185                 190

Pro Arg Gly Pro Pro Ser Phe Thr Ala Phe Asn Phe Val Thr Gln
            195                 200                 205

Val Val Glu Ile Ser Pro Glu Asn Ile Ala Arg Ile Lys Glu Asp Phe
210                 215                 220

Lys Ala Ala Thr Gly Gly Glu Thr Cys Ser Thr Phe Asp Ala Val Thr
225                 230                 235                 240

Ala Val Val Phe Lys Cys Arg Ala Leu Ala Val Glu Leu Pro Asp Thr
            245                 250                 255

Ala Glu Val Arg Leu Gly Phe Ala Ala Ser Thr Arg His Leu Leu Gln
            260                 265                 270

Gly Val Leu Pro Ser Val Asp Gly Tyr Tyr Gly Asn Cys Val Tyr Pro
            275                 280                 285

Val Gly Ile Thr Arg Ser Ser Lys Thr Ile Arg Glu Ala Ala Leu Thr
            290                 295                 300

Glu Val Val Gly Val Met Arg Glu Ala Lys Glu Ala Leu Thr Val Arg
305                 310                 315                 320

Phe Thr Asp Trp Met Arg Gly Ala Lys Asp Asp His Tyr Asn Val
            325                 330                 335

Pro Leu Asp Tyr Gly Thr Val Thr Val Ser Asp Trp Ser Arg Val Gly
            340                 345                 350

Phe Asn Glu Val Asp Tyr Gly Phe Gly Glu Pro Gly Tyr Val Phe Thr
            355                 360                 365

Leu Asn Asp Asp Val Asn
            370

<210> SEQ ID NO 35
<211> LENGTH: 445
<212> TYPE: PRT
<213> ORGANISM: Brachypodium distachyon

<400> SEQUENCE: 35

Thr Val Asn Arg Lys Ser Gln Ser Phe Val Lys Pro Ala Ala Pro Thr
1               5                   10                  15

Pro Thr Pro Gln Thr Pro Pro Leu Leu Glu Leu Ser Ala Ile Asp
            20                  25                  30

Arg Val Pro Gly Leu Arg His Thr Val Arg Ser Leu His Val Phe Arg
            35                  40                  45

Pro Pro Pro His Gly Asp Gly Ala Ala Cys Ser Arg Pro Ala Glu Val
            50                  55                  60

Ile Arg Ala Ala Leu Ala Arg Ala Leu Val Glu Tyr Pro Ala Phe Ala
65                  70                  75                  80

Gly Arg Leu Val Val Gly Gly Ser Gly Ser Asp Cys Gly Val Ala Cys
            85                  90                  95

Thr Gly Asp Gly Ala Trp Phe Val Glu Ala Ala Ala Gly Cys Asn Leu
            100                 105                 110

Glu Asp Val Asn Glu Leu Asp Tyr Pro Leu Val Val Cys Glu Glu Glu
            115                 120                 125

Leu Leu Pro Thr Ala Pro Glu Gly Glu Leu Asp Pro Thr Ser Ile Pro
            130                 135                 140

Val Met Met Gln Leu Met Ser Glu Met Thr Leu Trp His Lys Thr Val
145                 150                 155                 160

Thr Glu Phe Ser Cys Gly Gly Phe Val Val Gly Leu Val Ala Val His
            165                 170                 175

Thr Phe Ala Asp Gly Leu Gly Ala Ala Gln Phe Ile Asn Ala Ile Ala

```
            180                 185                 190
Glu Phe Ala Arg Gly Leu Asn Arg Pro Thr Val Asn Pro Ile Trp Ala
        195                 200                 205
Arg Ala Thr Ile Pro Asn Pro Pro Lys Phe Pro Pro Gly Pro Pro Pro
    210                 215                 220
Ser Phe Gln Ser Phe Gly Phe Gln His Phe Ala Thr Asp Ile Arg Pro
225                 230                 235                 240
Asp Arg Ile Ala His Ala Lys Ala Glu Tyr Leu Lys Ala Thr Gly Thr
                245                 250                 255
His Cys Ser Ala Phe Asp Val Ala Val Ala Lys Val Trp Gln Ala Arg
            260                 265                 270
Thr Arg Ala Val Arg Tyr Gly Pro Glu Ala Gln Val Gln Val Cys Phe
        275                 280                 285
Phe Ala Asn Thr Arg His Leu Leu Gly Glu Leu Pro Glu Gly Phe
    290                 295                 300
Tyr Gly Asn Cys Phe Phe Pro Val Thr Val Lys Ala Arg Ala Gly Asp
305                 310                 315                 320
Val Ala Gly Ser Lys Asp Leu Leu Gly Ile Ile Arg Met Ile Arg Asp
                325                 330                 335
Gly Lys Ala Arg Leu Pro Leu Glu Phe Ala Asp Trp Ala Ser Gly Leu
            340                 345                 350
Gly Gly Gly Gly Ala Gly Asp Lys Met Lys Phe Val Gln Asp Pro
        355                 360                 365
Tyr Glu Leu Arg Phe Glu His Asn Val Leu Phe Val Ser Asp Trp Thr
    370                 375                 380
Arg Leu Gly Phe Leu Glu Val Asp Tyr Gly Trp Gly Val Pro Ser His
385                 390                 395                 400
Val Ile Pro Phe Asn Tyr Ala Asp Tyr Met Ala Val Ala Val Leu Gly
                405                 410                 415
Ala Pro Pro Ala Pro Val Lys Gly Thr Arg Val Met Thr Gln Cys Val
            420                 425                 430
Glu Glu Lys His Leu Lys Glu Phe Arg Asp Glu Met Glu
        435                 440                 445

<210> SEQ ID NO 36
<211> LENGTH: 425
<212> TYPE: PRT
<213> ORGANISM: Oryza sativa

<400> SEQUENCE: 36

Thr Val Met Arg Lys Ser Arg Asn Phe Val Gly Pro Ser Pro Pro Thr
1               5                   10                  15
Pro Pro Ala Glu Ile Thr Thr Thr Leu Glu Leu Ser Ser Ile Asp Arg
            20                  25                  30
Val Pro Gly Leu Arg His Asn Val Arg Ser Leu His Val Phe Arg Arg
        35                  40                  45
His Lys Asn Ser Gly Pro Val Val Asp Gly Asp Ser Arg Arg Pro Ala
    50                  55                  60
Ala Val Ile Arg Ala Ala Leu Ala Arg Ala Leu Ala Asp Tyr Pro Ala
65                  70                  75                  80
Phe Ala Gly Arg Phe Val Gly Ser Leu Leu Ala Gly Asp Ala Cys Val
                85                  90                  95
Ala Cys Thr Gly Glu Gly Ala Trp Phe Val Glu Ala Ala Ala Asp Cys
            100                 105                 110
```

```
Ser Leu Asp Asp Val Asn Gly Leu Glu Tyr Pro Leu Met Ile Ser Glu
            115                 120                 125

Glu Glu Leu Leu Pro Ala Pro Glu Asp Gly Val Asp Pro Thr Ser Ile
        130                 135                 140

Pro Val Met Met Gln Val Thr Glu Phe Thr Cys Gly Gly Phe Ile Leu
145                 150                 155                 160

Gly Leu Val Ala Val His Thr Leu Ala Asp Gly Leu Gly Ala Ala Gln
                165                 170                 175

Phe Ile Thr Ala Val Ala Glu Leu Ala Arg Gly Met Asp Lys Leu Arg
            180                 185                 190

Val Ala Pro Val Trp Asp Arg Ser Leu Ile Pro Asn Pro Pro Lys Leu
        195                 200                 205

Pro Pro Gly Pro Pro Ser Phe Gln Ser Phe Gly Phe Gln His Phe
210                 215                 220

Ser Thr Asp Val Thr Ser Asp Arg Ile Ala His Val Lys Ala Glu Tyr
225                 230                 235                 240

Phe Gln Thr Phe Gly Gln Tyr Cys Ser Thr Phe Asp Val Ala Thr Ala
                245                 250                 255

Lys Val Trp Gln Ala Arg Thr Arg Ala Val Gly Tyr Lys Pro Glu Ile
            260                 265                 270

Gln Val His Val Cys Phe Phe Ala Asn Thr Arg His Leu Leu Thr Gln
        275                 280                 285

Val Leu Pro Lys Asp Gly Gly Tyr Tyr Gly Asn Cys Phe Tyr Pro Val
        290                 295                 300

Thr Val Thr Ala Ile Ala Glu Asp Val Ala Thr Lys Glu Leu Leu Asp
305                 310                 315                 320

Val Ile Lys Ile Ile Arg Asp Gly Lys Ala Arg Leu Pro Met Glu Phe
                325                 330                 335

Ala Lys Trp Ala Ser Gly Asp Val Lys Val Asp Pro Tyr Ala Leu Thr
            340                 345                 350

Phe Glu His Asn Val Leu Phe Val Ser Asp Trp Thr Arg Leu Gly Phe
        355                 360                 365

Phe Glu Val Asp Tyr Gly Trp Gly Thr Pro Asn His Ile Ile Pro Phe
    370                 375                 380

Thr Tyr Ala Asp Tyr Met Ala Val Ala Val Leu Gly Ala Pro Pro Met
385                 390                 395                 400

Pro Lys Lys Gly Thr Arg Ile Met Thr Gln Cys Val Glu Asn Lys Cys
                405                 410                 415

Ile Lys Glu Phe Gln Asp Glu Met Lys
            420                 425

<210> SEQ ID NO 37
<211> LENGTH: 432
<212> TYPE: PRT
<213> ORGANISM: Sorghum bicolor

<400> SEQUENCE: 37

Thr Val Thr Arg Lys Ser Gln Ser Phe Val Val Pro Ser Ser Ser Ser
1               5                   10                  15

Ala Pro Val Pro Thr Thr Ala Glu Thr Leu Glu Leu Ser Ala Ile Asp
            20                  25                  30

Arg Val Pro Gly Leu Arg His Thr Val Arg Ser Leu His Val Phe Arg
        35                  40                  45

Arg Lys Ala Asp Asp Ala Ala Ala Ala Ala Ala Ser Arg
    50                  55                  60
```

```
Arg Pro Ala Glu Val Ile Arg Ala Ala Leu Ser Arg Ala Leu Val Asp
 65                  70                  75                  80

Tyr Arg Pro Phe Ala Gly Arg Phe Val Gly Ser Leu Tyr Ala Gly Glu
                 85                  90                  95

Ala Cys Val Glu Cys Thr Asp Glu Gly Ala Trp Phe Glu Ala Val
            100                 105                 110

Ala Asp Cys Ser Leu Asp Asp Val Asn Gly Leu Asp Asp Tyr Pro Leu
            115                 120                 125

Met Val Ser Glu Glu Leu Leu Pro Ala Pro Glu Glu Gly Val Asp
130                 135                 140

Pro Thr Ser Ile Pro Met Met Met Gln Val Thr Glu Phe Ser Cys Gly
145                 150                 155                 160

Gly Phe Val Val Gly Leu Val Ala Val His Thr Leu Ala Asp Gly Leu
                165                 170                 175

Gly Ala Ala Gln Phe Ile Asn Ala Ile Ser Glu Phe Ala Arg Gly Leu
                180                 185                 190

Asp Lys Leu Thr Ile Ala Pro Val Trp Ala Arg Ser Leu Ile Pro Asn
            195                 200                 205

Pro Pro Lys Leu Pro Pro Ala Pro Pro Pro Ser Phe Glu Ser Phe Gly
210                 215                 220

Phe Lys His Phe Val Met Asp Val Thr Phe Asp Asn Ile Ala His Val
225                 230                 235                 240

Lys Thr Glu Tyr Phe Gln Ala Asn Gly Gln Tyr Cys Ser Thr Phe Asp
                245                 250                 255

Val Ala Ile Ala Lys Val Trp Gln Ala Arg Thr Arg Ala Ile Lys Tyr
            260                 265                 270

Asn Pro Asp Val Lys Val His Val Cys Phe Ala Asn Thr Arg His
            275                 280                 285

Leu Leu Thr Arg Glu Leu Pro Asn Asp Gly Phe Tyr Gly Asn Cys
290                 295                 300

Phe Tyr Pro Val Thr Val Thr Ala Thr Ala Glu Gly Val Ala Ser Gly
305                 310                 315                 320

Gly Leu His Asp Val Ile Arg Met Ile Arg Asp Gly Lys Ala Arg Leu
            325                 330                 335

Pro Leu Glu Phe Ala Lys Trp Ser Met Gly Asp Val Lys Val Asp Pro
            340                 345                 350

Tyr Gln Leu Thr Phe Lys His Asn Val Leu Phe Val Ser Asp Trp Thr
            355                 360                 365

Arg Leu Gly Phe Phe Glu Val Asp Tyr Gly Trp Gly Val Pro Asn His
370                 375                 380

Ile Ile Pro Phe Thr Tyr Ala Asp Tyr Met Ala Val Ala Val Leu Gly
385                 390                 395                 400

Ala Pro Pro Thr Thr Val Lys Asn Lys Gly Thr Arg Ile Met Thr Gln
            405                 410                 415

Cys Val Glu Glu Lys His Leu Met Glu Phe Lys Asp Glu Met Lys Ala
            420                 425                 430

<210> SEQ ID NO 38
<211> LENGTH: 413
<212> TYPE: PRT
<213> ORGANISM: Musa sapientum

<400> SEQUENCE: 38

Ala Val Thr Arg Thr Ser Arg Ser Leu Val Thr Pro Cys Gly Val Thr
```

```
1               5                    10                   15
Pro Thr Gly Ser Leu Gly Leu Ser Ala Ile Asp Arg Val Pro Gly Leu
            20                   25                   30
Arg His Met Val Arg Ser Leu His Val Phe Arg Gln Gly Arg Glu Pro
            35                   40                   45
Ala Arg Ile Ile Arg Glu Ala Leu Ser Lys Ala Leu Val Lys Tyr Tyr
 50                      55                   60
Pro Phe Ala Gly Arg Phe Val Asp Pro Glu Gly Gly Glu Val
 65                  70                   75                   80
Arg Val Ala Cys Thr Gly Glu Gly Ala Trp Phe Val Glu Ala Lys Ala
                     85                   90                   95
Asp Cys Ser Leu Glu Asp Val Lys Tyr Leu Asp Leu Pro Leu Met Ile
                    100                  105                  110
Pro Glu Asp Ala Leu Leu Pro Lys Pro Cys Pro Gly Leu Asn Pro Leu
                115                  120                  125
Asp Leu Pro Leu Met Leu Gln Val Thr Glu Phe Val Gly Gly Gly Phe
 130                      135                  140
Val Val Gly Leu Ile Ser Val His Thr Ile Ala Asp Gly Leu Gly Val
 145                      150                  155                  160
Val Gln Phe Ile Asn Ala Val Ala Glu Ile Ala Arg Gly Leu Pro Lys
                    165                  170                  175
Pro Thr Val Glu Pro Ala Trp Ser Arg Glu Val Ile Pro Asn Pro Pro
                180                  185                  190
Lys Leu Pro Pro Gly Gly Pro Pro Val Phe Pro Ser Phe Lys Leu Leu
                195                  200                  205
His Ala Thr Val Asp Leu Ser Pro Asp His Ile Asp His Val Lys Ser
 210                      215                  220
Arg His Leu Glu Leu Thr Gly Gln Arg Cys Ser Thr Phe Asp Val Ala
 225                      230                  235                  240
Ile Ala Asn Leu Trp Gln Ser Arg Thr Arg Ala Ile Asn Leu Asp Pro
                    245                  250                  255
Gly Val Asp Val His Val Cys Phe Phe Ala Asn Thr Arg His Leu Leu
                260                  265                  270
Arg Gln Val Val Leu Leu Pro Pro Glu Asp Gly Tyr Tyr Gly Asn Cys
                275                  280                  285
Phe Tyr Pro Val Thr Ala Thr Pro Ser Gly Arg Ile Ala Ser Ala
 290                      295                  300
Glu Leu Ile Asp Val Val Ser Ile Ile Arg Asp Ala Lys Ser Arg Leu
 305                      310                  315                  320
Pro Gly Glu Phe Ala Lys Trp Ala Ala Gly Asp Phe Lys Asp Pro
                    325                  330                  335
Tyr Glu Leu Ser Phe Thr Tyr Asn Ser Leu Phe Val Ser Asp Trp Thr
                340                  345                  350
Arg Leu Gly Phe Leu Asp Val Asp Tyr Gly Trp Gly Lys Pro Leu His
                355                  360                  365
Val Ile Pro Phe Ala Tyr Leu Asp Ile Met Ala Val Gly Ile Ile Gly
 370                      375                  380
Ala Pro Pro Ala Pro Gln Lys Gly Thr Arg Val Met Ala Gln Cys Val
 385                      390                  395                  400
Glu Lys Glu His Met Gln Ala Phe Leu Glu Glu Met Lys
                    405                  410
```

<210> SEQ ID NO 39

-continued

```
<211> LENGTH: 430
<212> TYPE: PRT
<213> ORGANISM: Oryza sativa

<400> SEQUENCE: 39

Val Val Arg Thr Asn Arg Glu Phe Val Arg Pro Ser Ala Ala Thr Pro
1               5                   10                  15

Pro Ser Ser Gly Glu Leu Leu Glu Leu Ser Ile Ile Asp Arg Val Val
            20                  25                  30

Gly Leu Arg His Leu Val Arg Ser Leu His Ile Phe Ser Ala Ala Ala
        35                  40                  45

Pro Ser Gly Gly Asp Ala Lys Pro Ser Pro Ala Arg Val Ile Lys Glu
    50                  55                  60

Ala Leu Gly Lys Ala Leu Val Asp Tyr Tyr Pro Phe Ala Gly Arg Phe
65                  70                  75                  80

Val Asp Gly Gly Gly Pro Gly Ser Ala Arg Val Glu Cys Thr Gly
                85                  90                  95

Glu Gly Ala Trp Phe Val Glu Ala Ala Gly Cys Ser Leu Asp Asp
            100                 105                 110

Val Asn Gly Leu Asp His Pro Leu Met Ile Pro Glu Asp Asp Leu Leu
        115                 120                 125

Pro Asp Ala Ala Pro Gly Val His Pro Leu Asp Leu Pro Leu Met Met
    130                 135                 140

Gln Val Thr Glu Phe Ser Cys Gly Gly Phe Val Val Gly Leu Ile Ser
145                 150                 155                 160

Val His Thr Met Ala Asp Gly Leu Gly Ala Gly Gln Phe Ile Asn Ala
                165                 170                 175

Val Gly Asp Tyr Ala Arg Gly Leu Asp Arg Pro Arg Val Ser Pro Val
            180                 185                 190

Trp Ala Arg Glu Ala Ile Pro Ser Pro Pro Lys Leu Pro Pro Gly Pro
        195                 200                 205

Pro Pro Glu Leu Lys Met Phe Gln Leu Arg His Val Thr Ala Asp Leu
    210                 215                 220

Ser Leu Asp Ser Ile Asn Lys Ala Lys Ser Ala Tyr Phe Ala Ala Thr
225                 230                 235                 240

Gly His Arg Cys Ser Thr Phe Asp Val Ala Ile Ala Lys Thr Trp Gln
                245                 250                 255

Ala Arg Thr Arg Ala Leu Arg Leu Pro Glu Pro Thr Ser Arg Val Asn
            260                 265                 270

Leu Cys Phe Phe Ala Asn Thr Arg His Leu Met Ala Gly Ala Ala Ala
        275                 280                 285

Trp Pro Ala Pro Ala Ala Gly Gly Asn Gly Gly Asn Gly Phe Tyr Gly
    290                 295                 300

Asn Cys Phe Tyr Pro Val Ser Val Ala Glu Ser Gly Ala Val Glu
305                 310                 315                 320

Ala Ala Asp Val Ala Gly Val Val Gly Met Ile Arg Glu Ala Lys Ala
                325                 330                 335

Arg Leu Pro Ala Asp Phe Ala Arg Trp Ala Val Ala Asp Phe Arg Glu
            340                 345                 350

Asp Pro Tyr Glu Leu Ser Phe Thr Tyr Asp Ser Leu Phe Val Ser Asp
        355                 360                 365

Trp Thr Arg Leu Gly Phe Leu Glu Ala Asp Tyr Gly Trp Gly Pro Pro
    370                 375                 380

Ser His Val Ile Pro Phe Ala Tyr Tyr Pro Phe Met Ala Val Ala Ile
```

Ile Gly Ala Pro Pro Val Pro Lys Thr Gly Ala Arg Ile Met Thr Gln
385                 390                 395                 400

Cys Val Glu Asp Asp His Leu Pro Ala Phe Lys Glu Glu Ile
            405                 410                 415

420                 425                 430

<210> SEQ ID NO 40
<211> LENGTH: 437
<212> TYPE: PRT
<213> ORGANISM: Brachypodium distachyon

<400> SEQUENCE: 40

Phe Thr Val Thr Arg Thr Ser Lys Ser Leu Val Pro Ser Ser Ser
1               5                   10                  15

Ser Pro Thr Pro Ala Ala Thr Glu Asp Asp Ala Pro Val Pro Val Ile
                20                  25                  30

Met Arg Leu Ser Thr Ile Asp Arg Val Pro Gly Leu Arg His Leu Val
            35                  40                  45

Leu Ser Leu His Ala Phe Asp Gly His Gly Val Val Ala Gly Glu Asp
    50                  55                  60

Asp Glu Glu Arg Ile Arg Trp Pro Ala Arg Val Val Arg Glu Ala Leu
65                  70                  75                  80

Gly Lys Ala Leu Val Asp Tyr Tyr Pro Phe Ala Gly Arg Phe Val Val
                85                  90                  95

Asp Glu Glu Gly Glu Val Gly Val Lys Cys Ser Gly Glu Gly Ala Trp
            100                 105                 110

Phe Val Glu Ala Lys Ala Glu Cys Ser Leu Glu Glu Ala Arg His Leu
        115                 120                 125

Asp Gly Asn Pro Met Glu Met Val Ile Pro Lys Glu Asp Leu Leu Pro
130                 135                 140

Glu Pro Ile Pro Gly Val Asp Pro Leu Asp Ile Pro Leu Ile Met Gln
145                 150                 155                 160

Val Thr Glu Phe Thr Cys Gly Gly Phe Val Val Gly Leu Ile Ser Val
                165                 170                 175

His Thr Ile Ala Asp Gly Leu Gly Ala Gly Gln Phe Ile Asn Ala Val
            180                 185                 190

Ala Asp Tyr Ala Arg Gly Leu Pro Lys Pro Arg Val Ser Pro Val Trp
        195                 200                 205

Ala Arg Asp Leu Val Pro Asp Pro Lys Met Pro Ala Pro Pro Pro
210                 215                 220

Lys Leu Glu Leu Leu Asp Leu Arg His Phe Thr Val Asp Leu Ser Pro
225                 230                 235                 240

Asp His Ile Ala Lys Val Lys Ser Gln Tyr Phe Ala Ser Thr Gly His
                245                 250                 255

Arg Cys Ser Ala Phe Asp Val Val Ala Val Thr Trp Gln Ser Arg
            260                 265                 270

Thr Arg Ala Leu Arg Leu Ala Gly Ala Gly Tyr Asp Val His Val
        275                 280                 285

Cys Phe Phe Ala Asn Thr Arg His Leu Met Leu His Gly Gly Ala Gly
290                 295                 300

Ala Ala Gly Phe Tyr Gly Asn Cys Phe Tyr Pro Val Arg Ala Thr Cys
305                 310                 315                 320

Gly Ser Ala Glu Val Ala Ser Asp Val Ala Gly Val Val Lys Val
                325                 330                 335

```
Val Arg Asp Ala Lys Ala Arg Leu Ala Gly Asp Val Ala Arg Trp Ala
            340                 345                 350

Val Gly Gly Phe Glu Gln Asp Pro Tyr Glu Leu Thr Phe Thr Tyr Asp
        355                 360                 365

Ser Leu Phe Val Ser Asp Trp Thr Arg Leu Gly Phe Leu Glu Ala Asp
    370                 375                 380

Tyr Gly Trp Gly Pro Pro Ala His Val Val Pro Phe Ser Tyr His Pro
385                 390                 395                 400

Phe Met Ala Val Ala Val Ile Gly Ala Pro Pro Lys Pro Lys Leu Gly
                405                 410                 415

Ser Arg Val Met Thr Met Cys Val Glu Glu Asp His Leu Pro Glu Phe
                420                 425                 430

Arg Asp Gln Met Asn
            435

<210> SEQ ID NO 41
<211> LENGTH: 421
<212> TYPE: PRT
<213> ORGANISM: Sorghum bicolor

<400> SEQUENCE: 41

Pro Val Thr Arg Thr Asn Arg Ser Leu Val Pro Pro Ser Ser Ala Thr
1               5                   10                  15

Pro Gln Glu Thr Leu Arg Leu Ser Val Ile Asp Arg Val Ala Gly Leu
            20                  25                  30

Arg His Leu Val Arg Ser Leu His Val Phe Ala Gly Gly Glu Asn Lys
        35                  40                  45

Lys Gln Ala Ala Pro Ala Lys Ser Leu Arg Glu Ala Leu Gly Lys
50                  55                  60

Ala Leu Val Asp Tyr Tyr Pro Phe Ala Gly Arg Phe Val Glu Glu Asp
65                  70                  75                  80

Gly Glu Val Arg Val Ala Cys Thr Gly Glu Gly Ala Trp Phe Val Glu
                85                  90                  95

Ala Ala Ala Ala Cys Ser Leu Glu Glu Val Arg His Leu Asp His Pro
                100                 105                 110

Met Leu Ile Pro Lys Glu Glu Leu Leu Pro Glu Pro Ala Pro Gly Val
            115                 120                 125

Asn Pro Leu Asp Met Pro Leu Met Met Gln Val Thr Glu Phe Thr Cys
130                 135                 140

Gly Gly Phe Val Val Gly Leu Ile Ser Val His Thr Ile Ala Asp Gly
145                 150                 155                 160

Leu Gly Ala Gly Gln Phe Ile Asn Ala Val Ala Asp Tyr Ala Arg Gly
                165                 170                 175

Gly Ala Thr Ala Gly Ala Val Thr Arg Pro Arg Ile Thr Pro Ile Trp
            180                 185                 190

Ala Arg Asp Val Ile Pro Asp Pro Lys Met Pro Ala Pro Pro
            195                 200                 205

Arg Leu Asp Leu Leu Asp Leu Val Tyr Phe Thr Thr Asp Leu Ser Pro
210                 215                 220

Asp His Ile Ala Lys Val Lys Ser Ser Tyr Leu Glu Ser Thr Gly Gln
225                 230                 235                 240

Arg Cys Ser Ala Phe Asp Val Cys Val Ala Arg Thr Trp Gln Ala Arg
                245                 250                 255

Val Arg Ala Leu Arg Leu Pro Asp Ala Ala Ala Pro Val His Val Cys
            260                 265                 270
```

```
Phe Phe Ala Asn Thr Arg His Leu Leu Pro Ala Thr Ala Ala Pro
        275                 280                 285

Ala Ser Gly Phe Tyr Gly Asn Cys Phe Tyr Thr Val Lys Ala Thr Arg
    290                 295                 300

Pro Ser Gly Glu Val Ala Ala Asp Ile Val Asp Val Val Arg Ala
305                 310                 315                 320

Ile Arg Asp Ala Lys Ala Arg Leu Ala Ala Asp Phe Ala Arg Trp Ala
                325                 330                 335

Ala Gly Gly Phe Asp Arg Asp Pro Tyr Glu Leu Thr Phe Thr Tyr Asp
                340                 345                 350

Ser Leu Phe Val Ser Asp Trp Thr Arg Leu Gly Phe Leu Glu Ala Asp
        355                 360                 365

Tyr Gly Trp Gly Thr Pro Thr His Val Val Pro Phe Ser Tyr His Pro
    370                 375                 380

Phe Met Ala Val Ala Val Ile Gly Ala Pro Ala Pro Lys Pro Gly
385                 390                 395                 400

Ala Arg Ile Met Thr Met Cys Val Gln Glu Gln His Leu Pro Glu Phe
                405                 410                 415

Gln Glu Gln Met Asn
            420

<210> SEQ ID NO 42
<211> LENGTH: 428
<212> TYPE: PRT
<213> ORGANISM: Oryza sativa

<400> SEQUENCE: 42

Phe Thr Val Thr Arg Thr Ser Arg Ser Leu Val Ala Pro Ser Ser Pro
1               5                   10                  15

Thr Pro Ala Glu Thr Leu Pro Leu Ser Val Ile Asp Arg Val Ala Gly
            20                  25                  30

Leu Arg His Leu Val Arg Ser Leu His Val Phe Glu Ala Gly Gly Arg
        35                  40                  45

Asn Gly Gly Gly Glu Pro Ala Arg Val Val Ile Arg Glu Ala Leu Gly
    50                  55                  60

Lys Ala Leu Val Glu Tyr His Pro Phe Ala Gly Arg Phe Val Glu Gly
65                  70                  75                  80

Asp Gly Gly Gly Glu Val Ala Val Ala Cys Thr Gly Glu Gly Ala Trp
                85                  90                  95

Phe Val Glu Ala Thr Ala Ala Cys Ser Leu Glu Glu Val Lys Leu Leu
            100                 105                 110

Asp His Pro Met Val Ile Pro Lys Glu Glu Leu Leu Pro Glu Pro Ala
        115                 120                 125

Pro Asp Val Gln Pro Leu Asp Ile Pro Leu Met Met Gln Val Thr Glu
    130                 135                 140

Phe Thr Cys Gly Gly Phe Val Gly Leu Ile Ser Val His Thr Ile
145                 150                 155                 160

Ala Asp Gly Leu Gly Ala Gly Gln Phe Ile Asn Ala Val Ala Asp Tyr
                165                 170                 175

Ala Arg Gly Leu Ala Lys Pro Arg Val Ser Pro Val Trp Ala Arg Asp
            180                 185                 190

Ala Ile Pro Asp Pro Pro Arg Met Pro Ala Pro Pro Arg Leu Glu
        195                 200                 205

Leu Leu Asp Leu Arg Tyr Phe Thr Val Asp Leu Ser Pro Asp His Ile
```

Ala Lys Val Lys Ser Ala Phe Phe Glu Ser Thr Gly His Arg Cys Ser
225                 230                 235                 240

Ala Phe Asp Val Cys Val Ala Lys Thr Trp Gln Ala Arg Thr Arg Ala
            245                 250                 255

Leu Val Ala Ala Ala Ala Ala Gly Asp Asp Gln Glu Arg Arg
        260                 265                 270

Thr Val Arg Val Cys Phe Phe Ala Asn Thr Arg His Leu Met Leu Lys
        275                 280                 285

Gly Asp Gly Ala Ala Ala Ala Thr Gly Phe Tyr Gly Asn Cys Phe
290                 295                 300

Tyr Pro Val Ala Ala Val Ala Ser Gly Gly Glu Val Ala Gly Ala Asp
305                 310                 315                 320

Ile Val Asp Val Val Arg Ile Val Arg Asp Ala Lys Ala Arg Leu Ala
            325                 330                 335

Ala Asp Val Ala Arg Trp Ala Val Gly Gly Phe Glu Glu Asp Pro Tyr
            340                 345                 350

Glu Leu Thr Phe Thr Tyr Asp Ser Leu Phe Val Ser Asp Trp Thr Arg
            355                 360                 365

Leu Gly Phe Leu Asp Ala Asp Tyr Gly Trp Gly Thr Pro Ser His Val
370                 375                 380

Val Pro Phe Ser Tyr His Pro Phe Met Ala Val Ala Val Ile Gly Ala
385                 390                 395                 400

Pro Pro Ala Pro Lys Leu Gly Ala Arg Val Met Thr Met Cys Val Glu
                405                 410                 415

Glu Ala His Leu Pro Glu Phe Arg Asp Gln Met Asn
            420                 425

<210> SEQ ID NO 43
<211> LENGTH: 22
<212> TYPE: DNA
<213> ORGANISM: Artificial Sequence
<220> FEATURE:
<223> OTHER INFORMATION: synthetic L0.5 5' primer for genotyping

<400> SEQUENCE: 43
ttggggatcc tctagagtcg ag                                              22

<210> SEQ ID NO 44
<211> LENGTH: 23
<212> TYPE: DNA
<213> ORGANISM: Artificial Sequence
<220> FEATURE:
<223> OTHER INFORMATION: synthetic iL1 5' primer for genotyping

<400> SEQUENCE: 44
tccgaaacta tcagtgtcta gct                                             23

<210> SEQ ID NO 45
<211> LENGTH: 20
<212> TYPE: DNA
<213> ORGANISM: Artificial Sequence
<220> FEATURE:
<223> OTHER INFORMATION: synthetic NGUS1 5' primer for genotyping

<400> SEQUENCE: 45
aacgctgatc aattccacag                                                 20

<210> SEQ ID NO 46

```
<211> LENGTH: 20
<212> TYPE: DNA
<213> ORGANISM: Artificial Sequence
<220> FEATURE:
<223> OTHER INFORMATION: synthetic Pam1-1F 5' primer for genotyping

<400> SEQUENCE: 46
gtggtggaaa gttgtgatcg                                              20

<210> SEQ ID NO 47
<211> LENGTH: 20
<212> TYPE: DNA
<213> ORGANISM: Artificial Sequence
<220> FEATURE:
<223> OTHER INFORMATION: synthetic Pam1-1R_15LB 3' primer for genotyping

<400> SEQUENCE: 47
cagggcatgt ttagttggtg                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic Pam1-3F 5' primer for genotyping

<400> SEQUENCE: 48
ctcaaccgcc atcatgttac                                              20

<210> SEQ ID NO 49
<211> LENGTH: 20
<212> TYPE: DNA
<213> ORGANISM: Artificial Sequence
<220> FEATURE:
<223> OTHER INFORMATION: synthetic Pam1-3R_15LB 3' primer for genotyping

<400> SEQUENCE: 49
gttcctatca catcggatgt                                              20

<210> SEQ ID NO 50
<211> LENGTH: 20
<212> TYPE: DNA
<213> ORGANISM: Artificial Sequence
<220> FEATURE:
<223> OTHER INFORMATION: synthetic Pam1-8F_15LB 5' primer for genotyping

<400> SEQUENCE: 50
gatgggacag tctctagtca                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic Pam1-8R 3' primer for genotyping

<400> SEQUENCE: 51
gtagtacgcg agatccgtat                                              20

<210> SEQ ID NO 52
<211> LENGTH: 19
<212> TYPE: DNA
<213> ORGANISM: Artificial Sequence
<220> FEATURE:
<223> OTHER INFORMATION: synthetic Pam1-12F_15RB 5' primer for
      genotyping
```

```
<400> SEQUENCE: 52
tgcagcctcg acgacgtga                                              19

<210> SEQ ID NO 53
<211> LENGTH: 19
<212> TYPE: DNA
<213> ORGANISM: Artificial Sequence
<220> FEATURE:
<223> OTHER INFORMATION: synthetic Pam1-12R 3' primer for genotyping

<400> SEQUENCE: 53
tgatccgtta gcgcgtgtt                                              19

<210> SEQ ID NO 54
<211> LENGTH: 20
<212> TYPE: DNA
<213> ORGANISM: Artificial Sequence
<220> FEATURE:
<223> OTHER INFORMATION: synthetic Pam1-13F 5' primer for genotyping

<400> SEQUENCE: 54
tgactgaagg tcgagaacga                                             20

<210> SEQ ID NO 55
<211> LENGTH: 21
<212> TYPE: DNA
<213> ORGANISM: Artificial Sequence
<220> FEATURE:
<223> OTHER INFORMATION: synthetic Pam1-13R_15LB 3' primer for
      genotyping

<400> SEQUENCE: 55
gttacatgat gccttgtcaa g                                           21

<210> SEQ ID NO 56
<211> LENGTH: 21
<212> TYPE: DNA
<213> ORGANISM: Artificial Sequence
<220> FEATURE:
<223> OTHER INFORMATION: synthetic Pam1-15F 5' primer for genotyping

<400> SEQUENCE: 56
gcagctcaac tcctgaaaat c                                           21

<210> SEQ ID NO 57
<211> LENGTH: 19
<212> TYPE: DNA
<213> ORGANISM: Artificial Sequence
<220> FEATURE:
<223> OTHER INFORMATION: synthetic Pam1-15R_72RB 3' primer for
      genotyping

<400> SEQUENCE: 57
gccagctgat ctgaagcag                                              19

<210> SEQ ID NO 58
<211> LENGTH: 19
<212> TYPE: DNA
<213> ORGANISM: Artificial Sequence
<220> FEATURE:
<223> OTHER INFORMATION: synthetic Pam1-16F_15LB 5' primer for
      genotyping

<400> SEQUENCE: 58
ccagagggag tacttccgt                                              19
```

```
<210> SEQ ID NO 59
<211> LENGTH: 20
<212> TYPE: DNA
<213> ORGANISM: Artificial Sequence
<220> FEATURE:
<223> OTHER INFORMATION: synthetic Pam1-16R 3' primer for genotyping

<400> SEQUENCE: 59
gcgagatggc tatacgtgag                                               20

<210> SEQ ID NO 60
<211> LENGTH: 20
<212> TYPE: DNA
<213> ORGANISM: Artificial Sequence
<220> FEATURE:
<223> OTHER INFORMATION: synthetic Pam1-17F 5' primer for genotyping

<400> SEQUENCE: 60
ccatcttaga gatgggagca                                               20

<210> SEQ ID NO 61
<211> LENGTH: 19
<212> TYPE: DNA
<213> ORGANISM: Artificial Sequence
<220> FEATURE:
<223> OTHER INFORMATION: synthetic Pam1-17R_15RB 3' primer for
      genotyping

<400> SEQUENCE: 61
cgtccttgga tctgggtca                                                19

<210> SEQ ID NO 62
<211> LENGTH: 20
<212> TYPE: DNA
<213> ORGANISM: Artificial Sequence
<220> FEATURE:
<223> OTHER INFORMATION: synthetic Pam1-19F 5' primer for genotyping

<400> SEQUENCE: 62
cagatgagct tatagctagt                                               20

<210> SEQ ID NO 63
<211> LENGTH: 20
<212> TYPE: DNA
<213> ORGANISM: Artificial Sequence
<220> FEATURE:
<223> OTHER INFORMATION: synthetic Pam1-19R_72LB 3' primer for
      genotyping

<400> SEQUENCE: 63
gacttgctca ccacaatgct                                               20

<210> SEQ ID NO 64
<211> LENGTH: 20
<212> TYPE: DNA
<213> ORGANISM: Artificial Sequence
<220> FEATURE:
<223> OTHER INFORMATION: synthetic Pam1-22F_15RB 5' primer for
      genotyping

<400> SEQUENCE: 64
gtggttagaa cctccctaga                                               20

<210> SEQ ID NO 65
<211> LENGTH: 20
<212> TYPE: DNA
```

```
<213> ORGANISM: Artificial Sequence
<220> FEATURE:
<223> OTHER INFORMATION: synthetic Pam1-22R 3' primer for genotyping

<400> SEQUENCE: 65
ctcatggatc ggatgctcga                                              20

<210> SEQ ID NO 66
<211> LENGTH: 20
<212> TYPE: DNA
<213> ORGANISM: Artificial Sequence
<220> FEATURE:
<223> OTHER INFORMATION: synthetic Pam1-25F_15RB 5' primer for
      genotyping

<400> SEQUENCE: 66
tcacgaacct ggactacatc                                              20

<210> SEQ ID NO 67
<211> LENGTH: 20
<212> TYPE: DNA
<213> ORGANISM: Artificial Sequence
<220> FEATURE:
<223> OTHER INFORMATION: synthetic Pam1-25R 3' primer for genotyping

<400> SEQUENCE: 67
accatctacc tgtaccctca                                              20

<210> SEQ ID NO 68
<211> LENGTH: 19
<212> TYPE: DNA
<213> ORGANISM: Artificial Sequence
<220> FEATURE:
<223> OTHER INFORMATION: synthetic Pam1-26F_07RB 5' primer for
      genotyping

<400> SEQUENCE: 68
gtgacggagg cagtgatga                                               19

<210> SEQ ID NO 69
<211> LENGTH: 20
<212> TYPE: DNA
<213> ORGANISM: Artificial Sequence
<220> FEATURE:
<223> OTHER INFORMATION: synthetic Pam1-26R 3' primer for genotyping

<400> SEQUENCE: 69
gcttaagtgc agcccaaact                                              20

<210> SEQ ID NO 70
<211> LENGTH: 20
<212> TYPE: DNA
<213> ORGANISM: Artificial Sequence
<220> FEATURE:
<223> OTHER INFORMATION: synthetic Pam1-28F 5' primer for genotyping

<400> SEQUENCE: 70
caagagggca taagtgaact                                              20

<210> SEQ ID NO 71
<211> LENGTH: 20
<212> TYPE: DNA
<213> ORGANISM: Artificial Sequence
<220> FEATURE:
<223> OTHER INFORMATION: synthetic Pam1-28R_15LB 3' primer for
      genotyping
```

<400> SEQUENCE: 71
catcggaagg tgattccaca					20

<210> SEQ ID NO 72
<211> LENGTH: 20
<212> TYPE: DNA
<213> ORGANISM: Artificial Sequence
<220> FEATURE:
<223> OTHER INFORMATION: synthetic Pam1-29F 5' primer for genotyping

<400> SEQUENCE: 72
cagttgcaga ccactgagaa					20

<210> SEQ ID NO 73
<211> LENGTH: 21
<212> TYPE: DNA
<213> ORGANISM: Artificial Sequence
<220> FEATURE:
<223> OTHER INFORMATION: synthetic Pam1-29R_72LB 3' primer for
      genotyping

<400> SEQUENCE: 73
cttgattctc gagttgaaag t					21

<210> SEQ ID NO 74
<211> LENGTH: 27
<212> TYPE: DNA
<213> ORGANISM: Artificial Sequence
<220> FEATURE:
<223> OTHER INFORMATION: synthetic Hyg-3 5' primer for genotyping

<400> SEQUENCE: 74
tccactatcg gcgagtactt ctacaca				27

<210> SEQ ID NO 75
<211> LENGTH: 24
<212> TYPE: DNA
<213> ORGANISM: Artificial Sequence
<220> FEATURE:
<223> OTHER INFORMATION: synthetic hyg 4 3' primer for genotyping

<400> SEQUENCE: 75
cactggcaaa ctgtgatgga cgac				24

<210> SEQ ID NO 76
<211> LENGTH: 22
<212> TYPE: DNA
<213> ORGANISM: Artificial Sequence
<220> FEATURE:
<223> OTHER INFORMATION: synthetic Os01g08380_F1 5' primer for RT-qPCR

<400> SEQUENCE: 76
aggccgggag gatgggtgga tt				22

<210> SEQ ID NO 77
<211> LENGTH: 22
<212> TYPE: DNA
<213> ORGANISM: Artificial Sequence
<220> FEATURE:
<223> OTHER INFORMATION: synthetic Os01g08380_R1 3' primer for RT-qPCR

<400> SEQUENCE: 77
accacgctcc acccacgagc tt				22

<210> SEQ ID NO 78

<211> LENGTH: 20
<212> TYPE: DNA
<213> ORGANISM: Artificial Sequence
<220> FEATURE:
<223> OTHER INFORMATION: synthetic os01g09010_832F 5' primer for RT-qPCR

<400> SEQUENCE: 78
cacctgctga agctggacag                                               20

<210> SEQ ID NO 79
<211> LENGTH: 22
<212> TYPE: DNA
<213> ORGANISM: Artificial Sequence
<220> FEATURE:
<223> OTHER INFORMATION: synthetic os01g09010_929R 3' primer for RT-qPCR

<400> SEQUENCE: 79
tccatcaccg acgacgacag ca                                            22

<210> SEQ ID NO 80
<211> LENGTH: 20
<212> TYPE: DNA
<213> ORGANISM: Artificial Sequence
<220> FEATURE:
<223> OTHER INFORMATION: synthetic 04g09260-2-f 5' primer for RT-qPCR

<400> SEQUENCE: 80
ggaagcacgt cggagccaag                                               20

<210> SEQ ID NO 81
<211> LENGTH: 22
<212> TYPE: DNA
<213> ORGANISM: Artificial Sequence
<220> FEATURE:
<223> OTHER INFORMATION: synthetic 04g09260-2-r 3' primer for RT-qPCR

<400> SEQUENCE: 81
cgacatgatg cagttgccgt ag                                            22

<210> SEQ ID NO 82
<211> LENGTH: 20
<212> TYPE: DNA
<213> ORGANISM: Artificial Sequence
<220> FEATURE:
<223> OTHER INFORMATION: synthetic os05g08640_F4qPCR 5' primer for
      RT-qPCR

<400> SEQUENCE: 82
aaaccagggg cacggctcat                                               20

<210> SEQ ID NO 83
<211> LENGTH: 22
<212> TYPE: DNA
<213> ORGANISM: Artificial Sequence
<220> FEATURE:
<223> OTHER INFORMATION: synthetic os05g08640_R4qPCR 3' primer for
      RT-qPCR

<400> SEQUENCE: 83
ttgatgtcca ccatggcgtc gt                                            22

<210> SEQ ID NO 84
<211> LENGTH: 23
<212> TYPE: DNA
<213> ORGANISM: Artificial Sequence
<220> FEATURE:
<223> OTHER INFORMATION: synthetic os05g19910_543F 5' primer for RT-qPCR

```
<400> SEQUENCE: 84
catcactgca gtagctgaat tgg                                               23

<210> SEQ ID NO 85
<211> LENGTH: 23
<212> TYPE: DNA
<213> ORGANISM: Artificial Sequence
<220> FEATURE:
<223> OTHER INFORMATION: synthetic os05g19910_634R 3' primer for RT-qPCR

<400> SEQUENCE: 85
gcttaggtgg gttcggtatc agc                                               23

<210> SEQ ID NO 86
<211> LENGTH: 25
<212> TYPE: DNA
<213> ORGANISM: Artificial Sequence
<220> FEATURE:
<223> OTHER INFORMATION: synthetic Os06g39370_F1 5' primer for RT-qPCR

<400> SEQUENCE: 86
tgcctcctag aaatctgaag cgtat                                             25

<210> SEQ ID NO 87
<211> LENGTH: 24
<212> TYPE: DNA
<213> ORGANISM: Artificial Sequence
<220> FEATURE:
<223> OTHER INFORMATION: synthetic Os06g39370_R1 3' primer for RT-qPCR

<400> SEQUENCE: 87
ttgctgtaca aactcgaact ctgc                                              24

<210> SEQ ID NO 88
<211> LENGTH: 24
<212> TYPE: DNA
<213> ORGANISM: Artificial Sequence
<220> FEATURE:
<223> OTHER INFORMATION: synthetic Os06g39380_F1 5' primer for RT-qPCR

<400> SEQUENCE: 88
acagaaaaac cacggcctaa taga                                              24

<210> SEQ ID NO 89
<211> LENGTH: 24
<212> TYPE: DNA
<213> ORGANISM: Artificial Sequence
<220> FEATURE:
<223> OTHER INFORMATION: synthetic Os06g39380_R1 3' primer for RT-qPCR

<400> SEQUENCE: 89
ctcttttcac tcccacccctt gtct                                             24

<210> SEQ ID NO 90
<211> LENGTH: 20
<212> TYPE: DNA
<213> ORGANISM: Artificial Sequence
<220> FEATURE:
<223> OTHER INFORMATION: synthetic 06g39390-RT2-5' 5' primer for RT-qPCR

<400> SEQUENCE: 90
gacccgttcc agatgacgtt                                                   20

<210> SEQ ID NO 91
```

```
<211> LENGTH: 20
<212> TYPE: DNA
<213> ORGANISM: Artificial Sequence
<220> FEATURE:
<223> OTHER INFORMATION: synthetic 06g39390-RT2-3' 3' primer for RT-qPCR

<400> SEQUENCE: 91
gatgaggtcg cagttcacca                                                 20

<210> SEQ ID NO 92
<211> LENGTH: 23
<212> TYPE: DNA
<213> ORGANISM: Artificial Sequence
<220> FEATURE:
<223> OTHER INFORMATION: synthetic Os06g39400_F1 5' primer for RT-qPCR

<400> SEQUENCE: 92
gcgcatggaa gggcaaaaac agc                                             23

<210> SEQ ID NO 93
<211> LENGTH: 25
<212> TYPE: DNA
<213> ORGANISM: Artificial Sequence
<220> FEATURE:
<223> OTHER INFORMATION: synthetic Os06g39400_R1 3' primer for RT-qPCR

<400> SEQUENCE: 93
ctgctccaga aaaagctcga tcggt                                           25

<210> SEQ ID NO 94
<211> LENGTH: 20
<212> TYPE: DNA
<213> ORGANISM: Artificial Sequence
<220> FEATURE:
<223> OTHER INFORMATION: synthetic os06g39470_359F 5' primer for RT-qPCR

<400> SEQUENCE: 94
agtacccgct catggtggac                                                 20

<210> SEQ ID NO 95
<211> LENGTH: 19
<212> TYPE: DNA
<213> ORGANISM: Artificial Sequence
<220> FEATURE:
<223> OTHER INFORMATION: synthetic os06g39470_467R 3' primer for RT-qPCR

<400> SEQUENCE: 95
aactgcgtga cctggacaa                                                  19

<210> SEQ ID NO 96
<211> LENGTH: 20
<212> TYPE: DNA
<213> ORGANISM: Artificial Sequence
<220> FEATURE:
<223> OTHER INFORMATION: synthetic CC55 R1-5' 5' primer for RT-qPCR

<400> SEQUENCE: 96
aaggagaaag ccgaacaacg                                                 20

<210> SEQ ID NO 97
<211> LENGTH: 23
<212> TYPE: DNA
<213> ORGANISM: Artificial Sequence
<220> FEATURE:
<223> OTHER INFORMATION: synthetic CC55 RT1-3' 3' primer for RT-qPCR

<400> SEQUENCE: 97
```

```
tcctcaagtt tcttcctgta ggc                                            23
```

<210> SEQ ID NO 98
<211> LENGTH: 21
<212> TYPE: DNA
<213> ORGANISM: Artificial Sequence
<220> FEATURE:
<223> OTHER INFORMATION: synthetic UBQ5 RT 1-5' 5' primer for RT-qPCR

<400> SEQUENCE: 98

```
accacttcga ccgccactac t                                              21
```

<210> SEQ ID NO 99
<211> LENGTH: 19
<212> TYPE: DNA
<213> ORGANISM: Artificial Sequence
<220> FEATURE:
<223> OTHER INFORMATION: synthetic UBQ5 RT 1-5' 5' primer for RT-qPCR

<400> SEQUENCE: 99

```
acgcctaagc ctgctggtt                                                 19
```

<210> SEQ ID NO 100
<211> LENGTH: 25
<212> TYPE: DNA
<213> ORGANISM: Artificial Sequence
<220> FEATURE:
<223> OTHER INFORMATION: synthetic Os06g39390-for-2 5' primer for
      cloning

<400> SEQUENCE: 100

```
caccagcagc agcagcagca gcagc                                          25
```

<210> SEQ ID NO 101
<211> LENGTH: 24
<212> TYPE: DNA
<213> ORGANISM: Artificial Sequence
<220> FEATURE:
<223> OTHER INFORMATION: synthetic Os06g39390-rev-stop2 3' primer for
      cloning

<400> SEQUENCE: 101

```
taccacgcat gtcacaaagc acgg                                           24
```

<210> SEQ ID NO 102
<211> LENGTH: 441
<212> TYPE: PRT
<213> ORGANISM: Angelica sinensis

<400> SEQUENCE: 102

Met Thr Ile Met Glu Val Gln Val Val Ser Lys Lys Met Val Lys Pro
1               5                   10                  15

Ser Val Pro Thr Pro Asp His His Lys Thr Cys Lys Leu Thr Ala Phe
                20                  25                  30

Asp Gln Ile Ala Pro Pro Asp Gln Val Pro Ile Ile Tyr Phe Tyr Asn
            35                  40                  45

Ser Ser Asn Ile His Asn Ile Arg Glu Gln Leu Val Lys Ser Leu Ser
        50                  55                  60

Glu Thr Leu Thr Lys Phe Tyr Pro Leu Ala Gly Arg Phe Val Gln Asp
65                  70                  75                  80

Gly Phe Tyr Val Asp Cys Asn Asp Glu Gly Val Leu Tyr Val Glu Ala
                85                  90                  95

-continued

```
Glu Val Asn Ile Pro Leu Asn Glu Phe Ile Gly Gln Ala Lys Lys Asn
                100                 105                 110
Ile Gln Leu Ile Asn Asp Leu Val Pro Lys Lys Asn Phe Lys Asp Ile
            115                 120                 125
His Ser Tyr Glu Asn Pro Ile Val Gly Leu Gln Met Ser Tyr Phe Lys
        130                 135                 140
Cys Gly Gly Leu Ala Ile Cys Met Tyr Leu Ser His Val Val Ala Asp
145                 150                 155                 160
Gly Tyr Thr Ala Ala Phe Thr Lys Glu Trp Ser Asn Thr Thr Asn
                165                 170                 175
Gly Ile Ile Asn Gly Asp Gln Leu Val Ser Ser Ser Pro Ile Asn Phe
            180                 185                 190
Glu Leu Ala Thr Leu Val Pro Ala Arg Asp Leu Ser Thr Val Ile Lys
        195                 200                 205
Pro Ala Val Met Pro Pro Ser Lys Ile Lys Glu Thr Lys Val Val Thr
    210                 215                 220
Arg Arg Phe Leu Phe Asp Glu Asn Ala Ile Ser Ala Phe Lys Asp His
225                 230                 235                 240
Val Ile Lys Ser Glu Ser Val Asn Arg Pro Thr Arg Val Glu Val Val
                245                 250                 255
Thr Ser Val Leu Trp Lys Ala Leu Ile Asn Gln Ser Lys Leu Pro Ser
            260                 265                 270
Ser Thr Leu Tyr Phe His Leu Asn Phe Arg Gly Lys Thr Gly Ile Asn
        275                 280                 285
Thr Pro Pro Leu Asp Asn His Phe Ser Leu Cys Gly Asn Phe Tyr Thr
    290                 295                 300
Gln Val Pro Thr Arg Phe Arg Gly Gly Asn Gln Thr Lys Gln Asp Leu
305                 310                 315                 320
Glu Leu His Glu Leu Val Lys Leu Leu Arg Gly Lys Leu Arg Asn Thr
                325                 330                 335
Leu Lys Asn Cys Ser Glu Ile Asn Thr Ala Asp Gly Leu Phe Leu Glu
            340                 345                 350
Ala Ala Ser Asn Phe Asn Ile Ile Gln Glu Asp Leu Glu Asp Glu Gln
        355                 360                 365
Val Asp Val Arg Ile Phe Thr Thr Leu Cys Arg Met Pro Leu Tyr Glu
    370                 375                 380
Thr Glu Phe Gly Trp Gly Lys Pro Glu Trp Val Thr Ile Pro Glu Met
385                 390                 395                 400
His Leu Glu Ile Val Phe Leu Leu Asp Thr Lys Cys Gly Thr Gly Ile
                405                 410                 415
Glu Ala Leu Val Ser Met Asp Glu Ala Asp Met Leu Gln Phe Glu Leu
            420                 425                 430
Asp Pro Thr Ile Ser Ala Phe Ala Ser
        435                 440
```

MODULATION OF EXPRESSION OF ACYLTRANSFERASES TO MODIFY HYDROXYCINNAMIC ACID CONTENT

CROSS-REFERENCE TO RELATED APPLICATIONS

This application is a divisional of Ser. No. 15/652,115, filed Jul. 17, 2017, now U.S. Pat. No. 10,450,578, issued on Oct. 22, 2019, which is a divisional of Ser. No. 14/746,779, filed Jun. 22, 2015, now U.S. Pat. No. 9,708,624, issued on Jul. 18, 2017, which is a continuation-in-part of PCT/US2013/077266, filed Dec. 20, 2013, which claims benefit of priority of U.S. provisional application no. 61/745,247, filed Dec. 21, 2012, each of which applications is herein incorporated by reference for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in this invention.

REFERENCE TO SUBMISSION OF A SEQUENCE LISTING

This application includes a Sequence Listing as a text file named "77429-1056139_SEQ" created Jul. 17, 2017 and containing 148,450 bytes. The material contained in this text file is incorporated by reference in its entirety for all purposes.

BACKGROUND OF THE INVENTION

Grasses constitute about 20% of natural land cover (Kellogg, 2001) and the majority of cultivated biomass (57%) that can be sustainably produced in the U.S. (US-DOE, 2011). Rice straw, for example, represents approximately 23% of all agricultural waste, globally (Lal, 2005). The inefficiency of deconstructing cell walls into their component sugars represents a key limitation for production of biofuels from biomass via biological conversion (Lynd et al., 2008). On the other hand, root and leaf litter composition significantly affects soil carbon storage (Zhou et al., 2012). The cell wall components of whole grains also have beneficial effects in human health and various impacts on food processing (Fincher, 2009). For these reasons, grass cell wall properties critically impact unmanaged and managed ecosystems and economic uses.

In contrast to the cell walls of dicotyledenous plants (type I), cell walls of grasses and other Commelinoid monocots (type II) consist of up to 40% dry weight of the polysaccharide xylan, even in primary walls (reviewed in: (Carpita, 1996; Vogel, 2008; Scheller and Ulvskov, 2010)). Grass xylan is substituted with arabinofuranose side chains and infrequently with glucuronic acid (Obel et al., 2006). Of apparent significance to the structure of grass cell walls, ferulic acid (FA, FIG. 1A) esterifies to a fraction of the arabinose sidechains of xylan (reviewed in (Buanafina, 2009)). Dehydrodimers of ferulate (diferulates) form through oxidative coupling likely mediated by peroxidases (Takahama and Oniki, 1994; Bunzel et al., 2008) and cross-link adjacent xylan strands to one another (Ishii, 1991; Allerdings et al., 2005). Furthermore, the observation of ether linkages between ferulate and monolignols suggests that ferulic acid on arabinoxylan may nucleate lignin polymerization (Bunzel et al., 2004). Another hydroxycinnamate, para-coumaric acid (p-CA, FIG. 1A), is also ester-linked to grass cell walls. p-Coumaryl esters are more abundant on lignin, but have also been found to be esterified to grass arabinoxylan (Mueller-Harvey et al., 1986; Ishii et al., 1990; Faulds et al., 2004; Ralph, 2010). Though p-CA is readily oxidized to its radical, p-CA dimers have not been observed (Ralph et al., 1994). Rather p-coumaryl substituents may act as "radical catalysts" rapidly passing the radical to synapyl alcohols and facilitating lignin polymerization (Takahama and Oniki, 1994; Ralph, 2010).

FA on arabinoxylan, and especially diferulates, are thought to act to strengthen primary and secondary cell walls. For example, diferulate accumulation anticorrelates with fescue leaf elongation (MacAdam and Grabber, 2002). Similarly, hydroxycinnamate amounts anticorrelate with rice internode expansion (Sasayama et al., 2011). Cell wall FA content inversely correlates with enzymatic sugar release parameters in vitro (Grabber et al., 1998; Grabber et al., 1998; Lam et al., 2003; Casler and Jung, 2006). In addition, both cell wall-associated diferulates and free and cell wall-associated FA and p-CA deter fungal pathogens and insect pests of grasses (Santiago et al., 2007; Santiago et al., 2008; Lanoue et al., 2009).

Despite their importance, the proteins that incorporate hydroxycinnamates into grass cell walls are not well-characterized. Recently, Mitchell et al. (2007) proposed that a subclade of proteins with the Pfam domain, PF02458, for which transcripts are more abundant in grasses relative to dicots, might incorporate FA into grass walls. PF02458 domain-containing proteins are acyl CoA-dependent acyltransferases present in plants, fungi, and a few bacteria. In plants, these enzymes have been named BAHD acyltransferase, based on the first biochemically characterized family members. They catalyze the addition of an acyl group from the thioester of coenzyme A primarily to oxygen nucleophiles of diverse acceptor molecules in plant secondary metabolism (reviewed in: (D'Auria, 2006)).

There are over 50 BAHD members in most sequenced vascular plants (Table I). The BAHD enzymes group robustly into five clades (D'Auria, 2006), though more recently subclades have been proposed (Tuominen et al., 2011). Several characterized members use hydroxycinnamoyl-CoAs as substrates, including the hydroxycinnamoyl-CoA:shikimate/quinate hydroxycinnamoyltransferase (HCT) involved in synthesis of lignin precursors (Hoffmann et al., 2003). Other recent reports have described suberin and cutin feruloyl transferases from *Arabidopsis thaliana* that act to transfer hydroxycinnamoyl-CoA ω-hydroxy fatty acids acyl acceptors (Molina et al., 2009; Rautengarten et al., 2012). Of importance for the possibility that the BAHD acyltransferase subclade identified by Mitchell, hereafter the "Mitchell clade", might be involved in arabinoxylan modification, other BAHD enzymes catalyze the addition of esters to sugar acceptors, such as in anthocyanin biosynthesis (Unno et al., 2007). Indeed, Piston et al. found that rice plants simultaneously engineered with reduced expression of four genes from this clade show a ~20% reduction in FA in young leaves (Piston et al., 2010). Furthermore, Withers et al. have recently described the biochemical characterization of one of the members of the "Mitchell clade", PMT or here called OsAT4, which possesses p-coumaryl-CoA:monolignol aclytransferase activity (Withers et al., 2012).

There is a need to increase the digestibility of grass plants. This invention addresses that need.

BRIEF SUMMARY OF THE INVENTION

The invention is based, in part, on the discovery that the "Mitchell clade" of BAHD acyltrasferases is expanded and diverged in grasses relative to dicots and more primitive plants. The invention is further based, in part, on the discovery that mutants in four of these genes have altered cell wall hydroxycinnamate content. Further, manipulating expression of these genes, e.g., overexpression AT10, AT15, AT7, and/or AT5; or decreasing expression of AT 5, increases arabinoxylan-associated ester-linked p-CA while simultaneously decreasing arabinoxylan-associated FA. Thus, in some aspects, the invention provides methods for engineering grass plants to reduce FA content and increase saccharification, recombinant plants produced by such engineering and methods of using the plants for improved biofuel and feed production.

In one aspect, the invention provides a method of engineering a plant to decrease the ferulic acid content in a plant, the method comprising: introducing an expression cassette into the plant, wherein the expression cassette comprises a polynucleotide encoding an AT10, AT7, AT15, or AT5 acyltransferase wherein the acyltranferase has at least 70% identity to a sequence selected from SEQ ID NO:2, SEQ ID NO:4, SEQ ID NO:6, or SEQ ID NO:8, and culturing the plant under conditions in which the acyltransferase is expressed. In some embodiments, the polynucleotide is operably linked to a promoter endogenous to the plant. In some embodiments, the expression cassette comprises a promoter to which the polynucleotide is operably linked. In some embodiments, the promoter is a tissue-specific promoter, e.g., a promoter that drives expression in cell wall. In some embodiments, the polynucleotide has at least 70% identity to SEQ ID NO:1, SEQ ID NO:3, SEQ ID NO:5, or SEQ ID NO:7.

In a further aspect, the invention provides a method of engineering a plant to decrease the ferulic acid content in a plant, the method comprising: modifying the plant to decrease expression of an AT5 polypeptide having at least 70% identity to SEQ ID NO:8.

In an additional aspect, the invention provides a grass plant, e.g., rice, corn, switchgrass, sorghum, millet, miscanthus, sugarcane, alfalfa, wheat, soy, rye, barley, turfgrass, hemp, bamboo, rape, sunflower, or brachypodium, genetically modified to over express AT10 AT15, AT7, and/or AT5. In some embodiments, a plant engineered in accordance with the invention, or progeny of said plant, comprises a polynucleotide encoding an AT10, AT15, AT7, or AT5 operably linked to a heterologous promoter. In some embodiments, the plant comprises a heterologous polynucleotide encoding an AT10, AT15, AT7, or AT5 protein.

In another aspect, the invention provides a plant, e.g., a grass plant, comprising a polynucleotide AT5 inhibitor that inhibits expression of a gene encoding AT5.

In a further aspect, the invention provides biomass comprising a plant or a part of a plant genetically modified as described herein to overexpress AT10, AT15, AT7, or AT5; or to disrupt AT5 expression. The invention additionally provides a method of obtaining an increased amount of soluble sugars from a plant in a saccharification reaction, the method comprising subjecting the plant biomass a saccharification reaction, thereby increasing the amount of soluble sugars that can be obtained from the plant as compared to a wild-type plant

BRIEF DESCRIPTION OF THE DRAWINGS

(FIG. 1A) Structures of relevant hydroxycinnamic acids. (FIG. 1B) Inferred Bayesian phylogeny of the rice "Mitchell Clade" BAHD acyl CoA-utilizing enzymes that includes the following: the rice acyltransferases (OsAT); the *Arabidopsis* gene, AT3G62160, that allowed this clade to be identified by Mitchell (2007); biochemically characterized BAHD-IV and BAHD-III proteins as an outgroup (ACT and VAAT, refs); *Arabidopsis* proteins that use hydroxycinnamoyl-CoA adducts (HCT and SFT) as substrates; and the rice genes that cluster with the *Arabidopsis* HCT (HCT-like). Proteins are identified by the locus ID that encodes them or their Genbank ID, followed by their designated abbreviations. Clade credibility values are 100 unless shown. The two major acyltransferase groups are designated clade i and ii. Color intensity of the circles indicates the level of RNA expression in terms of counts of Sanger ESTs and representation in massively parallel signature sequences (MPSS) data.

(FIG. 2A) Average ferulic acid content from an alcohol insoluble residue (AIR) preparation. (FIG. 2B) para-Coumaric acid content from AIR. (FIG. 2C) The ratio of ferulic acid (FA) to p-coumaric acid (p-CA), which is not subject to weighing errors. Error bars indicate standard deviations, 2 to 3 plants for each genotype were measured independently. Data are for homozygous negative segregant plants (solid bars) and homozygous mutant plants (hashed or striped bars). Light grey and cross-hatching indicate values for the leaf blade and dark red and horizontal stripes for the leaf sheath. Each plant line is designated by the repository ID and the putative target gene. The first three samples (2A-20021, 2A-40095, and 4A-03423) are from a side tiller harvested 7-weeks after transplanting to the greenhouse, which can be compared to indicate variation at this stage in hydroxycinnamic acid content. The last two, 1B-00523 and 5A-00394, were harvested 10-weeks after transplanting. A line putatively targeting a rice extosin, 5A-00394, demonstrates that heightened HCA levels are typical in older adult plants relative to younger adult plants.

(FIG. 3B) Average relative gene expression determined via qPCR shows that among genes within 20 kb of the insertion site only acyltransferase expression is altered significantly in young leaves of homozygous plants with the T-DNA insertion (hashed) compared with negative segregants (solid). The observed minor variations in other nearby genes were not consistent among the 3 biological replicates assayed (not shown). Error bars represent the standard deviation of 3-4 biological replicates. Genes with significantly higher expression (p<0.01, unpaired, 2-tailed, Student's t-test) are marked with an asterisk.

FIGS. 4A-4C. (FIG. 4A) OsAT10-D1 plants (4A-03423.5 progeny) are not significantly different in size compared with the negative segregant, wild type (4A-03423.1 progeny) at senescence, 7 months after planting. (FIG. 4B) dry biomass and (FIG. 4C) whole plant seed at senescence for OsAT10-D1 plants. Grey bars indicate wild type (WW, 4A-03423.1 progeny), and hatched bars indicate mutant (TT, 4A-03423.5 and 4A-03423.12 progeny). N=12. Error bars represent 2*SEM. '*' indicates significant differences at p<0.05 (unpaired, 2-tailed, Student's t-test).

(FIG. 5A) Ferulic acid content. (FIG. 5B) p-Coumaric acid content. (FIG. 5C) The ratio of ferulic acid (FA) to p-coumaric acid (p-CA), which is not subject to weighing or extraction efficiency errors. (FIG. 5D) FA dimer amounts and the ratio of FA:FA Dimer for young leaf samples from FIG. 5A-C.

(FIG. 6A) qRT-PCR shows that primary transgenic (Transg) Ubi:: OsAt10 lines 4 and 5 have increased expression of OsAt10 relative to the wild type (WT) Kitaake (Kit) and line 1, which lack the transgene. Relative expression is normalized to the average of the results with WT plants. (FIG. 6B) Hydroxycinnamic acid (i.e., ferulic acid, p-coumaric acid, and the sum of ferulic acid dimer peaks) content of a young leaf from wild type and primary transgenic plants. (FIG. 6C) FA:p-CA ratio, but not the FA:FA dimer ratio is altered in the OsAt10 over expression lines.

(FIG. 7A) Ferulic acid content in AIR. (FIG. 7B) p-Coumaric acid content in AIR. (FIG. 7C) The ratio of ferulic acid to p-coumaric acid.

(FIG. 8A) Liquid chromatography-mass spectrometry shows the total ion abundances in the ethyl acetate extracts for (a) wild type and (b) mutant after 50 mM TFA and 2 M NaOH and (c) wild type and (d) mutant after 50 mM TFA treatment only. Labeled peaks were consistent both with standards, when available, and with mass spectra. trans-Cinnamate was added as an extraction control. (FIG. 8B) The major ion in the mass spectrum for unknown peak 1 is consistent with a para-coumarylated five-carbon sugar. (FIG. 8C) The major ion in the mass spectrum for unknown peak 2 is consistent with a feruloylated five-carbon sugar.

(FIG. 9A) Mass analysis shows significant increases in glucose both after trifluoroacetate (TFA) and after additional treatment with sulfuric acid (TFA+H2SO4), as well as with the sum of the two treatments. (FIG. 9B) Analysis of the molecular fraction (mol %) of monomeric sugars released by TFA from various biomass fractions shows significant increases in mutant glucose and concomitant decreases in xylose, arabinose, and other sugars.

(FIG. 10A) First two components for total biomass (negative in PC1) and AIR (positive in PC1) for 4A-03423.1 pool (WT, diamonds and squares) and 4A-03423.1 pool (Mutant, triangles and X's). (FIG. 10B) Loadings plot for PC2 of A. The mass to charge ratios of the four most differentially identified ions are shown the ions that are overrepresented in mutant tissue are 120 (4-vinyl phenol or 2,3-Dihydrobenzofuran), 91 (fragment of 2,3-Dihydrobenzofuran and most phenols) and 94 (phenol). The ion that is underrepresented in the mutants is 150 (coumaryl alcohol/coniferyl alcohol). (FIG. 10C) For samples consisting of the residue remaining after 2 N NaOH extraction, PCA poorly distinguishes mutant and wild type, indicating that the principle components of variation are extractable and, therefore, cannot be polymeric lignin. Symbols are as in (FIG. 10A).

(FIG. 11A) An enzyme cocktail of cellulase and ß-glucosidase releases more sugar from destarched AIR from rice straw of OsAT10-D1 (red diamonds, 4A-03423.5 progeny) than from wild-type AIR (light grey circles, 4A-03423.1 progeny). AIR was pretreated at 100 degrees for one hour at pH 5.5 prior to addition of enzyme. Error bars show the values of the two technical replicates. (FIG. 11B) Penicillium sp. YT02 releases greater amounts of sugar from rice straw of OsAT10-D1 (diamonds, 4A-03423.5 progeny) than from wild type straw (circles, 4A-03423.1 T2 progeny) pretreated via acid-explosion. Grey symbols indicate glucose, red symbols xylose, and while symbols arabinose. Error bars show 2*SEM of five replicate cultures. (FIG. 11C) Xylanase activity (dashed lines, red symbols) in the fungal-straw slurry is enhanced in the presence of the mutant straw (diamonds) relative to the wild type straw (circles); whereas, carboxymethyl cellulase activity (solid lines, grey symbols) is unchanged. IU is nmoles of sugar per minute per mL. Error bars show 2*SEM of five replicate cultures.

FIG. 1B, are marked.

(FIG. 14A) Ferulic acid content in an alcohol insoluble residue (AIR) preparation. (FIG. 14B) p-Coumaric acid content from AIR. (FIG. 14C) The ratio of ferulic acid (FA) to p-coumaric acid (p-CA), which is not subject to weighing or extraction efficiency errors.

(FIG. 17A) Example gravimetric traces throughout heating. The first heating phase (red line, right axis) represents heating in the absence of oxygen and the second represents heating in the presence of oxygen (combustion). Data are normalized to values at 30 minutes (177° C.), which represent the initial dry weights. (FIG. 17B) Selected times report on biomass composition. WT and OsAT10-D1 are indistinguishable in terms of the mass of char (blue bars) remaining after pyrolysis at 800° C. (blue bars, t=112'), the ash content after combustion (red bars, t=250'), and, by extension, the fraction of the char that is combustible (yellow bars, difference between char and ash). This provides further evidence that there is no difference in the lignin composition or content between the two genotypes. Switchgrass, oak, and duckweed samples are shown for comparison. Values are % of the dry weight and averages were taken, when replicates were available. When shown, error bars are 2*SEM of 2-4 technical replicates.

(FIG. 19B) Average normalized gene expression determined via qPCR shows that among genes within 20 kbp of the insertion site only acyltransferase expression is altered significantly in young leaves of homozygous plants with the T-DNA insertion (hashed) compared with negative segregants (solid). Error bars represent the standard deviation of 3-4 biological replicates. Genes with significantly higher expression ($p<0.01$, Student's t-test) are marked with an asterisk.

(FIG. 20A) Ferulic acid content in an alcohol insoluble residue (AIR) preparation. (FIG. 20B) p-Coumaric acid content from AIR. (FIG. 20C) The ratio of ferulic acid (FA) to p-coumaric acid (CA), which is not subject to weighing or extraction efficiency errors. (FIG. 20D) Major FA dimer species and the ratio of FA to dimer for the Batch #1 expanded leaf samples.

FIGS. 21A-21C. Alignment of illustrative AT10 polypeptide sequences. (SEQ ID NOS:2 and 9-15)

FIGS. 22A-22C. Alignment of illustrative AT15 polypeptide sequences. (SEQ ID NOS:16, 17, 4, and 18-22)

FIGS. 23A-23E. Alignment of illustrative AT7 polypeptide sequences. (SEQ ID NOS:23, 24, 6, and 25-32)

FIGS. 24A-24D. Alignment of illustrative AT5 polypeptide sequences. (SEQ ID NOS:33-42)

(FIG. 25A) Representation of the portion of the rice chromosomes near the T-DNA insertion sites. Exons are represented by wide bars with the direction of transcription indicated by arrows. The insertion site is represented by the triangle, with the left border, nearest the transcriptional enhancer elements, represented by 'U. cDNA Regions targeted for amplification in qPCR are depicted as black bands. RT stands for retrotransposon and hypoth indicates hypothetical. (FIG. 25B) Average normalized gene expression determined via qPCR shows that among genes within 20 kbp of the insertion site only acyltransferase expression is altered significantly in young leaves of homozygous T2 plants with the T-DNA insertion (hashed) compared with negative segregants (solid). The observed minor variations in other nearby genes were not consistent among the 3 biological replicates assayed (not shown). Only 1 of 3 biological replicates for 0505g19920 in the absence of the insert gave a signal distinguishable from background, consistent with that locus' tentative annotation and lack of gene expression evidence. Error bars represent the standard deviation of 3-4 biological replicates. Genes with significantly higher expression ($p<0.01$, Student's t-test) are marked with an asterisk.

(FIG. 26A) Ferulic acid (FA) content in dsAIR. (FIG. 26B) p-Coumaric acid (pCA) content in dsAIR.

FIG. 27 provides an amino acid sequence alignment between AsFMT (14679; SEQ ID NO:102) and OsAT5 (14681; SEQ ID NO:8) run in NCBI with the CLUSTALW algorithm. Sequence identity is only 18% and similarity is 30%.

FIG. 29 provides a table showing a substrate specificity matrix. NA: No activity; $^1$Detected product with same retention time as ferulic acid adduct.

DETAILED DESCRIPTION OF THE INVENTION

I. Definitions

Figure 21B:
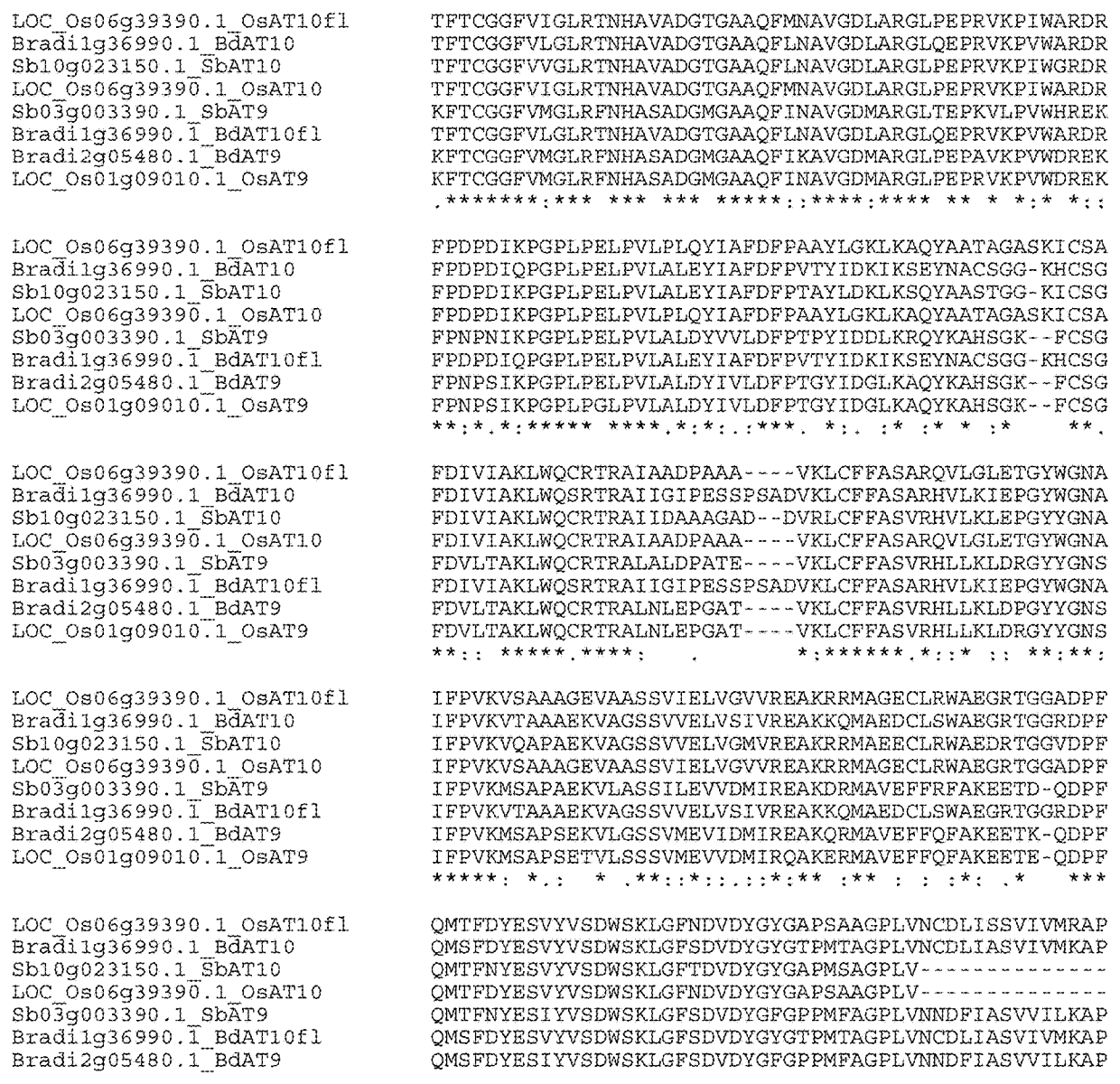
Figures 1A, 1B:
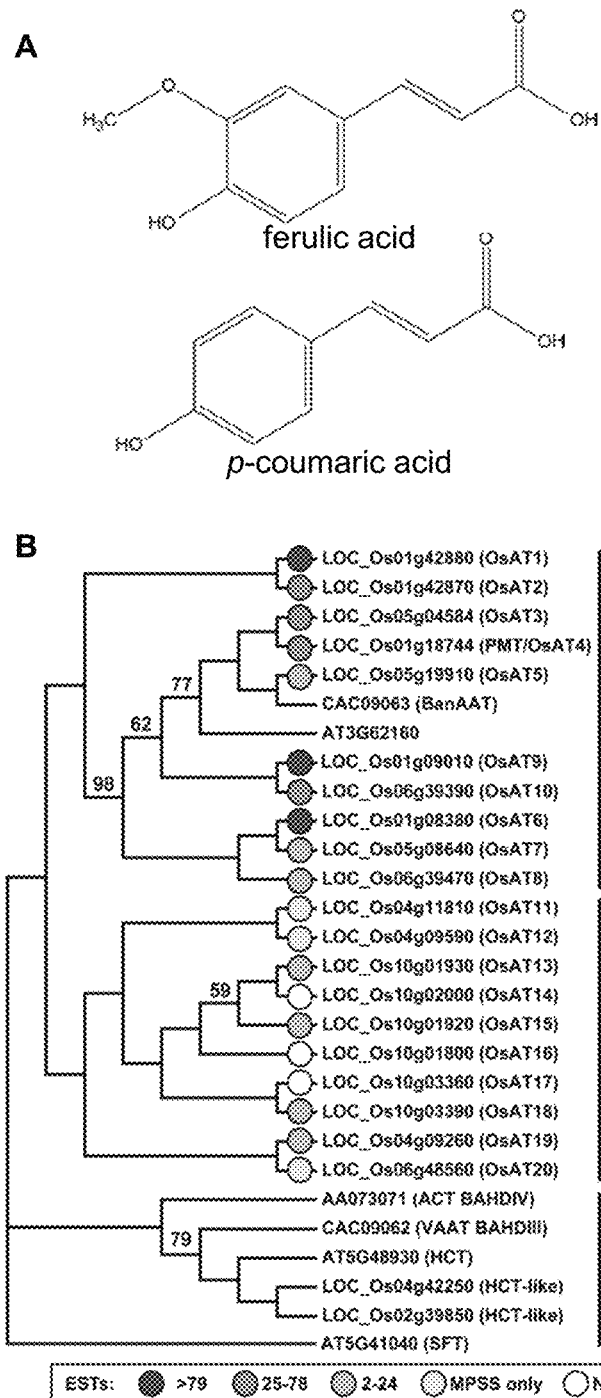
FIGS. 1A-1B.

As used herein, the term "AT10 acyl transferase" refers to a CoA p-coumaryl transferase that functions in the modification of grass arabinoxylan. The term encompasses variants and interspecies homologs to the specific polypeptides described herein. A nucleic acid that encodes an AT10 acyl transferase refers to a gene, pre-mRNA, mRNA, and the like, including nucleic acids encoding polymorphic variants, alleles, mutants, and interspecies homologs of the particular amino acid sequences described herein. Thus, in some embodiments, an At10 acyl transferase gene encodes a polypeptide having an amino acid sequence that has at least 70%, 75%, 80%, 85%, 90%, preferably 91%, 92%, 93%, 94%, 95%, 96%, 97%, 98% or 99% or greater, amino acid sequence identity, preferably over a region of at least about 25, 50, 100, 200 or more amino acids, or over the length of the entire polypeptide, to an amino acid sequence of SEQ ID NO:2; or to amino acids 4 to 434 of SEQ ID NO:2; or to any one of the AT10 amino acid sequences shown in FIGS. 21A-21C. Examples of AT 10 genes and the proteins encoded by the genes are shown in FIGS. 21A-21C.

As used herein, the term "AT15 acyl transferase" refers to a CoA feruloyl transferase that functions in the modification of a molecule that effects the amount of ferulic acid incorporated into grass cell wall. The term encompasses variants and interspecies homologs to the specific polypeptides described herein. A nucleic acid that encodes an AT15 acyl transferase refers to a gene, pre-mRNA, mRNA, and the like, including nucleic acids encoding polymorphic variants, alleles, mutants, and interspecies homologs of the particular amino acid sequences described herein. Thus, in some embodiments, an AT15 acyl transferase encodes a polypeptide having an amino acid sequence that has at least 70%, typically at least 75%, 80%, 85%, 90%, preferably 91%, 92%, 93%, 94%, 95%, 96%, 97%, 98% or 99% or greater, amino acid sequence identity, preferably over a region of at least about 25, 50, 100, 200 or more amino acids, or over the length of the entire polypeptide, to an amino acid sequence of SEQ ID NO:4, or to amino acid 5 to 429 of SEQ ID NO:4, or to any one of the AT15 amino acid sequences shown in FIGS. 22A-22C. Examples of AT15 genes and the proteins encoded by the genes are shown in FIGS. 22A-22C.

As used herein, the term "AT7 acyl transferase" refers to a CoA feruloyl transferase that functions in the modification of grass cell walls. The term encompasses variants and interspecies homologs to the specific polypeptides described herein. A nucleic acid that encodes an AT7 acyl transferase refers to a gene, pre-mRNA, mRNA, and the like, including nucleic acids encoding polymorphic variants, alleles, mutants, and interspecies homologs of the particular amino acid sequences described herein. Thus, in some embodiments, an AT7 acyl transferase encodes a polypeptide having an amino acid sequence that has at least 70%, typically at least 75%, 80%, 85%, 90%, preferably 91%, 92%, 93%, 94%, 95%, 96%, 97%, 98% or 99% or greater, amino acid sequence identity, preferably over a region of at least about 25, 50, 100, 200 or more amino acids, or over the length of the entire polypeptide, to an amino acid sequence of SEQ ID NO:6 or to amino acid residues 9 to 439 of SEQ ID NO:6, or to any one of the AT7 amino acid sequences shown in FIGS. 23A-23E. Examples of AT7 genes and the proteins encoded by the genes are shown in FIGS. 23A-23E.

As used herein, the term "AT5 acyl transferase" refers to a CoA feruloyl transferase that functions in the modification of grass cell wall components. The term encompasses variants and interspecies homologs to the specific polypeptides described herein. A nucleic acid that encodes an AT5 acyl transferase refers to a gene, pre-mRNA, mRNA, and the like, including nucleic acids encoding polymorphic variants, alleles, mutants, and interspecies homologs of the particular amino acid sequences described herein. Thus, in some embodiments, an AT7 acyl transferase encodes a polypeptide having an amino acid sequence that has at least 60%, 65%, 70%, 75%, 80%, 85%, 90%, preferably 91%, 92%, 93%, 94%, 95%, 96%, 97%, 98% or 99% or greater, amino acid sequence identity, preferably over a region of at least about 25, 50, 100, 200 or more amino acids, or over the length of the entire polypeptide, to an amino acid sequence of SEQ ID NO:8, or to amino acids 5 to 429 of SEQ ID NO:8, or to any one of the AT5 amino acid sequences shown in FIGS. 24A-24D. Examples of AT5 genes and the proteins encoded by the genes are shown in FIGS. 24A-24D.

The terms "increased level of activity," or "increased activity" refer interchangeably to an increase in the amount of activity of an AT10, AT15, AT7, or AT5 acyltransferase protein in a grass plant engineered to increase expression of the acyltransferase compared to the amount of activity in a wild-type (i.e., naturally occurring) plant. In some embodiments, increased activity results from increased expression levels. An increased level of activity or increased level of expression can be an increase in the amount of activity or expression of at least 10%, 20%, 30%, 40%, 50%, 60%, 70%, 80%, or 90% or greater, compared to a wildtype plant. In some embodiments, the increased acyltransferase activity or expression is localized to one or more tissues of the engineered plant, such as cell walls and/or leaves. Increased expression or activity of the acyltransferase gene or protein can be assessed by any number of assays, including, but not limited to, measuring the level of RNA encoded by the AT10, AT15, AT7, or AT5 acyltransferase gene, the level of AT10, AT15, AT7, or AT5 protein, the level of AT10, AT15, AT7, or AT5 enzymatic activity, or by measuring the cell wall ferulic acid and optionally, p-coumaric acid content in comparison to the amount in a wild-type plant.

The terms "reduced level of activity," "reduced activity" and "decreased activity" refer interchangeably to a reduction in the amount of activity of AT5 protein in a plant engineered to decrease AT5 compared to the amount of activity in a wild-type (i.e., naturally occurring) plant. In some embodiments, reduced activity results from reduced expression levels. A reduced level of activity or a reduced level of expression can be a reduction in the amount of activity or expression of AT5 of at least 10%, 20%, 30%, 40%, 50%, 60%, 70%, 80%, or 90% or greater. In some embodiments, the reduced level of activity or reduced level of expression occurs, throughout all the tissues of the engineered plant. In some embodiments, the reduction in the amount of activity or expression is localized to one or more tissues of the engineered plant, such as the cell wall. In some embodiments, the AT5 is not reduced in amount, but is modified in amino acid sequence so that the enzymatic activity is reduced directly or indirectly. Decreased expression or activity of an AT5 gene or protein can be assessed by any number of assays, including, but not limited to, measuring the level of RNA encoded by the AT5 gene, the level of AT5 protein, the level of AT5 enzymatic activity, or by measuring the cell wall ferulic acid and/or p-coumaric acid content.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, an AT10 polypeptide may have a sequence that is at least 70%, 75%, 80%, 85%, 90%, 91%, 92%, 93%, 94%, 95%, 96%, 97%, 98%, or 99% identical to a sequence of SEQ ID NO:2.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular plants species, but also encompasses a promoter from a corresponding gene in other plant species.

A "constitutive promoter" in the context of this invention refers to a promoter that is capable of initiating transcription in nearly all cell types, whereas a "cell type-specific promoter" or "tissue-specific promoter" initiates transcription only in one or a few particular cell types or groups of cells forming a tissue. In some embodiments, a promoter is tissue-specific if the transcription levels initiated by the promoter in the cell wall are at least 2-fold, 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in non-cell wall tissues A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a AT10 protein operably linked to a heterologous promoter. In some embodiments, an expression cassette comprises a polynucleotide sequence encoding a AT10 protein that is targeted to a position in a plant genome such that expression of the polynucleotide sequence is driven by a promoter that is present in the plant The term "plant" as used herein can refer to a whole plant or part of a plant, e.g., seeds, and includes plants of a variety of ploidy levels, including aneuploid, polyploid, diploid and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, bryophytes, and multicellular algae.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The term "decreased ferulic acid content" in the context of this invention refers to a decreased amount of ferulic acid present in cell wall or leaf in an engineered plant of the present invention as compared to a wild-type (i.e., naturally occurring) plant. In the current invention, ferulic acid is typically considered to be decreased when the amount of ferulic acid in the cell wall or leaf is decreased by at least 10%, at least 20, 30%, 40%, 50%, 60%, 70%, 80%, 90% or more relative to the amount of the ferulic acid in the cell wall or leaf in a wild-type plant. Ferulic acid content can be assessed using any method known in the art.

The term "decreased ferulic acid content" also encompasses embodiments where the ratio of ferulic acid to p-coumaric acid is decreased relative to a wild type plant. Thus, in some embodiments, the amount of ferulic acid may be the same as a wild-type plant, but relative to the to p-coumaric acid content, may be increased, thus decreasing the ration of ferulic acid to ferulic acid to p-coumaric acid when compared to a wildtype plant. In the current invention, the ratio of ferulic acid to p-coumaric acid is typically considered to be decreased when the ratio in the cell wall or leaf is decreased by at least 10%, at least 20, 30%, 40%, 50%, 60%, 70%, 80%, 90% or more relative to the ratio of the amount of the ferulic acid in the cell wall or leaf in a wild-type plant.

The term "saccharification reaction" refers to a process of converting biomass, usually cellulosic or lignocellulosic biomass, into monomeric sugars, such as glucose and xylose.

The term "soluble sugar" refers to monomeric, dimeric, or trimeric sugar that is produced from the saccharification of biomass.

The term "increased amount," when referring to an amount of sugar or soluble sugar obtained from an engineered plant of the present invention, refers to an increase in the amount or yield of sugar that is obtained from saccharification of biomass per amount of starting material, in comparison to corresponding biomass from a wild-type (i.e., naturally occurring) plant. In the context of the present invention, "corresponding biomass from a wild-type plant" refers to plant material that is from the same part of the plant as the biomass from a plant engineered to have modified hydroxycinnamic acid levels. As understood in the art, increased amount or increased yield is based upon comparisons of the same amount of corresponding plant material.

The term "conversion reaction," as used herein, refers to a reaction that converts biomass into a form of bioenergy. Examples of conversion reactions include, but are not limited to, combustion (burning), gasification, pyrolysis, and polysaccharide hydrolysis (enzymatic or chemical).

The term "increased production," when referring to an amount of bioenergy production obtained from an engineered plant of the present invention, refers to an increased amount of bioenergy that is produced from subjecting biomass from an engineered plant to a conversion reaction (e.g., combustion, gasification, pyrolysis, or polysaccharide hydrolysis) as compared to the amount of bioenergy that is produced from corresponding biomass from a wild-type (i.e., naturally occurring) plant.

II. Introduction

The invention relates to acyltransferases that modify the hydroxycinnamic acid content in grass plant cell walls. These acyltranferases include AT10, AT15, AT7, and AT5. Plants, e.g., grasses, that are modified to overexpress AT10, AT15, and AT7; and/or are modified to decrease expression of AT5 have reduced ferulic acid content and accordingly, provide an increased yield, relative to a wild-type plant, in obtaining sugars from plant wall material. In some embodiments, plants, e.g., grass plants, may be modified to overexpress AT5, resulting in an increase of feruloyl esters. Not to be bound by theory, depending on the cell wall precursor that is modified, increasing the level of feruloyl esters present may introduce relatively easily broken bonds that reduce cell wall recalcitrance. For example, increasing ester linkages within the lignin polymer may improve the solubilization of lignin under mild alkaline conditions compared to native lignin. Accordingly, in this embodiment, increasing ferulic acid content of a plant, such as a grass plan, may provide an increased yield, relative to a wild-type plant in which AT5 is not modified, in obtaining sugars from plant wall material.

Plants can be engineered to overexpress an acyltransferase by genetically modifying a plant to overexpress one or more of AT5, AT10, AT15, or AT7 acyltransferase genes as described herein. In some embodiments, overexpresson is targeted to various tissues, e.g., cell wall and/or leaf, using a tissue-specific promoter. An example of a method for fine-tuning AT5, AT10, AT15, or AT7 expression to increase expression in the cell wall is taught in PCT/US2012/023182, which is incorporated by reference. Similarly, ferulic acid content in a plant, e.g., a grass plant, can be increased by genetically modifying a cell to decrease expression of AT5 as described herein.

In some embodiments, a plant may be genetically modified, to disrupt expression of an endogenous AT10, AT15, AT7, and/or AT5 gene and then further modified to express the AT10, AT15, AT7, and/or AT5 gene in a tissue of interest, e.g., cell wall and/or leaf.

The invention additionally provides methods of generating genetically modified plants that overexpress or have reduced levels of AT10, AT15, AT7, and/or AT5 acyltransferase activity and methods of using such plants, e.g., as biomass for degradation reactions to produce soluble sugars or as forage plants.

As used herein in describing nucleic acids and polypeptides of the invention, an "AT" nucleic acid or polypeptides refers to an AT10, AT15, AT7, or AT5 polynucleotide or polypeptide.

Acyltransferase Nucleic Acid and Polypeptide Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009).

AT10

AT10 nucleic acid and polypeptide sequences suitable for use in the invention include AT10 nucleic acid sequences that encode a plant AT10 polypeptide as illustrated by the sequences shown in FIGS. 21A-21C, or a substantially identical variant. Such a substantially identical variant typically has at least 70%, or at least 75%, 80%, 85%, 90%, or 95% identity to SEQ ID NO:2. In some embodiments, the variant has at least 70%, or at least 75%, 80%, 85%, 90%, or 95% identity to an AT10 sequence shown in FIGS. 21A-21C. In some embodiments, a nucleic acid that encodes an AT10 polypeptide of the invention has at least 60%, often at least 70%, or at least 75%, 80%, 85%, or 90% identity to the nucleic acid sequence of SEQ ID NO:1. The Pfam domain of SEQ ID NO:2 corresponds to amino acids 4 to 434 of SEQ ID NO:2. AT10 proteins are additionally characterized by the presence of a motif HXXXD at positions 182-186 of SEQ ID NO:2.

A comparison of AT10 sequences is provided in FIGS. 21A-21C. As shown in FIGS. 21A-21C, there are highly conserved regions of the polypeptide sequences. These conserved sequences are not strictly conserved 100% across the various plant protein sequences. For example, one of skill can obtain a variant by using the sequence alignments to identify residues within the conserved sequences that would be expected to retain AT10 function as well as residues outside of the conserved regions that would be expected to be tolerant to substitution.

AT10 activity can be assessed using any number of assays, including assays that evaluate the hydroxycinnamic acid content of cell wall and/or leaf. AT10 activity can be assessed by increasing the expression of AT10 in plant cells. Examples of assays include, but are not limited to the following illustrative assays. Activity may assayed by creation of a transgenic plant by incorporation into the plant genome of an AT10 gene that is associated with a promoter that increases AT10 expression compared to wild-type levels. Alternatively, transient expression assays, such as through infiltration or dipping of plant cells into an *Agrobacterium* solution, can be used. For both of these assays the read out is measurement of an increase in the cell wall content of p-coumaryl esters associated with cell wall matrix polysaccharide. For this assay, biomass, or a cell wall extraction thereof, is treated with 2M NaOH. The resulting supernatant, or an extract there of, can be analyzed for changes in hydroxycinnamate content via high performance liquid chromatography with UV absorbance detection or another similar method. Alternatively, an in vitro assay can be used to indicate activity of AT10 in attachment of a hydroxycinnamate (e.g., FA or pCA) onto a 5-carbon sugar. This activity can be measured again via liquid chromatography (LC)-UV detection or LC-mass spectrometry, among others

AT15

AT15 nucleic acid and polypeptide sequences suitable for use in the invention include AT15 nucleic acid sequences that encode a plant AT15 polypeptide as illustrated by the sequences shown in FIGS. 22A-22C, or a substantially identical variant. Such a variant typically has at least 75%, 80%, 85%, 90%, or 95% identity to SEQ ID NO:4. In some embodiments, the variant has at least 75%, 80%, 85%, 90%, or 95% identity to an AT15 sequence shown in FIGS. 22A-22C. In some embodiments, a nucleic acid that encodes an AT15 polypeptide of the invention has at least 60%, often at least 70%, or at least 75%, 80%, 85%, or 90% identity to SEQ ID NO:3. The Pfam domain of SEQ ID NO:4 corresponds to amino acids 5 to 411 of SEQ ID NO:4. AT15 proteins are additionally characterized by the presence of a motif, HXXXD. This motif occurs near position 164 in SEQ ID NO:4.

A comparison of AT15 sequences is provided in FIGS. 22A-22C. As shown in FIGS. 22A-22C, there are highly conserved regions of the polypeptide sequences. These conserved sequences are not strictly conserved 100% across the various plant protein sequences. For example, one of skill can obtain a variant by using the sequence alignments to identify residues within the conserved sequences that would be expected to retain AT15 function as well as residues outside of the conserved regions that would be tolerant to substitution.

AT15 activity can be assessed using any number of assays, including assays that evaluate the hydroxycinnamic acid content of cell wall and/or leaf. Examples of assays include, but are not limited to the following illustrative assays. AT15 activity can be assessed by increasing the expression of AT15 in plant cells. This can be accomplished through creation of a transgenic plant by incorporation into the plant genome of an AT15 gene that is associated with a promoter that increases AT15 expression compared to wild-type levels. Alternatively, transient expression assays, such as through infiltration or dipping of plant cells into an *Agrobacterium* solution, can be used. For both of these assays the read out is measurement of an decrease in the cell wall content of hydroxycinnamyl esters associated with cell wall matrix polysaccharide. For this assay, biomass, or a cell wall extraction thereof, is treated with 2M NaOH. The resulting supernatant, or an extract thereof, can be analyzed for changes in hydroxycinnamate content via high performance liquid chromatography with UV absorbance detection or another similar method.

AT7

AT7 nucleic acid and polypeptide sequences suitable for use in the invention include AT7 nucleic acid sequences that encode a plant AT7 polypeptide as illustrated by the sequences shown in FIGS. 23A-23E, or a substantially identical variant. Such a variant typically has at least 70%, or at least 75%, 80%, 85%, 90%, or 95% identity to SEQ ID NO:6. In some embodiments, the variant has at least 75%, 80%, 85%, 90% or 95% identity to identity to an AT7 sequence shown in FIGS. 23A-23E. In some embodiments, a nucleic acid that encodes an AT7 polypeptide of the invention has at least 60%, often at least 70%, or at least 75%, 80%, 85%, or 90% identity to SEQ ID NO:5. The Pfam domain of SEQ ID NO:6 corresponds to amino acids 9 to 439 of SEQ ID NO:6. AT7 polypeptides are additionally characterized by the presence of a motif HXXXD. This motif occurs near position 176 in SEQ ID NO:6.

A comparison of AT7 sequences is provided in FIGS. 23A-23E. As shown in FIGS. 23A-23E, there are highly conserved regions of the polypeptide sequences. These conserved sequences are not strictly conserved 100% across the various plant protein sequences. For example, one of skill can obtain a variant by using the sequence alignments to identify residues within the conserved sequences that would be expected to retain AT7 function as well as residues outside of the conserved regions that would be tolerant to substitution.

AT7 activity can be assessed using any number of assays, including assays that evaluate the hydroxycinnamic acid content of cell wall and/or leaf. Examples of assays include, but are not limited to the following illustrative assays. AT7 activity can be assessed by increasing the expression of AT7 in plant cells. This can be accomplished through creation of a transgenic plant by incorporation into the plant genome of an AT7 gene that is associated with a promoter that increases AT7 expression compared to wild-type levels. Alternatively, transient expression assays, such as through infiltration or dipping of plant cells into an *Agrobacterium* solution, can be used. For both of these assays the read out is measurement of an decrease in the cell wall content of hydroxycinnamyl esters associated with cell wall matrix polysaccharide. For this assay, biomass, or a cell wall extraction thereof, is treated with 2M NaOH. The resulting supernatant, or an extract thereof, can be analyzed for changes in hydroxycinnamate content via high performance liquid chromatography with UV absorbance detection or another similar method.

AT5

AT5 nucleic acid and polypeptide sequences that are targeted for disruption in accordance with the invention include AT5 nucleic acid sequences that encode a plant AT5 polypeptide as illustrated by the sequences shown in FIGS. 24A-24D, or a substantially identical variant. Such a variant typically has at least 60% identity, or at least 65%, 70%, 75%, 80%, 85%, 90%, or 95% identity to SEQ ID NO:8. In some embodiments, the variant has at least 70%, 75%, 80%, 85%, 90% or 95% identity to identity to an AT5 sequence shown in FIGS. 24A-24D. In some embodiments, a nucleic acid that encodes an AT5 polypeptide of the invention has at least 60%, often at least 70%, or at least 75%, 80%, 85%, or 90% identity to SEQ ID NO:7. The Pfam domain of SEQ ID NO:8 corresponds to amino acids 5 to 429 of SEQ ID NO:8. AT5 polypeptides are additionally characterized by the presence of a motif, HXXXD. This motif occurs near position 170 in SEQ ID NO:8.

A comparison of AT5 amino acid sequences is provided in FIGS. 24A-24D. As shown in FIGS. 24A-24D, there are highly conserved regions of the polypeptide sequences. These conserved sequences are not strictly conserved 100% across the various plant protein sequences. For example, one of skill can obtain a nucleic acid encoding a variant polypeptide by using the sequence alignments to identify residues within the conserved sequences that would be expected to retain AT5 function as well as residues outside of the conserved regions that would be tolerant to substitution.

AT5 activity can be assessed using any number of assays, including assays that evaluate the hydroxycinnamic acid content of cell wall and/or leaf. Examples of assays include, but are not limited to the following illustrative assays. AT5 activity can be assessed by increasing the expression of AT5 in plant cells. This can be accomplished through creation of a transgenic plant by incorporation into the plant genome of an AT5 gene that is associated with a promoter that increases AT5 expression compared to wild-type levels. Alternatively, transient expression assays, such as through infiltration or dipping of plant cells into an *Agrobacterium* solution, can be used. For both of these assays the read out is measurement of an decrease in the cell wall content of hydroxycinnamyl esters associated with cell wall matrix polysaccharide. For this assay, biomass, or a cell wall extraction thereof, is treated with 2M NaOH. The resulting supernatant, or an extract thereof, can be analyzed for changes in hydroxycinnamate content via high performance liquid chromatography with UV absorbance detection or another similar method.

Isolation or generation AT polynucleotide sequences can be accomplished by a number of techniques. Cloning and expression of AT genes in accordance with the invention are generally discussed in the context of AT10 genes. One of skill understands that these techniques can be employed to overexpress AT7, AT15, or AT5 genes. Recombinant expression techniques can also be used to disrupt AT5 expression. In some embodiments, oligonucleotide probes based on the sequences disclosed here can be used to identify the desired polynucleotide in a cDNA or genomic DNA library from a desired plant species. Probes may be used to hybridize with genomic DNA or cDNA sequences to isolate homologous genes in the same or different plant species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a AT10 gene from plant cells such as moss or spikemoss, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990).

AT10, AT15, AT7, and AT5 nucleic acid sequences for use in the invention includes genes and gene products identified and characterized by techniques such as hybridization and/or sequence analysis using exemplary nucleic acid sequences, e.g., SEQ ID NO:1, SEQ ID NO:3, SEQ ID NO:5, and SEQ ID NO:7.

Preparation of Recombinant Vectors

To use isolated sequences in the above techniques, recombinant DNA vectors suitable for transformation of plant cells, such as grass crop plant cells, are prepared.

Techniques for transformation are well known and described in the technical and scientific literature. For example, a DNA sequence encoding an AT10, AT7, AT15, or AT5 polypeptide (described in further detail below), can be combined with transcriptional and other regulatory sequences which will direct the transcription of the sequence from the gene in the intended cells, e.g., grass or other crop plant cells. In some embodiments, an expression vector that comprises an expression cassette that comprises the AT10, AT7, AT15, or AT5 gene further comprises a promoter operably linked to the AT10, AT7, AT15, or AT5 gene. In other embodiments, a promoter and/or other regulatory elements that direct transcription of the AT10, AT7, AT15, or AT5 gene are endogenous to the plant and an expression cassette comprising the AT10, AT7, AT15, or AT5 gene is introduced, e.g., by homologous recombination, such that the heterologous AT10, AT7, AT15, or AT5 gene is operably linked to an endogenous promoter and is expression driven by the endogenous promoter.

Regulatory sequences include promoters, which may be either constitutive or inducible, or tissue-specific.

In some embodiments, recombinant vectors may be prepared to disrupt gene expression, e.g., AT5 gene expression. For example, such a recombinant vector may encode an RNA that disrupts expression of an endogenous gene. Such embodiments are described in greater detail in the section below relating to engineering of plants to decrease expression of an AT gene of interest.

Tissue-Specific Promoters

In some embodiments, a plant promoter to direct expression of an AT gene, e.g., AT10, AT7, AT15, or AT5 gene. in a specific tissue is employed (tissue-specific promoters). Tissue-specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, cell walls, including e.g., roots or leaves. A variety of promoters specifically active in vegetative tissues, such as leaves, stems, roots and tubers are known. For example, promoters controlling patatin, the major storage protein of the potato tuber, can be used (see, e.g., Kim, *Plant Mol. Biol.* 26:603-615, 1994; Martin, *Plant J.* 11:53-62, 1997). The ORF13 promoter from *Agrobacterium rhizogenes* that exhibits high activity in roots can also be used (Hansen, Mol. Gen. Genet. 254:337-343, 1997). Other useful vegetative tissue-specific promoters include: the tarin promoter of the gene encoding a globulin from a major taro (*Colocasia esculenta* L. Schott) corm protein family, tarin (Bezerra, *Plant Mol. Biol.* 28:137-144, 1995); the curculin promoter active during taro corm development (de Castro, *Plant Cell* 4:1549-1559, 1992) and the promoter for the tobacco root-specific gene TobRB7, whose expression is localized to root meristem and immature central cylinder regions (Yamamoto, Plant Cell 3:371-382, 1991).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier, *FEBS Lett.* 415:91-95, 1997). A ribulose bisphosphate carboxylase promoters expressed almost exclusively in mesophyll cells in leaf blades and leaf sheaths at high levels (e.g., Matsuoka, *Plant J.* 6:311-319, 1994), can be used. Another leaf-specific promoter is the light harvesting chlorophyll a/b binding protein gene promoter (see, e.g., Shiina, *Plant Physiol.* 115:477-483, 1997; Casal, *Plant Physiol.* 116:1533-1538, 1998). The *Arabidopsis thaliana* myb-related gene promoter (AtmybS) (Li, et al., *FEBS Lett.* 379:117-121 1996), is leaf-specific. The AtmybS promoter is expressed in developing leaf trichomes, stipules, and epidermal cells on the margins of young rosette and cauline leaves, and in immature seeds. AtmybS mRNA appears between fertilization and the 16 cell stage of embryo development and persists beyond the heart stage. A leaf promoter identified in maize (e.g., Busk et al., *Plant J.* 11:1285-1295, 1997) can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, (e.g., Di Laurenzio, et al., Cell 86:423-433, 1996; and, Long, et al., Nature 379:66-69, 1996); can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, Plant Cell.

7:517-527, 1995). Also useful are kn1-related genes from maize and other species which show meristem-specific expression, (see, e.g., Granger, *Plant Mol. Biol.* 31:373-378, 1996; Kerstetter, *Plant Cell* 6:1877-1887, 1994; Hake, Philos. Trans. R. Soc. Lond. B. Biol. Sci. 350:45-51, 1995). For example, the *Arabidopsis thaliana* KNAT1 promoter (see, e.g., Lincoln, *Plant Cell* 6:1859-1876, 1994) can be used.

In some embodiments, the promoter is substantially identical to the native promoter of a promoter that drives expression of a gene involved in secondary wall deposition. Examples of such promoters are promoters from IRX1, IRX3, IRX5, IRX8, IRX9, IRX14, IRX7, IRX10, GAUT13, or GAUT14 genes. Specific expression in fiber cells can be accomplished by using a promoter such as the NST1 promoter and specific expression in vessels can be accomplished by using a promoter such as VND6 or VND7. (See, e.g., PCT/US2012/023182 for illustrative promoter sequences).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Constitutive Promoters

A promoter, or an active fragment thereof, can be employed which will direct expression of a nucleic acid encoding a fusion protein of the invention, in all or most transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191, 1997); the 1'- or 2'-promoter derived from T-DNA of *Agrobacterium tumefaciens* (see, e.g., Mengiste supra (1997); O'Grady, Plant Mol. Biol. 29:99-108, 1995); the promoter of the tobacco mosaic virus; the promoter of Figwort mosaic virus (see, e.g., Maiti, *Transgenic Res.* 6:143-156, 1997); actin promoters, such as the *Arabidopsis* actin gene promoter (see, e.g., Huang, *Plant Mol. Biol.* 33:125-139, 1997); alcohol dehydrogenase (Adh) gene promoters (see, e.g., Millar, *Plant Mol. Biol.* 31:897-904, 1996); ACT11 from *Arabidopsis* (Huang et al., *Plant Mol. Biol.* 33:125-139, 1996), Cat3 from *Arabidopsis* (GenBank No. U43147, Zhong et al., *Mol. Gen. Genet.* 251:196-203, 1996), the gene encoding stearoyl-acyl carrier protein desaturase from *Brassica napus* (Genbank No. X74782, Solocombe et al., *Plant Physiol.* 104:1167-1176, 1994), GPc1 from maize (GenBank No. X15596, Martinez et al., *J. Mol. Biol.* 208:551-565, 1989), Gpc2 from maize (GenBank No. U45855, Manjunath et al., *Plant Mol. Biol.* 33:97-112, 1997), other transcription initiation regions from various plant genes known to those of skill. See also Holtorf, "Comparison of different constitutive and inducible promoters for the overexpression of transgenes in *Arabidopsis thaliana*," Plant Mol. Biol. 29:637-646, 1995).

Inducible Promoters

In some embodiments, a plant promoter may direct expression of the nucleic acids under the influence of changing environmental conditions or developmental conditions. Examples of environmental conditions that may effect transcription by inducible promoters include anaerobic conditions, elevated temperature, drought or other environmental stress, or the presence of light. Examples of developmental conditions that may effect transcription by inducible promoters include senescence and embryogenesis. Such promoters are referred to herein as "inducible" promoters. For example, the invention can incorporate drought-specific promoter such as the drought-inducible promoter of maize (Busk et al., *Plant J,* 11: 1285-95, 1997); or alternatively the cold, drought, and high salt inducible promoter from potato (Kirch *Plant Mol. Biol.* 33:897-909, 1997).

Suitable promoters responding to biotic or abiotic stress conditions include the pathogen inducible PRP1-gene promoter (Ward et al., *Plant. Mol. Biol.* 22:361-366, 1993), the heat inducible hsp80-promoter from tomato (U.S. Pat. No. 5,187,267), cold inducible alpha-amylase promoter from potato (PCT Publication No. WO 96/12814) or the wound-inducible pinII-promoter (European Patent No. 375091). For other examples of drought, cold, and salt-inducible promoters, such as the RD29A promoter, see, e.g., Yamaguchi-Shinozalei et al., *Mol. Gen. Genet.* 236:331-340, 1993 are also known.

Alternatively, plant promoters which are inducible upon exposure to plant hormones, such as auxins, may be used to express an AT10, AT7, AT15, or AT5 gene. For example, the invention can use the auxin-response elements E1 promoter fragment (AuxREs) in the soybean (*Glycine max* L.) (Liu, *Plant Physiol.* 115:397-407, 1997); the auxin-responsive *Arabidopsis* GST6 promoter (also responsive to salicylic acid and hydrogen peroxide) (Chen, Plant J. 10: 955-966, 1996); the auxin-inducible parC promoter from tobacco (Sakai, 37:906-913, 1996); a plant biotin response element (Streit, *Mol. Plant Microbe Interact.* 10:933-937, 1997); and, the promoter responsive to the stress hormone abscisic acid (Sheen, *Science* 274:1900-1902, 1996).

Plant promoters inducible upon exposure to chemicals reagents that may be applied to the plant, such as herbicides or antibiotics, are also useful for expressing an AT10, AT7, AT15, or AT5 gene in accordance with the invention. For example, the maize In2-2 promoter, activated by benzenesulfonamide herbicide safeners, can be used (De Veylder, *Plant Cell Physiol.* 38:568-577, 19997); application of different herbicide safeners induces distinct gene expression patterns, including expression in the root, hydathodes, and the shoot apical meristem. An AT10, AT7, AT15, or AT5 coding sequence can also be under the control of, e.g., a tetracycline-inducible promoter, such as described with transgenic tobacco plants containing the *Avena sativa* L. (oat) arginine decarboxylase gene (Masgrau, *Plant J.* 11:465-473, 1997); or, a salicylic acid-responsive element (Stange, *Plant J.* 11:1315-1324, 1997; Uknes et al., *Plant Cell* 5:159-169, 1993); Bi et al., *Plant J.* 8:235-245, 1995).

Examples of useful inducible regulatory elements include copper-inducible regulatory elements (Mett et al., *Proc. Natl. Acad. Sci. USA* 90:4567-4571, 1993); Furst et al., *Cell* 55:705-717, 1988); tetracycline and chlor-tetracycline-inducible regulatory elements (Gatz et al., *Plant J.* 2:397-404, 1992); Roder et al., *Mol. Gen. Genet.* 243:32-38, 1994); Gatz, *Meth. Cell Biol.* 50:411-424, 1995); ecdysone inducible regulatory elements (Christopherson et al., *Proc. Natl. Acad. Sci. USA* 89:6314-6318, 1992; Kreutzweiser et al., *Ecotoxicol. Environ. Safety* 28:14-24, 1994); heat shock inducible regulatory elements (Takahashi et al., *Plant Physiol.* 99:383-390, 1992; Yabe et al., *Plant Cell Physiol.* 35:1207-1219, 1994; Ueda et al., *Mol. Gen. Genet.* 250:533-539, 1996); and lac operon elements, which are used in combination with a constitutively expressed lac repressor to confer, for example, IPTG-inducible expression (Wilde et al., *EMBO J.* 11:1251-1259, 1992). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)).

Expression Using a Positive Feed Back Loop

In further embodiments, a plant can be engineered to overexpress AT10, AT7, AT15, or AT5 using a positive feedback loop to express AT10, AT7, AT15, or AT5 in a desired tissue. In such an embodiment, a promoter for use in an AT10, AT7, AT15, or AT5 expression construct is responsive to a transcription factor that mediates expression in the desired tissue. The AT10, AT7, AT15, or AT5 expression construct is used in a genentically modified plant comprising an expression construct encoding a transcription factor were expression is also driven by a promoter that is responsive to the transcription factor. Examples of such expression systems are provided in PCT/US2012/023182.

In some embodiments in which a positive feed back loop is employed, the plant is genetically modified to express a transcription factor that regulates the production of secondary cell wall. Examples of such transcription factors include NST1, NST2, NST3, SND2, SND3, MYB103, MBY85, MYB46, MYB83, MYB58, and MYB63 (See, e.g., Mitsuda et al., *Plant Cell* 17:2993-3006 (2005); Mitsuda et al., *Plant Cell* 19:270-80 (2007); Ohashi-Ito et al., *Plant Cell* 22:3461-73 (2010); Zhong et al., *Plant Cell* 20:2763-82 (2008); Zhong et al., *Plant Cell* 19:2776-92 (2007); Ko et al., *Plant J.* 60:649-65 (2009); and McCarthy et al., *Plant Cell Physiol.* 50:1950-64 (2009)).

Illustrative examples of gene and protein sequences and/or accession numbers for NST1, NST2, NST3, SND2, SND3, MYB103, MBY85, MYB46, MYB83, MYB58, and MYB63 are provided in PCT/US2012/023182.

In some embodiments, the polynucleotide encoding the transcription factor that regulates secondary cell wall production is operably linked to a promoter that is a downstream target of the transcription factor. Similarly, the AT10, AT7, AT15, or AT5 nucleic acid sequence is also linked to a promoter that is a downstream target of the transcription factor. The promoter may be the same promoter or different promoters. In such an embodiment, a promoter is suitable for use with the transcription factor that regulates secondary cell wall production if expression of the promoter is induced, directly or indirectly, by the transcription factor to be expressed, and if the promoter is expressed in the desired location, e.g., the stem of the plant.

In some embodiments, a native IRX1, IRX3, IRX5, IRX8, IRX9, IRX14, IRX7, or IRX10, GAUT13, or GAUT14 promoter, or active variant thereof, is employed.

Additional Embodiments for Expressing AT10, AT7, AT15, or AT5

In another embodiment, the AT10, AT7, AT15, or AT5 polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai, *Proc. Natl. Acad. Sci. USA* 92:1679-1683, 1995); the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer, *Plant Mol. Biol.* 31:1129-1139, 1996).

A vector comprising an AT10, AT7, AT15, or AT5 nucleic acid sequence will typically comprise a marker gene that confers a selectable phenotype on the cell to which it is introduced. Such markers are known. For example, the marker may encode antibiotic resistance, such as resistance to kanamycin, G418, bleomycin, hygromycin, and the like.

AT10, AT7, AT15, or AT5 nucleic acid sequences of the invention are expressed recombinantly in plant cells as described. As appreciated by one of skill in the art, expression constructs can be designed taking into account such properties as codon usage frequencies of the plant in which the AT nucleic acid is to be expressed. Codon usage frequencies can be tabulated using known methods (see, e.g., Nakamura et al. *Nucl. Acids Res.* 28:292, 2000). Codon usage frequency tables are available in the art (e.g., from the Codon Usage Database at the internet site for kazusa.or.jp/codon/.)

Additional sequence modifications may be made that are also known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence may also be modified to avoid predicted hairpin secondary mRNA structures.

Production of Transgenic Plants

As detailed herein, the present invention provides for transgenic plants comprising recombinant expression cassettes either for expressing heterologous AT10, AT7, AT15, or AT5 for overexpressing endogenous AT10, AT7, AT15, or AT5 using recombinant technology. It should be recognized that the term "transgenic plants" as used here encompasses the plant or plant cell in which the expression cassette is introduced as well as progeny of such plants or plant cells that contain the expression cassette, including the progeny that have the expression cassette stably integrated in a chromosome.

Once an expression cassette comprising a polynucleotide encoding an AT10, AT7, AT15, or AT5 polypeptide (or a polynucleotide sequence designed to suppress or inhibit expression of an AT gene, e.g., AT5, as described below) has been constructed, standard techniques may be used to introduce the polynucleotide into a plant in order to modify gene expression. See, e.g., protocols described in Ammirato et al. (1984) Handbook of Plant Cell Culture—Crop Species. Macmillan Publ. Co. Shimamoto et al. (1989) Nature 338: 274-276; Fromm et al. (1990) Bio/Technology 8:833-839; and Vasil et al. (1990) *Bio/Technology* 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175;

5,510,471; 5,750,386; 5,597,945; 5,589,615; 5,750,871; 5,268,526; 5,780,708; 5,538,880; 5,773,269; 5,736,369 and 5,610,042.

Transformed plant cells derived by any of the above transformation techniques can be cultured to regenerate a whole plant that possesses the transformed genotype and thus the desired phenotype such as enhanced drought-resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally, e.g., in Klee et al. *Ann. Rev. of Plant Phys.* 38:467-486, 1987.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In some embodiments, the plant into which the expression construct comprising a nucleic acid sequence that encodes AT10, AT7, AT15, or AT5 (or that is designed to inhibit expression of AT5) is introduced is the same species of plant from which the AT sequence, and/or the promoter driving expression of the AT sequence, is obtained. In some embodiments, the plant into which the expression construct is introduced is a different species of plant compared to the species from which the AT and/or promoter sequence was obtained.

Plants that overexpress AT10, AT7, AT15, or AT5 can be identified using any known assay, including analysis of RNA, protein, or hydroxycinnamic ester content. With respect to this aspect of the invention, the plants have altered hydroxycinnamic acid levels, e.g., decreased ferulic acid. Hydroxycinnamic ester levels can be determined directly or indirectly. An example of an assay measuring hydroxycinnamic ester levels in the cell wall is provided in the Examples section. For this assay, biomass, or a cell wall extraction thereof, is treated with 2M NaOH. The resulting supernatant, or an extract thereof, can be analyzed for changes in hydroxycinnamate content via high performance liquid chromatography with UV absorbance detection or another similar method.

Modification of Plants to Decrease AT Expression

In one aspect, the invention also provides a plant in which expression of an AT gene as described herein, e.g., an AT5 gene is inhibited, thereby resulting in modified levels of hydroxycinnamic acid in the plant. As understood in the art, in some embodiments, it may be desirable to inhibit expression of AT10, AT7, or AT15 generally in a plant and restore expression in tissue of interests, e.g., grass cell wall. Techniques described in this section with reference to inhibition of AT5 can also be used to inhibit AT10, AT7, and/or AT15, if desired.

In some embodiments, the plant is modified to have a level of AT5 activity that is reduced throughout the entire plant. In some embodiments, the plant is modified to reduce AT5 activity in a subset of cells or tissues of the plant. The genetic background of the plant can be modified according to any method known in the art, such as antisense, siRNA, microRNA, dsRNA, sense suppression, mutagenesis, or use of a dominant negative inhibition strategy. In some embodiments, the level of expression of the protein is reduced.

Gene Silencing Techniques

In some embodiments, expression of a AT5 is inhibited by an antisense oligonucleotide. In antisense technology, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of an AT5-encoding sequence can be useful for producing a plant in which expression of AT5 is inhibited. For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 20, 25, 30, 50, 100, 200, or more continuous nucleotides (up to mRNA full length) substantially identical to a AT5 mRNA, or a complement thereof, can be used.

Catalytic RNA molecules or ribozymes can also be used to inhibit expression of a gene encoding an AT5 polypeptide. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585-591 (1988).

Another method by which expression of a gene encoding an AT5 polypeptide can be inhibited is by sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes, see Napoli et al., *The Plant Cell* 2:279-289 (1990); Flavell, *Proc. Natl. Acad.*

*Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous AT5 sequence intended to be repressed. This minimal identity will typically be greater than about 65%, but a higher identity can exert a more effective repression of expression of the endogenous sequences. In some embodiments, sequences with substantially greater identity are used, e.g., at least about 80%, at least about 95%, or 100% identity are used. As with antisense regulation, further discussed below, the effect can be designed and tested to apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct Genom* 5: 240-244 (2004); Lu, et al., *Nucleic Acids Res.* 32(21):e171 (2004)).

Thus, in some embodiments, inhibition of a gene encoding an AT5 polypeptide is accomplished using RNAi techniques. For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting plants may then be screened for a phenotype associated with the target protein, for example, screening for an increase in the extractability of sugar from the plants as compared to wild-type plants, and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

Yet another way to suppress expression of an endogenous AT5 gene is by recombinant expression of a microRNA that suppresses a target (e.g., a gene encoding a lignin or xylan biosynthesis enzyme). Artificial microRNAs are single-stranded RNAs (e.g., between 18-25-mers, generally 21-mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

Another example of a method to reduce levels of AT5 employs riboswitch techniques (see, e.g., U.S. Patent Application Publication Nos. US20100286082, and US20110245326).

In some embodiments, the level of expression of AT5 is reduced by generating a plant that has a mutation in a gene encoding an AT5 enzyme. One method for abolishing or decreasing the expression of a gene encoding AT5 is by insertion mutagenesis using the T-DNA of *Agrobacterium tumefaciens*. After generating the insertion mutants, the mutants can be screened to identify those containing the insertion in the gene of interest. Mutants containing a single mutation event at the desired gene may be crossed to generate homozygous plants for the mutation (Koncz et al. (1992) Methods in *Arabidopsis* Research. World Scientific).

Alternatively, random mutagenesis approaches may be used to generate new alleles that will generate truncated or defective (non-functional or poorly active) enzymes or unstable RNA, or to disrupt or "knock-out" the expression of a gene encoding an AT5 enzyme using either chemical or insertional mutagenesis or irradiation.

Methods of Using Plants Having Modified AT10, AT15, AT7 and/or AT5 Expression

The nucleic acid constructs of the invention can be used to modulate the hydroxycinnamic acid of cell walls of essentially any plant, but in particular grass plants. The plant may be a monocotyledonous plant or a dicotyledonous plant. In some embodiments of the invention, the plant is a green field plant. In some embodiments, the plant is a gymnosperm or conifer. Thus, the invention has use over a broad range of plants, including species from the genera Asparagus, *Atropa, Avena, Brassica, Cannabis, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is corn, switchgrass, sorghum, miscanthus, sugarcane, poplar, pine, wheat, rice, soy, cotton, barley, turf grass, tobacco, potato, bamboo, rape, sugar beet, sunflower, willow, and eucalyptus. In further embodiments, the plant is reed canarygrass (*Phalaris arundinacea*), *Miscanthus×giganteus, Miscanthus* sp., sericea lespedeza (*Lespedeza cuneata*), millet, ryegrass (*Lolium multiflorum, Lolium* sp.), timothy, *Kochia (Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, or Kentucky bluegrass among others. In some embodiments, the plant is an ornamental plant. In some embodiment, the plant is a vegetable- or fruit-producing plant. In some embodiments, the plant is a plant that is suitable for generating biomass, including plants as noted above, e.g., *Arabidopsis*, poplar, *eucalyptus*, rice, corn, switchgrass, sorghum, millet, miscanthus, sugarcane, pine, alfalfa, wheat, soy, barley, turfgrass, tobacco, hemp, bamboo, rape, sunflower, willow, *Jatropha*, and *Brachypodium*.

Plants, parts of plants, or plant biomass material from plants having modified AT10, AT15, AT7 and/or AT5 expression can be used for a variety of purposes. In embodiments, the plants, parts of plants, or plant biomass material may be used in a conversion reaction to generate an increased amount of bioenergy as compared to wild-type plants. For example, the plants, parts of plants, or plant biomass material can be used in a saccharification reaction to generate an increased amount of soluble and fermentable sugar compared to wild-type plants. In some embodiments, the plants, parts of plants, or plant biomass material are used to increase biomass yield or simplify downstream processing for wood industries (such as paper, pulping, and construction) as compared to wild-type plants. In some embodiments, the plants, parts of plants, or plant biomass material are used to increase the quality of wood for construction purposes. In some embodiments the plants, or parts of plants are used to improve the quality of textile fiber or simplify the downstream processing for textile industry. In some embodiments the plants, or parts of plants, are used as a raw material for pectin production.

Methods of conversion, for example biomass gasification, are known in the art. Briefly, in gasification plants or plant biomass material (e.g., leaves and stems) are ground into small particles and enter the gasifier along with a controlled amount of air or oxygen and steam. The heat and pressure of the reaction break apart the chemical bonds of the biomass, forming syngas, which is subsequently cleaned to remove impurities such as sulfur, mercury, particulates, and trace materials. Syngas can then be converted to products such as ethanol or other biofuels.

Methods of enzymatic saccharification are also known in the art. Briefly, plants or plant biomass material (e.g., leaves and stems) are optionally pre-treated with hot water, dilute acid, alkali, or ionic liquid followed by enzymatic saccharification using a mixture of cellulases and hemicellulases and pectinases in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher sugar yield as compared to wild-type plants.

In some embodiments, grass plants having modified AT10, AT15, AT7, or AT5 expression are used as forage plants for application in which an improvement in digestibility is desired.

EXAMPLES

The following examples are provided to illustrate, but not limit the claimed invention.

Example 1. The "Mitchell Clade" of BAHD Acyltransferases is Expanded and Diverged in Grasses Mitchell et al. (2007) identified what is referred to in this examples section as the "Mitchell clade" of BAHD acyl CoA acyltransferases on the basis of high gene expression in grasses relative to dicots. We systematically characterized the distribution of this clade in selected plant species and compared the clade with other characterized BAHD proteins. We identified BAHD proteins from a diverse set of sequenced plants and analyzed the phylogenetic relationships among them and a reference set of BAHDs (Table I). To gain higher sensitivity relative to local sequence alignment (i.e., BLAST) for recognizing sequences with low, but potentially still significant, homology, we used a hidden Markov model to identify putative BAHD proteins (Finn et al., 2011). We then inferred an initial model of the phylogenetic relationships among the putative BAHD proteins from each genome and the set of biochemically characterized BAHD proteins cataloged by D'Auria (2006) with a neighbor-joining algorithm (Tamura et al., 2011). Active BAHD proteins can be identified by a HXXXD motif. A variation of this motif can also be present in an active protein in which the histidine is replaced by a serine (see, e.g., one of the known biochemically active proteins for the family, BAPT (NCBI ID: AAL92459) involved in taxol biosynthesis (Walker et al., 2002).

As observed by Tuominen et al., the distribution of BAHD proteins varies among species (Table I, FIG. 12). The "Mitchell clade" is embedded within Clade V, or Clade Va of Tuominen et al. The analysis revealed that the "Mitchell clade" includes a biochemically characterized banana alcohol CoA acyltransferase, BanAAT (Beekwilder et al., 2004), and is also related to a group of BAHD proteins that participate in taxol biosynthesis (FIGS. 1A-1B and FIG. 12).

Using Bayesian analysis, we found that multiple proteins with similarity to the "Mitchell clade" are present in the grass genomes that were available at the time of the analysis, Sorghum bicolor and Brachypodium dystachion (Table I, FIG. 12). In contrast, the annotated genomes of Arabidopsis thaliana, Glycine max, and Medicago truncatula encode only single members of this clade. The other recently characterized cutin- and suberin-feruloyl transferases (Molina et al., 2009; Rautengarten et al., 2012), though part of clade V, are not part of the "Mitchell clade". The clade is entirely absent from the annotated proteins of Populus trichocarpa and the primitive plants, Selaginella and Physcomietrella. Thus, the "Mitchell clade" appears to be conserved and expanded in grasses and banana relative to dicotyledonous species and more primitive plants. This is consistent with this clade functioning in aspects of Commelinoid metabolism that diverge from metabolism of dicot and more basal plants, such as synthesis of type II cell walls.

Figure 12A:
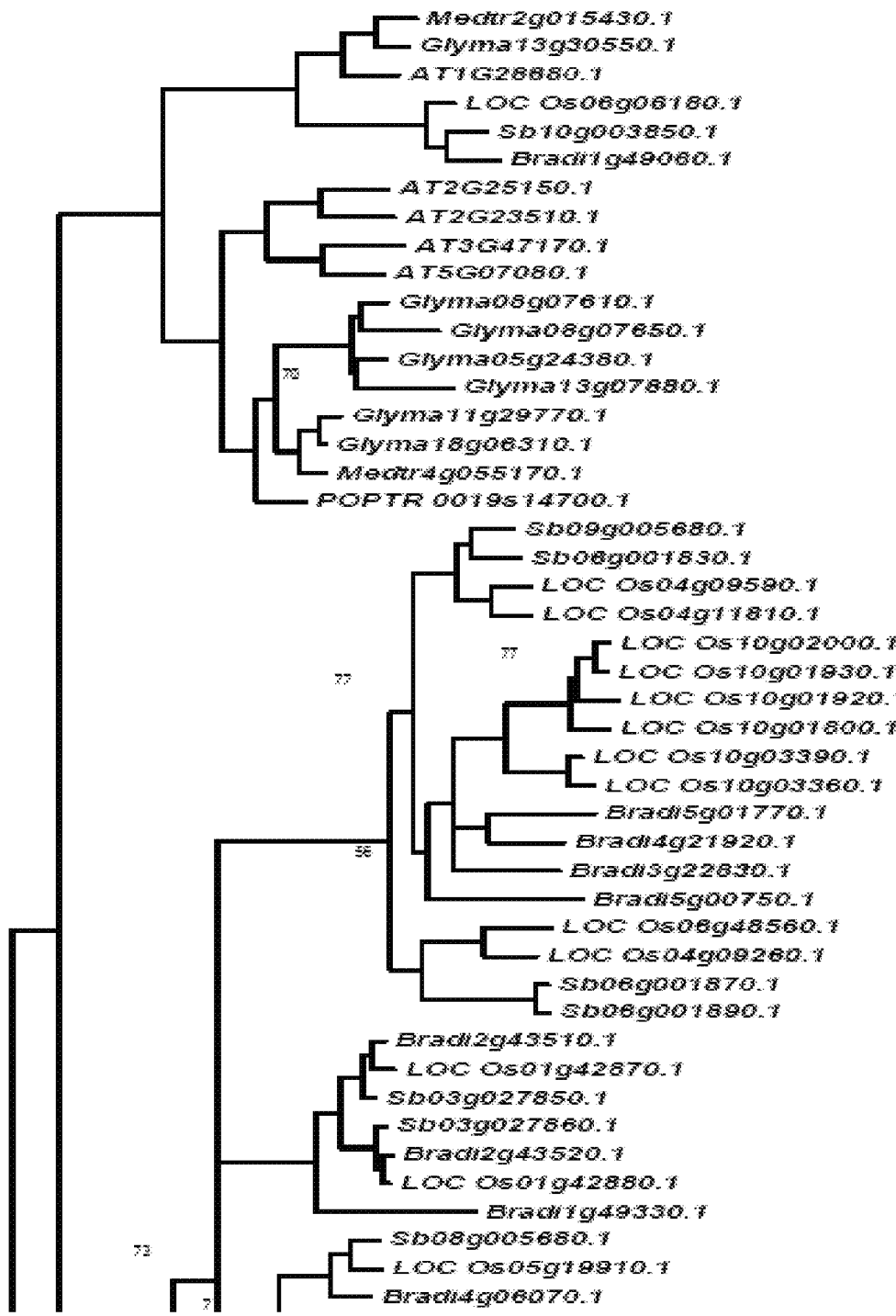
FIGS. 12A-12B. Inferred Bayesian phylogeny for clade V BAHD CoA acyltransferases identified from diverse species based on grouping closely with the biochemically characterized proteins that are similar to the "Mitchell clade" of BAHD proteins, namely BanAAT, and the taxol biosynthesis genes. Branch likelihood scores are >95% if not specified. The phylogeny was built using Mr.Bayes3.1.2 with 1.5×106 generations, until the split frequencies decreased below 0.01. Subclades i and ii, described in the text and Suppl.
Figure 12B:
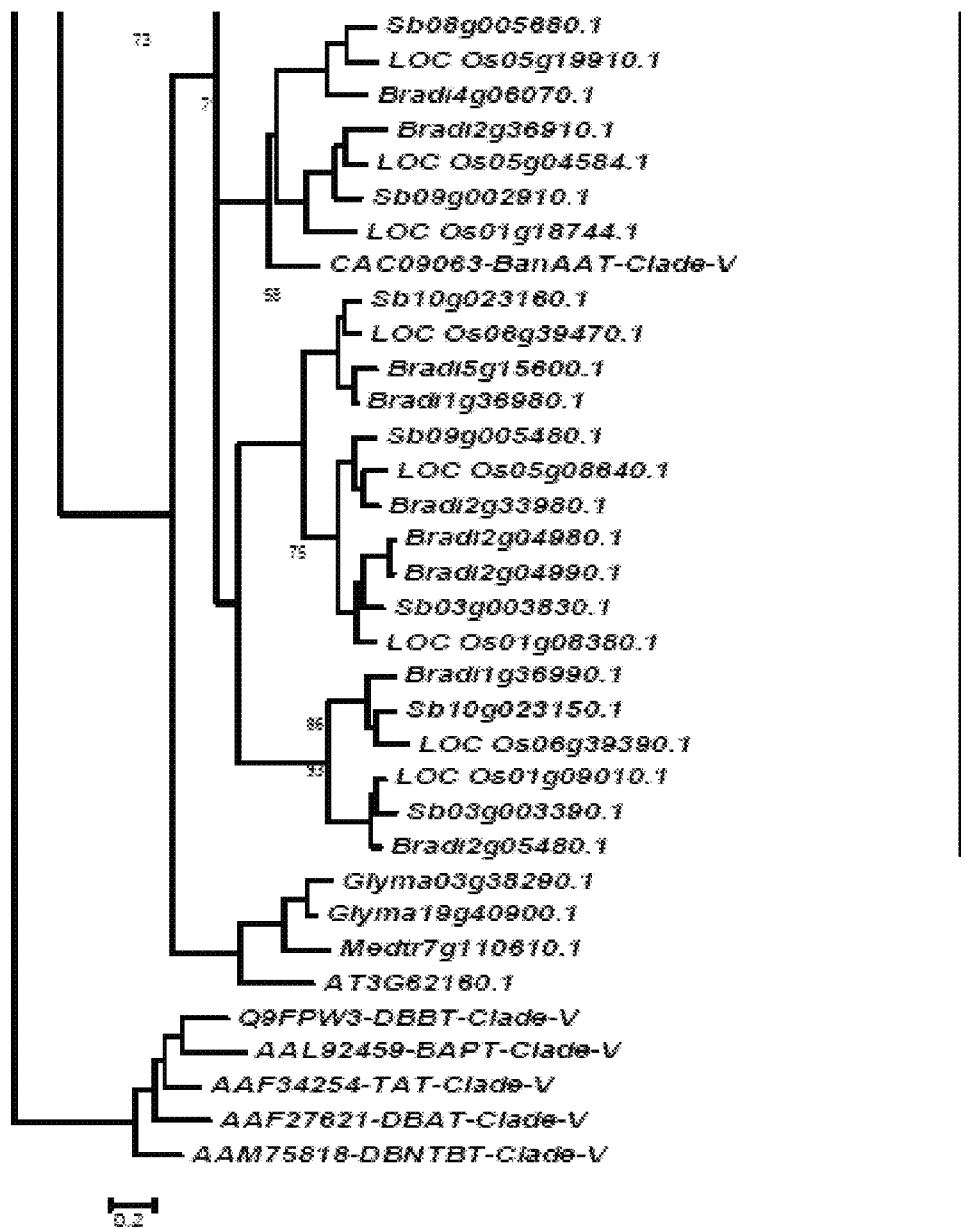

The analysis described above also revealed that the "Mitchell clade" of BAHD acyltransferases was missing several members. Instead of possessing 12 members in rice (Mitchell et al., 2007; Piston et al., 2010), the group consists of 20 closely related members that are further subdivided into two subclades (i and ii, FIG. 1). In rice, the 10 genes in subclade i are all supported by Sanger-based expressed sequence tag (EST)-evidence; whereas, only 3 of the 10 members of subclade ii were identified via traditional EST sequencing (FIG. 1). In addition, the multi-species tree reveals that most proteins of subclade i are represented in all three grass species examined and are more similar to the non-grass proteins (FIGS. 12A-12B). In contrast, subclade ii contains more species-specific expansions and/or contractions, consistent with the possibility that some of the members are pseudogenes. To facilitate communication about the putative "Mitchell clade" acyltransferases, we have given the clade members of rice preliminary names with the format Oryza sativa acyltransferase, OsAT1 through OsAT20. As mentioned above, OsAT4 was recently named PMT and found to be capable of esterifying monolignols (Withers et al., 2012).

Screen of Mutants for Altered Cell Wall Hydroxycinnamic Acid Content

We screened indexed rice mutants related to Mitchell clade" of BAHD CoA acyltransferases for altered cell wall content. Table II describes the mutant lines that we characterized. We screened progeny of each of these lines for the presence of the insertion, did not detect an insert in four lines, and for two lines, did not identify any progeny that were homozygous for the insert (Table II).

Figure 2A:
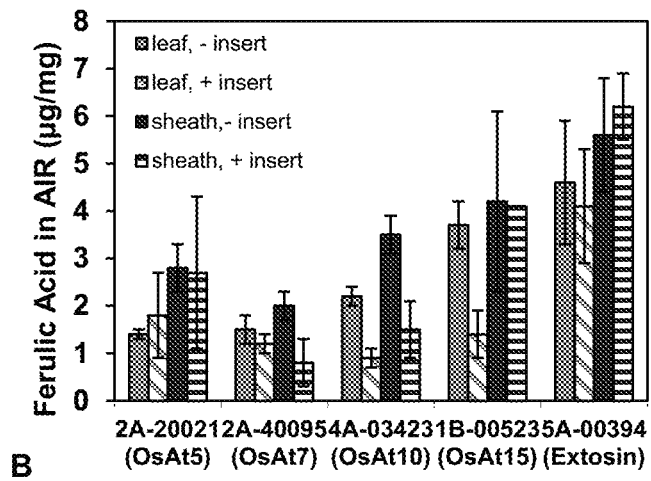
FIGS. 2A-2C. Screening results of the cell wall soluble hydroxycinnamate composition of selected T-DNA mutant rice lines.
Figure 2B:
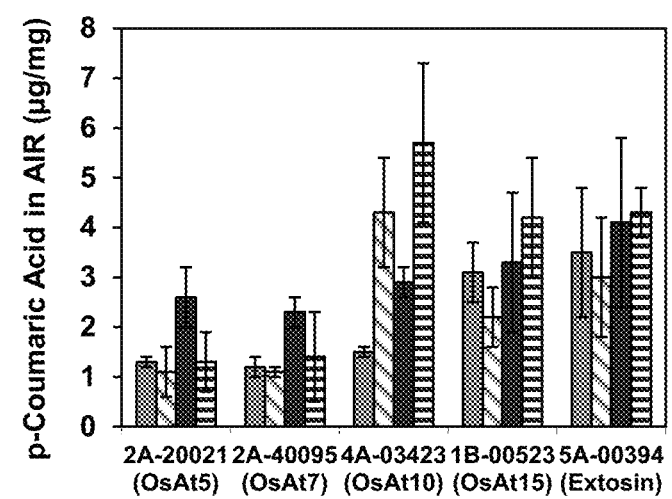
Figure 2C:
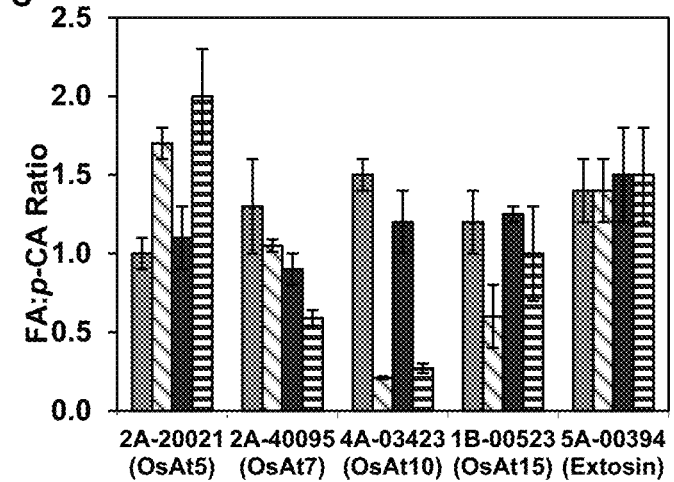

For the remaining 11 lines, we characterized the alkali-labile hydroxycinnamoyl ester content of cell wall alcohol insoluble residue (AIR) from leaves and leaf sheaths. We compared side tillers of homozygous, mutant and negative segregant, wild-type plants seven to ten weeks after planting. From this, we found four possible cell wall hydroxycinnamic acid phenotypes (Table II, FIG. 2). Three of the preliminary phenotypes were in putative mutants of subclade i proteins, and one was a mutant in a subclade ii protein. Homozygous mutant progeny of 2A-20021, predicted to increase expression of OsAt5, exhibited reduced p-CA in leaf sheaths relative to negative segregant wild-type progeny (50% less). Homozygous mutant progeny of 2A-40095, possessing the transcriptional activator sequences but inserted toward the end of the coding sequence for OsAt7, exhibited reduced FA in leaf sheaths (~60% less). Homozygous mutant progeny of 4A-03423 (OsAT10-D1), however, which were predicted to increase expression of OsAt10, exhibited reduced FA (~60% less) and increased p-CA (~300% more) in sheaths and leaves. Homozygous mutant progeny of 1B-00523, which were predicted to increase expression of OsAT15, a subclade ii member, exhibited reduced FA in leaves relative to negative segregant, wild-type progeny (60% less). In contrast, the other lines showed no change in FA or p-CA in the developmental stages and tissues examined. For example, our experiment included line 5A-00394, which is predicted to have activated expression of a putative rice exostosin (GT47) gene, LOC_Os10g10080. This line showed no alteration in cell wall hydroxycinnamic acids in leaf blades or sheaths (FIG. 2).

Gene Expression and Developmental Phenotypes of OsAT10-D1

Figures 3A, 3B:
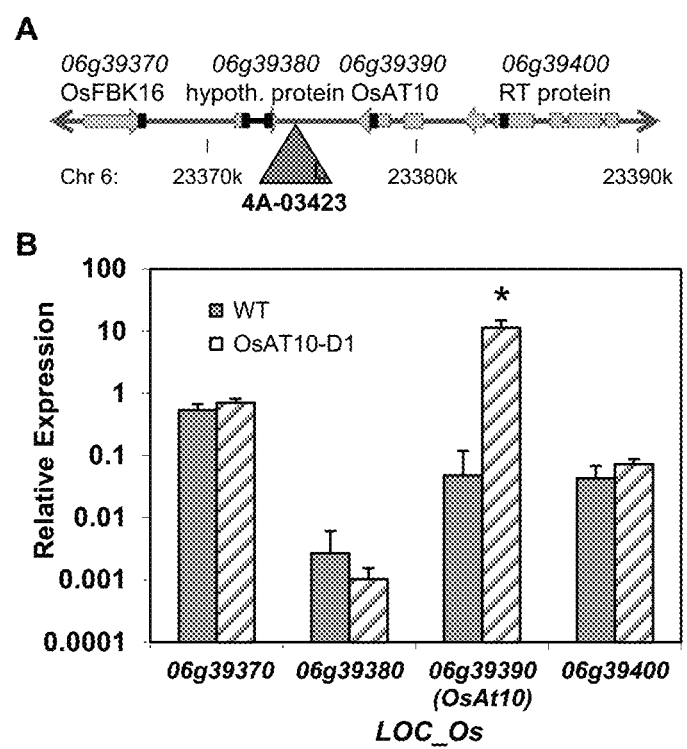
FIGS. 3A-3B. Genomic positions and gene expression data for OsAT10-D1 activation tagged lines (FIG. 3A) Representation of the portion of the rice chromosomes near the T-DNA insertion sites. Exons are represented by wide bars with the direction of transcription indicated by arrows. The insertion site is represented by the triangle, with the left border, nearest the CaMV 35S transcriptional enhancer elements, represented by 'L'. cDNA regions targeted for amplification in qPCR are depicted as black bands. 'RT' stands for retrotransposon and 'hypoth.' indicates hypothetical. OsFBK16 is an F-box and kelch-domain containing protein.
Figure 13:
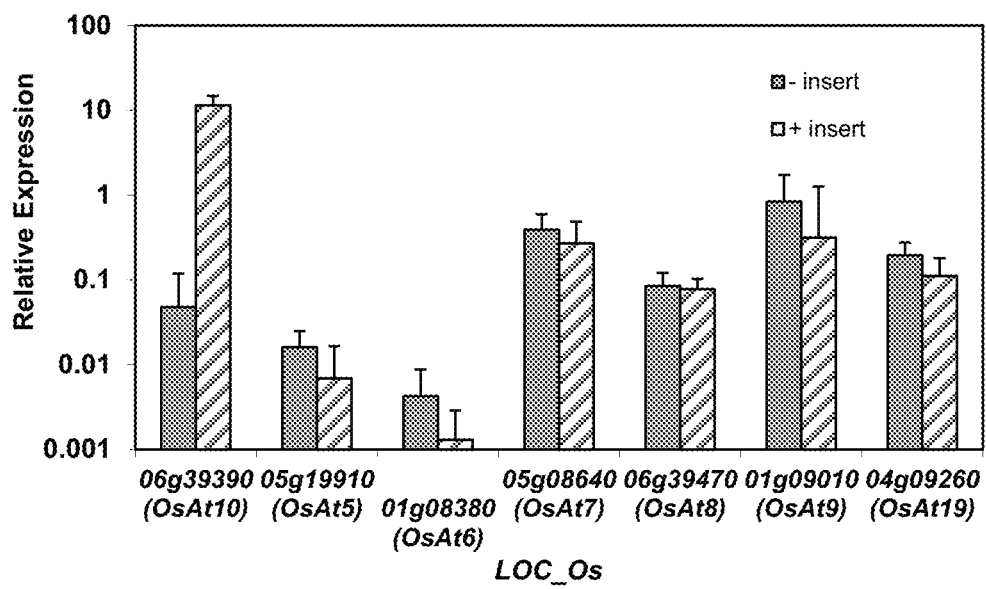
FIG. 13. Quantitative gene expression analysis suggests no change in the expression of other closely related acyltransferases the OsAT10-D1(4A-03423.5, + insert, cross-hatched bars) and negative segregant lines (4A-03423.1, − insert, solid bars). Shown are the average relative expression data for each target gene and related BAHD acyltransferases in young leaves. Error bars are 2*SEM of three to four biological replicates.
Figure 14A:
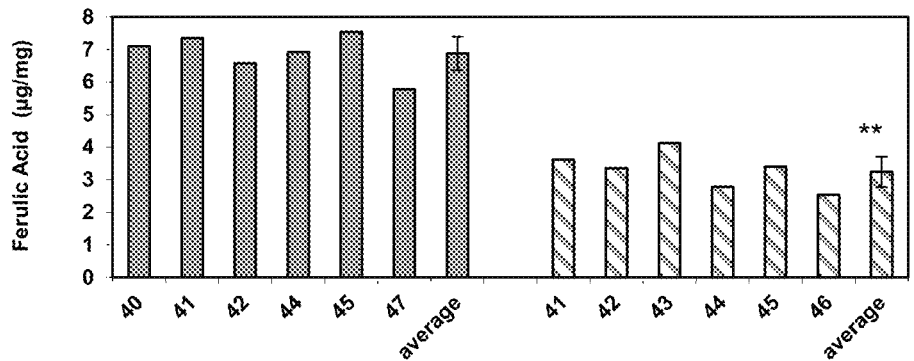
FIGS. 14A-14C. OsAT10-D1 shows consistent alterations in cell wall hydroxycinnamic acids. Data are for young leaves from progeny of negative segregant (NS) wild-type line (4A-03423.1.9, grey bars) and a line that is homozygous for the insert (4A-03423.5.6, crosshatched bars). The average and error bars indicate 2*SEM for the shown biological young leaf replicates. * indicates significance via Student's t-test at $p<0.05$ and ** indicates significance at $p<0.01$.
Figure 14B:
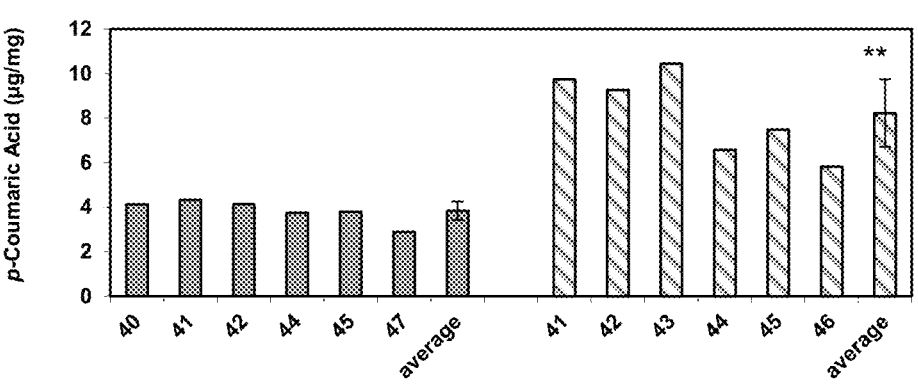
Figure 14C:
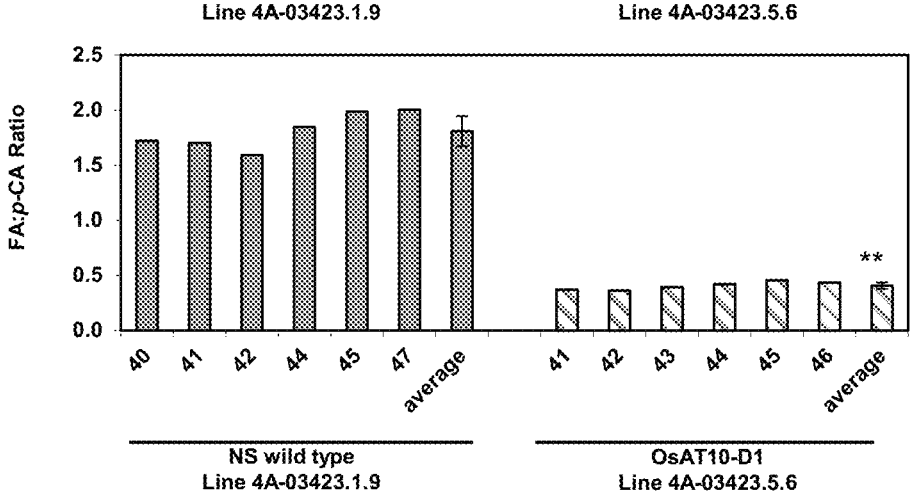
Figure 15:
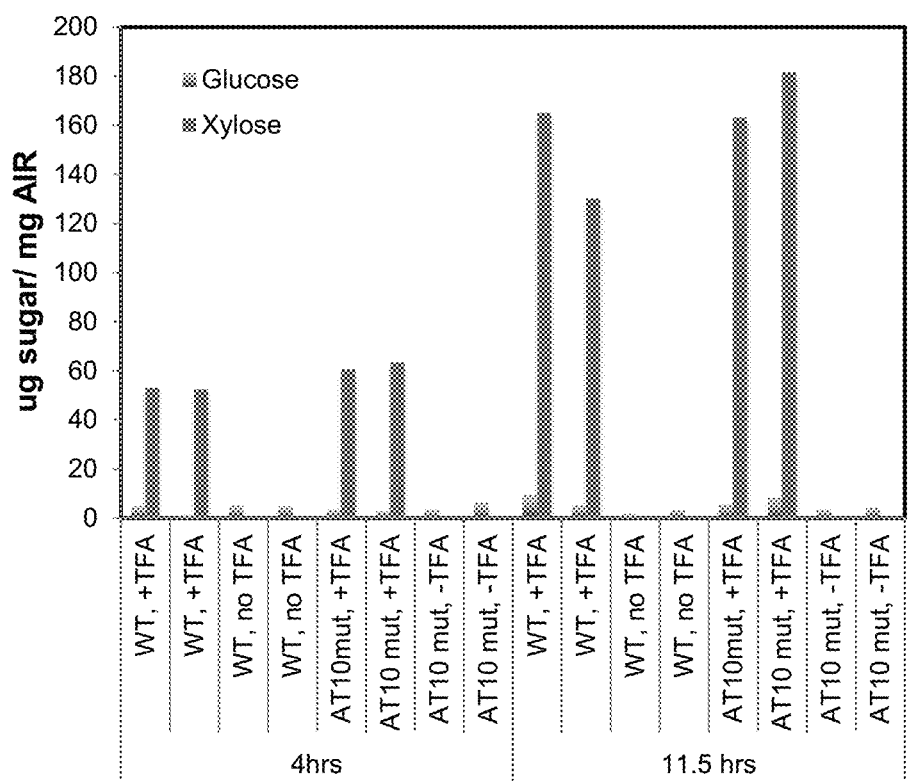
FIG. 15. Sugar analysis confirms that xylose, not glucose, is a major constituent released by the 50 mM TFA treatments.

The T-DNA insertion site for line 4A-03423, hereafter referred to as OsAT10-D1, is approximately 8.5 kb downstream of the transcriptional start site for OsAt10 (FIG. 3A). The insert is oriented so that the activating sequences are proximate to OsAt10 and thus is in range observed to activate expression (Jeong et al., 2006). RT-qPCR indicated that the expression of OsAt10 was indeed increased by >100-fold in the leaves of homozygous OsAT10-D1 plants (FIG. 3B). In OsAT10-D1, the expression genes other than OsAt10 that were proximate to the site of the T-DNA insertion did not vary significantly relative to the wild type (FIG. 3B). The expression of related OsAt genes did not vary significantly in OsAT10-D1 (FIG. 13), reducing the possibility that the observed phenotype is due to compensation at the level of gene expression of a related acyltransferase. OsAT10-D1 lines exhibited no change in size and dry mass at maturity (FIGS. 4A-4B). However, a ~20 to 30% decrease in total seed mass per plant for the mutant compared to the wild type (FIG. 4C) was observed.

Figures 5A, 5B, 5C, 5D:
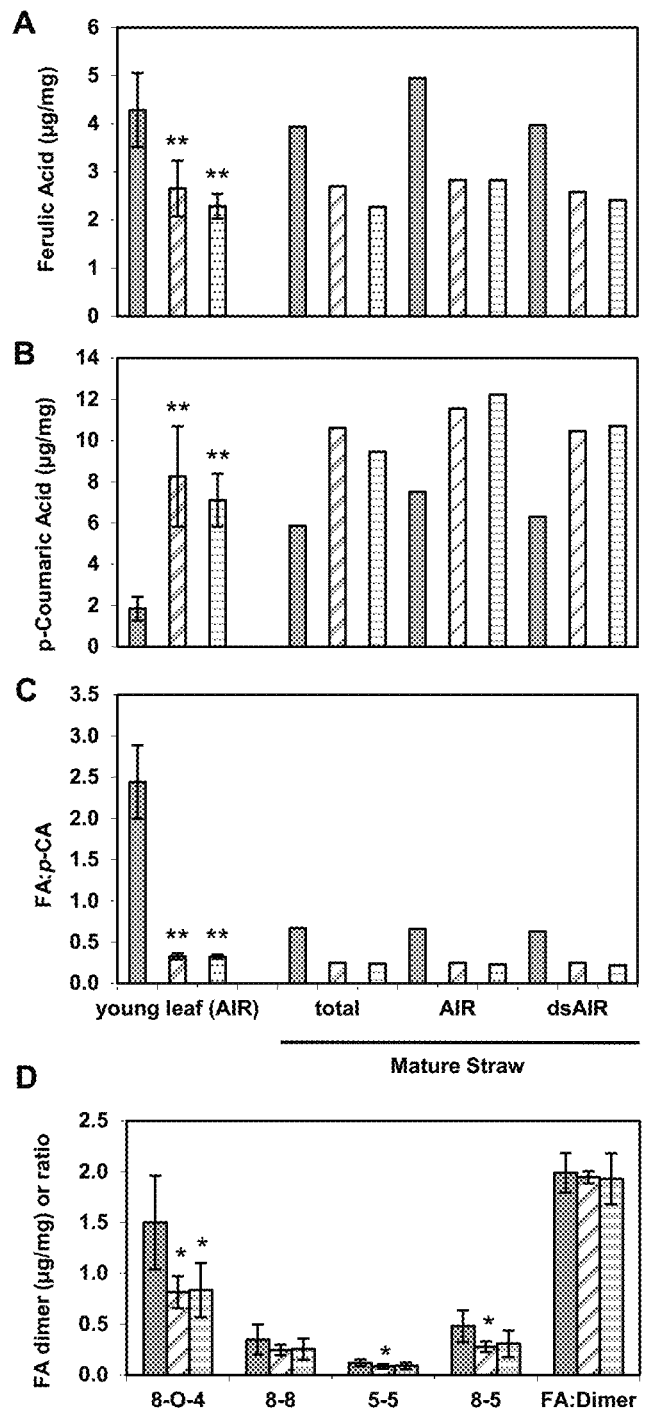
FIGS. 5A-5D. OsAT10-D1 shows alterations in cell wall hydroxycinnamic acids. Data are for a negative segregant family lacking the insert (grey bars, progeny of 4A-03423.1) and two mutant families homozygous for the insert (cross hatched bars, progeny of 4A-03423.5; and horizontal hatched bars, progeny of 4A-03423.12) for young leaves and a pool of mature aerial, vegetative material (i.e., mature straw). AIR is alcohol insoluble residue. dsAIR is destarched alcohol insoluble residue. Error bars are 2*SEM of 3 to 5 biological replicates. * indicates significance via two-tailed, unpaired Student's t-test at p<0.05 and ** indicates significance at p<0.01.

Cell Walls of OsAt10 Over Expression Lines are Heritable Altered in Ester-Linked Hydroxycinnamic Acids For OsAT10-D1, we confirmed the inheritance of the altered cell wall hydroxycinnamate phenotype in young leaves and mature tillers of plants from two subsequent generations (FIGS. 5A-5D and FIGS. 14A-15C). This line has a ~50% decrease in ester-linked FA in young leaf tissue (FIG. 5A). The same tissue shows an ~300% increase in ester-linked p-CA (FIG. 5B). The change in both components is most clearly exhibited as a change in the ratio of FA to p-CA (FIG. 5C). The ratio is the most reliable as it is independent of potential variation in the absolute amounts due to variation in sample mass and extraction efficiency. We were also able to quantify the four most abundant ferulate dimers. Although signals were low for some dimer species, most showed decreases compared to wild-type amounts (FIG. 5D). We found that the dimers decreased proportionally to the decrease in FA in the young leaf tissues (FIG. 5D). This can be most clearly seen as the similar ratio of FA compared to the sum of the dimer species (FIG. 5D). In addition, we found similar trends but less extreme changes in pools of total aerial tissues harvested after senescence for the same plants from each genotype (FIGS. 5A-5D). These mature straw samples possessed a ~40% less FA and ~80% more p-CA. Measurements were independent of whether total, AIR or destarched AIR preps were used, but these different samples do show the technical replicate-ability of the analysis.

Figure 6A:
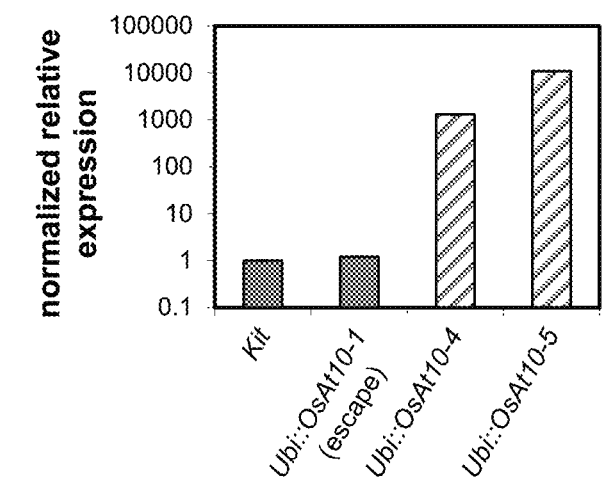
FIGS. 6A-6C. Independent OsAt10 over expression lines (cross-hatch) also show altered ratios of hydroxycinnamic acids (HCA) relative to wild-type lines (solid).
Figure 6B:
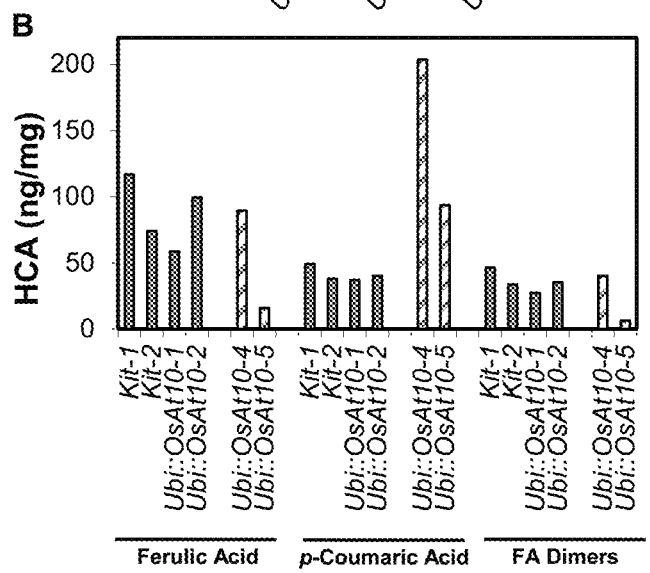
Figure 6C:
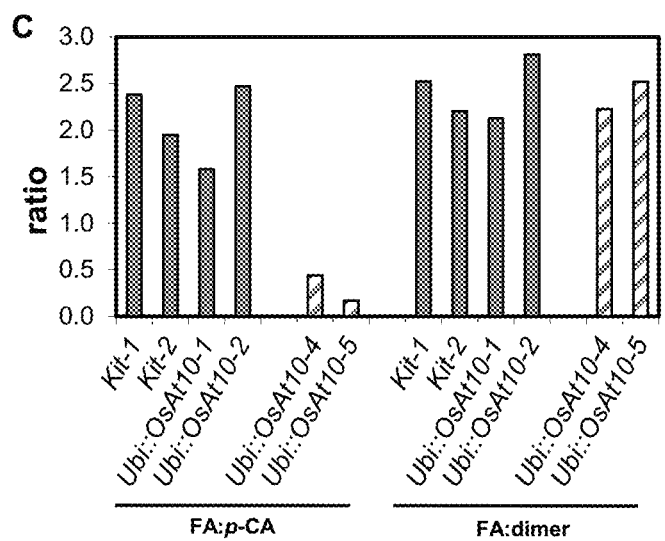

To gather further evidence that the phenotype in the activation tagged line was due to over expression of OsAt10, we generated two additional OsAt10 over expression lines utilizing the maize ubiquitin1 promoter (FIGS. 6A-6C). Contrary to our typical experience for high efficiency transformation with the japonica cultivar, Kitaake (Jung et al., 2008), we were only able to regenerate two independent transformants that possessed the transgene from tissue culture (FIG. 6A). This result suggest that the OsAt10 construct interferes with transformation efficiency. Both of the confirmed transgenic lines did show increased expression of OsAt10 compared to the non-transgenic plants (FIG. 6A). Furthermore, AIR from young leaf tissue of the primary transgenics also exhibited a qualitatively similar change in hydroxycinnamic acids compared with the OsAT10-D1 line (FIG. 6B). In particular, the ratio of FA:p-CA was dramatically decreased in both lines, though the absolute amounts of FA and p-CA varied relative to the non-transgenics. Specifically, Ubi::OsAt10-4 has a sharp decrease in FA, with a relatively smaller increase in p-CA and Ubi::OsAt10-5 showed no change in FA, but a dramatic increase in p-CA (FIG. 6B). As with the other over expression lines, the FA:diferulate ratios do not vary from those observed for the non-transgenics (FIG. 6C).

Figures 7A, 7B, 7C:
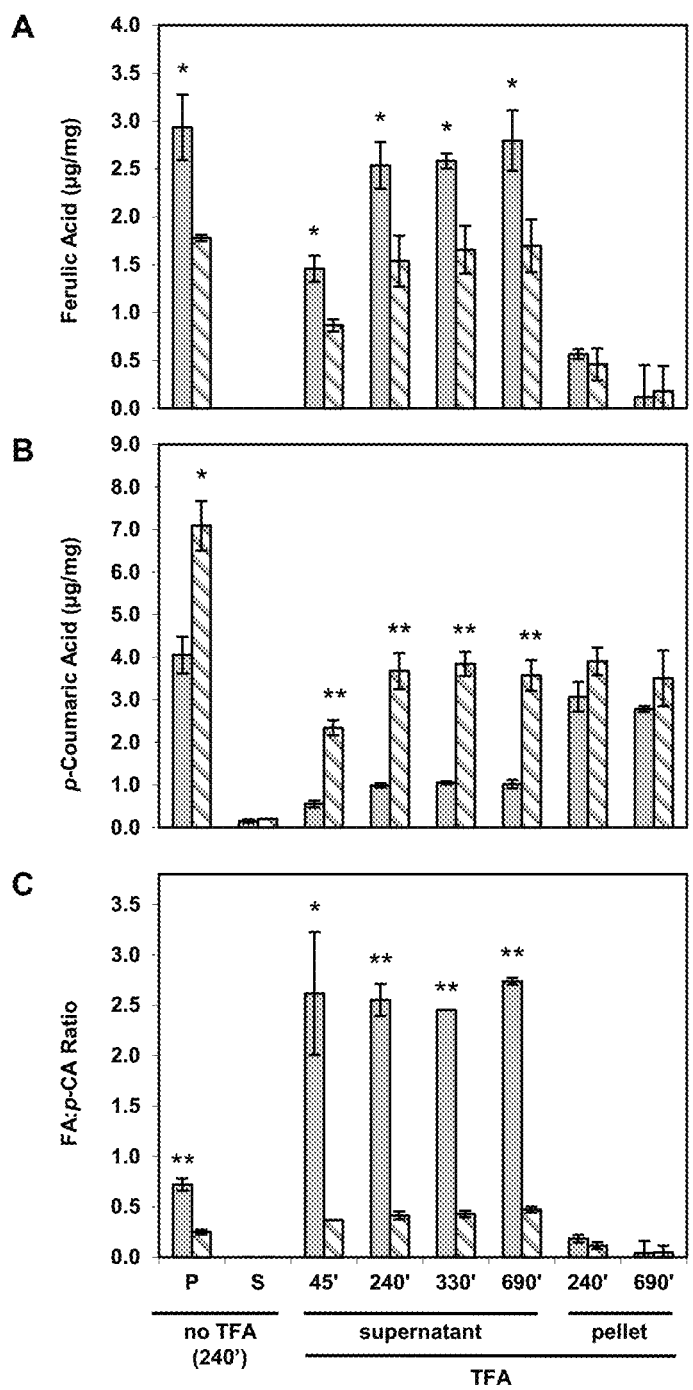
FIGS. 7A-7C. The cell wall alteration in OsAT10-D1 hydroxcinnamates is predominantly in the TFA-soluble fraction. Data are for mature straw from wild type (solid, 4A-03423.5 progeny) and mutant (hatched, 4A-03423.1 progeny). P indicates the pellet and S the supernatant after trifluoroacetate treatment (TFA) or mock (no TFA). The times indicates the minutes of TFA treatment. * indicates significance via unpaired, 2-tailed Student's t-test at p<0.05 and ** indicates significance at p<0.01.

The Difference in OsAT10-D1 Hydroxycinnamates is Predominantly TFA-Soluble and is Linked to a 5-Carbon Sugar In grasses, hydroxycinnamoyl esters have been found to be attached to matrix polysaccharides, glucuranoarabinoxylan or xyloglucan, or to lignin. We examined which cell wall fraction harbored the alteration in FA and p-CA in the OsAT10-D1 mutant. To accomplish this, we subjected AIR from mutant and wild-type mature rice straw with a relatively mild, 50 mM trifluoroacetate (TFA) treatment to release the matrix polysaccharides. At multiple time points, we removed a fraction of the supernatant. We then saponified both the supernatants and pellet with the typical 2 N NaOH treatment followed by HPLC analysis of the products. The results demonstrated that the alteration in FA and p-CA amounts in OsAT10-D1 is primarily in the matrix polysaccharide fraction of the cell wall (FIGS. 7A-7C). For both the wild type and OsAT10-D1, the FA is predominantly associated with the TFA fraction, with less than 20% of the FA remaining in the pellet after TFA treatment for both genotypes (FIG. 7A). The reverse is observed for the p-CA for the wild type, in which ~70% of the p-CA remains in the pellet (FIG. 7B). However, for the mutant only 55% of the p-CA is in the pellet after TFA treatment, though the absolute amount of p-CA in the TFA pellet are very similar for the wild type and mutant (FIG. 7B). Thus, we conclude the additional p-CA in the cell wall of the OsAT10-D1 is in the TFA-soluble matrix polysaccharide fraction. This can be clearly seen in the FA:p-CA ratio plot, in which the ratio of FA:p-CA is most drastically changed in the supernatants after TFA treatment; whereas, the FA:p-CA ratio is the same within error for the mutant and wild type in the residue remaining after TFA treatment (i.e., pellet, FIG. 7C). These data suggest that in mature rice straw, the change in p-CA in the matrix polysaccharide fraction approaches a ~300% increase of OsAT10-D1 over the wild type, rather than the smaller ~70% increase when total ester-linked p-CA is considered. Consistent with the typical location of p-CA on lignin, this magnitude of increase in the mutant compared to the wild type is more similar to that seen in young leaf tissue, which in the wild type possess a relatively lower percentage of p-CA compared to FA (FIGS. 5A-5D).

Figure 8A:
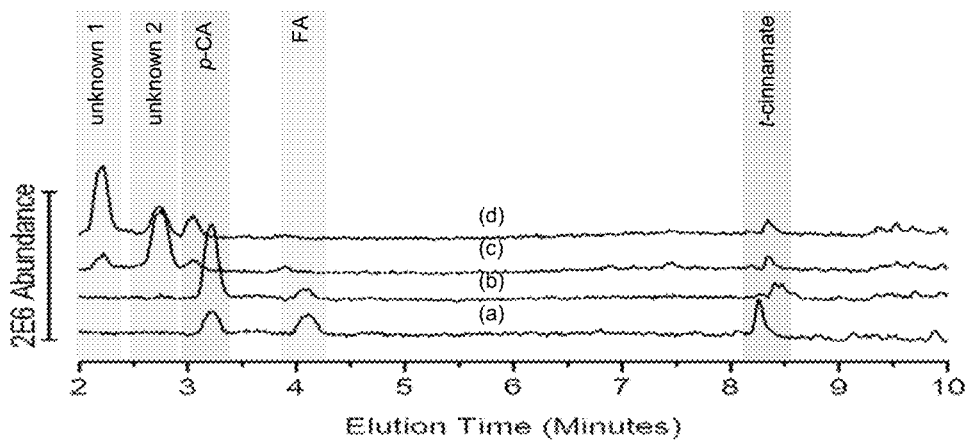
FIGS. 8A-8C. The modified hydroxycinnamates in OsAT10-D1 are attached to a five-carbon sugar.
Figure 8B:
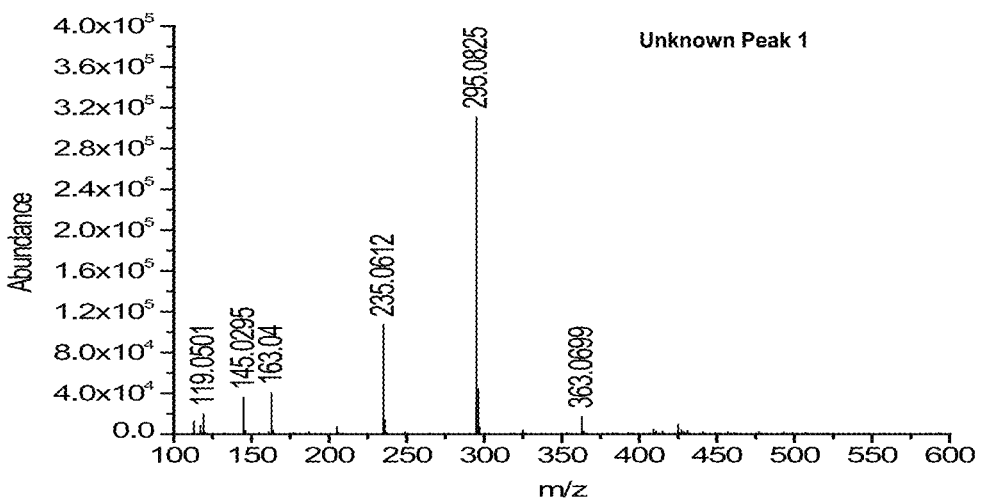
Figure 8C:
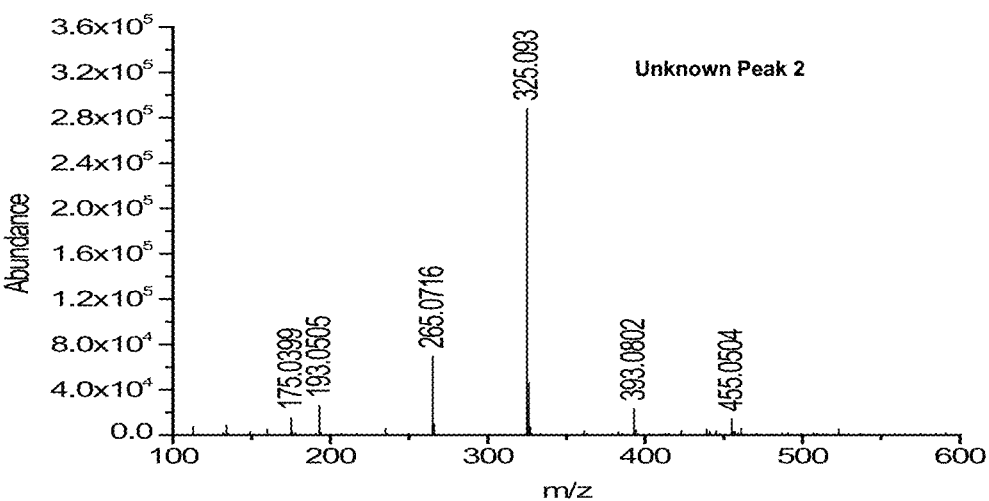

Further analysis of the TFA soluble fractions supports the assertion that the glucuranoarabinoxylan is modified by OsAt10 activation. First, the sugars released by TFA treatment in this experiment predominantly consist of xylose, consistent with the model that OsAT10 functions in arabinoxylan modification FIG. 15. In contrast, the pellet contains less than 20% of the total amount of xylose. Furthermore, via LC-MS, we detected two major new ion peaks in the TFA-solubilized ethylacetate extract compared to extract that had been treated with NaOH or with hydroxycinnamate standards (FIG. 8A). The mass spectra of these peaks are consistent with the major unknown peak in the mutant (unknown peak 1) consisting of p-CA esterified to a five-carbon sugar (m/z=295.0285, FIG. 8B); whereas, the predominant peak in the wild type (unknown peak two) is consists of FA esterified to a five carbon sugar (m/z=325.083, FIG. 8C). Because arabinose and xylose have the same molecular weight they are indistinguishable in this experiment; however, our strong expectation from nuclear magnetic resonance (NMR) data from the literature is that the esterified sugar is arabinose (Buanafina, 2009; Ralph, 2010). Relative quantification of the ion counts of each of these peaks in the mutant vs. the wild type is consistent with the results measured via HPLC. That is, compared with the wild type, OsAT10-D1 has ~4.6-fold more pCA-sugar and 2.5-fold less FA-sugar (FIG. 8A). The relative amounts of FA and p-CA after saponification are also consistent with our previous results (FIG. 8A).

The OsAT10-D1 Line has an Increase in Cell Wall Glucose Content

Figures 9A, 9B:
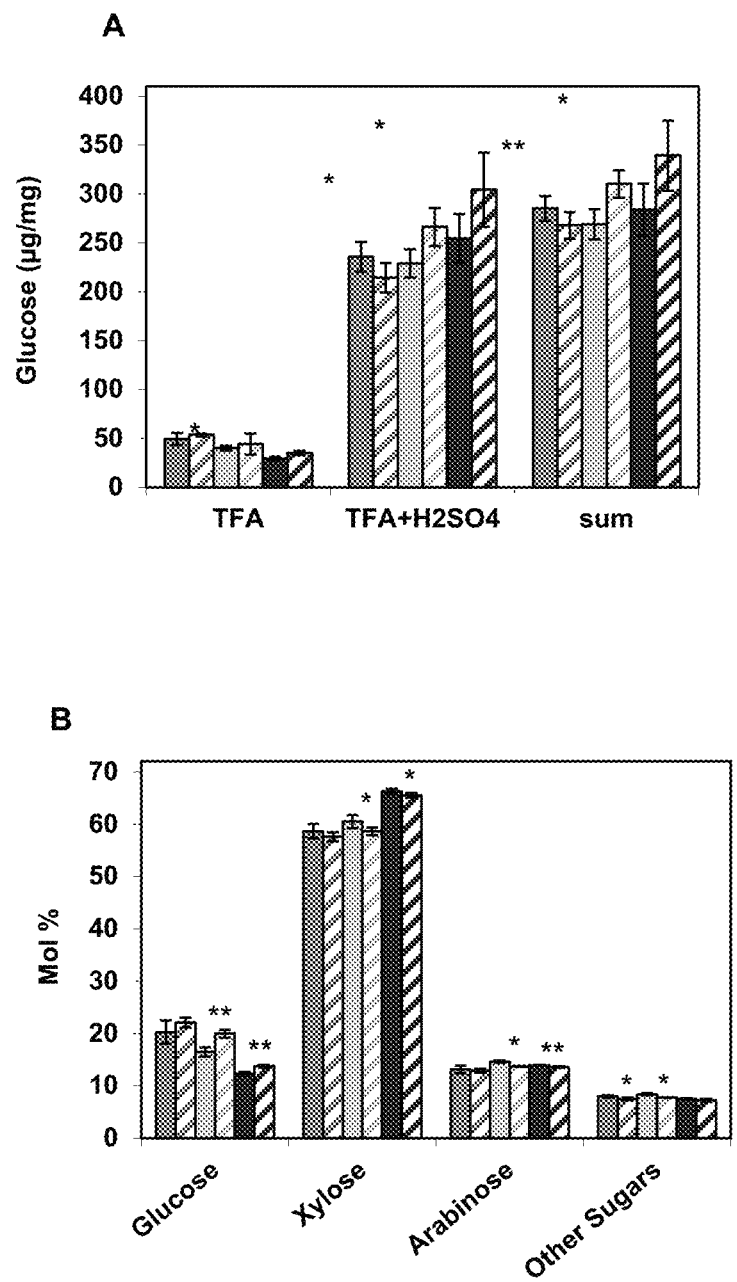
FIGS. 9A-9B. OsAT10-D1 mature straw has increased glucose content relative to wild type (4A-03423.5 progeny vs. 4A-03423.1 progeny, respectively). Wild-type samples are solid and mutant samples are hatched. Grey is from whole tissue, blue is AIR, and maroon is destrached AIR. Error bars show 2*SEM of three replicates. '**' indicates a difference at p<0.01 and '*' at p<0.05 via unpaired, 2-tailed, Student's t-test.
Figure 16:
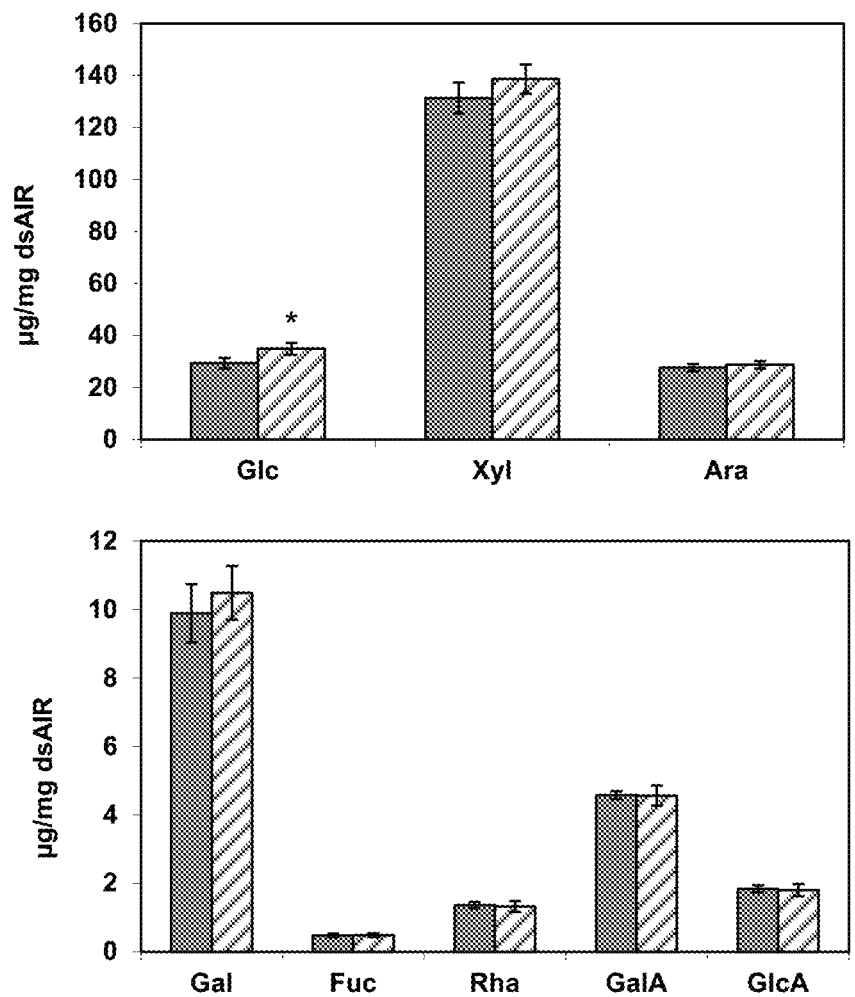
FIG. 16. Destarched AIR from OsAT10-D1 mature straw has increased glucose content relative to that of the wild type, but no other significant changes by mass. Wild-type (4A-03423.1 progeny) samples are solid and mutant (4A-03423.5 progeny) samples are hatched. Error bars show 2*SEM of three replicates. '*' indicates a difference at $p<0.05$ via unpaired, two-tailed Student's t-test. (A) Mass analysis shows significant increases in glucose (Glc), but not xylose (Xyl) and arabinose (Ara). (B) Mass analysis shows no significant changes in galactose (Gal), fucose (Fuc), rhammnose (Rha), galacturonic acid (GalA), or glucuronic acid (GlcA).

Compensatory changes are often seen among the components of the cell wall (Humphrey et al., 2007). Quantification of sugars released by acid treatment of total, AIR, and destarched (ds) AIR preparations suggests that the glucose content is increased by ~20% (weight/weight) in AIR and dsAIR for the mutant relative to the wild type (FIG. 9A). We observed the difference both with TFA treatment, which liberates matrix polysaccharides and amorphous cellulose, and when the TFA residue is further treated with sulfuric acid, which liberates cellulose (FIG. 9A). That the difference persists after destarching is consistent with a change in the cell wall content, not starch. By mass, we did not observe any other significant changes in sugar amounts in the mutant compared to the wild type FIG. 16). Expressing sugar data as percent of molecules (mol %) is more precise because it excludes weighing and other experimental errors. When the TFA-solubilized sugars are expressed in terms of mol %, the data also indicate an increase in glucose content, on the order of 10 to 20% (FIG. 9B). Xylose, arabinose, and the sum of minor cell wall sugars decrease proportionally to the glucose increase (10-20%), suggesting that the change in cell wall polysaccharide content in the mutant is isolated to the glucose-containing polymers.

The OsAT10-D1 Shows No Alterations in Lignin Content or Composition

To further explore the extent of cell wall changes in the mutants relative to the wild type, we also measured lignin content and composition. We hypothesized that the possible alteration in pools of hydroxycinnamyl-CoA adducts in the OsAT10-D1 line might lead to alterations in lignin amount or content, in terms of syringyl (S), guiacyl (G), and coumaryl (H) subunits. Due to the presence of H residues in grass lignin, all methods of lignin analysis are not equally accurate for grasses relative to dicots. For our analysis, we used two methods suitable for grasses—acetylbromide solubilization (Grabber et al., 1996; Fukushima and Hatfield, 2004) and pyrolysis-molecular beam mass spectrometry (py-MBMS) (Evans and Milne, 1987; Agblevor et al., 1994). "Lignin" analyses of whole tissue or AIR typically include all classes of phenylpropanoids, both esterified and non-esterified, though some esterified hydroxycinnamates are associated soley with arabinoxylan. Since our previous analysis had determined that there is a difference in OsAT10-D1 in ester-linked phenolics, we quantified lignin content and composition with and without removing esterified hydroxycinnimates via saponification.

Figure 10A:
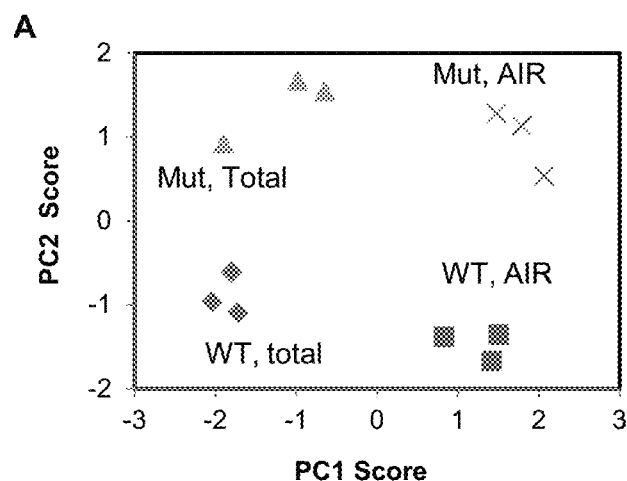
FIGS. 10A-10C. Principal component analysis of pyrolysis-molecular beam-mass spectrometry data for 4A-03423 corroborate the change in extractable phenolics, but show no difference in lignin composition.
Figure 10B:
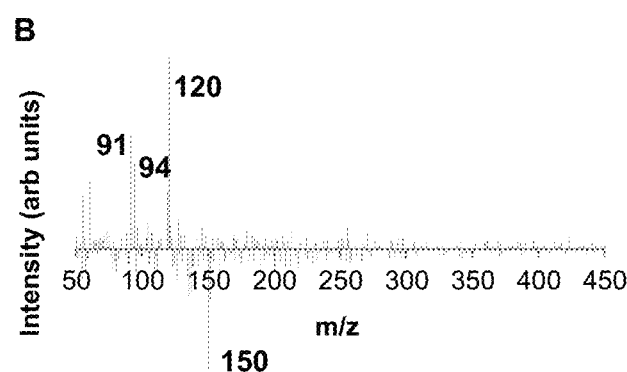
Figure 10C:
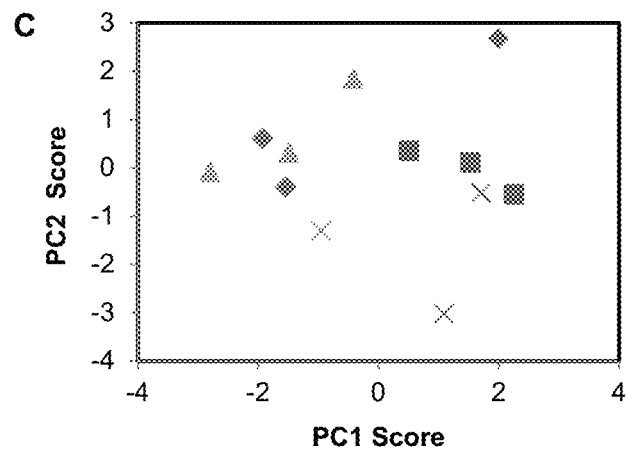

OsAT10-D1 mature aerial tissue, and separate, young leaf and sheath samples show no significant difference in mass percent acetylbromide soluble lignin after saponification relative to the wild type. We obtained a similar result via py-MBMS, which also revealed no difference in the S:G lignin ratio in the mutant compared to the wild type after saponification. For OsAT10-D1, we also collected py-MBMS data for unprocessed straw and AIR. When analyzed together via principle component analysis (PCA), the first component clearly separates the saponified and unsaponified samples and explains 85% of the variation between the samples (not shown). Separate analysis of the saponified and unsaponified samples reveals distinctions between the wild type and mutant in the unsaponified samples (FIG. 10A). Principle component 1 (PC1) explains the alcohol extraction (30% of the variation) and principle component 2 (PC2) explains differences between the wild-type and mutant samples (19% of the variation). The loadings for PC2 show that the major ions that distinguish the wild-type and mutant samples are phenolics (FIG. 10B). Thus, the MS fragmentation pattern is consistent with an interpretation in which there is an increase of p-CA, as reflected by peaks 120, 94, and 91, and a decrease in ferulic acid, as reflected in the drop in the coniferyl ion, peak 150 (Evans and Milne, 1987). Note that the "tails" of phenylpropanoid molecules are typically absent in these spectra due to MS fragmentation. The observed differences in phenylpropanoids between OsAT10-D1 and the wild type are likely associated with ester-linked hydroxycinnamates and not lignin, because PCA no longer distinguishes the samples after saponification (FIG. 10C).

Figures 17A, 17B:
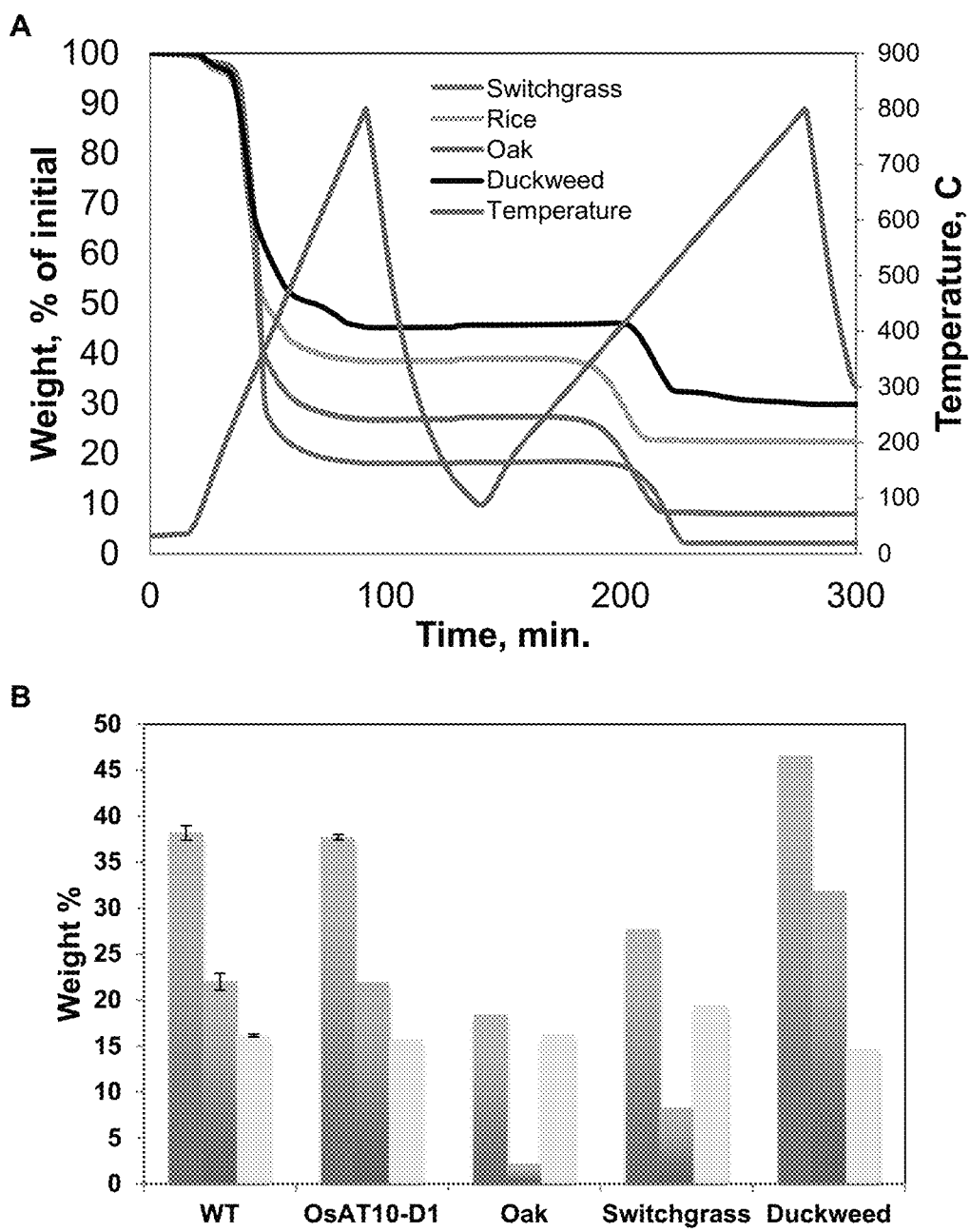
FIGS. 17A-17B. Thermogravimetric analysis detects no mass difference upon heating between wild-type and mutant mature straw.

A limitation of the pyrolysis method for determining lignin composition is that it inaccurately measures H-lignin, which volatilizes poorly and instead turns to char upon heating. Because of the increase in p-CA, a precursor of H-lignin, in OsAT10-D1 cell walls relative to the wild type, we sought to determine whether there is an increase in the char content of OsAT10-D1 using a thermogravimetric (TG) pyrolysis instrument. Duplicate runs per genotype of the TG did not detect a difference in the mass remaining from mature straw after pyrolysis FIGS. 17A-17B), again consistent with there being no difference in core lignin composition or content between OsAT10-D1 and the wild type.

The OsAT10-D1 Line Shows an Increase in Saccharification

Figure 11A:
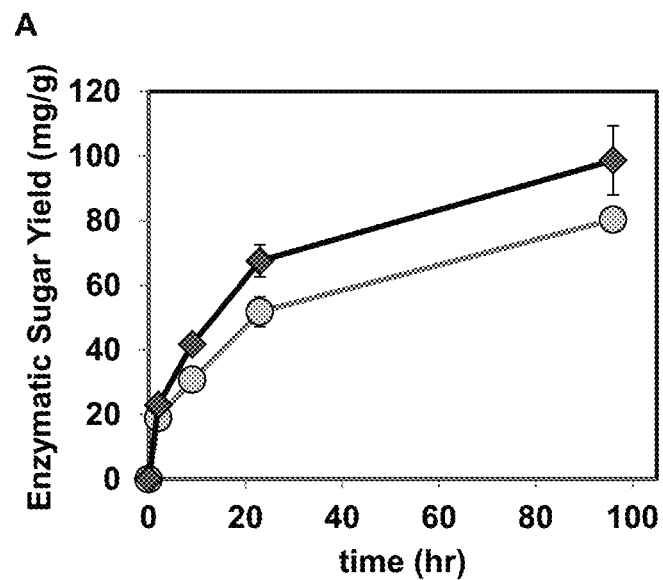
FIGS. 11A-11C. OsAT10-D1 exhibits increased enzymatic and fungal deconstructability.

Several researchers have observed a correlation between ferulate esters in grass biomass and digestibility among diverse canarygrass and lolium accessions (Lam et al., 2003; Casler and Jung, 2006). The phenotype of the OsAt10-D1 line provided the opportunity to determine whether there is also an increase in enzymatic digestibility with reduced FA content when comparing two near-isogenic plant lines, with little to no variation besides the difference in cell wall hydroxycinnamic acid content. We found that destarched AIR after mild pre-treatment followed by incubation with a cellulase cocktail and ß-glucosidase resulted in the release of approximately 20% more reducing sugar from the mutant compared with the wild type at all time points examined (FIG. 11A). We note that this might be explained solely by the increase in glucose content, which is quantitatively similarity.

Figure 11B:
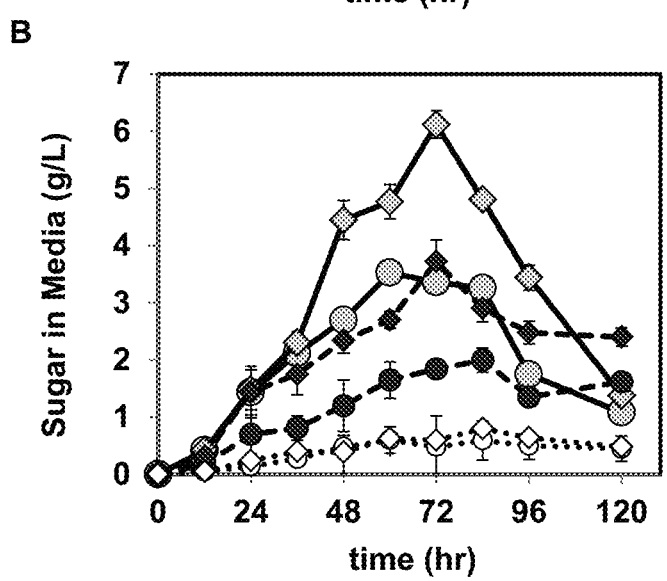
Figure 11C:
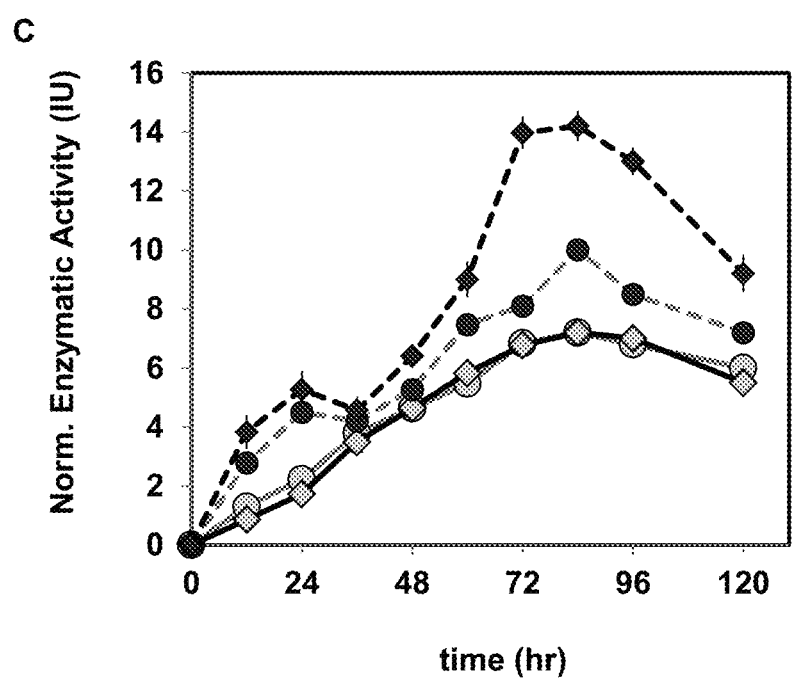
Figure 18:
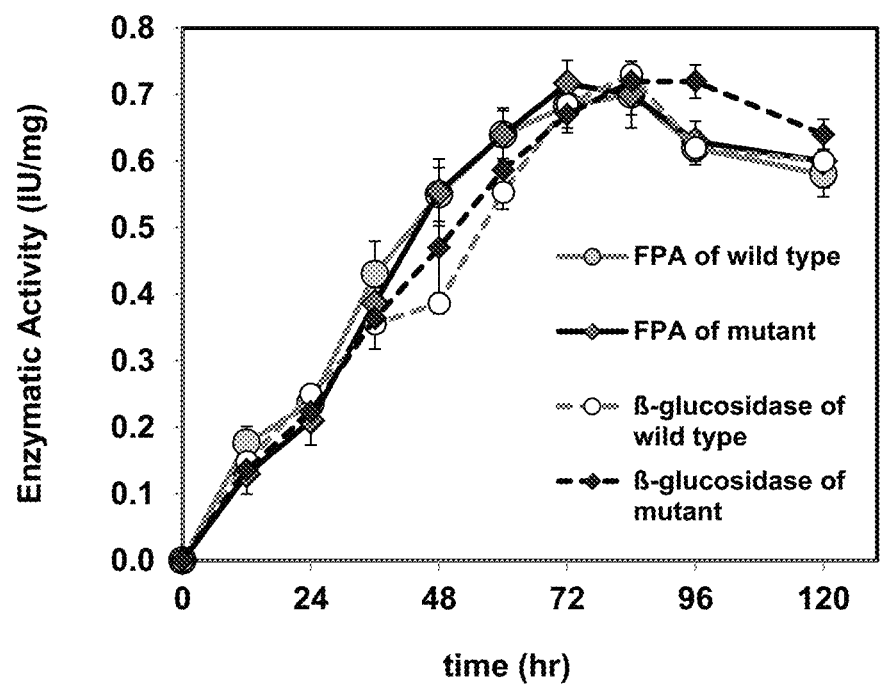
FIG. 18. Enzymatic activity in media during *Penicillium* sp. YT02 incubation with wild-type (circles) and OsAT10-D1 mutant (diamonds) straw. FPA (dashed lines, red symbols) is the activity on cellulose filter paper. ß-glucosidase activity uses cellobiose as a substrate. IU is nmoles of sugar per minute per mL. Data are normalized for mg of total protein. Error bars show 2*SEM of five replicate cultures.

We also determined if the improvement in digestibility impacted a biological saccharification agent. For this, we exposed acid-explosion pretreated, coarsely chopped rice straw from the wild type and OsAT10-D1 to the mesophilic fungus, *Penicillium* sp. YT02. This recently characterized fungus shows significantly higher xylanase and ß-glucosidase with various insoluble lignocellulosic substrates in comparison with the commonly used fungal strain, *Trichoderma reesei* (ATCC 24449) (Kovacs et al., 2009), and may be a promising strain for industrial bioprocessing of cellulosic plant biomass (L. Gao and J. Zhou, in prep). Qualitatively consistent with the enzymatic deconstruction results, YT02 incubation released more glucose, xylose, and arabinose into the medium from acid explosion pretreated OsAT10-D1 straw than from wild-type straw (FIG. 11B). Averaged over the entire time course (12 to 120 hours), the improvement in yield is more dramatic with the fungus than with enzymes alone, with the fungus releasing 46% more glucose, 82% more xylose, and 25% more arabinose for a total sugar yield increase of ~40%. In the fungal treatments, the biomass-derived sugars initially accumulate, due to the action of enzymes excreted by the fungus. At later time points (>72 hrs.), the fungus metabolizes the sugars, incorporating them into fungal biomass. Cellulase and ß-glucosidase enzymatic activity in the slurry is unchanged on the mutant straw (FIG. 11C and FIG. 18), suggesting that the fungus grew similarly on both. In contrast and of relevance to the nature of the change caused by the increased expression of OsAT10, xylanase activity is dramatically enhanced, especially at later time points (FIG. 11C).

OsAT5

Figure 19A:
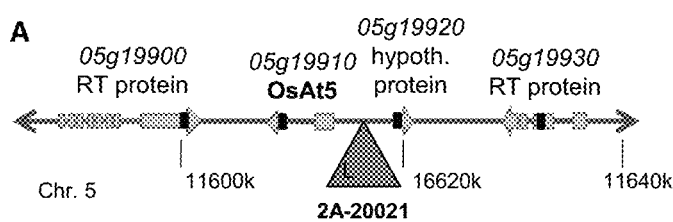
FIGS. 19A-19B. Genomic positions and gene expression data of the OsAT5-D1 activation tagged line. Genomic positions and gene expression data for the OsAT5-D1 activation tagged line (FIG. 19A) Representation of the portion of the rice chromosome near the T-DNA insertion site. Exons are represented by wide bars with the direction of transcription indicated by arrows. The insertion site is represented by the triangle, with the left border, nearest the transcriptional enhancer elements, represented by 'L'. cDNA Regions targeted for amplification in qPCR are depicted as black bands. RT stands for retrotransposon and hypoth indicates hypothetical.
Figure 19B:
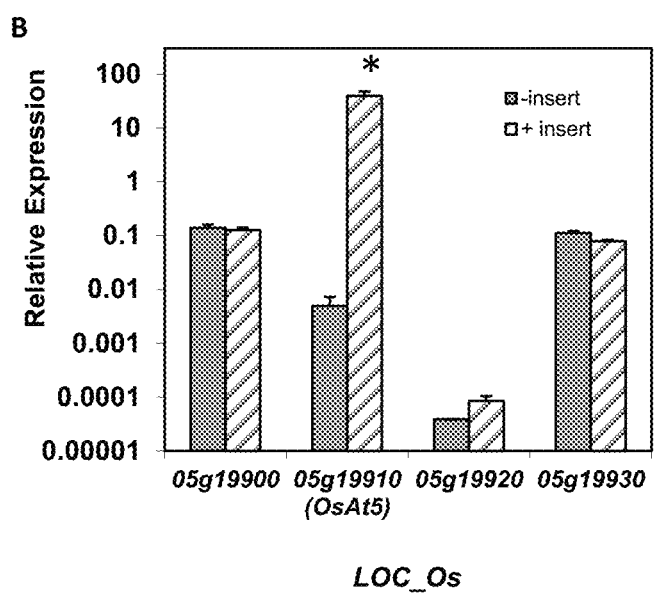
Figures 20A, 20B, 20C, 20D:
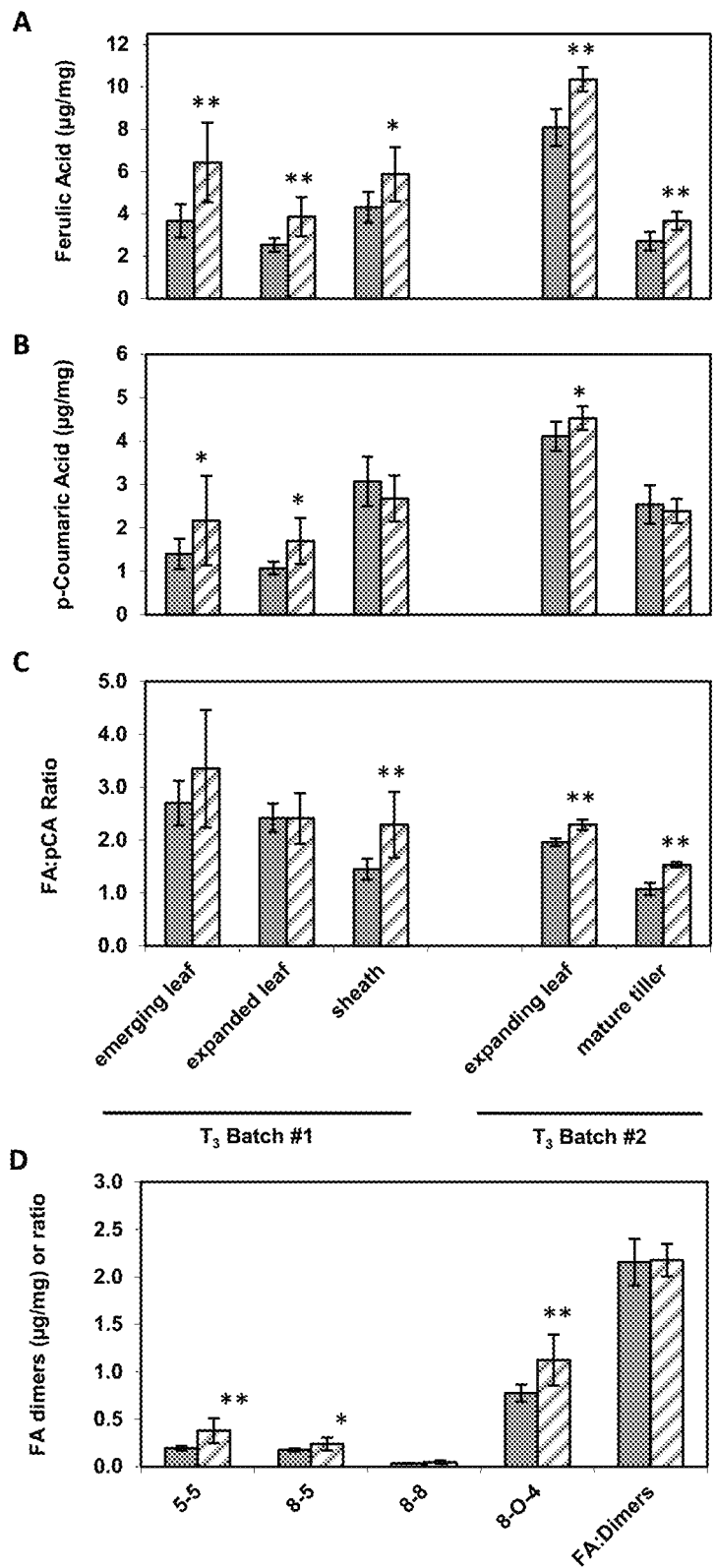
FIGS. 20A-20D. OsAT5-D1 shows alterations in cell wall hydroxycinnamic acids. Data are for two separately grown batches (#1 and #2) of plants of a near isogenic family lacking the insert (grey bars, progeny of the near isogenic wild type line 2A-20021.10.2) and a family homozygous for the insert (cross-hatched bars, progeny of the OsAT5-D1 mutant line 2A-20021.11.7). Samples for batch #1 were harvested from seedlings 35 days post germination. The expanding leaf samples for batch #2 were harvested at 8 weeks post germination and the mature tiller at 16 weeks post germination. Values are the average of 5 to 12 individual plants. Error bars mark the 95% confidence interval for the mean. * indicates significance via Student's t-test at $p<0.05$ and ** indicates significance at $p<0.01$.

FIGS. 19A-19B provide the genomic positions and gene expression data of the OsAT5-D1 activation tagged line. Genomic positions and gene expression data for the OsAT5-D1 activation tagged line (FIG. 19A) Representation of the portion of the rice chromosome near the T-DNA insertion site. Exons are represented by wide bars with the direction of transcription indicated by arrows. The insertion site is represented by the triangle, with the left border, nearest the transcriptional enhancer elements, represented by 1'. cDNA Regions targeted for amplification in qPCR are depicted as black bands. RT stands for retrotransposon and hypoth indicates hypothetical. (FIG. 19B) Average normalized gene expression determined via qPCR shows that among genes within 20 kbp of the insertion site only acyltransferase expression is altered significantly in young leaves of homozygous plants with the T-DNA insertion (hashed) compared with negative segregants (solid). Error bars represent the standard deviation of 3-4 biological replicates. Genes with significantly higher expression (p<0.01, Student's t-test) are marked with an asterisk.

FIGS. 20A-20D provides data demonstrating that OsAT5-D1 shows alterations in cell wall hydroxycinnamic acids. Data are for two separately grown batches (#1 and #2) of plants of a near isogenic family lacking the insert (grey bars, progeny of the near isogenic wild type line 2A-20021.10.2) and a family homozygous for the insert (cross-hatched bars, progeny of the OsAT5-D1 mutant line 2A-20021.11.7). Samples for batch #1 were harvested from seedlings 35 days post germination. The expanding leaf samples for batch #2 were harvested at 8 weeks post germination and the mature tiller at 16 weeks post germination. Values are the average of 5 to 12 individual plants. Error bars mark the 95% confidence interval for the mean. * indicates significance via Student's t-test at p≤0.05 and ** indicates significance at p≤0.01. (FIG. 20A) Ferulic acid content in an alcohol insoluble residue (AIR) preparation. (FIG. 20B) p-Coumaric acid content from AIR. (FIG. 20C) The ratio of ferulic acid (FA) to p-coumaric acid (CA), which is not subject to weighing or extraction efficiency errors. (FIG. 20D) Major FA dimer species and the ratio of FA to dimer for the Batch #1 expanded leaf samples.

FIGS. 19A-19B. Genomic positions and gene expression data of the OsAT5-D1 activation tagged line. Genomic positions and gene expression data for the OsAT5-D1 activation tagged line (FIG. 19A) Representation of the portion of the rice chromosome near the T-DNA insertion site. Exons are represented by wide bars with the direction of transcription indicated by arrows. The insertion site is represented by the triangle, with the left border, nearest the transcriptional enhancer elements, represented by cDNA Regions targeted for amplification in qPCR are depicted as black bands. RT stands for retrotransposon and hypoth indicates hypothetical. (FIG. 19B) Average normalized gene expression determined via qPCR shows that among genes within 20 kbp of the insertion site only acyltransferase expression is altered significantly in young leaves of homozygous plants with the T-DNA insertion (hashed) compared with negative segregants (solid). Error bars represent the standard deviation of 3-4 biological replicates. Genes with significantly higher expression ($p \leq 0.01$, Student's t-test) are marked with an asterisk.

FIGS. 20A-20D. OsAT5-D1 shows alterations in cell wall hydroxycinnamic acids. Data are for two separately grown batches (#1 and #2) of plants of a near isogenic family lacking the insert (grey bars, progeny of the near isogenic wild type line 2A-20021.10.2) and a family homozygous for the insert (cross-hatched bars, progeny of the OsAT5-D1 mutant line 2A-20021.11.7). Samples for batch #1 were harvested from seedlings 35 days post germination. The expanding leaf samples for batch #2 were harvested at 8 weeks post germination and the mature tiller at 16 weeks post germination. Values are the average of 5 to 12 individual plants. Error bars mark the 95% confidence interval for the mean. * indicates significance via Student's t-test at $p \leq 0.05$ and ** indicates significance at $p \leq 0.01$. (FIG. 20A) Ferulic acid content in an alcohol insoluble residue (AIR) preparation. (FIG. 20B) p-Coumaric acid content from AIR. (FIG. 20C) The ratio of ferulic acid (FA) to p-coumaric acid (CA), which is not subject to weighing or extraction efficiency errors. (FIG. 20D) Major FA dimer species and the ratio of FA to dimer for the Batch #1 expanded leaf samples.

Discussion

Hydroxycinnamyl esters in cell walls influence basic and applied plant traits including growth properties, disease resistance, and food and feed quality (Santiago et al., 2007; Buanafina, 2009). The molecular mechanism of incorporation of hydroxycinnamates into cell walls remains largely obscure. Here, we present results showing that over expression of OsAt10 in the OsAT10-D1 line decreases FA and increases p-CA in leaf blades, leaf sheaths, and mature straw (FIG. 5). We have also confirmed that over expression of OsAt10 in two other independent lines, Ubi::OsAt10-4 and Ubi::OsAt10-5, alters the ratio of FA to p-CA in a manner similar to OsAT10-D1, namely by causing a dramatic decrease in the FA:p-CA ratio relative to wild-type genotypes (FIGS. 6A-6C).

Distribution of BAHD CoA Acyltransferases Across Plants

Our phylogenetic analysis shows that, with one exception, sequenced angiosperms that we examined have annotated proteins within the "Mitchell clade" of BAHD acyl CoA-utilizing acyltransferase proteins, identified by being highly expressed in grasses (Mitchell et al., 2007). However, there has been a distinct expansion of this clade in grasses, with 12-20 members in grasses compared to 0-2 in other species (Table I). The presence and expression of a protein in the Mitchell clade in banana (order Zingerberales, BanAAT (Beekwilder et al., 2004)), is consistent with the presence of hydroxycinnamates in banana cell walls (Carpita, 1996).

A mutant in the most closely related *Arabidopsis* protein, AT3G62160, was recently examined for a change in hydroxycinnamates in the cell wall and other extracellular polymers, though no differences were identified (Rautengarten et al., 2012). Though the function of the *Arabidopsis* protein remains to be determined, that result is consistent with a model of neofunctionalization or subneofunctionalization of the "Mitchell clade" of BAHD acyltransferases in Commelinoid monocots (He and Zhang, 2005). In this model, a duplicated "Mitchell clade" member in the progenitor of Commelinoids acquired the ability to modify a cell wall-related substrate. Subsequently, the conservation of additional clade members that we observe is consistent with selection for further additional gene duplication events.

The Cell Wall Target of OsAT10 is Arabinoxylan

Previous results have found that p-coumaroyl esters are almost exclusively bonded to lignin; whereas, FA is predominantly esterfied to glucuranoarabinoxylan. However, enzymatic release experiments have provided some prior evidence that p-CA is also incorporated into the polysaccharides of grass cell walls (Mueller-Harvey et al., 1986; Ishii et al., 1990; Faulds et al., 2004). We find that mature rice straw has ~20% of p-CA associated with matrix polysaccharide (FIGS. 7A-7C). This may also be the location of the p-CA in the young leaf tissue, which we expect to have very low lignin amounts (FIGS. 6A-6C). We found that the hydroxycinnamic acid changes in OsAT10-D1 are predominantly on the TFA-soluble matrix polysaccharide fraction, not the acid-resistant lignin (FIGS. 7A-7C). Indeed, we were able to confirm that the hydroxycinnamoyl groups in the TFA-released fraction are ester-linked to a 5-carbon sugar. Since this sugar-hydroxycinnamoyl species migrate in narrow bands in the LC-MS analysis, we strongly suspect that these represent only arabinose esters, which have been commonly described (Mueller-Harvey et al., 1986; Buanafina, 2009). Thus, it is unlikely that this peak also consists of feruloylated-xylose, which has been described from bamboo xyloglucan (Ishii et al., 1990). Furthermore, we have no evidence to suggest that OsAT10 functions as a p-coumaroyl CoA monolignol acyltransferase that has been described in recent publications (Hatfield et al., 2009; Withers et al., 2012). Rather, it seems likely that the native function of OsAT10 is to incorporate p-CA into cell wall 5-carbon sugars, likely the arabinose of arabinoxylan. This is consistent with the notion that different "Mitchell clade" members may have different functions.

We observed that OsAT10-D1 had an ~300-fold increase in gene expression, but only a 3-fold increase in p-CA. While this could be caused by the cell wall phenotype being an indirect result of increased OsAt10 expression, this trivial explanation is unlikely based on previous results. The observations that silencing "Mitchell clade" members decreases rice cell wall hydroxycinnamate content (Piston et al., 2010) and that biochemical analysis of one of them, PMT (OsAT4), demonstrates function on a cell wall substrate makes the trivial explanation unlikely. Instead, the difference suggests that other parts of the cell wall hemicellulose-incorporation pathway are limiting in the presence of the excess amount of acyltransferase. Indeed, dramatic changes in, for example, the monolignol biosynthesis enzymes, 4-coumaryl CoA ligase of *Arabidopsis*, cause comparatively small changes in enzyme activity and lignin composition (Lee et al., 1997). Assuming that the altered polysaccharide is arabinoxylan, one possibility is that the frequency of hydroxycinnamoyl-arabinose incorporation is controlled by the glycosyltransferases that synthesize arabinoxylan. Another observation that remains to be completely resolved is the decrease in sugar-feruloylation that accompanies the increase in p-coumarylation in cell walls of mutant plants. Some specificity in the level of modification of arabinose may explain this observation. Alternatively or in addition, since p-CA is a precursor of FA, the increased activity of the putative p-CA transferase, OsAT10, may reduce the amount of feruloyl-CoA available for modification of the hemicellulose. Further experiments will be needed to test these models.

"Mitchell Clade" Acyltransferase have Different Effects on Cell Wall Hydroxycinnamoyl Esters Both our data and that of Piston et al. (2010) provide genetic evidence that changing the expression of "Mitchell clade" CoA acyltransferases alters the amounts of cell wall hydroxycinnamyl esters. Superficially, our result that OsAT10 over expression decreases cell wall ferulate appears to conflict with that of Piston et al. (2010), who reported that simultaneous reduced expression of OsAT6 through OsAT10 (i.e., construct pAFT-B) causes a ~20% reduction in the amount of FA in mature leaves. One possibility is that in OsAT10-D1 a change in expression of other related acyltransferases causes the observed phenotype. However, our results showing that there is no measurable change in selected related acyltransferases in the over expression lines (Supp FIG. 2), make this model less likely.

Instead, the various results with "Mitchell clade" members is consistent with the model that differing OsATs have different functions. First, this model explains the apparent conflict between Piston et al.'s results and ours. If all of the OsATs function to incorporate FA into arabinoxylan, it seems likely that the effect of reducing expression 2- to 5-fold for four to five OsAT members would give greater than the observed 20% reduction in FA. Further, Piston et al. detected no effect on wall hydroxycinnamates in lines with simultaneously reduced expression of OsAt1, OsAt2, OsAt11, and OsAt12 (i.e., construct pAFT-A). Thus, we suspect that Piston et al. observed small or no effects because their constructs caused multiple small effects. Indeed, while several studies have found that BAHD acyltransferases often have promiscuous specificities (D'Auria, 2006), work with anthocyanidin-malonyl transferases (Dm3MAT1), have measured discrimination for a hydroxylated substrate over a maloynated one (Unno et al., 2007). Thus, it is not improbable to hypothesize that different acyltransferases may have differential affinities for the two hydroxycinnamyl CoA adducts. This is also consistent with the report of Withers et al. that OsAT4 (PMT) acts on monolignols (Withers et al., 2012), rather than polysaccharides.

Glucose Polysaccharide, but not Lignin, Compensation in OsAT10-D1

Several cases of compensatory changes in plant cell wall composition have been observed. For example, the cell walls of an *Arabidopsis* mutant with dramatically reduced xylan, irx10irx10L, possess by mass more glucose, arabinose, and galactose compared with those of wild-type plants (Wu et al., 2009). Also, other *Arabidopsis* and rice xylan mutants have reduced lignin content (Scheller irx 9 and irx 7 paper, (Chen et al., in prep)). Similarly, poplar saplings (*Populus tremuloides*) in which a phenylpropanoid biosynthesis gene for 4-coumaryl-CoA ligase is silenced produce less lignin but more cellulose (Hu et al., 1999). However, compensatory changes are not uniformly observed in response to reduced amounts of a particular cell wall component. For example, no consistent changes in polysaccharide content are observed in switchgrass plants with lignin reduced by silencing of the phenylpropanoid biosynthesis genes that encode caffeic acid 3-O-methyltransferase or cinnamyl alcohol dehydrogenase (Fu et al., 2011; Fu et al., 2011).

The mature cell walls of OsAT10-D1 exhibits a ~15 to 20% increase by mass and mol % in both TFA-soluble glucose, corresponding to mixed linkage glucose and amorphous cellulose, and TFA-insoluble glucose, representing crystalline cellulose (F). The increase in crystalline cellulose is of a similar magnitude to that observed in poplar silenced for 4-coumaryl-CoA ligase (15%, (Hu et al., 1999)). In contrast, chemical, mass spectrometry, and thermogravimetric assays did not detect alterations in lignin content or composition in the OsAT10-D1 mutant line (Table III, FIGS. 9A-9B, and FIGS. 17A-17B). This suggests that lignin amounts are not sensitive to changes in phenylpropanoid pathway flux that may be caused by increased OsAT10 activity. The observations that FA and glucose levels change but lignin does not might be due to spatial and temporal separation of the incorporation of hydroxycinnamates into a precursor of arabinoxylan and the synthesis of lignin. Generally, our results contribute to an emerging view that plants possess specific molecules that are able to sense and trigger responses to specific changes in cell wall composition and/or function; however, the nature of those sensors remains obscure (Humphrey et al., 2007).

Cell Wall Hydroxycinnamyl Esters May Contribute to Plant Reproduction

Correlative studies suggest that FA dimerization has a role in halting plant growth via inhibition of cell wall elongation and expansion (MacAdam and Grabber, 2002; Obel et al., 2002; Sasayama et al., 2011). Thus, we might have expected plants with reduced FA dimer content to either be smaller, due to decreased ability to support themselves, or be larger, due to greater expansion of cells during growth. Indeed, the progeny of a maize line with reduced ferulate esters at the seedling stage, has recently been found to increase biomass by ~8% in field trials (Jung and Phillips, 2010). However, we observed no effect on vegetative growth for greenhouse-grown OsAt10 over expression lines (FIG. 4). We were also unable to detect changes in the breaking force of OsAT10-D1 seedling leaves compared with those of the negative segregant (FL, R. Gan, and LEB unpublished), suggesting that this modification does not cause changes in leaf biophysics. OsAT10-D1 does exhibit reduced seed yields per plant by ~20% (FIG. 4). This observation correlates with the difficulty of isolating homozygous knockout lines for various OsATs (Table II, F. Piston and J. Dubcovsky personal communication). On the other hand the low ferulate maize lines did not exhibit a change in ear mass at the stage examined (Jung and Phillips, 2010). From a practical perspective, restoring grain yield in plants engineered to over express OsAt10 would be an important consideration for development of a dual-use crop for both food and biofuel/feed purposes, but would be less crucial for dedicated fuel and feed grasses. One way to accomplish this might be to use a promoter with low expression in reproductive tissues.

Heightened Saccharification of OsAT10-D1

A major impetus for this work was to understand if a specific genetic reduction of the amount of cell wall-associated FA would improve the yields of cell wall sugars from modified plants for biofuel and feed production. We found that the decreased amount of FA and proportional decrease in FA dimers releasable from OsAT10-D1, did indeed lead to greater sugar yields in both enzymatic and fungal saccharification assays (FIGS. 11A-11C). However, the quantitative similarity between the improvement in cellulose-mediated digestion and cell wall glucose content (20%) suggest that with the mild pretreatment conditions used the improvement in enzymatic digestibility may not be due to altered cellulose accessibility, but rather cellulose content. On the other hand, the larger improvement in glucose yield (~45%) from acid pretreatment and fungal digestion is consistent with improvements in the accessibility of glucose-containing polysaccharides. The improvement in fungal xylose release was particularly dramatic (85%) and correlates with an increase in fungal xylanase production (FIGS. 11A-11C), as if due to a positive feedback loop between xylose and xylanase expression. The enhanced xylanase activity of YT02 on the mutant straw is consistent with the model that the modifications in the mutants are on the xylan polymer, which is made more accessible by reduced ability to cross-link with each other and lignin. The acid-based pretreatment and the synthesis by the fungus of a suite of enzymes, presumably including diverse xylanases, in the fungal assay might have accentuated the effects of the reduced ferulate content of the mutant relative to the wild type. In contrast, we do not expect that there is a major improvement in the quality of the xylan of the OsAT10-D1 because the xylan in the mutant appears to have higher absolute hydroxycinnamyl esters substitution rates compared with the wild type.

Summary

We find that over expression of members of a grass-diverged and expanded clade of BAHD CoA acyltransferases alter the amounts of hydroxycinnamic acids in grass cell walls. In particular, increased expression of OsAt10 increased p-CA content but decreased FA content of rice matrix polysaccharide, consistent with the tentative assignment of this enzyme as a p-coumaryl CoA transferase. Similarly, increased expression of AT15 and AT7 resulted in decreased FA. Together with the recent report that OsAT4 has p-coumaryl CoA:monolignol transferase activity, this suggests that other members of the "Mitchell clade" of CoA acyltransferases likely possess feruloyl transferase activity. Of practical importance toward improving the efficiency of biofuel production and animal feed from grass biomass, we have found that the increased OsAt10 expression increases the glucose content of and improves the digestibility of mature straw. The fact that this is an over expression effect will facilitate rapid transfer to and testing of this gene in other grass species.

Materials and Methods

Acyltransferase Identification and Phylogenetic Analysis

To identify putative BAHD acyltransferases, we downloaded the hidden Markov model profile for PF02458 from the Pfam database and then searched the annotated coding sequences of diverse plant genomes to identify potential domains using HMMER v3.0 (Finn et al., 2011). We used the following genome annotation sources and versions, which were current at the time of the analysis: *Arabidopsis thaliana*, TAIR v10; *Brachypodium dystachyon*, Phytozome v7.0; Soybean, Phytozome v7.0; *Medicago truncatula*, Mt3.5; Rice, MSU v6.1; *Physcomitrella patens*, Phytozome v7.0; Poplar, Phytozome v7.0; Sorghum, Phytozome v7.0; *Selaginella moellendorffii*, Phytozome v7.0. To serve as a reference for phylogenetic analysis, we downloaded the sequences of 46 previously characterized BAHD enzymes from NCBI, and identified their conserved PF02458 domains as described above. e refer to these proteins as the D'Auria set (D'Auria, 2006). In addition, we randomly selected an outgroup of three PF02458-containing proteins from fungi. All phylogenetic analyses were conducted only with the Pfam domain protein sequences. If HMMER3 identified multiple segments with similarity to the PF02458 domain for a single protein, those segments were concatenated. Redundant sequences, such as from alternative splice versions of a single locus, were noted in the sequence name and only represented once in subsequent analyses.

We determined the BAHD clade of each predicted protein via comparison to the D'Auria set. To do this, we used Clustal2 (Larkin et al., 2007) with default settings to build an alignment of the D'Auria set followed by limited manual adjustments with BioEdit. We used this alignment as a profile for alignment of each species' predicted BAHD enzymes. Based on these alignments, we omitted sequences that lack the region immediately surrounding the highly conserved active-site motif, HXXXD, and also those that lack either the H or the D, or include of an extra amino acid between them. We then used MEGA5.05 (Tamura et al., 2011) to infer and visualize neighbor-joining phylogenetic trees for each species' BAHD proteins in conjunction with the D'Auria set and the outgroup sequences. Parameters were: amino acid substitutions according to the Jones-Taylor-Thorton model, gamma distribution of mutation rate among sites, distribution shape parameter of one, and gaps treated by pair-wise deletion. Five hundred bootstraps were used to identify a consensus tree for each species. Though the bootstrap values were often lower than 50%, the previously delineated BAHD clades unfailingly grouped together (D'Auria, 2006). The proteins encoded by the highly grass-expressed genes belong to Clade V. From the species BAHD trees, we identified clade V proteins, to which, from each species for further analysis.

Clade V proteins from the diverse plant species examined were aligned, then the alignments manually edited. To achieve a high level of confidence we analyzed the relationships among the rice acyltransferase proteins of interest using Bayesian analysis, in addition to the methods described above. Using MrBayes3.1.2 (Huelsenbeck and Ronquist, 2001), the parameters for that analysis were as follows: the WAG model for amino acid substitutions (analysis with a subset of the data showed that this was the most probably fixed rate model for the data set), with a gamma rate distribution with some invariable residues. We ran the simulation for 125,000 generation until the average standard deviation of split frequencies stabilized below 0.01.

Plant Lines and Growth Conditions

We selected mutant lines for the target genes from RiceGE, which summarizes rice T-DNA flanking sequence database (An et al., 2005; Jeong et al., 2006). The initial screen was conducted on the segregating progeny of the primary transgenics, the line numbers for which are listed in Table II. Seeds from the stock center were sterilized with a 40% commercial bleach solution and germinated on a half-strength Murashige and Skoog (MS) medium containing 1.5% sucrose, 0.55 mM myo-inositol and 0.2% phytagel at 28° C. with continuous white light. After seven days, the seedlings were transplanted into topsoil and grown in a greenhouse (20-30° C., 60 to 80% relative humidity). Natural day lengths <14 hours were supplemented with artificial lighting. For genotyping, 10-20 mg leaf samples from 10-24 segregating progeny of the first generation were harvested, frozen in liquid nitrogen, and ground with a Qiagen Tissuelyser (17 Hz, 1 minute). The samples were vortexed in 200 µL DNA extraction buffer containing 100 mM Tris-HCl (pH 9.5), 1 M KCl, and 10 mM EDTA (pH 8.0), incubated at 65° C. for 30 mM, diluted with 1 mL of H2O, and centrifuged for 10 min at the maximum speed. The supernatant was used as template the template for genotyping by PCR. PCR conditions were as follows: 94° C., 5 min; 35 cycles of 95° C. for 35 sec, 56° C. for 45 sec, and 72° C. for 45 sec; 72°

C. for 5 minutes. Genotyping primers are described in Table IV. We confirmed and further characterized the next two generations in selfed progeny of homozygous mutant and negative segregant, wild-type plants of line 4A-03423, which we have named OsAT10-D1. Specifically we characterized mutant progeny of 4A-03423.5, 4A-03423.12, and 4A-03423.1.9 and negative segregant progeny of 4A-03423.5 and 4A-03423.5.6. In this nomenclature, the period indicates each new generation and the numbers following the period indicate the parent plant of the analyzed progeny.

Generation of Ubi:OsAt10 Lines

We amplified a 1541 base pair fragment encoding OsAT10 (LOC_Os06g39390.1) including both the start and stop codons from Nipponbare seedling cDNA with the cloning primers listed in Table IV. The PCR fragment was gel purified, cloned into pENTR-DTOPO (Invitrogen), and confirmed by sequencing. We then recombined the gene into the final pCAMBIA1300-Ubi-GW-Nos construct (Park et al., 2010). This binary vector contains a Gateway cassette, flanked by the maize Ubi1 promoter and the 3'-terminator of nopaline synthase from *Agrobacterium tumefaciens*, and the Hpt2 gene, which confers resistance to hygromycin. We used *Agrobacterium tumefaciens* EHA105 to transform fresh calli from the rice *japonica* cultivar, Kitaake, as previously described (Cheng et al., 1997). After regeneration of plantlets, plants were transferred to the greenhouse under conditions described above, and genotyped with primers for Hpt2 (Table IV).

Quantitative RT-PCR

We measured gene expression in young leaf samples. The samples were harvested 33 days after transplanting to the greenhouse and consisted of the top recently emerged or greater-than two-thirds emerged leaf of the 2nd or 3rd tiller. We attempted to choose morphologically and developmentally similar leaves for analysis, based on leaf length and degree of emergence/expansion. Leaves were split vertically down the mid-vein and one half dried for hydroxycinnamic acid analysis, as described below. The other half was frozen in liquid nitrogen, ground to a powder and the RNA extracted with 1 mL of Trizol reagent (Invitrogen) with subsequent processing according the manufacturer's protocol. The resulting total RNA was then purified by digestion with DNaseI and cleaned up on a Nucleospin RNA II column (Macherey-Nagel) according to the manufacturer's protocol. RNA quality was checked on a 1.4% agarose gel after denaturation with glyoxal reagent (Ambion). We synthesized cDNA from 1 μg of total RNA with VILO-Superscript (Invitrogen).

We used quantitative real time PCR to measure the expression of each target gene and potential off targets. Using an established procedure for identifying control primers (Vandesompele et al., 2002), we screened primers for three highly expressed rice genes (Ubq5, eEf1α, and 18S rRNA (Jain et al., 2006)) and two moderately expressed genes (Abp and Cc55 (Jain, 2009)) for stability of expression across a set of cDNAs made from 28 rice, aerial vegetative samples collected throughout development (Table IV, LEB and PCR in prep). Based on geNORM analysis, we used primers for Ubq5 and Cc55, the two most stably expressed genes for our samples, for internal controls in the qPCR reactions. Reactions were run in a Bio-Rad CFX thermocycler, using SsoFAST EvaGreen mastermix (Bio-Rad). Reaction efficiencies were calculated with Lin-RegPCR, which calculates the average efficiency for each primer pair based on all the reactions using those primers per plate (Ruijter et al., 2009). Efficiency-adjusted gene expression was normalized with the geometric mean of the control primers (Vandesompele et al., 2002), using the following equation: $EAt10Cq(At10)/SQRT(ECc55Cq(Cc55) \times Eubq5Cq(Ubq5))$, where E and Cq indicates the average reaction efficiency and cycle number at which the threshold fluorescence level was exceeded for the designated genes, respectively.

Cell Wall Analyses

Preparation of Alcohol Insoluble Residue (AIR)

Due to the significant changes in cell wall content across development, we took care to harvest developmentally similar plant organs and parts for comparisons between wild-type and mutant plants in all experiments. Samples harvested for the initial screen were dried at 65° C. and samples from subsequent generations at 45° C. for 72 hours. Immature tissue was ground by two rounds of shaking at 1200 rpm with two stainless steal balls 90 sec each. Mature aerial tissue was milled with a Wiley Mill with a 5 mm screen followed by and Udy mill with a 1 mm screen. Ground tissue (5 to 500 mg) was treated with 95% ethanol (1:4 w/v) at 100° C. for 30 min. After the treatment, the supernatant was removed by centrifugation (10,000 g, 10 min) and the residue was subsequently washed three to five times with 70% ethanol and dried at ~35° C. under vacuum using a centrivap. The dried powder obtained after 70% ethanol wash is designated as alcohol insoluble residue (AIR). The AIR was destarched as described by Obro et al. (2004). AIR was treated with amylase (0.3 U/10 mg biomass Termamyl, Novozymes, Bagsværd, Denmark) in 3-(N-morpholino) propanesulfonic acid (MOPS) buffer (50 mM, pH 7.0) at 85° C. for 1 h followed by amyloglucosidase (0.33 U/10 mg biomass) and pullulanase (0.04 U/10 mg biomass) in acetate buffer, 200 mM, pH 4.5 for 2 h at 50° C. Amyloglucosidase and pullulanase were purchased from Megazyme (Bray, Ireland). The reactions were stopped by adding 3 volumes of cold 95% ethanol, vortexed, and centrifuged at 10,000 g for 10 mM The residue obtained after centrifugation was washed three times with 70% ethanol and dried at 32° C. using a CentriVap Vacuum Concentrator (Labconco Corp, MO).

Analysis of Hydroxycinnamic Acids

To release esterified hydroxycinnamic acids from the cell wall, AIR (1 to 10 mg, depending on the experiment, typically 3 mg) was saponified with 500 μl of 2 N NaOH for 24 h at 25° C. with mixing at 300 rpm. For analysis of later generations, we doped reactions with an extraction standard, trans-cinnamic acid, but this improvement had not yet been developed for the initial screening. After saponification, the supernatant was acidified (pH<2) with 100 μL concentrated HCl, vortexed, and extracted three times with 300 μL ethyl acetate. The extracts were combined and evaporated to dryness using a CentriVap at 32° C. The samples were dissolved in 50% (v/v) methanol prior to HPLC analysis. Care was taken to shield the samples from light during the entire process of extraction to prevent the isomerization of hydroxycinnamates in light.

Quantification of hydroxycinnamic acids was carried out on a Dionex Ultimate 3000 high pressure liquid chromatography (HPLC) system (Thermofisher-Dionex, Sunnyvale, Calif., USA) with UV detection. Samples were separated on a reverse-phase C18 column a Synergy 4u Fusion-RP 80 Å column (250×2 mm, Phenomenex, Torrance, Calif.) with a flow of 0.3 ml min-1 and a gradient of solvent A (0.2%, v/v, TFA) and solvent B (acetonitrile) as follows: 0-5 min, 10% B isocratic; 5-25 min, 10-30% B linear; 25-40 min, 30% B isocratic; 40-45 min, 30-35% B linear; 45-46 min, 35-100% B linear; 46-51 min, 100% B isocratic; 51-53 min 100-10%

B linear; 53-60 min 10% B isocratic. The column temperature was maintained at 30° C. and detection was carried out at 320 nm. Drs. J. Ralph and F. Lu kindly provided the ferulate dehydrodimers, which were treated with 2 N NaOH prior to running as standards (Ralph et al., 1994). To confirm that the species with corresponding retention times were diferulates, we also collected the two major dimer peaks from the HPLC and then their identity verified their mass by LC-MS.

Hydroxycinnamate Fractionation

To determine whether the changes in hydroxycinnamate content were associated with the matrix polysaccharide or the lignin fractions, 6 mg of destarched AIR were mixed with 600 uL of either 0.05 M trifluoroacetate (TFA) or water. Samples were incubated with shaking at 100° C. for up to 690 minutes. At each time point, a fraction of the sample was removed and frozen. Once all the samples were collected, they were thawed and treated with 2 N NaOH for 24 hrs at 25° C. followed by neutralization with concentrated HCl. (Control duplicates remained frozen during the NaOH incubation and then were treated with NaOH and HCl). trans-Cinnamic acid was doped into the samples before they were extracted three times with 300 uL of ethyl acetate. Combined extracts were dried with no heat via speed vac and resuspended in 50:50 MeOH before HPLC analysis. For quantification of sugars released by TFA, D-xylose was measured using a D-xylose test kit (Megazyme) and D-glucose was measured using a D-fructose/D-glucose (LQR) kit (Megazyme). Both kits were used essentially according to manufacturer's directions, but with reduced volumes for use with a microplate reader. Xylose and glucose supplied with the kits were used to generate standard curves for quantification.

High Performance Liquid Chromatography-Electrospray Ionization-Mass Spectrometry HPLC separation of the 50 mM TFA-treated samples was performed using an Agilent (Santa Clara, Calif.) 1290 HPLC system equipped with a Phenomenex (Torrance, Calif.) Kinetex reversed phase column (ODS-18, 100 mm×2.1 mm, 2.6 μm particle size). Mobile phase A consisted of 5% acetonitrile and 0.1% formic acid in HPLC-grade submicron filtered water (Fisher Scientific, Pittsburgh, Pa.). Mobile phase B consisted of 0.1% formic acid in 100% acetonitrile. These mobile phase solutions were filtered and vacuum-degassed prior to use. A binary gradient at 0.3 mL/min flow rate was applied as follows: 90% solvent A and 10% solvent B from 0 to 4 min, linear gradient to 30% solvent B from 4 to 8 min, linear gradient to 50% solvent B from 8 to 9 min, 50% solvent B from 9 to 12 min, linear gradient from 12 to 13 100% solvent B, 100% solvent B from 13 to 15 min, and linear gradient to return the mobile phase to 90% solvent A and 10% solvent B from 15 to 16 min, which was maintained for an additional 5 min before the next sample was injected. The HPLC column eluent was introduced into an Agilent 6538 UHD Accurate Mass QTOF (Santa Clara, Calif.) equipped with an electrospray ionization source operated in negative ion mode. Nitrogen gas was used as a nebulizing and drying gas with a drying gas temperature of 325° C. and 10 L/min flow rate. Fragmentor voltage was 160V and capillary voltage was 3500V. Data was collected with Mass Hunter Acquisition (B.04.00, 2011) and analyzed with Mass Hunter Qualitative (B.04.00, 2011).

Monosaccharide Composition by HPAEC

Destarched AIR (2-5 mg) was treated with 2 M TFA at 120° C. for 1 h. Next the hydrolysate was completely dried using a CentriVap at 32° C. Monosaccharides produced by TFA hydrolysis were then redissolved in nanopure water and analyzed by high-performance anion exchange chromatography (HPAEC) with pulsed amperometric detection on an Dionex UltimateICS-3000 system equipped with an electrochemical detector and a 4×250 mm CarboPac PA20 column (ØBro et al., 2004). The monosaccharides used as the external standards were obtained from Sigma Aldrich, USA and Alfa Aesar, MA, USA.

Lignin Quantification Using Acetyl Bromide

Lignin was quantified via acetylbromide solubilization (Fukushima and Hatfield, 2004), followed by quantification in a 96-well plate as described. Breifly, AIR (5 mg) was incubated with 300 μL of freshly prepared acetyl bromide (25% v/v in acetic acid, Alfa Aesar, MA, USA)) in screw-capped eppendorf tubes (VWR#16466-044) at 50° C. for 3 h in a thermomixer at 1050 rpm, with vortexing every 15 min for the last hour. After centrifuging, 100 μL of the solution was transferred to a fresh tube, followed by addition of 400 μL of 2 N NaOH and 70 μL of freshly prepared 0.5 M hydroxylamine hydrochloride. Next, 57 μL of the solution was transferred to a uv-compatible 96-well plate, followed by addition of 200 μL of glacial acetic acid. Absorption was measured at 280 nm with a BioTek SynergyHT. The lignin content in the samples was determined with an extinction coefficient of 17.75 Lg-1 cm-1 corresponding to average values for grass samples (Fukushima and Hatfield, 2004). Pathlength was determined by measuring the height of the plate.

Pyrolysis Molecular Beam Mass Spectrometry

A commercially available molecular beam mass spectrometer (MBMS) designed specifically for biomass analysis was used for pyrolysis vapor analysis (Skyes et al., 2010). Approximately 4 mg of air-dried 20 mesh biomass was introduced into the quartz pyrolysis reactor via 80 μL deactivated stainless steel Eco-Cups provided with the autosampler. Mass spectral data from m/z 30-450 were acquired on a Merlin Automation data system version 3.0 using 17 eV electron impact ionization. Lignin estimates and S:G ratios were determined by summing the intensities of peaks assigned to lignin compounds as described (Skyes et al., 2010). Several lignin peaks were omitted in the syringyl or guaiacyl summations due to individual peaks having associations with both S and G precursors (Evans and Milne, 1987).

Thermogravimetric Analysis

Thermogravimetric experiments were run using a Netzsch STA 449 F3 TG-DTA instrument. Approximately 50 mg of the ground samples were weighed and then loaded into the thermal analyzer. The samples were measured in 50 mL/min gas flow. The gas was initially He; and the temperature was held at 35° C. for 15 minutes and then increased to 800° C. at 10 K/min. The samples were then cooled to 140° C. and the gas flow was switched to 60% air in He. The samples were then again heated to 800° C. at 5 K/min and then cooled to 290° C. and the gas flow was switched back to He. The weight data reported in FIG. 16 was corrected for variations in water content by normalizing to the weight at 177° C., 30 minutes into the experiment.

Enzymatic Saccharification Assay

AIR (2-5 mg) was pretreated by shaking at 30° C. in 500 μL of 100 mM Citrate buffer (pH 5.0) followed by incubation at 100° C. for 1 hour. After cooling on the bench, 1:2000 (final dilution) NS50013, which contain a cellulose cocktail, and 1:10,000 (final dilution) NS50010, which contains ß-glucosidase, from the Novozymes Biomass Kit were added to the slurry. Reactions were incubated at 50° C. with shaking with periodic removal of timepoints, which were stopped by freezing. Released reducing sugars were quantified by 3,5-dinitrosalicilate (DNS) assay (Ghose, 1987).

Fungal Deconstruction and Enzymatic Assays

Pretreatment of rice straw. Prior to steam pre-treatment, wild-type and mutant rice straw were soaked in 1.2% H2SO4 overnight. Steam-based pretreatment was performed by loading the samples into an autoclave gun and treating them at 191° C. with a residence time of 2 min. Pretreated materials were then released by rapid depressurization to allow the material to explode, breaking apart the lignin and hemi-cellulose from the cellulose. The pre-treated materials were collected, filtered, washed with distilled water, and stored at 4° C. for subsequent degradation experiments using a modified Hägglund's method (Hägglund, 1951).

Rice straw degradation. The pretreated wild-type and mutant rice straw was supplemented with 100 mL of Mandel's media in 500-mL flasks (Mandels et al., 1970). Spores from *Penicillium* sp. YT02 were collected from agar plates with a 0.9% NaCl solution, the adjusted to a concentration of $5.0 \times 10^{12}$ spores mL-1, and used as inoculum [10% (v/v)] for fungal degradation.

Protein content. Fungal growth was estimated by the protein content in the supernatant. Mid-log fungal cell culture suspension was collected by centrifugation ($14,000 \times$ g) for 20 min at room temperature. The supernatant was collected and protein content was determined via the Bradford method.

Enzymatic activities. Total cellulase activity was determined against Whatman no. 1 filter paper (Sigma-Aldrich, St. Louis, Mo.) using the DNS method (Xiao et al. 2004). Total endoglucanase activity was determined with carboxymethylcellulose (CMC) (Claeyssens and Aerts, 1992) followed by reducing sugar measurements with DNS (Ghose, 1987). β-glucosidase activity was determined with p-nitrophenyl-β-d-glucoside and the liberation of p-nitrophenol was accompanied by absorption spectroscopy at 410 nm (Ghose, 1987). Xylanase activity was assayed as described elsewhere (Gessesse and Gashe, 1997). One international unit (IU) was defined as the enzymatic activity needed for the release of 1 mmol of sugar equivalents per unit volume per minute. To improve accuracy, activity values are expressed relative to the protein concentration in the media (IU/mg).

Saccharides. Fungal cultures were centrifuged and the supernatants analyzed for saccharide content by HPLC using an Aminex HPX-87H (Bio-Rad, Hercules, Calif., USA) organic acid column at 65° C. The mobile phase was 5 mM sulphuric acid at a flow rate of 0.5 mL min-1. A refractive index detector was used.

Example 2. Expression of OsAT10 in Switchgrass

Switchgrass plants were transformed with a pUbi:OsAT10 construct, where pUbi is the maize ubiquitin promoter. Transformation was performed using *Agrobacterium*-mediated transformation of calli, and several transgenic calli were selected. A number of lines were transplanted to soil and grown for 5 to 6 months in a greenhouse. Stem material was harvested from the plants and analyzed for hydroxycinnamate content. This analysis showed a decrease of ferulic acid esters from 35.7 nmol/mg biomass in the control plants to 26.4 nmol/mg in the selected transgenic lines, corresponding to a 26% decrease in ferulate esters. Coumaroyl esters showed an increase from 32.9 nmol/mg in the wild type to 64.6 nmol/mg in the transformants. Dried stem material was pretreated with hot water at 100 C for 1 hr, and subsequently subjected to saccharification with Novozymes CTec2 enzyme cocktail for 24 hrs. Released sugars were determined by dinitrosalicylate assays. Under these conditions the wild type plants released 39.9 μg sugar per mg dry biomass whereas the transformants released 56.4 μg per mg dry biomass, corresponding to a 40% increase in released sugars.

Example 3. Increased Expression of AT5

Figures 25A, 25B:
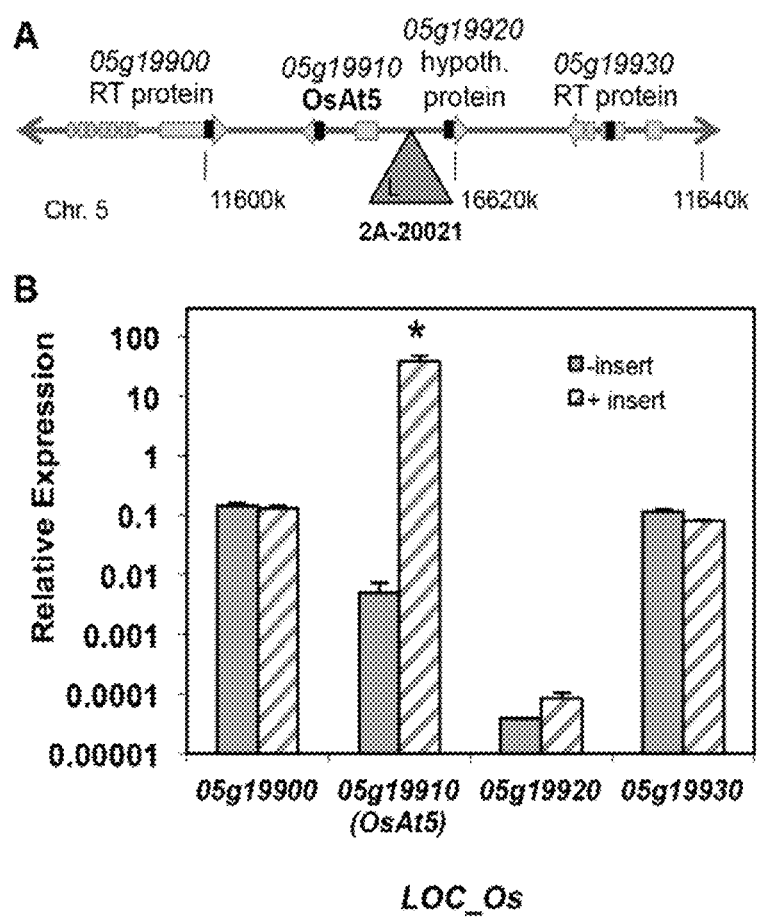
FIGS. 25A-25B shows the Genomic positions and gene expression data for the OsAT5 activation tagged line.
Figures 26A, 26B:
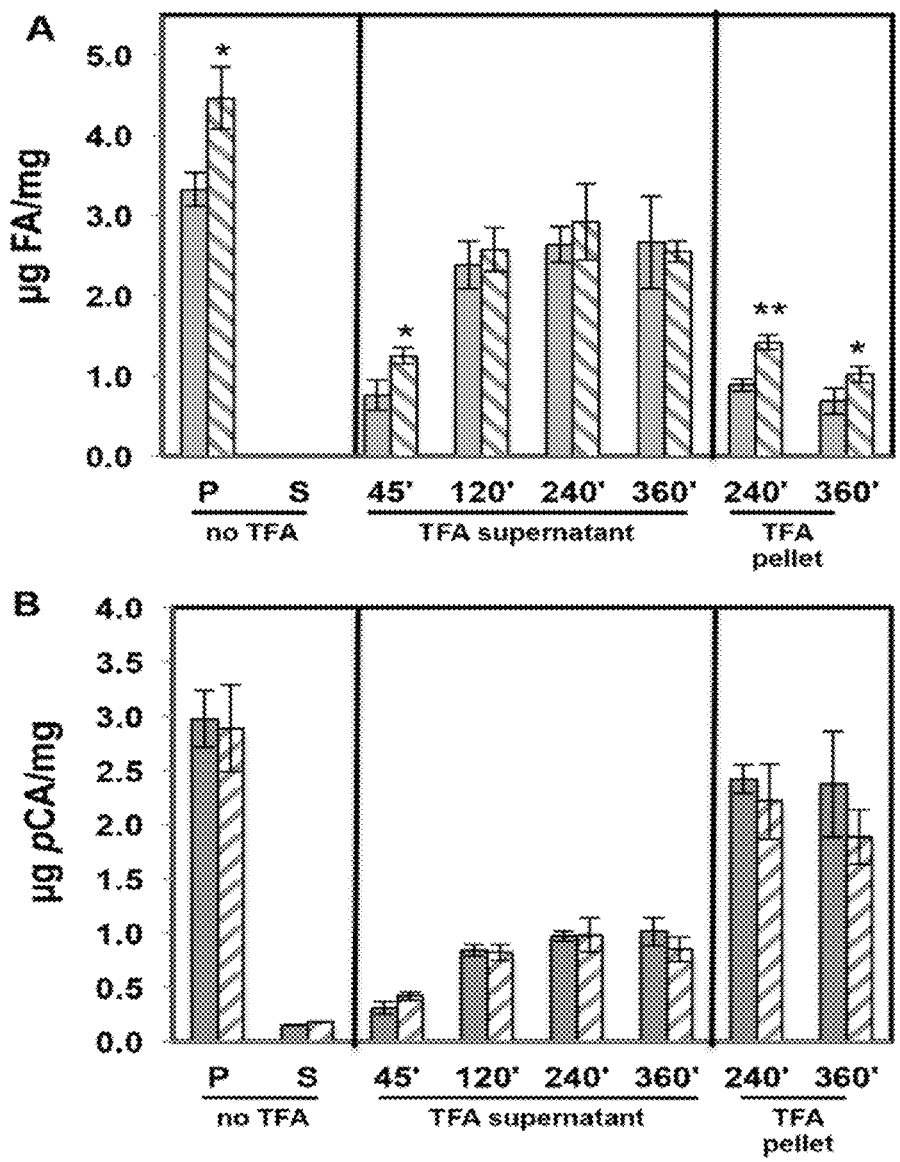
FIGS. 26A-26B illustrates that the cell wall alteration in OsAT5-D1 straw is predominantly to the (50 mM TFA, 100° C.)-insoluble fraction. Wild type samples are (solid) and mutant samples (hatched). P indicates the pellet and S the supernatant after TFA treatment (TFA) or mock (no TFA). The numbers indicate the minutes of TFA treatment.

AT5-D1 is the result of insertion of a T-DNA that includes a transcriptional enhancer cassette near the At5 locus (LOC_Os05g19910) in rice. FIGS. 25A-25B shows quantitative reverse transcriptase PCR data indicating that At5 is over expressed, unlike other loci close to the site of insertion. Previously, we reported that this line showed enhanced cell wall ferulic acid content. FIGS. 26A-26B shows that, unlike At10-over expression lines (Bartley et al. 2013), the increased ferulic acid content of AT5-D1 is not associated with the acid-labile polysaccharide cell wall, but rather fractionates with the acid-resistant, lignin and cellulose pellet. The results of expression of the AT5 and 4-coumaryl ligase (4CL) proteins in yeast show that this causes the novel accumulation of ferulate-monolignol adducts (see below), suggesting that in AT5-D1 the modification to the lignin & cellulose fractions resides on the lignin. AT5-D1 plants grow normally in the greenhouse, under most conditions, but show reduced growth under some undefined stresses (not shown). That AT5 acts as an FMT suggests that over expression of this enzyme in bioenergy crops or crop plant organs that do not normally contain ferulated lignin, can be used to introduce ester linkages into the lignin that can be easily cleaved with weak base pretreatment for subsequent saccharification and biofuel production. Although this concept was shown (Wilkerson et al, 2014). However, AT5 shows only very low sequence similarity to the AsFMT gene described in the Ralph work (18% identity, 30% similarity, FIG. 27), consistent with convergent evolution of the FMT activity in monocots and dicots, and the possibility at AT5 represents a different approach to the problem of introducing ester linkages into lignin.

Plant Lines and Growth Conditions

Plants were grown in (1:1) Turface Athletics medium: vermiculite mix supplemented with fertilizer (JACKS PROFESSIONAL LX 15-5-15 4Ca 2Mg) 3 times a week at a temperature of 85° F.–87° F. during daytime and 75° F.–77° F. during night. Natural day lengths less than 13 h were supplemented with artificial lighting.

OsAT5-D1 qRT-PCR

We measured gene expression in young leaf samples. The samples were harvested 5 weeks after transplanting to the greenhouse and consisted of the top, recently emerged or greater than two-thirds emerged leaf of the second or third tiller. We attempted to choose morphologically and developmentally similar leaves for analysis, based on leaf length and degree of emergence/expansion. Leaves were split vertically down the midvein, and one-half was dried for hydroxycinnamic acid analysis, as described below. The other one-half was frozen in liquid nitrogen, ground to a powder, and the RNA was extracted with 1 mL of Trizol reagent (Invitrogen) with subsequent processing according to the manufacturer's protocol. The resulting total RNA was then purified by digestion with DNaseI and cleaned up on a Nucleospin RNA II column (Macherey-Nagel) according to the manufacturer's protocol. RNA quality was checked on a 1.4% agarose gel after denaturation with glyoxal reagent (Ambion). We synthesized cDNA from 1 mg of total RNA with VILO-Superscript (Invitrogen).

We used quantitative real-time PCR to measure the expression of each target gene and potential off targets.

Using an established procedure for identifying control primers (Vandesompele et al., 2002), we screened primers for threehighly expressed rice genes (Ubq5, eEf1a, and 18S rRNA; Jain et al., 2006) and two moderately expressed genes (Abp and Cc55; Jain, 2009) for the stability of expression across a set of cDNAs made from 28 rice aerial vegetative samples collected throughout development (Table IV; L. E. Bartley and P. C. Ronald, unpublished data). Based on geNORM analysis, we used primers for Ubq5 and Cc55, the two most stably expressed genes for our samples, for internal controls in the quantitative PCR. Reactions were run in a Bio-Rad CFX96 thermocycler using SsoFAST EvaGreen Mastermix (Bio-Rad). Reaction efficiencies were calculated with LinRegPCR, which calculates the aver-age efficiency for each primer pair based on all the reactions using those primers per plate (Ruijter et al., 2009). Efficiency-adjusted gene expression was normalized with the geometric mean of the control primers (Vandesompele et al. 2002) using the following equation: $SQRT(E_{Cc55}^{Cq(Cc55)} \times E_{Ubq5}^{Cq(Ubq5)})/E_{goi}^{Cq(goi)}$, where E and Cq indicate the average reaction efficiency and cycle number at which the threshold fluorescence level was exceeded for the designated genes, respectively, and goi indicates the experimental "gene of interest."

OsAT5-D1 Hydroxycinnamate Fractionation

To determine whether the changes in hydroxycinnamate content were associated with the matrix polysaccharide or the lignin fractions, 6 mg of destarched AIR was mixed with 600 mL of either 0.05 M TFA or water, similar to a previously described method (Saulnier et al., 1995). Samples were incubated with shaking at 100° C. for up to 690 min. At each time point, a fraction of the sample was removed and frozen. Thawed samples were treated with 2 N NaOH for 24 h at 25° C. followed by neutralization with concentrated HCl. trans-Cinnamic acid was doped into the samples prior to three extractions with 300 mL of ethyl acetate. Combined extracts were dried with a CentriVap without heat and resuspended in 50:50 methanol for HPLC analysis. The multiple time points show that the reaction that liberates the matrix poly-saccharide goes approximately to completion. Longer times or higher acid concentrations caused degradation of the hydroxycinnamates.

In further experiments, AT5 and *Arabidopsis thaliana* 4-coumarate-CoA ligase (4CL) and AT5 were co-expressed in *Saccharamycetes cerevisiae*. The yeast were fed various permutations of hydroxycinnamic acids and monolignols as acyl donors and acceptors, respectively. Monolignol ester conjugate formation in the yeast intracellular fraction was detected using liquid chromatography-mass spectrometry (LC/MS).

Figures 28A, 28B, 28C:
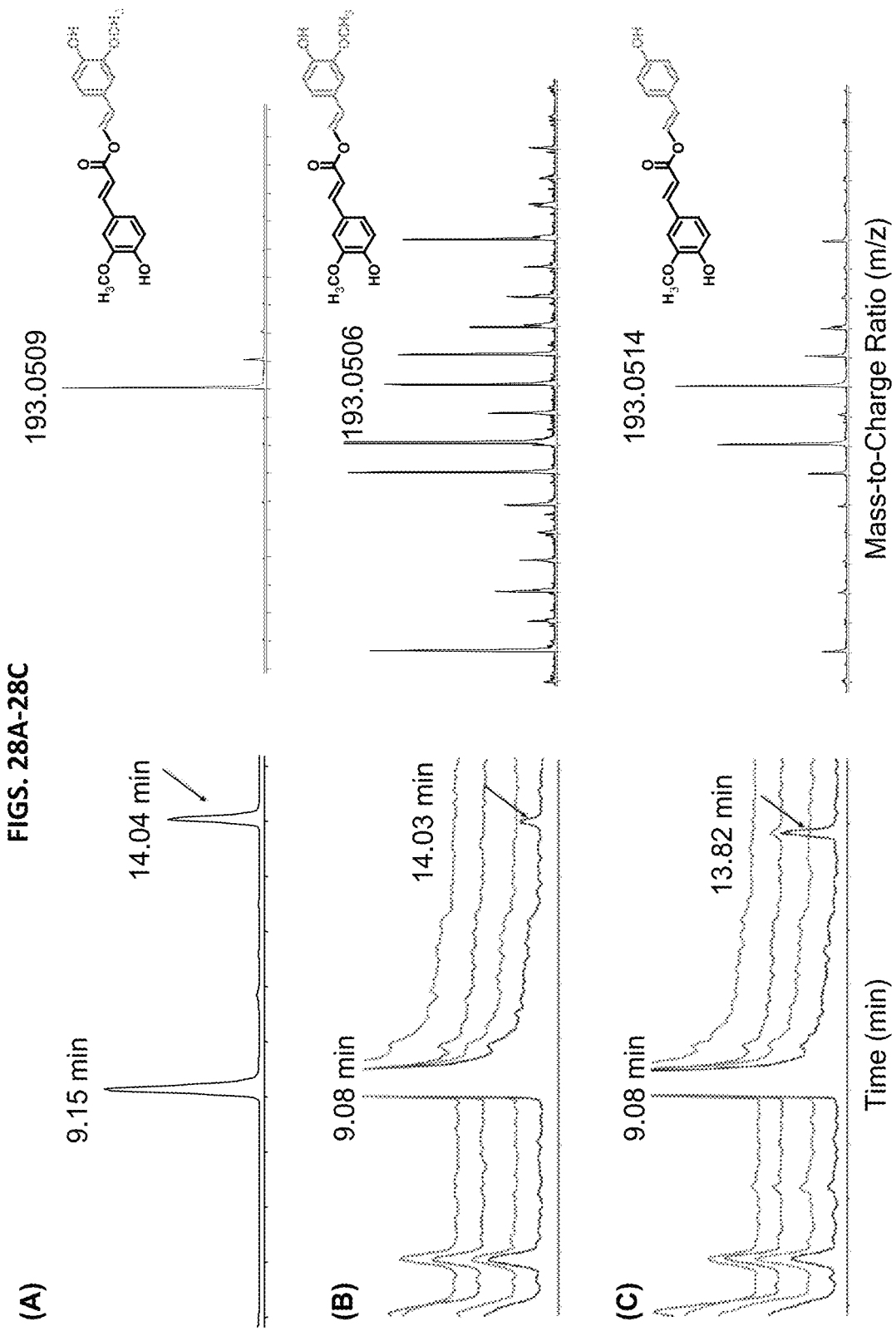
FIGS. 28A-28C shows LC/MS spectra of yeast metabolite analyses for (FIG. 28A) authentic coniferyl ferulate, (FIG. 28B) yeast fed with ferulic acid and coniferyl alcohol, and (FIG. 28C) yeast fed with ferulic acid and coumaryl alcohol. The chromatogram correspond to: yeast carrying empty vector (top line); yeast expressing 4CL ($2^{nd}$ line from the top); yeast expressing AT5 ($3^{rd}$ line from the top); and yeast expressing both 4CL and AT5 (bottom line). The MS spectra correspond to the peaks indicated by the arrows.

The results show that only the feruloyl adduct of monolignol ester was detected, not the monolignol ferulate conjugate. Expression of AT4/PMT in the yeast assay yielded coumaryl-ester conjugate, consistent with previous results (data not shown). This demonstrates that AT5 transfers feruloyl-CoA to monolignol moieties (FIGS. 28A-28C) and that AT5 specifically used ferulic acid as acyl donor (FIG. 29).

Additional Reference Cited

Agblevor F A, Evans R J, Johnson K D (1994) Molecular-beam mass-spectrometric analysis of lignocellulosic materials: I. Herbaceous biomass. Journal of Analytical and Applied Pyrolysis 30: 125-144

Allerdings E, Ralph J, Schatz P F, Gniechwitz D, Steinhart H, Bunzel M (2005) Isolation and structural identification of diarabinosyl 8-O-4-dehydrodiferulate from maize bran insoluble fibre. Phytochemistry 66: 113-124

An G, Lee S, Kim S H, Kim SR (2005) Molecular genetics using T-DNA in rice. Plant Cell Physiol 46: 14-22

Beekwilder J, Alvarez-Huerta M, Neef E, Verstappen F W, Bouwmeester H J, Aharoni A (2004) Functional characterization of enzymes forming volatile esters from strawberry and banana. Plant Physiol 135: 1865-1878

Buanafina MMdO (2009) Feruloylation in Grasses: Current and Future Perspectives. Mol Plant 2: 861-872

Bunzel M, Heuermann B, Kim H, Ralph J (2008) Peroxidase-catalyzed oligomerization of ferulic acid esters. J Agric Food Chem 56: 10368-10375

Bunzel M, Ralph J, Lu F, Hatfield R D, Steinhart H (2004) Lignins and ferulate-coniferyl alcohol cross-coupling products in cereal grains. J Agric Food Chem 52: 6496-6502

Carpita N C (1996) Structure and Biogenesis of the Cell Walls of Grasses. Annu Rev Plant Physiol Plant Mol Biol 47: 445-476

Casler M D, Jung H-J G (2006) Relationships of fibre, lignin, and phenolics to in vitro fibre digestibility in three perennial grasses. Animal Feed Science and Technology 125: 151-161

Chen X, Vega-Sánchez M, Bartley L E, Verhertbruggen Y, Chiniquy D, Canlas P E, Fagerström A, Prak L, Christensen U, Oikawa A, Chern M, Zuo S, Auer M, Willats W G, Harholt J, Scheller H V, Ronald PC (in prep) The OsIRX10 glycosyltansferase is critical for xylan biosynthesis in rice.

Cheng X, Sardana R, Altosaar I (1997) Rice transformation by *Agrobacterium* infection. In C Cunningham, A J R Porter, eds, Methods in Biotechnology: Recombinant Proteins from Plants—Production and Isolation of Clinically Useful Compounds, Vol 3. Humana, Totowa, N.J., pp 1-9

Claeyssens M, Aerts G (1992) Characterisation of cellulolytic activities in commercial *Trichoderma reesei* preparations: An approach using small, chromogenic substrates. Bioresource Technology 39: 143-146

D'Auria J C (2006) Acyltransferases in plants: a good time to be BAHD. Current Opinion in Plant Biology 9: 331-340

Evans R J, Milne T A (1987) Molecular characterization of the pyrolysis of biomass. Energy & Fuels 1: 123-137

Faulds C B, Mandalari G, LoCurto R, Bisignano G, Waldron K W (2004) Arabinoxylan and mono- and dimeric ferulic acid release from brewer's grain and wheat bran by feruloyl esterases and glycosyl hydrolases from <i> Humicola insolens</i>. Applied Microbiology and Biotechnology 64: 644-650

Fincher G B (2009) Revolutionary times in our understanding of cell wall biosynthesis and remodeling in the grasses. Plant Physiol 149: 27-37

Finn R D, Clements J, Eddy S R (2011) HMMER web server: interactive sequence similarity searching. Nucleic Acids Res Fu C, Mielenz J R, Xiao X, Ge Y, Hamilton C Y, Rodriguez M, Chen F, Foston M, Ragauskas A, Bouton J, Dixon R A, Wang Z-Y (2011) Genetic manipulation of lignin reduces recalcitrance and improves ethanol production from switchgrass. Proceedings of the National Academy of Sciences 108: 3803-3808

Fu C, Xiao X, Xi Y, Ge Y, Chen F, Bouton J, Dixon R, Wang Z-Y (2011) Downregulation of Cinnamyl Alcohol Dehydrogenase (CAD) Leads to Improved Saccharification Efficiency in Switchgrass. BioEnergy Research 4: 153-164

Fukushima R S, Hatfield R D (2004) Comparison of the Acetyl Bromide Spectrophotometric Method with Other Analytical Lignin Methods for Determining Lignin Concentration in Forage Samples. Journal of Agricultural and Food Chemistry 52: 3713-3720

Gessesse A, Gashe B A (1997) Production of alkaline xylanase by an alkaliphilic Bacillus sp. isolated from an alkaline soda lake. Journal of Applied Microbiology 83: 402-406

Ghose T K (1987) Measurement of Cellulase Activities. Pure and Applied Chemistry 59: 257-268

Grabber J H, Hatfield R D, Ralph J (1998) Diferulate cross-links impede the enzymatic degradation of non-lignified maize walls. Journal of the Science of Food and Agriculture 77: 193-200

Grabber J H, Quideau S, Ralph J (1996) p-coumaroylated syringyl units in maize lignin: Implications for [beta]-ether cleavage by thioacidolysis. Phytochemistry 43: 1189-1194

Grabber J H, Ralph J, Hatfield R D (1998) Ferulate Cross-Links Limit the Enzymatic Degradation of Synthetically Lignified Primary Walls of Maize. Journal of Agricultural and Food Chemistry 46: 2609-2614

Hagglund E (1951). In E Hagglund, ed, Chemistry of Wood. Academic, New York, N.Y., pp 374-379

Hatfield R, Marita J, Frost K, Grabber J, Ralph J, Lu F, Kim H (2009) Grass lignin acylation: p-coumaroyl transferase activity and cell wall characteristics of C3 and C4 grasses. Planta 229: 1253-1267

He X, Zhang J (2005) Rapid Subfunctionalization Accompanied by Prolonged and Substantial Neofunctionalization in Duplicate Gene Evolution. Genetics 169: 1157-1164

Hoffmann L, Maury Sp, Martz Fß, Geoffroy P, Legrand M (2003) Purification, Cloning, and Properties of an Acyltransferase Controlling Shikimate and Quinate Ester Intermediates in Phenylpropanoid Metabolism. Journal of Biological Chemistry 278: 95-103

Hu W J, Harding S A, Lung J, Popko J L, Ralph J, Stokke D D, Tsai C J, Chiang V L (1999) Repression of lignin biosynthesis promotes cellulose accumulation and growth in transgenic trees. Nat Biotechnol 17: 808-812

Huelsenbeck J P, Ronquist F (2001) MRBAYES: Bayesian inference of phylogenetic trees. Bioinformatics 17: 754-755

Humphrey T V, Bonetta D T, Goring D R (2007) Sentinels at the wall: cell wall receptors and sensors. New Phytologist 176: 7-21

Ishii T (1991) Isolation and characterization of a diferuloyl arabinoxylan hexasaccharide from bamboo shoot cell-walls. Carbohydrate Research 219: 15-22

Ishii T, Hiroi T, Thomas J R (1990) Feruloylated xyloglucan and p-coumaroyl arabinoxylan oligosaccharides from bamboo shoot cell-walls. Phytochemistry 29: 1999-2003

Jain M (2009) Genome-wide identification of novel internal control genes for normalization of gene expression during various stages of development in rice. Plant Science 176: 702-706

Jain M, Nijhawan A, Tyagi A K, Khurana J P (2006) Validation of housekeeping genes as internal control for studying gene expression in rice by quantitative real-time PCR. Biochem Biophys Res Commun 345: 646-651

Jeong D H, An S, Park S, Kang H G, Park G G, Kim S R, Sim J, Kim Y O, Kim M K, Kim J, Shin M, Jung M, An G (2006) Generation of a flanking sequence-tag database for activation-tagging lines in japonica rice. Plant J 45: 123-132

Jung H G, Phillips R L (2010) Putative Seedling Ferulate Ester (sfe) Maize Mutant: Morphology, Biomass Yield, And Stover Cell Wall Composition And Rumen Degradability. Crop Sci. 50: 403-418

Jung K H, An G, Ronald P C (2008) Towards a better bowl of rice: assigning function to tens of thousands of rice genes. Nat Rev Genet 9: 91-101

Kellogg E A (2001) Evolutionary History of the Grasses. Plant Physiol. 125: 1198-1205

Kovacs K, Macrelli S, Szakacs G, Zacchi G (2009) Enzymatic hydrolysis of steam-pretreated lignocellulosic materials with Trichoderma atroviride enzymes produced in-house. Biotechnology for Biofuels 2

Lal R (2005) World crop residues production and implications of its use as a biofuel. Environment International 31: 575-584

Lam T B-T, Iiyama K, Stone B A (2003) Hot alkali-labile linkages in the walls of the forage grass Phalaris aquatica and Lolium perenne and their relation to in vitro wall digestibility. Phytochemistry 64: 603-607

Lanoue A, Burlat V, Henkes G J, Koch I, Schurr U, Rose U S (2009) De novo biosynthesis of defense root exudates in response to Fusarium attack in barley. New Phytol Larkin M A, Blackshields G, Brown N P, Chenna R, McGettigan P A, McWilliam H, Valentin F, Wallace I M, Wilm A, Lopez R, Thompson J D, Gibson T J, Higgins D G (2007) Clustal W and Clustal X version 2.0. Bioinformatics 23: 2947-2948

Lee D, Meyer K, Chapple C, Douglas C J (1997) Antisense suppression of 4-coumarate:coenzyme A ligase activity in Arabidopsis leads to altered lignin subunit composition. Plant Cell 9: 1985-1998

Lynd L R, Laser M S, Bransby D, Dale B E, Davison B, Hamilton R, Himmel M, Keller M, McMillan J D, Sheehan J, Wyman C E (2008) How biotech can transform biofuels. Nat Biotechnol 26: 169-172

MacAdam J W, Grabber J H (2002) Relationship of growth cessation with the formation of diferulate cross-links and p-coumaroylated lignins in tall fescue leaf blades. Planta 215: 785-793

Mandels M, Andreotti R, Roche C (1970) Measurement of saccharifying cellulase. Biotechnology and Bioengineering Symposium 6: 21-33

Mitchell R A, Dupree P, Shewry P R (2007) A novel bioinformatics approach identifies candidate genes for the synthesis and feruloylation of arabinoxylan. Plant Physiol 144: 43-53

Molina I, Beisson-Li Y, Beisson F, Ohlrogge J B, Pollard M (2009) Identification of an Arabidopsis Feruloyl-CoA Transferase Required for Suberin Synthesis. Plant Physiol Mueller-Harvey I, Hartley R D, Harris P J, Curzon E H (1986) Linkage of p-coumaroyl and feruloyl groups to cell-wall polysaccharides of barley straw. Carbohydrate Research 148: 71-85

Obel N, Nuemetzler L, Pauly M (2006) Hemicelluloses and cell expansion. In J-P Verbelen, K Vissenberg, eds, Plant Cell Monographs: The Expanding Cell, Vol 5. Springer, Berlin, pp 57-88

Obel N, Porchia A C, Scheller H V (2002) Dynamic changes in cell wall polysaccharides during wheat seedling development. Phytochemistry 60: 603-610

ØBro J, Harholt J, Scheller H V, Orfila C (2004) Rhamnogalacturonan I in Solanum tuberosum tubers contains complex arabinogalactan structures. Phytochemistry 65: 1429-1438

Park C J, Bart R, Chern M, Canlas P E, Bai W, Ronald P C (2010) Overexpression of the endoplasmic reticulum chaperone BiP3 regulates XA21-mediated innate immunity in rice. PLoS ONE 5: e9262

Piston F, Uauy C, Fu L, Langston J, Labavitch J, Dubcovsky J (2010) Down-regulation of four putative arabinoxylan feruloyl transferase genes from family PF02458 reduces ester-linked ferulate content in rice cell walls. Planta 231: 677-691

Ralph J (2010) Hydroxycinnamates in lignification. Phytochemistry Reviews 9: 65-83

Ralph J, Quideau S, Grabber J H, Hatfield R D (1994) Identification and synthesis of new ferulic acid dehydrodimers present in grass cell walls. Journal of the Chemical Society, Perkin Transactions 1: 3485-3498

Rautengarten C, Ebert B, Ouellet M, Nafisi M, Baidoo E E, Benke P, Stranne M, Mukhopadhyay A, Keasling J D, Sakuragi Y, Scheller H V (2012) Arabidopsis Deficient in Cutin Ferulate encodes a transferase required for feruloylation of omega-hydroxy fatty acids in cutin polyester. Plant Physiol 158: 654-665

Ruijter J M, Ramakers C, Hoogaars W M, Karlen Y, Bakker 0, van den Hoff M J, Moorman A F (2009) Amplification efficiency: linking baseline and bias in the analysis of quantitative PCR data. Nucleic Acids Res 37: e45

Santiago R, Reid L M, Arnason J T, Zhu X, Martinez N, Malvar R A (2007) Phenolics in Maize Genotypes Differing in Susceptibility to Gibberella Stalk Rot (Fusarium graminearum Schwabe). Journal of Agricultural and Food Chemistry 55: 5186-5193

Santiago R, Sandoya G, Butrón A, Barros J, Malvar R A (2008) Changes in Phenolic Concentrations during Recurrent Selection for Resistance to the Mediterranean Corn Borer (Sesamia nonagrioides Lef.). Journal of Agricultural and Food Chemistry 56: 8017-8022

Sasayama D, Azuma T, Itoh K (2011) Involvement of cell wall-bound phenolic acids in decrease in cell wall susceptibility to expansins during the cessation of rapid growth in internodes of floating rice. J Plant Physiol 168: 121-127

Scheller H V, Ulvskov P (2010) Hemicelluloses. Annu Rev Plant Biol 61: 263-289

Skyes R, Yung M, Novaes E, Kirst M, Peter G, Davis M (2010) High-Throughput Screening of Plant Cell-Wall Composition Using Pyrolysis Molecular Beam Mass Spectroscopy. In J R Mielenz, ed, Biofuels: Methods and Protocols, Vol 581. Humana Press, pp 169-183

Takahama U, Oniki T (1994) Effects of Ascorbate on the Oxidation of Derivatives of Hydroxycinnamic Acid and the Mechanism of Oxidation of Sinapic Acid by Cell Wall-Bound Peroxidases. Plant and Cell Physiology 35: 593-600

Tamura K, Peterson D, Peterson N, Stecher G, Nei M, Kumar S (2011) MEGA5: molecular evolutionary genetics analysis using maximum likelihood, evolutionary distance, and maximum parsimony methods. Molecular biology and evolution 28: 2731-2739

Tuominen L, Johnson V, Tsai C-J (2011) Differential Phylogenetic Expansions in BAHD Acyltransferases Across Five Angiosperm Taxa and Evidence of Divergent Expression Among Populus Paralogues. BMC Genomics 12: 236

Unno H, Ichimaida F, Suzuki H, Takahashi S, Tanaka Y, Saito A, Nishino T, Kusunoki M, Nakayama T (2007) Structural and mutational studies of anthocyanin malonyltransferases establish the features of BAHD enzyme catalysis. J Biol Chem 282: 15812-15822

US-DOE (2011) U.S. Billion-Ton Update: Biomass Supply for a Bioenergy and Bioproducts Industry. In R D Perlack, B J Stokes, eds. Oak Ridge National Labs, Oak Ridge, Tenn., p 227

Vandesompele J, De Preter K, Pattyn F, Poppe B, Van Roy N, De Paepe A, Speleman F (2002) Accurate normalization of real-time quantitative RT-PCR data by geometric averaging of multiple internal control genes. Genome Biol 3: RESEARCH0034

Vogel J (2008) Unique aspects of the grass cell wall. Curr Opin Plant Biol 11: 301-307

Walker K, Long R, Croteau R (2002) The final acylation step in taxol biosynthesis: cloning of the taxoid C13-side-chain N-benzoyltransferase from Taxus. Proc Natl Acad Sci USA 99: 9166-9171

Withers S, Lu F, Kim H, Zhu Y, Ralph J, Wilkerson C G (2012) Identification of grass-specific enzyme that acylates monolignols with p-coumarate. J Biol Chem 287: 8347-8355

Wu A M, Rihouey C, Seveno M, Hornblad E, Singh S K, Matsunaga T, Ishii T, Lerouge P, Marchant A (2009) The Arabidopsis IRX10 and IRX10-LIKE glycosyltransferases are critical for glucuronoxylan biosynthesis during secondary cell wall formation. Plant J 57: 718-731

Zhou J Z, Xue K, Xie J P, Deng Y, Wu L Y, Cheng X H, Fei S F, Deng S P, He Z L, Van Nostrand J D, Luo Y Q (2012) Microbial mediation of carbon-cycle feedbacks to climate warming. Nature Climate Change 2: 106-110

Bartley, et al., (2013). "Overexpression of a Band Acyltransferase, Osat10, Alters Rice Cell Wall Hydroxycinnamic Acid Content and Saccharification." Plant Physiol 161(4): 1615-1633.

Wilkerson, et al., (2014). "Monolignol Ferulate Transferase Introduces Chemically Labile Linkages into the Lignin Backbone." Science 344(6179): 90-93.

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

```
ILLUSTRATIVE SEQUENCES
AT10 Acyltransferase cDNA Sequence
LOC_OS06G39390.1
                                                        SEQ ID NO: 1
ATGGGCGTCTTCGCCGTCACCAAGGTGTCCGAGGGCCCCGTCCGGCCGTCCGCAGCGACG

CCGTCGGAGACGCTGCCGCTCGCCTGGGTCGACCGCTACCCGACGCACCGCGGCCTCGTC

GAGTCCGTGCACATCTACCTCCGCCGCGACGACGCCGCCGTCGAGGCGCCGTGCGCCGAC
```

-continued

```
GGCGGCGTCATCGTCGAGGGAAAGAAGAAGAATAATAAGCCGGCGGCGGCGGTGGTGCGC

GGCGCGCTGGCGGACGCGCTGGTGCACTACTACCCGTTCGCGGGGCGGATCGTGGAGGAC

GAGCGGTCGCCGGGGCGGCCTGCCGTGCTGTGCTCCGGCGAGGGCGTCTACTTCGTGGAG

GCCGCCGCCAACTGCACCCTCGCCGACGTCAACCACCTGGAGCGGCCGCTGCTGCTGTCC

AAGGAGGACCTCGTGCCGTGCCCGACGCCGGAGCAGTGGCCCGTCGAGCCGCACAACAGC

CTCGCCATGATCCAGGTGACGACGTTCACCTGCGGCGGCTTCGTGATCGGGCTGCGCACC

AACCACGCGGTGGCGGACGGCACCGGCGCCGCCCAGTTCATGAACGCCGTCGGCGACCTC

GCCCGCGGCCTCCCCGGAGCCGCGGGTGAAGCCGATCTGGGCGCGCGACCGCTTCCCGGAC

CCGGACATCAAGCCCGGCCCGCTGCCGGAGCTCCCCGTGCTGCCGCTCCAGTACATCGCC

TTCGACTTCCCCGCCGCCTACCTCGGCAAGCTCAAGGCGCAGTACGCCGCCACCGCCGGC

GCCAGCAAGATCTGCTCCGCCTTCGACATCGTCATCGCCAAGCTCTGGCAGTGCCGGACG

CGCGCCATCGCCGCCGACCCCGCCGCGGCCGTCAAGCTCTGCTTCTTCGCCAGCGCCCGC

CAGGTGCTCGGCCTGGAGACCGGCTACTGGGGCAACGCCATCTTCCCGGTGAAGGTGTCC

GCGGCGGCGGGGAGGTGGCGGCGTCGTCGGTGATCGAGCTCGTCGGCGTGGTCCGGGAG

GCGAAGCGGCGGATGGCCGGCGAGTGCCTGCGCTGGGCGGAGGGGCGCACCGGCGGCGCC

GACCCGTTCCAGATGACGTTCGACTACGAGTCCGTGTACGTGTCGGACTGGAGCAAGCTC

GGGTTCAACGACGTCGACTACGGGTACGGCGCGCCGTCGGCGGCGGGGCCGCTGGTGAAC

TGCGACCTCATCTCGTCGGTGATCGTCATGCGGGCGCCGGCGCCGCTCGCCGGCACGCGG

CTGCTGGCGAGCTGCGTCACCAAGGAGCACGCCGACGACTTCGCCGCCAGGATGAGGGAG

GATCTCGTCTAA

AT10 Acyltransferase Protein Sequence
LOC_Os06g39390.1 (encoded by SEQ ID NO: 1)
                                                   SEQ ID NO: 2
MGVFAVTKVSEGPVRPSAATPSETLPLAWVDRYPTHRGLVESVHIYLRRDDAAVEAPCAD

GGVIVEGKKKNNKPAAAVVRGALADALVHYYPFAGRIVEDERSPGRPAVLCSGEGVYFVE

AAANCTLADVNHLERPLLLSKEDLVPCPTPEQWPVEPHNSLAMIQVTTFTCGGFVIGLRT

NHAVADGTGAAQFMNAVGDLARGLPEPRVKPIWARDRFPDPDIKPGPLPELPVLPLQYIA

FDFPAAYLGKLKAQYAATAGASKICSAFDIVIAKLWQCRTRAIAADPAAAVKLCFFASAR

QVLGLETGYWGNAIFPVKVSAAAGEVAASSVIELVGVVREAKRRMAGECLRWAEGRTGGA

DPFQMTFDYESVYVSDWSKLGFNDVDYGYGAPSAAGPLVNCDLISSVIVMRAPAPLAGTR

LLASCVTKEHADDFAARMREDLV*

AT15 Acyltransferase cDNA Sequence
LOC_OS10G01920.1
                                                   SEQ ID NO: 3
ATGAGTATTGTGGTGAGCAAGTCAGCGCCGGTGGTCGTCCGGCCATCGGAGCCGGCCACA

TCGACGGCCGACAAGATCCTTCTGTCAACTTTGGACAAGCCTGTTGCCACGATACCAGTG

ACCGTGCTACTTGCGTTCGACCACCCCATCCATGACGCCACCGCGGAGACCATCAAGACG

GCTCTCGCTCAATCACTCGTCCACTACTATCCTATCGCCGGCCGCATTTCCTGCGACAAT

GACGACGGCGGCCATTTCTACATCGACTGCACCGGCGAGGATCTCGGGGTCACGTTCGTG

GCCGCGTCCGCCAACTGCACCATGGAGGAGCTCATGTGTCTCGTCGACGACCAGGCTCCC

GACGACGAGACAGCGGTGGTGCAGCAGCTCGCCTTCAACTGCACGCCCGACGACCTTCAT

CACCGTCTGCTGTGGGTGCAGGTCACCACTCTCAACTGTGGAGGCTTCGTCGTCGGGGTG

ACATGGAGCCATGGCGTGGCTGACGGTCCCGGCATAGCACAGTTCATACAAGCCGTCGGC
```

-continued

```
GAGCTCGCCCGTGGCCTGCCATCGCCGTCCGTCGTCCCGGTCAGGTTGGACGACAAGATC

GCAACCCAAGCCGTACCTCCCTTCACCATGGCCGTTCATCGCTTCATATCCGGCCTCAAG

CCAGTATCAAACCTCGACGTACGCAACGTCACCGTCTCATCTAGCCTTATCAACCACATC

ATCGTCGGAGCTCGTCGTCGTGCCACCGTGTTCGAGGCGGTCGCCGCCGTGCTCTGGCAG

TGCCGTACACGGGTGGTGATGACGGATCCTGAGGCCCCCGCCGTGCTGCTCTTCGCGGTG

AACGCACGCAAGTACCTCGGCGCCAAGGACGGCTACTACGGATGCTGCACCGCCATGCAC

ATGGCCGTGTCCAAGTCCGGCACGGTGGCCAACGGCGACATCATGAAGTTGGTCGGCATC

ATACGCCGCGCCAAGGAGCAGATACCGGAGCAGCTGAAGGCAGACGACGGCGAGATGATG

CTACGGACGATGGTAGGGGAGAAGCAGGTGAATGGATACGAGAGCCTGCTCTACTTGACA

TCCTGGCGAAACATCGGGTTCGAGGACGTCGATTTCGGCAGCGGGAAGACGGCGAGGGTG

ATGACCTACCCGCCGAGGATGCTGTCCATGATGCCCAGGATTGCGCCCATCTGCTTCATG

CTCAAGGCCACAGAGGAAGGGGTCAGGGTCATGTCAGACTGTGTTACGGCTGACCACGCC

GATGCCTTCTATCAAGAAATAGCCAAGCTCAAAGCCACCACCTGA
```

AS15 Acyltransferase Protein Sequence
LOC_OS10G01920.1 (encoded by SEQ ID NO: 3)

SEQ ID NO: 4

```
MSIVVSKSAPVVVRPSEPATSTADKILLSTLDKPVATIPVTVLLAFDHPIHDATAETIKT

ALAQSLVHYYPIAGRISCDNDDGGHFYIDCTGEDLGVTFVAASANCTMEELMCLVDDQAP

DDETAVVQQLAFNCTPDDLHHRLLWVQVTTLNCGGFVVGVTWSHGVADGPGIAQFIQAVG

ELARGLPSPSVVPVRLDDKIATQAVPPFTMAVHRFISGLKPVSNLDVRNVTVSSSLINHI

IVGARRRATVFEAVAAVLWQCRTRVVMTDPEAPAVLLFAVNARKYLGAKDGYYGCCTAMH

MAVSKSGTVANGDIMKLVGIIRRAKEQIPEQLKADDGEMMLRTMVGEKQVNGYESLLYLT

SWRNIGFEDVDFGSGKTARVMTYPPRMLSMMPRIAPICFMLKATEEGVRVMSDCVTADHA

DAFYQEIAKLKATT*
```

AT7 Acyltransferase cDNA Sequence
LOC_Os05g08640.1

SEQ ID NO: 5

```
ATGGCGGCGGCGGCGCCGGACAAGGCGGTGGAGCGGCTGTCCCAGAAGCTGGTGCACCCG

TCGTCCCCACGCCGTCGGCCCCGCTCCGCCTCTCCTGGCTCGACCGCTACCCCACCCAG

ATGGCGCTCATCGAGTCGCTCCACGTCTTCAAGCCCGACCCGGCGAGGGACGCCGCGGGG

CAGGGGCTCGCCCCCGCGCGCGCCATCGAGACGGCCCTCGCGAGAGCCCTCGTCGAGTAC

TACCCGCTCGCCGGGAGGCTCGCCGTCTCCCGGGACTCCGGCGAGCTCCAGGTGGATTGC

TGCGGCGGCGCCGGCGGCCATGGCGGGGTGTGGTTCATCGAGGCGGCTGTCCCGTGCCGG

CTCGAGGACGTGGATTACCTCGAGTACCCTCTCGCCATCTCCAAGGACGAGCTGCTCCCC

CACCCGCGCCCCGCCCCACCCGCGACGAGGAAGACAAGCTCATCCTGCTCGTCCAGGTG

ACGACGTTCGCGTGCGGCGGGTTCGTGGTGGGGTTCAGGTTCAGCCACGCGGTGGCGGAC

GGCCCGGGGGCGGCGCAGTTCATGGGCGCGGTCGGCGAGCTCGCCCCGCGGCGGCGAGCGC

ATCACGGTGGCCCCGTCGTGGGGGCGCGACGCGGTGCCCGACCCGGCCGGCGCCATGGTC

GGCGCCCTCCCGGAGCCGGCCGGCGCGTCCCGCCTCGAGTACCTCGCCATCGACATCTCC

GCCGACTACATCAACCACTTCAAGTCCCAGTTCGCGGCGGCCACCGGCGGCGCCCGCTGC

TCCGCCTTCGAGGTGCTCATCGCCAAGGCATGGCAGAGCCGCACCCGCGCCGCCGCGTTC

GACCCCTCGACGCCGATCAACCTCTCCTTCGCCATGAACGCCCGGCCGCTCCTCCTCCCG

CGCGGCGGCGCCGGGTTCTACGGCAACTGCTACTACATCATGCGGGTGGCCTCCACCGCC

GGGAGGGTGGCGACGGCGAGCGTCACCGACGTGGTGAGGATGATCCGGGAGGGGAAGAAG
```

```
CGGCTCCCGTCGGAGTTCGCGCGGTGGGCCGCCGGAGAGATGGCCGGAGTCGACCCGTAC

CAGATCACCTCCGACTACCGGACGCTGCTGGTCTCCGACTGGACGCGGCTGGGCTTCGCC

GAGGTGGACTACGGGTGGGGCCCACCGGGCCACGTCGTGCCGCTCACGAACCTGGACTAC

ATCGCCACGTGTATCCTCGTCAAGCCCTGGGCCCACAAACCAGGGGCACGGCTCATCACC

CAGTGCGTCACACCCGACCGCGTCACCGCCTTCCACGACGCCATGGTGGACATCAACTAA
```

AT7 Protein Sequence
LOC_Os05g08640.1 (encoded by SEQ ID NO: 5)

SEQ ID NO: 6

```
MAAAAPDKAVERLSQKLVHPSSPTPSAPLRLSWLDRYPTQMALIFSLHVFKPDPARDAAG

QGLAPARAIETALARALVEYYPLAGRLAVSRDSGELQVDCCGGAGGHGGVWFIEAAVPCR

LEDVDYLEYPLAISKDELLPHPRPRPTRDEEDKLILLVQVTTFACGGFVVGFRFSHAVAD

GPGAAQFMGAVGELARGGERITVAPSWGRDAVPDPAGAMVGALPEPAGASRLEYLAIDIS

ADYINHFKSQFAAATGGARCSAFEVLIAKAWQSRTRAAAFDPSTPINLSFAMNARPLLLP

RGGAGFYGNCYYIMRVASTAGRVATASVTDVVRMIREGKKRLPSEFARWAAGEMAGVDPY

QITSDYRTLLVSDWTRLGFAEVDYGWGPPGHVVPLTNLDYIATCILVKPWAHKPGARLIT

QCVTPDRVTAFHDAMVDIN*
```

AT5 cDNA sequence
LOC_Os05g19910.1

SEQ ID NO: 7

```
ATGGTCGCTGTCACCGTGATGAGGAAGTCCCGGAACTTCGTCGGGCCGTCTCCTCCGACG

CCGCCGGCCGAGATCACGACGACGCTCGAGCTGTCGTCCATCGACCGCGTGCCCGGGCTG

CGCCACAACGTGCGGTCCCTGCACGTGTTCCGCCGCCACAAGAACAGCGGGCCCGTCGTC

GACGGTGATAGCAGGAGGCCGGCCGCCGTGATCCGCGCGGCGCTCGCCCGGGCGCTGGCG

GACTACCCGGCGTTCGCCGGCCGATTCGTCGGCTCCCTGCTGGCCGGCGACGCCTGCGTC

GCGTGCACCGGCGAGGGCGCGTGGTTCGTGGAGGCAGCCGCGGACTGCAGCCTCGACGAC

GTGAACGGCCTCGAGTACCCGCTCATGATCTCCGAGGAGGAGCTGCTGCCTGCCCCCGAG

GACGGCGTCGACCCTACCAGTATTCCAGTCATGATGCAGGTGACTGAATTCACTTGTGGA

GGATTTATCTTGGGCCTTGTGGCAGTCCACACCCTTGCTGATGGACTTGGAGCAGCACAA

TTCATCACTGCAGTAGCTGAATTGGCCCGTGGCATGGACAAGCTCAGGGTGGCTCCCGTG

TGGGATCGCTCGCTGATACCGAACCCACCTAAGCTCCCTCCTGGGCCACCACCATCGTTC

CAGTCCTTTGGTTTTCAGCATTTCTCCACAGATGTCACCTCTGACCGTATAGCTCACGTG

AAGGCTGAGTACTTCCAGACCTTTGGCCAGTATTGTTCCACCTTTGATGTTGCTACTGCT

AAGGTTTGGCAGGCCAGGACACGGGCCGTCGGGTACAAACCGGAGATCCAGGTCCATGTG

TGTTTCTTTGCAAACACGCGTCACCTGCTCACGCAGGTTCTCCCAAAAGATGGGGCTAC

TATGGCAACTGCTTTTATCCAGTGACTGTGACAGCAATAGCTGAGGATGTTGCCACCAAA

GAGTTGCTTGATGTGATCAAGATAATTCGGGATGGAAAGGCGAGGCTCCCCATGGAGTTT

GCAAAGTGGGCTTCAGGGGATGTGAAAGTTGATCCCTACGCATTGACATTTGAACACAAT

GTGCTTTTTGTGTCTGATTGGACGAGGTTAGGATTCTTCGAGGTAGACTATGGGTGGGGT

ACACCTAATCACATCATACCATTCACTTATGCAGACTACATGGCAGTCGCAGTGCTTGGT

GCTCCACCAATGCCAAAGAAAGGGACCCGGATTATGACACAGTGTGTGGAGAACAAGTGT

ATCAAGGAGTTCCAAGATGAGATGAAGGCCTTCATATAA
```

-continued

AT5 polypeptide sequence
LOC_Os05g19910.1 (encoded by SEQ ID NO: 7)

SEQ ID NO: 8

MVAVTVMRKSRNFVGPSPPTPPAEITTTLELSSIDRVPGLRHNVRSLHVFRRHKNSGPVV

DGDSRRPAAVIRAALARALADYPAFAGRFVGSLLAGDACVACTGEGAWFVEAAADCSLDD

VNGLEYPLMISEEELLPAPEDGVDPTSIPVMMQVTEFTCGGFILGLVAVHTLADGLGAAQ

FITAVAELARGMDKLRVAPVWDRSLIPNPPKLPPGPPPSFQSFGFQHFSTDVTSDRIAHV

KAEYFQTFGQYCSTFDVATAKVWQARTRAVGYKPEIQVHVCFFANTRHLLTQVLPKDGGY

YGNCFYPVTVTAIAEDVATKELLDVIKIIRDGKARLPMEFAKWASGDVKVDPYALTFEHN

VLFVSDWTRLGFFEVDYGWGTPNHIIPFTYADYMAVAVLGAPPMPKKGTRIMTQCVENKC

IKEFQDEMKAFI*

TABLE I

BAHD CoA acyltransferases encoded in some sequenced plant genomes.

| Species | # putative BAHD proteins: Total (# Perfect HXXXD)[a] | Clade V: Total (# Perfect HXXXD)[a,b] | AT Clade i[c] | AT Clade ii[c] |
|---|---|---|---|---|
| Physcomitrella patens | 17 (16) | 8 (7) | 0 | 0 |
| Selaginella moellendorffii | 74 (65) | 19 (19) | 0 | 0 |
| Oryza sativa | 122 (117) | 61 (60) | 10 | 10 |
| Sorghum biocolor | 89 (85) | 49 (48) | 8 | 4 |
| Brachypodium dystachion | 83 (78) | 38 (38) | 12 | 4 |
| Arabidopsis thaliana | 64 (61) | 25 (25) | 1 | 0 |
| Populus tricocarpa | 125 (121) | 25 (24) | 0 | 0 |
| Medicago truncatula | 89 (83) | 30 (27) | 1 | 0 |
| Glycine max | 142 (135) | 70 (65) | 2 | 0 |

[a] Consists of nonredundant predicted protein sequences identified via HMMER3.0 based on PFAM v. 25 and that contain the region surrounding the conserved active site motif, HXXXD, though proteins with single amino acid variations in either the H or D are included. The number in parentheses is the number with the strict HXXXD motif. See Results for justification.
[b] As in D'Auria 2006.
[c] Acyltransferase (AT) protein clades delineated in FIGS. 1A-1B and FIG. 12.

TABLE II

Summary of the rice acyltransferase mutant analysis.

| Gene Name[a] | Locus ID (LOC_)[b] | EST Count[c] | Mutant Line ID (PFG_) | cv[d] | Line Class (putative) | Insert Detected | Immature leaf and sheath cell wall hydroxycinnamic acid phenotype[e] |
|---|---|---|---|---|---|---|---|
| OsAt1 | Os01g42880 | 86 | 3A-13924 | DJ | AT[f] | No | ND[g] |
| OsAt2 | Os01g42870 | 25 | NA[h] | | | | |
| OsAt3 | Os05g04584 | 49 | 3A-02783 | DJ | AT | No | ND |
| OsAt4 | Os01g18744 | 50 | 3A-02300 | DJ | Insert/AT[i] | Yes, no homozygotes | ND |
| | | | 3A-09297 | DJ | Insert/AT | No | ND |
| OsAt5 | Os05g19910 | 17 | 2A-20021[j] | DJ | AT | Yes | Leaf and sheath: increase in FA:p-CA ratio |
| | | | 1C-03624 | HY | Insert[k] | No | ND |
| OsAt6 | Os01g08380 | 76 | 1C-06931 | HY | Insert | No | ND |
| | | | 3A-08459 | DJ | AT | No | ND |
| | | | 2D-40810 | HY | AT | Yes | None |
| OsAt7 | Os05g08640 | 15 | 2A-40095 | HY | Insert/AT | Yes | Sheath: decrease FA |
| OsAt8 | Os06g39470 | 5 | NA | | | | |
| OsAt9 | Os01g09010 | 200 | NA | | | | |
| OsAt10 | Os06g39390 | 41 | 4A-03423[l] | DJ | AT | Yes | Leaf: decrease FA, increase p-CA Sheath: decrease FA, increase p-CA |
| OsAt11 | Os04g11810 | 0 | NA | | | | |
| OsAt12 | Os04g09590 | 0 | 3A-16373 | DJ | AT | Yes | None |
| | | | 2D-41616 | HY | AT | Yes | None |
| OsAt13 | Os10g01930 | 0 | 2D-10182 | DJ | Insert/AT | Yes, no homozygotes | ND |
| OsAt14 | Os10g02000 | 9 | NA | | | | |
| OsAt15 | Os10g01920 | 0 | 1B-00523 | DJ | AT | Yes | Leaf: decrease FA |

TABLE II-continued

Summary of the rice acyltransferase mutant analysis.

| Gene Name [a] | Locus ID (LOC_) [b] | EST Count [c] | Mutant Line ID (PFG_) | cv [d] | Line Class (putative) | Insert Detected | Immature leaf and sheath cell wall hydroxycinnamic acid phenotype [e] |
|---|---|---|---|---|---|---|---|
| OsAt16 | Os10g01800 | 0 | 2D-40243 | DJ | AT | Yes | None |
| OsAt17 | Os10g03360 | 0 | NA | | | | |
| OsAt18 | Os10g03390 | 1 | 4A-04176 | DJ | AT | Yes | None |
| OsAt19 | Os04g09260 | 7 | NA | | | | |
| OsAt20 | Os06g48560 | 0 | NA | | | | |
| Totals | | 20 | 17 (for 11 genes) | | | 11 confirmed, 2 no homozyg. for insert | 4 phenotypes |

[a] *Oryza sativa* (Os) acyltransferase (At) gene names were assigned arbitrarily based on an early phylogenic analysis, that has since been revised.
[b] Annotation MSUv6
[c] Sum of ESTs from all organs/stages from rice Sanger EST data available through 2009.
[d] DJ and HW indicate *O. sativa* var. *japonica* cv. Dongjin and cv. Hwayoung, respectively
[e] For homozygous mutants relative to negative segregant wild-type siblings. CA signifies para-coumaric acid. FA signifies ferulic acid. A change in FA:CA ratio is only mentioned when a phenotype in neither FA nor CA alone appear to change.
[f] AT signifies a putative activation tagged line in the T-DNA insert possesses transcription activation sequences.
[g] ND signifies not determined.
[h] NA signifies that no rice activation lines were available at the inception of the study.
[i] Insert/AT signifies that the T-DNA possesses transcription activation sequences and is inserted within, or <300 base pairs away from, the gene.
[j] OsAT5-D1
[k] Insert signifies that the T-DNA is inserted within, or <300 base pairs away from, the gene.
[l] OsAT10-D1

TABLE III

Lignin Amounts and S:G Ratios from AIR after 2N NaOH extraction for greenhouse grown mutant and wildtype plants.

| Line | Parental Genotype | Material | ABSL [a] (% mass) | S/G ratio [b] | Standardized Lignin [c] (% mass) |
|---|---|---|---|---|---|
| WT [d] | 4A-03423.1 | mature straw | 5.5 ± 0.5 | 0.67 ± 0.01 | 5.7 ± 0.2 |
| AT10-D1 | 4A-03423.5 | mature straw | 5.5 ± 0.5 | 0.75 ± 0.11 | 5.5 ± 0.1 |
| AT10-D1 | 4A-03423.12 | mature straw | 5.7 ± 0.6 | ND [e] | ND |
| WT | 4A-03423 | leaf sheath | ND | 0.39 ± 0.05 | 5.9 ± 0.1 |
| AT10-D1 | 4A-03423 | leaf sheath | ND | 0.36 ± 0.13 | 5.5 ± 0.7 |
| WT | 4A-03423 | leaf blade | ND | 0.52 ± 0.13 | 3.4 ± 0.1 |
| AT10-D1 | 4A-03423 | leaf blade | ND | 0.52 ± 0.09 | 3.4 ± 0.3 |

[a] Acetylbromide soluble lignin expressed in terms of mg/mg for pools of straw, measured in triplicate, or 2 to 3 individual bioreplicates, measured in duplicate. Errors are standard deviations.
[b] Average ± standard deviation of singlicate measurements of 2 to 3 plants for the earlier generation, and two technical replicates of pools of 12 plants for the later generation samples, as determined by py-MBMS.
[c] As determined via py-MBMS and calibrated for each type of rice sample (i.e., straw, leaf, sheath) based on the ABSL data.
[d] negative segregant, wild type.
[e] ND = not determined

TABLE IV

Primers used in examples

A. Primers used for genotyping (SEQ ID NOS: 43-75).

| Line | 5' primer name | 5' primer sequence (5->3) | 3' primer name | 3' primer sequence (5->3) | primer pair for T-DNA:: plant junction |
|---|---|---|---|---|---|
| | L0.5 | TTGGGGATCCTCTAGAGTCGAG | | | |
| | iL1 | TCCGAAACTATCAGTGTCTAGCT | | | |
| | NGUS1 | AACGCTGATCAATTCCACAG | | | |
| 1A-19542 | Pam1-1F | GTGGTGGAAAGTTGTGATCG | Pam1-1R_15LB | CAGGGCATGTTTAGTTGGTG | Pam1-1R_15LB/L0.5 |
| 5A-00394 | Pam1-3F | CTCAACCGCCATCATGTTAC | Pam1-3R_15LB | GTTCCTATCACATCGGATGT | Pam1-3R_15LB/L0.5 |

TABLE IV-continued

Primers used in examples

| | | | | | |
|---|---|---|---|---|---|
| 1B-00523 | Pam1-8F_15LB | GATGGGACAGTCTCTAGTCA | Pam1-8R | GTAGTACGCGAGATCCGTAT | Pam1-8F_15LB/L0.5 |
| 3A-02300 | Pam1-12F_15RB | TGCAGCCTCGACGACGTGA | Pam1-12R | TGATCCGTTAGCGCGTGTT | Pam1-12F_15RB/NGUS1 |
| 2A-20021 | Pam1-13F_15LB | TGACTGAAGGTCGAGAACGA | Pam1-13R_15LB | GTTACATGATGCCTTGTCAAG | Pam1-13R_15LB/L0.5 |
| 2D-40818 | Pam1-15F | GCAGCTCAACTCCTGAAAATC | Pam1-15R_72RB | GCCAGCTGATCTGAAGCAG | Pam1-15R_72RB/NGUS1 |
| 4A-03423 | Pam1-16F_15LB | CCAGAGGGAGTACTTCCGT | Pam1-16R | GCGAGATGGCTATACGTGAG | Pam1-16F_15LB/L0.5 |
| 3A-13924 | Pam1-17F | CCATCTTAGAGATGGGAGCA | Pam1-17R_15RB | CGTCCTTGGATCTGGGTCA | Pam1-17R_15RB/NGUS1 |
| 2D-10182 | Pam1-19F | CAGATGAGCTTATAGCTAGT | Pam1-19R_72LB | GACTTGCTCACCACAATGCT | Pam1-19R_72LB/iL1 |
| 4A-04176 | Pam1-22F_15RB | GTGGTTAGAACCTCCCTAGA | Pam1-22R | CTCATGGATCGGATGCTCGA | Pam1-22F_15RB/NGUS1 |
| 2A-40095 | Pam1-25F_15RB | TCACGAACCTGGACTACATC | Pam1-25R | ACCATCTACCTGTACCCTCA | Pam1-25F_15RB/NGUS1 |
| 1C-03624 | Pam1-26F_07RB | GTGACGGAGGCAGTGATGA | Pam1-26R | GCTTAAGTGCAGCCCAAACT | Pam1-26F_07RB/NGUS1 |
| 3A-16373 | Pam1-28F | CAAGAGGGCATAAGTGAACT | Pam1-28R_15LB | CATCGGAAGGTGATTCCACA | Pam1-28R_15LB/L0.5 |
| 2D-41616 | Pam1-29F | CAGTTGCAGACCACTGAGAA | Pam1-29R_72LB | CTTGATTCTCGAGTTGAAAGT | Pam1-29R_72LB/iL1 |
| Ubi::OsAt10 | Hyg-3 | TCCACTATCGGCGAGTACTTCTACACA | hyg 4 | CACTGGCAAACTGTGATGGACGAC | |

B. RT-qPCR primers (SEQ ID NOS: 76-99)

| ID | 5' primer name | 5' primer sequence | 3' primer name | 3' primer sequence | purpose |
|---|---|---|---|---|---|
| LOC_Os01g08380 | Os01g08380F1 | AGGCCGGGAGGATGGGTGGATT | Os01g08380R1 | ACCACGCTCCACCCACGAGCT | experimental |
| LOC_Os01g09010 | os01g09010_832F | cacctgctgaagctggacag | os01g09010_929Ra | tccatcaccgacgacgacagc | experimental |
| LOC_Os04g09260 | 04g09260-2-f | GGAAGCACGTCGGAGCCAAG | 04g09260-2-r | CGACATGATGCAGTTGCCGTAG | experimental |
| LOC_Os05g08640 | os05g08640F4qPCR | AAACCAGGGGCACGGCTCAT | os05g08640R4qPCR | TTGATGTCCACCATGGCGTCGT | experimental |
| LOC_Os05g19910 | os05g19910_543F | catcactgcagtagctgaattgg | os05g19910_634R | gcttaggtgggttcggtatcagc | experimental |
| LOC_Os06g39370 | Os06g39370F1 | TGCCTTCTAGAAATCTGAAGCGTAT | Os06g39370R1 | TTGCTGTACAAACTCGAACTCTGC | experimental |
| LOC_Os06g39380 | Os06g39380F1 | ACAGAAAAACCACGGCCTAATAGA | Os06g39380R1 | CTCTTTTCACTCCCACCCTTGTCT | experimental |
| LOC_Os06g39390 | Os06g39390RT2-5' | GACCCGTTCCAGATGACGTT | 06g39390-RT2-3' | GATGAGGTCGCAGTTCACCA | experimental |
| LOC_Os06g39400 | Os06g39400F1 | GCGCATGGAAGGGCAAAACAGC | Os06g39400R1 | CTGCTCCAGAAAAAGCTCGATCGGT | experimental |
| LOC_Os06g39470 | Os06g39470_359F | agtacccgctcatggtggac | os06g39470_467R | aactgcgtgacctggacaa | experimental |

TABLE IV-continued

Primers used in examples

| LOC_Os04g35910 | CC55 R1-5' | AAGGAGAAAGCCGAACAACG | CC55 RT1-3' | TCCTCAAGTTTCTTCCTGTAGGC | control |
| LOC_Os01g224901 | UBQ5 RT-5' | ACCACTTCGACCGCCACTACT | UBQ5 RT1-3' | ACGCCTAAGCCTGCTGGTT | control |

C. Cloning primers (SEQ ID NOS: 100-101)

| gene targeted | 5' primer name | 5' primer sequence | 3' primer name | 3' primer sequence |
|---|---|---|---|---|
| LOC_Os06g39390 | Os06g39390for-2 | CACCAGCAGCAGCAGCAGCAGCAG | Os06g39390rev-stop2 | TACCACGCATGTCACAAAGCACGG |

TABLE V

Average ± standard deviation of sugar composition of the media during the course of *Penicillium* sp. YT02 incubation with OsAT10-D1 and negative segregant, wild type. N = 5.

| | Glucose | | | Xylose | | | Arabinose | | |
|---|---|---|---|---|---|---|---|---|---|
| Time (hrs) | WT (mg/mL) | Mut (mg/mL) | Δ % | WT (mg/mL) | Mut (mg/mL) | Δ % | WT (mg/mL) | Mut (mg/mL) | Δ % |
| 12 | 0.42 ± 0.01 | 0.42 ± 0.02 | 0 | 0.17 ± 0.03 | 0.32 ± 0.04 | 88 | 0.05 ± 0.02 | 0.05 ± 0.01 | 0 |
| 24 | 1.4 ± 0.1 | 1.5 ± 0.4 | 3 | 0.7 ± 0.3 | 1.4 ± 0.5 | 106 | 0.14 ± 0.05 | 0.24 ± 0.01 | 71 |
| 36 | 2.1 ± 0.1 | 2.3 ± 0.2 | 9 | 0.8 ± 0.2 | 1.8 ± 0.4 | 116 | 0.27 ± 0.03 | 0.40 ± 0.01 | 48 |
| 48 | 2.7 ± 0.1 | 4.4 ± 0.3 | 65 | 1.2 ± 0.5 | 2.3 ± 0.2 | 95 | 0.5 ± 0.1 | 0.39 ± 0.02 | — |
| 60 | 3.5 ± 0.1 | 4.7 ± 0.3 | 35 | 1.7 ± 0.3 | 2.7 ± 0.2 | 64 | 0.6 ± 0.2 | 0.63 ± 0.02 | 5 |
| 72 | 3.4 ± 0.1 | 6.1 ± 0.2 | 82 | 1.8 ± 0.1 | 3.7 ± 0.4 | 102 | 0.5 ± 0.5 | 0.60 ± 0.03 | 25 |
| 84 | 3.3 ± 0.1 | 4.8 ± 0.1 | 47 | 2.0 ± 0.2 | 2.9 ± 0.2 | 45 | 0.6 ± 0.3 | 0.80 ± 0.05 | 35 |
| 96 | 1.8 ± 0.1 | 3.4 ± 0.2 | 97 | 1.4 ± 0.1 | 2.5 ± 0.2 | 84 | 0.5 ± 0.2 | 0.64 ± 0.03 | 28 |
| 120 | 1.1 ± 0.1 | 1.4 ± 0.1 | 28 | 1.6 ± 0.1 | 2.4 ± 0.2 | 48 | 0.5 ± 0.2 | 0.48 ± 0.03 | 7 |
| Avg | | | 46 | | | 82 | | | 25 |

| | Galactose | | | Mannose | | | Cellobiose | | |
|---|---|---|---|---|---|---|---|---|---|
| Time (hrs) | WT (mg/mL) | Mut (mg/mL) | Δ % | WT (mg/mL) | Mut (mg/mL) | Δ % | WT (mg/mL) | Mut (mg/mL) | Δ % |
| 12 | 0.02 ± 0.01 | 0.02 ± 0.01 | 0 | 0.04 ± 0.01 | 0.04 ± 0.01 | 0 | 0.20 ± 0.01 | 0.09 ± 0.01 | −55 |
| 24 | 0.11 ± 0.02 | 0.04 ± 0.01 | −62 | 0.18 ± 0.02 | 0.16 ± 0.01 | −9 | 0.38 ± 0.01 | 0.36 ± 0.02 | −4 |
| 36 | 0.09 ± 0.03 | 0.10 ± 0.01 | 11 | 0.14 ± 0.06 | 0.20 ± 0.03 | 48 | 0.54 ± 0.01 | 0.35 ± 0.02 | −35 |
| 48 | 0.18 ± 0.06 | 0.16 ± 0.01 | −13 | 0.42 ± 0.04 | 0.23 ± 0.04 | −44 | 0.70 ± 0.01 | 0.55 ± 0.04 | −22 |
| 60 | 0.15 ± 0.02 | 0.27 ± 0.03 | 80 | 0.38 ± 0.03 | 0.45 ± 0.03 | 20 | 0.85 ± 0.02 | 0.81 ± 0.05 | −5 |
| 72 | 0.16 ± 0.04 | 0.12 ± 0.02 | −25 | 0.24 ± 0.04 | 0.48 ± 0.02 | 100 | 0.95 ± 0.01 | 1.2 ± 0.2 | 27 |
| 84 | 0.15 ± 0.02 | 0.40 ± 0.03 | 170 | 0.15 ± 0.03 | 0.30 ± 0.02 | 103 | 0.73 ± 0.03 | 0.80 ± 0.05 | 10 |
| 96 | 0.65 ± 0.01 | 0.24 ± 0.01 | −63 | 0.10 ± 0.02 | 0.40 ± 0.02 | 300 | 0.60 ± 0.02 | 0.80 ± 0.04 | 34 |
| 120 | 0.36 ± 0.01 | 0.03 ± 0.02 | −17 | 0.36 ± 0.05 | 0.30 ± 0.01 | −17 | 0.37 ± 0.03 | 0.78 ± 0.02 | 110 |
| Avg | | | 10 | | | 63 | | | 14 |

What is claimed is:

1. A method of engineering a plant to increase the ferulic acid content in the plant, the method comprising: introducing an expression cassette into the plant, wherein the expression cassette comprises a polynucleotide encoding an AT5 acyltransferase, wherein the acyltransferase has at least 95% identity to SEQ ID NO:8, and culturing the plant under conditions in which the acyltransferase is expressed.

2. The method of claim 1, wherein the acyltransferase has at least 99% identity to SEQ ID N0:8.

3. The method of claim 2, wherein the acyltransferase comprises SEQ ID NO:8.

4. The method of claim 1, wherein the polynucleotide is operably linked to a promoter endogenous to the plant.

5. The method of claim 1, wherein the expression cassette comprises a promoter to which the polynucleotide is operably linked.

6. The method of claim 5, wherein the promoter is a tissue-specific promoter.

7. The method of claim 1, wherein the polynucleotide has at least 95% identity to SEQ ID NO:7.

8. The method of claim 7, wherein the polynucleotide has at least 99% identity to SEQ ID NO:7.

9. The method of claim 8, wherein the polynucleotide comprises SEQ ID NO:7.

10. The method of claim 1, wherein the plant is a grass plant.

11. The method of claim 10, wherein the grass plant is rice, corn, switchgrass, sorghum, millet, miscanthus, sugarcane, alfalfa, wheat, soy, rye, barley, turfgrass, hemp, bamboo, rape, sunflower, or brachypodium.

12. A plant engineered by the method of claim 1, or a progeny of the plant.

13. A plant cell comprising a polynucleotide encoding an AT5 operably linked to a heterologous promoter; or a plant comprising a heterologous polynucleotide encoding an AT5 protein.

14. Biomass comprising the plant or a part of the plant of claim 12.

15. A method of obtaining an increased amount of soluble sugars from a plant in a saccharification reaction, the method comprising:
   subjecting the plant of claim 12 to a saccharification reaction, thereby increasing the amount of soluble sugars that can be obtained from the plant as compared to a wild-type plant.

* * * * *